US009664683B2

(12) United States Patent
Singh et al.

(10) Patent No.: US 9,664,683 B2
(45) Date of Patent: May 30, 2017

(54) PROFILING OF SIGNAL PATHWAY PROTEINS TO DETERMINE THERAPEUTIC EFFICACY

(71) Applicant: Nestec S.A., Vevey (CH)

(72) Inventors: Sharat Singh, Rancho Santa Fe, CA (US); Phillip Kim, Irvine, CA (US)

(73) Assignee: PIERIAN HOLDINGS, INC., Franklin, TN (US)

( * ) Notice: Subject to any disclaimer, the term of this patent is extended or adjusted under 35 U.S.C. 154(b) by 0 days.

(21) Appl. No.: 14/194,323

(22) Filed: Feb. 28, 2014

(65) Prior Publication Data

US 2015/0017659 A1    Jan. 15, 2015

Related U.S. Application Data

(63) Continuation of application No. PCT/US2012/053505, filed on Aug. 31, 2012.

(60) Provisional application No. 61/562,338, filed on Nov. 21, 2011, provisional application No. 61/553,124, filed on Oct. 28, 2011, provisional application No. 61/530,621, filed on Sep. 2, 2011.

(51) Int. Cl.
   *G01N 33/574* (2006.01)
   *G01N 33/50* (2006.01)
   *G01N 33/542* (2006.01)

(52) U.S. Cl.
   CPC ... *G01N 33/57492* (2013.01); *G01N 33/5011* (2013.01); *G01N 33/5041* (2013.01); *G01N 33/542* (2013.01); *G01N 2333/9121* (2013.01)

(58) Field of Classification Search
   None
   See application file for complete search history.

(56) References Cited

U.S. PATENT DOCUMENTS

| | | | |
|---|---|---|---|
| 4,233,402 A | 11/1980 | Maggio et al. | |
| 4,690,890 A | 9/1987 | Loor et al. | |
| 4,975,532 A | 12/1990 | Rowley et al. | |
| 5,089,419 A | 2/1992 | Kuniyuki | |
| 5,120,660 A | 6/1992 | Kuniyuki | |
| 5,192,660 A * | 3/1993 | Reed-Gitomer | 435/7.21 |
| 5,445,944 A | 8/1995 | Ullman | |
| 5,516,931 A | 5/1996 | Giese et al. | |
| 5,527,684 A | 6/1996 | Mabile et al. | |
| 5,876,944 A | 3/1999 | Kuo | |
| 6,201,109 B1 | 3/2001 | Avnur et al. | |
| 6,335,173 B1 | 1/2002 | Kaplan | |
| 6,406,913 B1 | 6/2002 | Ullman et al. | |
| 6,511,809 B2 | 1/2003 | Baez et al. | |
| 6,627,400 B1 | 9/2003 | Singh et al. | |
| 6,649,351 B2 | 11/2003 | Matray et al. | |
| 6,770,439 B2 | 8/2004 | Singh et al. | |
| 6,818,399 B2 | 11/2004 | Singh et al. | |
| 6,949,347 B2 | 9/2005 | Singh et al. | |
| 6,972,198 B2 | 12/2005 | Craig et al. | |
| 7,101,682 B2 | 9/2006 | Ullman et al. | |
| 7,279,286 B2 | 10/2007 | Kannt et al. | |
| 7,402,399 B2 | 7/2008 | Mukherjeei et al. | |
| 7,537,938 B2 | 5/2009 | Kirakossian et al. | |
| 7,695,924 B2 | 4/2010 | Perez et al. | |
| 7,695,926 B2 | 4/2010 | Perez et al. | |
| 8,163,499 B2 | 4/2012 | Singh et al. | |
| 8,609,349 B2 | 12/2013 | Singh et al. | |
| 8,658,388 B2 | 2/2014 | Harvey et al. | |
| 9,250,243 B2 | 2/2016 | Singh et al. | |
| 9,274,116 B2 | 3/2016 | Singh et al. | |
| 9,285,369 B2 | 3/2016 | Harvey et al. | |
| 2002/0142361 A1 | 10/2002 | Emmert-Buck | |
| 2002/0168641 A1 | 11/2002 | Mortensen et al. | |
| 2003/0059811 A1 | 3/2003 | Djaballah et al. | |
| 2003/0087311 A1 | 5/2003 | Wolf | |
| 2003/0153013 A1 | 8/2003 | Huang | |
| 2003/0153014 A1 | 8/2003 | Shen et al. | |
| 2003/0190689 A1 | 10/2003 | Crosby et al. | |
| 2004/0077090 A1 | 4/2004 | Short | |
| 2004/0106161 A1 | 6/2004 | Bossenmaier et al. | |
| 2004/0157271 A1 | 8/2004 | Kirakossian et al. | |
| 2004/0175696 A1 | 9/2004 | Ullman et al. | |
| 2004/0235002 A1 | 11/2004 | Holmes et al. | |
| 2004/0265923 A1 | 12/2004 | Gilmore et al. | |
| 2004/0265938 A1 | 12/2004 | Remacle et al. | |
| 2005/0069962 A1 | 3/2005 | Archer et al. | |
| 2005/0153342 A1 | 7/2005 | Chen | |

(Continued)

FOREIGN PATENT DOCUMENTS

CA    2 588 992 A1    6/2006
EP    0 310 132 A2    4/1989

(Continued)

OTHER PUBLICATIONS

Cao et al. (J. Biol. Chem. 1996 vol. 271, p. 3154-3162).*
Ahn, S. et al., "Molecular Markers for Individualized Therapy in Colorectal Cancer: Progress Towards a Pharmacogenomics Array," Curr Pharma and Personalized Medicine, 7:70-80, 2009.
Angenendt, P. et al. "3D Protein microarrays: performing multiplex immunoassays on a single Chip," Anal. Chem., 75:4368-4372, 2003.
Annex to EPO Form 2004, Communication Pursuant to Rule 71(3) EPC; European Patent Application No. 07 842 865.3; May 8, 2012 (7 pgs).
Arpino, G. et al., "Infiltrating lobular carcinoma of the breast: tumor characteristics and clinical outcome," Breast Cancer Research, 6:R149-156, 2003.

(Continued)

*Primary Examiner* — Jacob Cheu
(74) *Attorney, Agent, or Firm* — Kilpatrick Townsend & Stockton LLP

(57) ABSTRACT

The present invention provides methods for detecting, measuring and quantitating the activation states of components of the PI3K signaling pathway in cells such as tumor cells. In particular embodiments, the present invention enable the determination of tumor adaptation to anticancer therapy. Accordingly, the present invention provides methods for improved cancer therapy selection/adjustment and disease monitoring.

27 Claims, 53 Drawing Sheets

(56) References Cited

U.S. PATENT DOCUMENTS

| | | | |
|---|---|---|---|
| 2006/0013819 A1* | 1/2006 | Kelsey | A61K 31/4745 424/155.1 |
| 2006/0024723 A1 | 2/2006 | Hussa et al. | |
| 2006/0024846 A1 | 2/2006 | Singh et al. | |
| 2006/0127945 A1 | 6/2006 | Preaudat et al. | |
| 2007/0111944 A1 | 5/2007 | Scrofani et al. | |
| 2007/0269902 A1 | 11/2007 | Beechem et al. | |
| 2008/0096235 A1 | 4/2008 | Kimberly et al. | |
| 2008/0176229 A1 | 7/2008 | Agus et al. | |
| 2008/0187948 A1 | 8/2008 | Chan-Hui et al. | |
| 2008/0261829 A1* | 10/2008 | Harvey | G01N 33/574 506/13 |
| 2009/0035792 A1* | 2/2009 | Singh | G01N 33/5041 435/7.23 |
| 2009/0124511 A1 | 5/2009 | Archer et al. | |
| 2010/0021457 A1 | 1/2010 | Pfleger et al. | |
| 2010/0167945 A1 | 7/2010 | Singh et al. | |
| 2010/0311185 A1 | 12/2010 | Schelp et al. | |
| 2011/0275097 A9 | 11/2011 | Singh et al. | |
| 2011/0281748 A1 | 11/2011 | Singh et al. | |
| 2012/0231965 A1 | 9/2012 | Kim et al. | |
| 2012/0270745 A1 | 10/2012 | Singh et al. | |
| 2013/0045880 A1 | 2/2013 | Singh et al. | |
| 2013/0216523 A1* | 8/2013 | Wallweber et al. | 424/133.1 |
| 2013/0315933 A1* | 11/2013 | Renner et al. | 424/173.1 |
| 2013/0324430 A1 | 12/2013 | Kim et al. | |
| 2014/0187445 A1 | 7/2014 | Harvey et al. | |
| 2014/0349865 A1 | 11/2014 | Singh et al. | |
| 2015/0051107 A1 | 2/2015 | Harvey et al. | |
| 2016/0123984 A1 | 5/2016 | Singh et al. | |

FOREIGN PATENT DOCUMENTS

| | | |
|---|---|---|
| EP | 1 145 004 B1 | 4/2004 |
| EP | 1 673 635 B1 | 4/2009 |
| EP | 2 065 475 A1 | 6/2009 |
| JP | 60-228962 | 11/1985 |
| JP | 62-501892 | 7/1987 |
| JP | 01-163661 | 6/1989 |
| JP | H06-109734 A | 4/1994 |
| JP | 07-216000 A2 | 8/1995 |
| JP | H10-501070 A | 1/1998 |
| JP | 2002-214237 A | 7/2002 |
| JP | 2002-530629 | 9/2002 |
| JP | 2005-500045 | 1/2005 |
| JP | 2006-521821 | 9/2006 |
| JP | 2007-510910 | 4/2007 |
| JP | 2008-503476 | 2/2008 |
| JP | 2008-292424 A | 12/2008 |
| JP | 2010-504532 | 2/2010 |
| RU | 2149404 C1 | 5/2000 |
| RU | 2165081 C | 4/2001 |
| WO | 86/04822 | 8/1986 |
| WO | 96/07103 A1 | 3/1996 |
| WO | 00/29609 | 5/2000 |
| WO | 01/27611 A2 | 4/2001 |
| WO | 02/090964 A1 | 11/2002 |
| WO | 03/006104 | 1/2003 |
| WO | 03/087761 A2 | 10/2003 |
| WO | 2004/071572 A2 | 8/2004 |
| WO | 2004/092353 | 10/2004 |
| WO | 2005/037071 A2 | 4/2005 |
| WO | 2005/044794 | 5/2005 |
| WO | 2005/095965 A1 | 10/2005 |
| WO | 2006/007398 | 1/2006 |
| WO | 2006/031815 A1 | 3/2006 |
| WO | 2006/044748 A2 | 4/2006 |
| WO | 2006/045991 A1 | 5/2006 |
| WO | 2006/054991 A | 5/2006 |
| WO | 2006/055739 A2 | 5/2006 |
| WO | 2006/105642 A1 | 10/2006 |
| WO | 2006/119980 A1 | 11/2006 |
| WO | 2007/130677 A2 | 11/2007 |
| WO | 2008/019375 A2 | 2/2008 |
| WO | 2008/036802 A2 | 3/2008 |
| WO | 2008/064884 A1 | 6/2008 |
| WO | 2009/012140 A2 | 1/2009 |
| WO | 2009/108637 A1 | 9/2009 |
| WO | 2011/008990 A1 | 1/2011 |

OTHER PUBLICATIONS

Bachleitner-Hofmann, T. et al., "Her kinase activation confers resistance to MET tyrosine kinase inhibition in MET oncogene-addicted gastric cancer cells," Molecular Cancer Therapeutics, 7(11):3499-3508, 2008.

Bartling, B. et al., "Comparative application of antibody and gene array for expression profiling in human squamous cell lung carcinoma," Lung Cancer, 49(2):145-154, 2005.

Becker et al., "Role of receptor tyrosine kinases in gastric cancer: new targets for a selective therapy," World J of Gasteroenterol, 12(21):3297-3305, 2006.

Blume-Jensen, P. and Hunter, T., "Oncogenic kinase signalling," Nature, 411:355-365, 2001.

Daly et al., "Evaluating concentration estimation errors in ELISA microarray experiments," BMC Bioinformatics, 6:17, 2005, printed as pp. 1/11 to 11/11.

Dorland's Medical Dictionary for Healthcare Consumers (non-small cell carcinoma, Merck Sharp & Dohme Corp.) 2007, 1 page.

Engelman, J. et al., "ErbB-3 mediates phosphoinositide 3-kinase activity in gefitinib-sensitive non-small cell lung cancer cell lines," PNAS, 102(10):3788-93, 2005.

Engelman, J. et al., "Met amplification leads to gefitinib resistance in lung cancer by activating ERBB3 signaling," Science, 316(5827):1039-1043, 2007.

Fiore et al., "Clinical relevance of KRAS mutation detection in metastatic colorectal cancer treated by Cetuximab plus chemotherapy," British Journal of Cancer 96:1166-69, 2007.

Gembitsky, D. et al., "A prototype antibody microarray platform to monitor changes in protein tyrosine phosphorylation," Molecular & Cellular Proteomics, 3(11):1102-1118, 2004.

Glucose Oxidase (MeSH http://www.ncbi.nlm.nih.gov/mesh/?term=glucose+oxidase, 1964), "MeSH".

Granted Claims of European Patent Application No. 07 842 865.3; claims 1-20 (3 pgs), 2011.

Haab, B., "Antibody arrays in cancer research," Molecular & Cellular Proteomics, 4(4):377-383, 2005.

Haab, B., "Applications of antibody array platforms," Current Opinion in Biotechnology, 17:415-421, 2006.

Huang, F. et al., "The mechanisms of differential sensitivity to an insulin-like growth factor-1 receptor inhibitor (BMS-536924) and rationale for combining with EGFR/HER2 inhibitors," Cancer Research, 69(1):161-170, 2009.

Hudelist, G. et al. "Use of high-throughput protein array for profiling of differentially expressed proteins in normal and malignant breast tissue," Breast Cancer Research and Treatment, 86:281-291, 2004.

Humblet, Y., "Cetuximab: an $IgG_1$ monoclonal antibody for the treatment of epidermal growth factor receptor-expressing tumours," Expert Opin. Pharmacother, 5(7): 1621-1633, 2004.

Kelkar, S. et al., "Cytoplasmic Dynein Mediates Adenovirus Binding to Microtubules," J. Virol., 78(18):10122-10132, 2004.

Kim, P. et al., "Highly sensitive proximity mediated immunoassay reveals HER2 status conversion in the circulating tumor cells of metastatic breast cancer patients," Proteome Science, 9:75, 2011, 15 pgs.

Kopf, E. et al. "Antibody arrays—An emerging tool in cancer proteomics," The International Journal of Biochemistry & Cell Biology, 39:1305-1317, 2007.

Kuhlmann, W.D. et al., "Glucose oxidase as label in histological immunoassays with enzyme-amplification in a two-step technique: coimmobilized horseradish peroxidase as secondary system enzyme for chromogen oxidation," Histochemistry, 85:13-17, 1986.

Langer, C.J., "Emerging Role of Epidermal Growth Factor Receptor Inhibition in Therapy for Advanced Malignancy: Focus on NSCLC," Int. J. Radiation Oncology boil. Phys., 58(3):991-1002, 2004.

(56) References Cited

OTHER PUBLICATIONS

Langry, K. et al., "Chemiluminescence assay for the detection of biological warfare agents," U.S. Dept. of Energy Report No. UCRL-ID-136797, Nov. 5, 1999, 30 pages.

Litt et al., Chapter 10, "Tyramide signal amplification: applications in detecting infectious agents," in Rapid Detection of Infectious Agents, Ed. Specter et al., Plenum Press, New York, 1998, pp. 159-173.

Lu, Z. et al., "Construction of an antibody microarray based on agarose-coated slides," Electrophoresis, 28:406-413, 2007.

Mouridsen, H. et al., "Phase III study of letrozole versus tamoxifen as first line therapy of advanced breast cancer in postmenopausal women: analysis of survival and update of efficiency from the international letrozole breast cancer group," Journal of Clinical Oncology, 21:2101-2109, 2003.

Nielsen, U. et al. "Multiplexed sandwich assays in microarray format," Journal of Immunological Methods, 290:107-120, 2004.

Nielsen, U. et al. "Profiling receptor tyrosine kinase activation by using Ab microarrays," PNAS, 100(16):9330-9335, 2003.

Pearce, S. et al., "Modulation of estrogen receptor α function and stability by tamoxifen and a critical amino acid (asp-538) in helix 12," Journal of Biological Chemistry, 278:7630-7638, 2003.

Restriction Requirement mailed on Jun. 25, 2010 in U.S. Appl. No. 12/046,381, filed Mar. 11, 2008; 12 pages.

Samuilov, V.D., Immunofermentnyi analiz [Immunoenzyme analysis], Sorosovskii obrazovatelnyi zhurnal, 12:9-15, 1999.

Sanchez-Carbayo, M., "Antibody arrays: technical considerations and clinical applications in cancer," Clinical Chemistry, 52:1651-1659, 2006.

Sathyanarayanan, S. et al., "229 Anti-IGF1R therapy with dalotuzumab is efficacious in a sub-set of KRAS mutant cetuximab refractory CRC models," Eur J Cancer, Supplement, 8(7):75, Nov. 16, 2010, p. 75.

Scaltriti, M. et al., "Expression of p95HER2, a truncated form of the HER2 receptor and response to anti-HER2 therapies in breast cancer," Journal of the National Cancer Institute, 99(8):628-638, 2007.

Siena, Salvatore et al., "Biomarkers Predicting Clinical Outcome of Epidermal Growth Factor Receptor-Targeted Therapy in Metastatic Colorectal Cancer," J Natl Cancer Inst, 101(19):1308-1324, 2009.

Stern, David F., "Phosphoproteomics for Oncology discovery and treatment," Expert Opinion on Therapeutic Targets, 9(4):851-860, 2005.

Ubersax et al., "Mechanisms of specificity in protein phosphorylation," Nature, 8:530-541, 2007.

Wiese et al., "Simultaneous multianylyte ELISA performed on a microarray platform," Clinical Chemistry, 47(8):1450-1457, 2001.

Woodbury et al., "Elevated HGF levels in sera from breast cancer patients detected using a protein microarray ELISA," Journal of Proteome Research, 1:233-237, 2002.

Yan, Jing et al., "Role of antibody chip in analysis of inflammatory cytokine expression in severe sepsis," Chin. J. Emerg. Med., 15(9):830-833, 2006.

Yasui, W. et al., "Expression of epidermal growth factor receptor in human gastric and colonic carcinomas," Cancer Res, Jan. 1, 1988, 48(1), 137-141.

Yonemura, Y. et al., "Role of vascular endothelial growth factor C expression in the development of lymph node metastasis in gastric cancer," Clinical Cancer Research, 5:1823-1829, 1999.

Zhou, B. et al., "Targeting ADAM-mediated ligand cleavage to inhibit HER3 and EGFR pathways in non-small cell lung cancer," Cancer Cell, 10:39-50, 2006.

De Roock, W. et al., "Association of KRAS p. G13D mutation with outcome in patients with chemotherapy-refractory metastatic colorectal cancer treated with Cetuximab," JAMA, 304(16):1812-1820, 2010.

Lemmon, M. et al., "Cell signaling by receptor tyrosine kinases," Cell, 141:1117-1134, 2010.

* cited by examiner

FIG. 4A
FIG. 4B
FIG. 4C
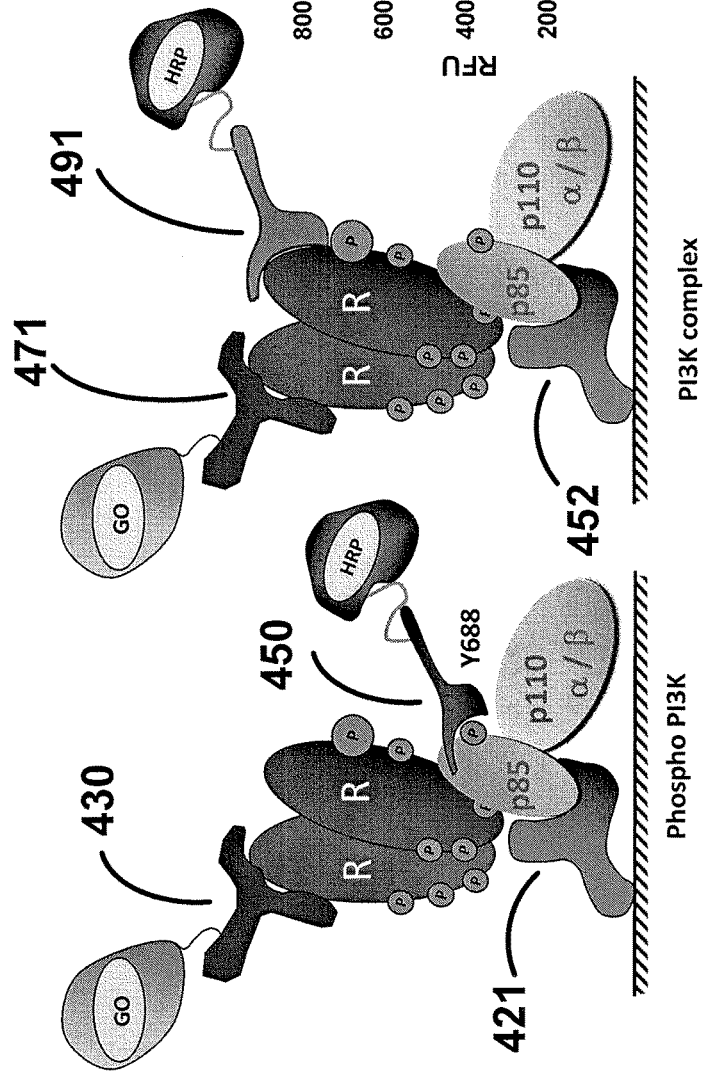
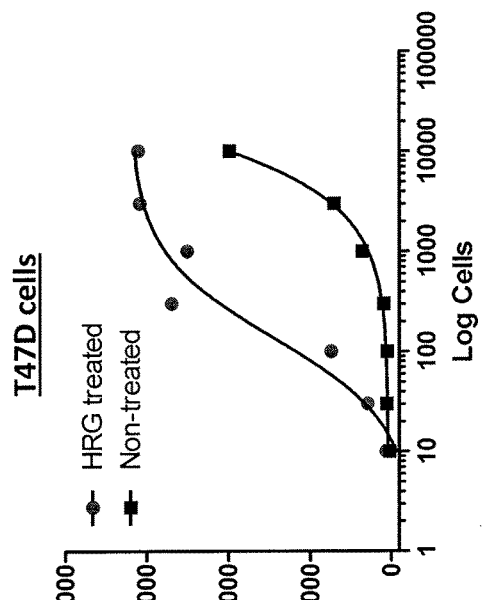

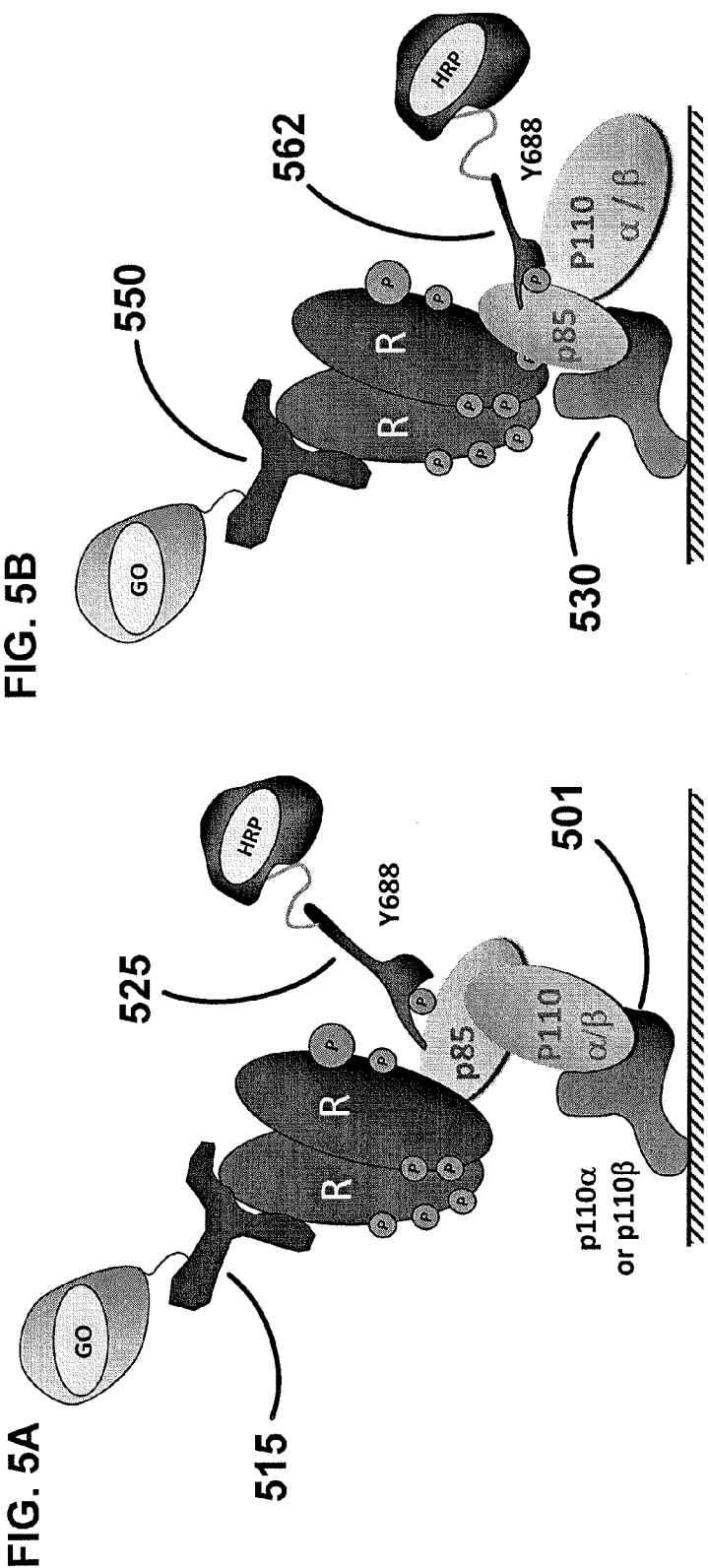

| PI3K & AKT (PI3K cutoff ≥ 60) | ✓✓ | ✓✗ | ✗✓ | ✗✗ | count PI3K pos | count AKT pos | p-value |
|---|---|---|---|---|---|---|---|
| AKT cutoff ≥ 24 | 17 | 4 | 20 | 19 | 21 | 37 | 0.0222 |
| AKT cutoff ≥ 8 | 19 | 2 | 26 | 13 | 21 | 45 | 0.0385 |

And just to show using the same cutoff for PI3K and AKT (although that does not make sense based on assay limits):

| PI3K & AKT (PI3K cutoff ≥ 24) | ✓✓ | ✓✗ | ✗✓ | ✗✗ | PI3K pos | AKT pos | p-value |
|---|---|---|---|---|---|---|---|
| AKT ≥ 24 | 24 | 6 | 13 | 17 | 30 | 37 | 0.00364 |

FIG. 6

| PI3K & HER3-P | PI3K↑HER3-P ✓✓ | PI3K↑HER3-P↓ ✓✗ | PI3K↓HER3-P↑ ✗✓ | PI3K↓HER3-P↓ ✗✗ | # PI3K + | # HER3-P + | # samples | p-value |
|---|---|---|---|---|---|---|---|---|
| *PI3K cutoff ≥ 30* | | | | | | | | |
| HER3-P ≥ 30 | 24 | 3 | 11 | 22 | 27 | 35 | 60 | 0.0000116 |
| *PI3K cutoff ≥ 60* | | | | | | | | |
| HER3-P ≥ 30 | 20 | 1 | 15 | 24 | 21 | 35 | 60 | 0.0000105 |
| *PI3K cutoff ≥ 90* | | | | | | | | |
| HER3-P ≥ 30 | 13 | 0 | 22 | 25 | 13 | 35 | 60 | 0.000286 |

FIG. 9

| | HER3-P cutoff ≥ 30 | | | | p-value |
|---|---|---|---|---|---|
| HER3-P & AKT | HER3 ↑<br>AKT ↑<br>✓✓ | HER3 ↑<br>AKT ↓<br>✓✗ | HER3 ↓<br>AKT ↑<br>✗✓ | HER3 ↓<br>AKT ↓<br>✗✗ | |
| AKT cutoff ≥ 4 | 33 | 2 | 18 | 7 | 0.022 |

FIG. 10

| HER2-P | HER2-P↑PI3K↑ ✓✓ | HER2-P↑PI3K↓ ✓✗ | HER2-P↓PI3K↑ ✗✓ | HER2-P↓PI3K↓ ✗✗ | # HER2-P + | #PI3K+ | # samples | p-value |
|---|---|---|---|---|---|---|---|---|
| | | HER2-P cutoff ≥ 30 | | | | | | |
| PI3K cutoff ≥ 90 | 9 | 9 | 4 | 38 | 18 | 13 | 60 | 0.0679 |
| PI3K cutoff ≥ 60 | 12 | 6 | 9 | 33 | 18 | 21 | 60 | 0.00117 |
| PI3K cutoff ≥ 30 | 14 | 4 | 13 | 29 | 18 | 27 | 60 | 0.000998 |

| HER2-P | HER2-P↑AKT↑ ✓✓ | HER2-P↑AKT↓ ✓✗ | HER2-P↓AKT↑ ✗✓ | HER2-P↓AKT↓ ✗✗ | # HER2-P + | #AKT + | # samples | p-value |
|---|---|---|---|---|---|---|---|---|
| AKT cutoff ≥ 16 | 17 | 1 | 24 | 18 | 18 | 41 | 60 | 0.00333 |
| AKT cutoff ≥ 8 | 18 | 0 | 27 | 15 | 18 | 45 | 60 | 0.00185 |
| AKT cutoff ≥ 4 | 18 | 0 | 33 | 9 | 18 | 51 | 60 | 0.0302 |

| HER2-P | HER2-P↑PI3K↑ ✓✓ | HER2-P↑PI3K↓ ✓✗ | HER2-P↓PI3K↑ ✗✓ | HER2-P↓PI3K↓ ✗✗ | # HER2-P + | #PI3K+ | # samples | p-value |
|---|---|---|---|---|---|---|---|---|
| | | HER2-P cutoff ≥ 1 | | | | | | |
| PI3K cutoff ≥ 90 | 11 | 17 | 2 | 30 | 28 | 13 | 60 | 0.00226 |
| PI3K cutoff ≥ 60 | 17 | 11 | 4 | 28 | 28 | 21 | 60 | 0.000105 |
| PI3K cutoff ≥ 30 | 21 | 7 | 6 | 26 | 28 | 27 | 60 | 0.0000131 |

| HER2-P | HER2-P↑AKT↑ ✓✓ | HER2-P↑AKT↓ ✓✗ | HER2-P↓AKT↑ ✗✓ | HER2-P↓AKT↓ ✗✗ | # HER2-P + | #AKT + | # samples | p-value |
|---|---|---|---|---|---|---|---|---|
| AKT cutoff ≥ 16 | 25 | 3 | 16 | 16 | 28 | 41 | 60 | 0.00107 |
| AKT cutoff ≥ 8 | 26 | 2 | 19 | 13 | 28 | 45 | 60 | 0.00273 |
| AKT cutoff ≥ 4 | 26 | 2 | 25 | 7 | 28 | 51 | 60 | 0.108 |

FIG. 12

| HER2-P | HER2-P cutoff ≥ 1 | | | | # HER2-P + | #PI3K+ | # samples | p-value |
|---|---|---|---|---|---|---|---|---|
| | HER2-P↑PI3K↑ ✓✓ | HER2-P↑PI3K↓ ✓x | HER2-P↓PI3K↓ x✓ | HER2-P↓PI3K↓ xx | | | | |
| PI3K cutoff ≥ 30 | 5 | 1 | 3 | 15 | 6 | 8 | 24 | 0.00686 |

| HER2-P | HER2-P↑AKT↑ ✓✓ | HER2-P↑AKT↓ ✓x | HER2-P↓AKT↑ x✓ | HER2-P↓AKT↓ xx | # HER2-P + | #AKT + | # samples | p-value |
|---|---|---|---|---|---|---|---|---|
| AKT cutoff ≥ 16 | 5 | 1 | 9 | 9 | 6 | 14 | 24 | 0.171 |
| AKT cutoff ≥ 8 | 5 | 1 | 11 | 7 | 6 | 16 | 24 | 0.319 |
| AKT cutoff ≥ 4 | 5 | 1 | 15 | 3 | 6 | 20 | 24 | 0.749 |

FIG. 13

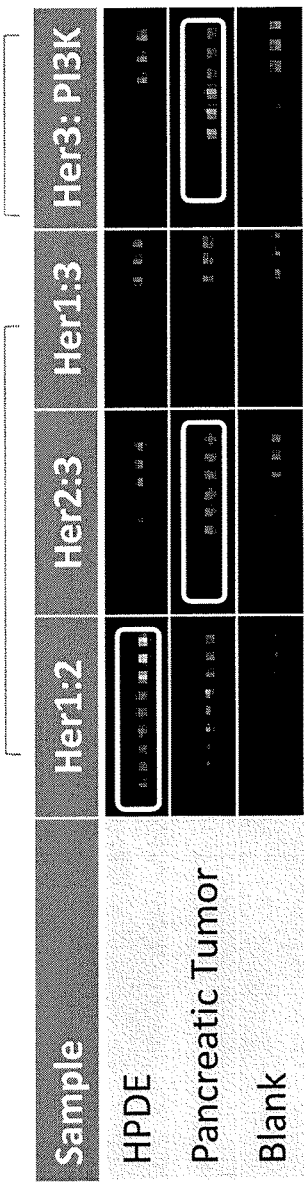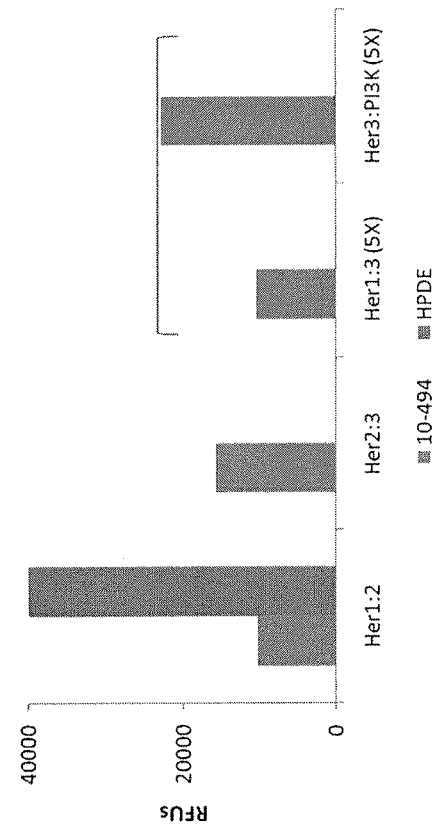

Figure xx. Heterodimer complexes for HDPE cells and tumor sample 10-494. CEER™ dimer assay is performed at 10μg, 5μg, and 2μg using a combination of capture and multiple detection antibodies. 5μg data is shown for all except for Her3:PI3K complex at 10μg. HPDE cells and tumor sample 10-494 form 1:2 and 2:3 complexes respectively. Relative to the HPDE cells, tumor sample has higher levels of phospho Her3 and associate with PI3K to form a Her3: PI3K complex.

FIG. 19

| IGF1R-P cutoff ≥ 30 | | | | | | | |
|---|---|---|---|---|---|---|---|
| IGF1R-P | IGF1R-P↑AKT↑ ✓✓ | IGF1R-P↑AKT↓ ✓× | IGF1R-P↓AKT↑ ×✓ | IGF1R-P↓AKT↓ ×× | #IGF1R-P + | #AKT + | # samples | p-value |
| AKT cutoff ≥ 16 | 15 | 2 | 26 | 17 | 17 | 41 | 60 | 0.0335 |
| AKT cutoff ≥ 8 | 16 | 1 | 29 | 14 | 17 | 45 | 60 | 0.0279 |
| AKT cutoff ≥ 4 | 17 | 0 | 34 | 9 | 17 | 51 | 60 | 0.0381 |

| IGF1R-T cutoff ≥ 30 | | | | | | | |
|---|---|---|---|---|---|---|---|
| IGF1R-T | IGF1R-T↑AKT↑ ✓✓ | IGF1R-T↑AKT↓ ✓× | IGF1R-T↓AKT↑ ×✓ | IGF1R-T↓AKT↓ ×× | # IGF1R-T+ | #AKT + | # samples | p-value |
| AKT cutoff ≥ 16 | 19 | 3 | 22 | 16 | 22 | 41 | 60 | 0.0203 |
| AKT cutoff ≥ 8 | 20 | 2 | 25 | 13 | 22 | 45 | 60 | 0.0278 |
| AKT cutoff ≥ 4 | 21 | 1 | 30 | 8 | 22 | 51 | 60 | 0.0838 |

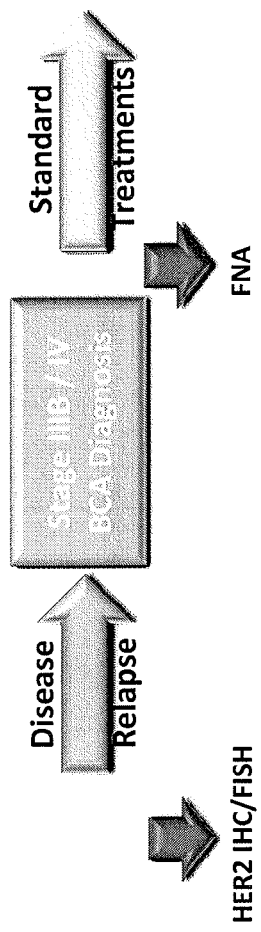

- Multinational / Multicenter Study
- 124 Stage IIIB and IV Breast Cancer Patients (pts) Enrolled
- FNA collected from various metastatic sites for each patient (multiple sites if possible)
  - Sites of Mets:
    - liver, bone, axilar and other lymph nodes, lung, skin, chest wall, brain, sternal mass
- FNA collected in 100 ml of "ProteinLater" 23 gauge needle or EUS-FNA
  - FNA stored and shipped at ambient temperature
- Interim Analysis was performed on 58 patients for multiple pathway proteins

FIG. 42

- Sufficient Materials were present in FNA-ProteinLater for multiplexed analysis.
  - 58 our of 58 (100%) : 4 to 8 μl (out of ~100 μl ) of FNA lysate was sufficient to profile RTK and down stream signal proteins (* much greater than ~70% success rate for RNA based analysis)

- Proteins were well preserved for functional pathway profiling + genotyping
  - Robust pathway expression patterns were observed
  - Phosphorylated sites were well preserved for functional analysis
  - Single sample source for both mutation / pathway profiling possible!

Markers Analyzed for FNA
- ❖ Expression:
  HER1, HER2, p95HER2, HER3, cMET, IGF1R, CK
- ❖ Phosphorylation:
  HER1, HER2, p95HER2, HER3, cMET, IGF1R, PI3K, SHC, AKT, ERK
- ❖ Somatic Mutations:
  PIK3CA: E542K, E545D, E545K, H1047R

FIG. 43

FNA samples are obtained by using a 23 or 25 gauge needle from LN or from axilar region and EUS-FNA /Cores → Comprehensive data from minimal amounts of sample

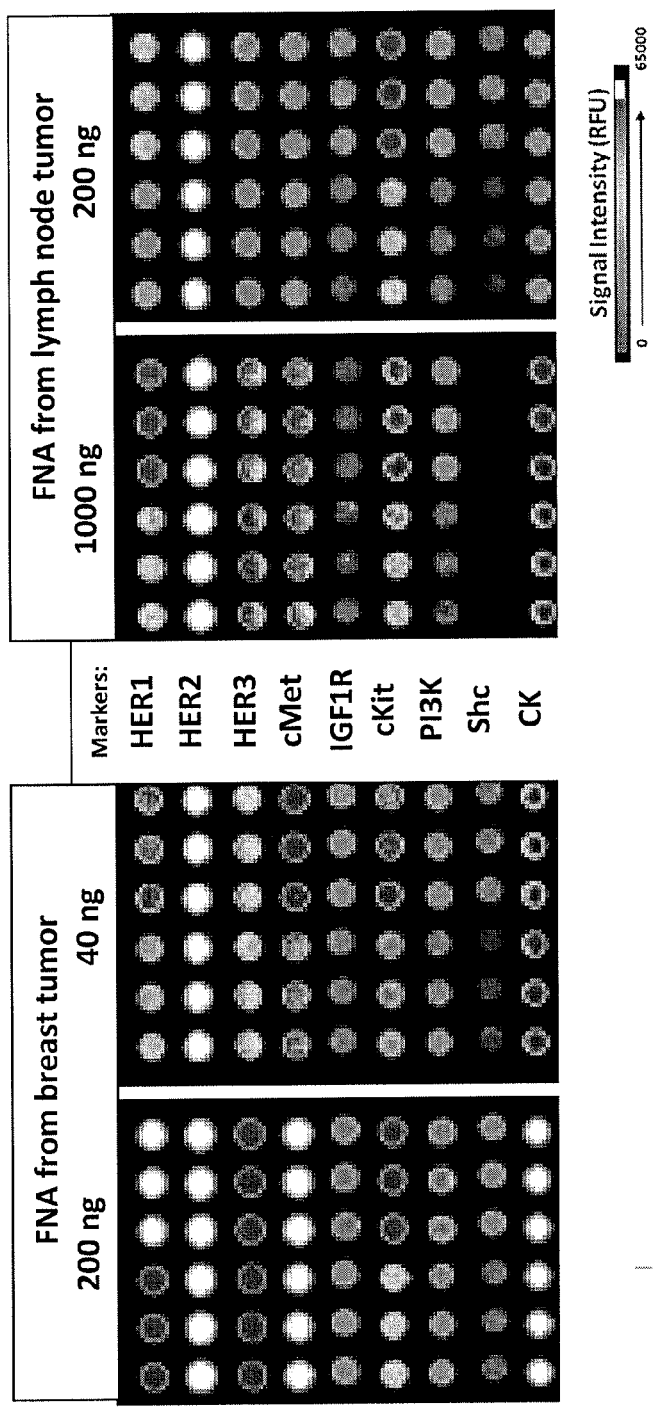
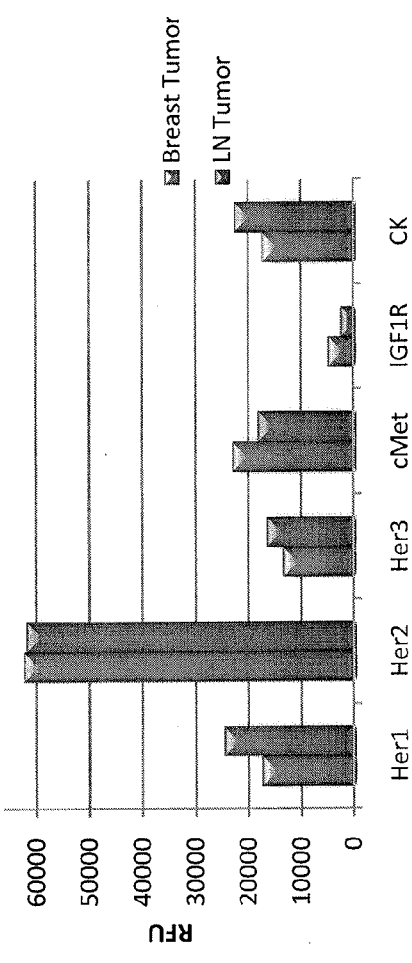
FIG. 46A
FIG. 46B

| Marker 1 | Marker 2 | P value | % Patients |
|---|---|---|---|
| P-HER 2 in HER 2 Over-expressed (+3) patients | P-AKT | 0.0031 | 23% |
| P-HER 2 in HER 2 Over-expressed (+3) patients | Activated PI3K | 0.0011 | 20% |
| Activated PI3K | P-AKT | 0.022 | 32% |
| Activated PI3K (Mutant) | P-AKT | 0.0072 | 13% |
| P-HER 2 in HER 2 (+1 and +2) patients | Activated PI3K | 0.00023 | 18% |
| P-HER 2 in HER 2 (+1 and +2) patients | P-AKT | 0.019 | 22% |
| P-HER3 | P-AKT | 0.00007 | 37% |
| P-HER3 | Activated PI3K | 0.0012 | 20% |

FIG. 47

Patient 14003-3004

Patient Test Result Summary

| | | | | | |
|---|---|---|---|---|---|
| Activation | HER1 | Low | Expression | HER1 | Low |
| | HER2 | High | | HER2 | High |
| | HER3 | High | | HER3 | High |
| | cMET | Low | | cMET | Moderate |
| | PI3K | High | | PTEN | Positive |
| | AKT | Present | Mutations | PIK3CA | NO |
| | ERK | Present | | BRAF | NO |
| | RPS6 | Present | | | |

| | HER1-P | HER2-P | HER3-P | cMET-P | PI3K | AKT-P | ERK-P | RPS6-P |
|---|---|---|---|---|---|---|---|---|
| CU (or pg) | 12.9 | 135.7 | 391.8 | L | 60.2 | Present | Present | Present |
| # pRTK | 1,290,867 | 13,569,590 | 2,742,578 | | | | | |

| | HER1-T | HER2-T | HER3-T | cMET-T | CK |
|---|---|---|---|---|---|
| CU | 55.3 | 169.3 | 698.5 | 137.1 | 284.3 |
| # RTK | 27,633,071 | 169,296,016 | 6,984,590 | 54,839,345 | |

FIG. 48

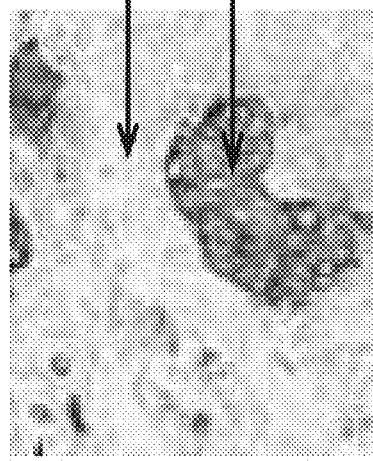
FIG. 49A
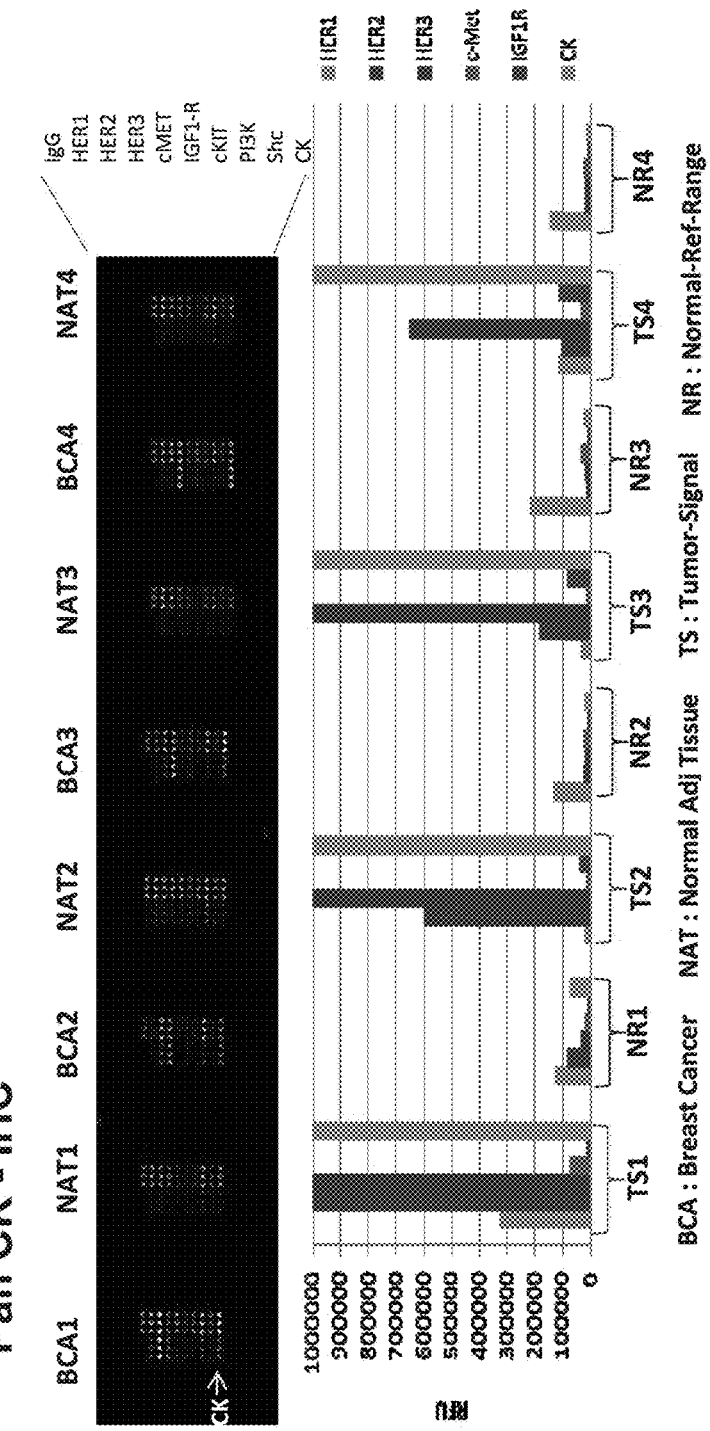
FIG. 49B
FIG. 49C

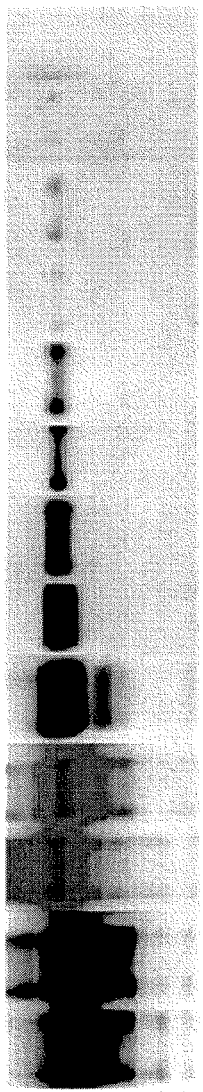
FIG. 50A
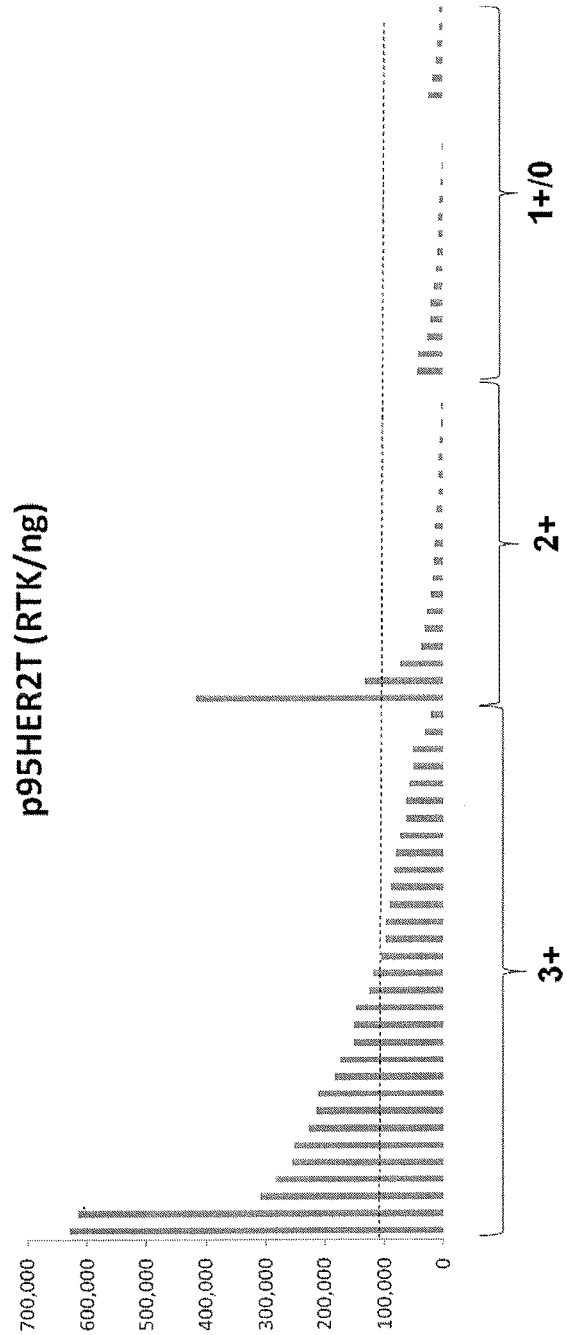
FIG. 50B
FIG. 50C

|  | Positive (+3) | Negative (+2/+1/0) | *Primary IHC information available for final analysis |
|---|---|---|---|
| IHC (N) | 6 | 21 | 27 |
| CEER + | 6 | 2 | 7 |
| % Concordance | 100% | 90.5% | |
| % Conversion | | 9.5% | |

- Interim analysis on 58 FNA samples performed by CEER
- 100% Concordance for IHC HER2 positive samples with CEER
- 90.5% Concordance for IHC HER2 negative tumor with CEER
- 8 specimens had PI3K (PIK3CA) mutations

FIG. 51

PROFILING OF SIGNAL PATHWAY PROTEINS TO DETERMINE THERAPEUTIC EFFICACY

CROSS REFERENCE TO RELATED APPLICATIONS

The present application is a continuation of PCT/US2012/053505 filed Aug. 31, 2012, which claims priority to U.S. Provisional Application Nos. 61/530,621 filed Sep. 2, 2011; 61/553,124 filed Oct. 28, 2011; and 61/562,338 filed Nov. 21, 2011, the disclosures of which are hereby incorporated by reference in their entireties for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file-220-3.TXT, created on May 16, 2014, 73,728 bytes, machine format IBM-PC, MS-Windows operating system, is hereby incorporated by reference in its entirety for all purposes.

BACKGROUND OF THE INVENTION

Signal transduction pathways that mediate cell growth and survival are targets for cancer therapy, as tumorigenesis often involves dysfunctional signal transduction pathways. Signaling abnormalities provide cancer cells increased growth potential, and the ability to avert apoptosis induced by DNA damaging agents.

One well characterized signal transduction pathway is the phosphatidylinositol 3-kinase (PI3K) pathway, which is implicated in a variety of cellular processes, e.g., malignant transformation, growth factor signaling, inflammation, and immunity. The enzyme was originally identified as an activity associated with viral oncoproteins and growth factor receptor tyrosine kinases that phosphorylate phosphatidylinositol (PI) and its phosphorylated derivatives at the 3'-hydroxyl of the inositol ring. Phosphoinositide 3-kinases (PI3K) are lipid kinases that phosphorylate lipids at the 3-hydroxyl residue of an inositol ring. The 3-phosphorylated phospholipids (PIP3s) generated by PI3-kinases act as second messengers recruiting kinases with lipid binding domains, such as AKT and phosphoinositide-dependent kinase-1 (PDK1).

The class I PI3 kinases are heterodimers composed of 2 subunits: a 110 kDa catalytic subunit (p110) and an 85 kDa regulatory subunit (p85). The regulatory subunit contains SH2 domains and binds to tyrosine residues phosphorylated by growth factor receptors with a tyrosine kinase activity or oncogene products, thereby inducing the PI3K activity of the p110 catalytic subunit, which in turn phosphorylates its lipid substrate.

Class I PI3 kinases are involved in important signal transduction events downstream of cytokines, integrins, growth factors and immunoreceptors, which suggests that control of this pathway may lead to important therapeutic effects such as modulating cell proliferation and carcinogenesis. Activation of class I PI3 kinases is initiated when a growth factor or ligand binds to its cognate receptor tyrosine kinase (RTK). These receptors include members of the human epidermal growth factor receptor family (HER, EGFR or ErbB), platelet-derived growth factor (PDGF) receptor, insulin and insulin-like growth factor 1 (IGF-1) receptors. Subsequent RTK dimerization and phosphorylation enable the PI3K heterodimer to bind directly to activated RTKs and/or adaptor proteins. Activated PI3K catalyzes the phosphorylation of phosphatidylinositol-4,5-biphosphate (PI(4,5)P2 or PIP2) to phosphatidylinositol-3,4,5-triphosphate (P(3,4,5)P3 or PIP3). PIP3 facilitates the phosphorylation of AKT which is the central effector of the PI3K pathway. AKT transmits signals to a host of downstream substrates, this controlling a variety of key cellular function, including growth, metabolis, proliferation and survival.

Inappropriate co-opting of the PI3K pathway commonly occurs in human cancer. The PI3K pathway is frequently hyperactivated in breast cancer, as well as other tumor types. It has been shown that 70% of breast cancers have a dysregulated PI3K pathway (Lopez-Knowles et al. *Int. J. Cancer,* 126, 1121-1131 (2010)). It has been well established that mutations in the PIK3CA gene (encodes for the PI3K p110 subunit) are common in tumors, including breast, colon and endometrial cancers, and glioblastomas. Additionally, in many cancers, RTKs are often mutated, amplified, or overexpression, thereby causing aberrant PI3K activation. Taken together, these findings have made components of the PI3K pathway attractive targets for cancer therapeutics.

Currently several PI3K pathway inhibitors are under investigation in preclinical studies and the results appear promising (Markman et al., *Annls. Oncol.* 21(4), 683-691 (2010)). Inhibition of cancer cell proliferation was seen in some patients receiving PI3K inhibitors (Courtney et al. *J Clin. Oncol.* 28(6), 1075-1083 (2010)). While these PI3K therapies have demonstrated success in the treatment of cancers (Baselga et al., *J. Clin. Oncol.,* 28:15s, abstract 3003, (2010); Burris et al., *J. Clin. Oncol.,* 28:15s, abstract 3005, (2010)), it is important to recognize that not all subjects treated respond, or respond well. There is a need for methods to predict those likely to respond well to targeted inhibitor. Unfortunately, the presence of PI3K somatic mutations can not adequately predict therapeutic response. Thus, there is a need for predictive biomarker assays that interrogate key signaling pathways that can be used to determine the clinical sensitivity to PI3K inhibitors and PI3K inhibitor-combination therapy. The present invention satisfies this and other needs.

BRIEF SUMMARY OF THE INVENTION

The PI3K pathway has been implicated in numerous cancers, such as breast, lung, gastric, colorectal and pancreatic cancers and is a useful therapeutic target for cancers, even those no longer responsive to existing anti-cancer therapy. PI3K inhibitors are under development and have shown some promise in some patient studies. The present invention provides assay methods to monitor PI3K pathway in patients with cancer or solid tumors.

As such, the present invention provides methods to detect and quantitate activated PI3K pathway components and/or proteins of associated or nearby signaling pathways. The methods are also useful to evaluate tumor adaption, such as shunting activation and/or expression to associated or nearby pathways not directly targeted by an existing therapy. The methods are used to predict a patient's clinical benefit from a PI3K inhibitor or a PI3K inhibitor combination therapy. Information derived from practice of the present invention can be used for cancer diagnosis, prognosis, and in the design of cancer treatments or regimens.

In one aspect, the present invention provides an assay for detecting and/or quantitating homo- or heterodimerization of receptor tyrosine kinases (e.g., a dimer pair) including, but not limited to, HER1/HER2 dimers, HER1/HER3 dimers, HER2/HER3 dimers, HER2/HER2 dimers, HER2/HER4 dimers, p95HER2/HER3 dimers, p95HER2/HER2 dimers, and the like.

In certain aspects, the assay comprises 3 antibodies:
(1) a capture antibody specific for one member of the dimer pair;
(2) a first detection antibody specific for a first member of the dimer pair, wherein the first detection antibody is specific for a different domain than the capture antibody; and a
(3) a second detection antibody specific for a second member of the dimer pair.

In one particular embodiment, the proximity assay for detecting and/or quantitating dimerization of receptor tyrosine kinases, comprises:
(i) incubating a cellular extract with one or a plurality of dilution series of capture antibodies to form a plurality of captured analytes;
(ii) incubating the plurality of captured analytes with detection antibodies comprising a first or a plurality of first activation state-independent antibodies and a second or a plurality of second activation state-independent antibodies specific for a first member and a second member, respectively, of a dimerized pair of analytes to form a plurality of detectable captured dimerized analytes,
wherein the first detection antibodies are labeled with a facilitating moiety, the second detection antibodies are labeled with a first member of a signal amplification pair, and the facilitating moiety generates an oxidizing agent which channels to and reacts with the first member of the signal amplification pair;
(iii) incubating the plurality of detectable captured dimerized analytes with a second member of the signal amplification pair to generate an amplified signal; and
(iv) detecting the amplified signal generated from the first and second members of the signal amplification pair.

In a preferred aspect, the amount of amplified signal is correlative to the amount of dimerized receptor tyrosine kinase.

The capture antibodies and detection antibodies are preferably selected to minimize competition between them with respect to analyte binding (i.e., both capture and detection antibodies can simultaneously bind their corresponding signal transduction molecules).

In some embodiments, the methods of the present invention are used to determine the RTK activation (e.g., phosphorylation) status of one or more oncogenic RTKs (e.g., HER1, HER2, HER3, p95HER2, cMET and IGF-1R) in patients at risk of developing, suspected of having, or diagnosed with a solid tumor cancer, such as breast, colorectal, gastric, lung or pancreatic cancer.

In one aspect, the present invention provides methods for selecting a treatment for a subject having or suspected of having cancer, wherein the method comprises:
(a) measuring the dimerization of at least two receptor tyrosine kinases (RTKs), wherein measuring comprises: (i) incubating a cellular extract with one or a plurality of dilution series of capture antibodies to form a plurality of captured analytes; (ii) incubating the plurality of captured analytes with detection antibodies comprising a first or a plurality of first activation state-independent antibodies and a second or a plurality of second activation state-independent antibodies specific for a first member and a second member, respectively, of a dimerized pair of analytes to form a plurality of detectable captured dimerized analytes, wherein the first activation state-independent antibodies are labeled with a facilitating moiety, the second activation state-independent antibodies are labeled with a first member of a signal amplification pair, and the facilitating moiety generates an oxidizing agent which channels to and reacts with the first member of the signal amplification pair; (iii) incubating the plurality of detectable captured dimerized analytes with a second member of the signal amplification pair to generate an amplified signal; and (iv) detecting the amplified signal generated from the first and second members of the signal amplification pair; and
(b) selecting an anticancer drug by comparing the dimerization of at least two RTKs to a reference dimerization profile of the same two RTK wherein the reference dimerization profile is generated in the absence of the anticancer drug.

In some embodiments, the method further comprises calibrating the level of dimerization of at least two RTKs against a standard curve generated for said at least two RTKs.

In some embodiments, the cellular extract is isolated from a subject having cancer after administration of an anticancer drug. In some embodiments, the cellular extract is contacted with an anticancer drug. In some embodiments, the anticancer drug is selected from the consisting of a PI3K modulating compound, a RTK modulating compound, or a combination thereof.

In some embodiments, the cellular extract is isolated from a subject having or suspected of having a cancer selected from the group consisting of breast, lung, pancreatic, colorectal, or gastric cancer.

In some embodiments, at least two RTKs is a member selected form the group consisting of a HER1/HER2 dimer, a HER1/HER3 dimer, a HER2/HER3 dimer, a HER2/HER2 dimer, a HER2/HER4 dimer, a p95HER2/HER3 dimer, and a p95HER2/HER2 dimer.

In some embodiments, the first activation state-independent antibodies are directly labeled with the facilitating moiety. In some embodiments, the facilitating moiety is glucose oxidase. In some embodiments, the glucose oxidase and the activation state-independent antibodies are conjugated to a sulfhydryl-activated dextran molecule. In some embodiments, the sulfhydryl-activated dextran molecule has a molecular weight of about 500 kDa. In some embodiments, the first member of the binding pair is biotin and/or the second member of the binding pair is streptavidin.

In some embodiments, the second activation state-independent antibodies are directly labeled with the first member of the signal amplification pair.

In some embodiments, the second activation state-independent antibodies are labeled with the first member of the signal amplification pair via binding between a first member of a binding pair conjugated to the activation state-independent antibodies and a second member of the binding pair conjugated to the first member of the signal amplification pair.

In some embodiments, the capture antibodies are on a solid support, selected from the group consisting of glass, plastic, chips, pins, filters, beads, paper, membrane, fiber bundles, and combinations thereof. In some embodiments, capture antibodies are restrained on the solid support in an addressable array.

In some embodiments, the first member of the signal amplification pair is a peroxidase. In some embodiments, the peroxidase is horseradish peroxidase (HRP). In some embodiments, the second member of the signal amplification pair is a tyramide reagent. In some embodiments, the tyramide reagent is biotin-tyramide.

In some embodiments, the amplified signal is generated by peroxidase oxidization of the biotin-tyramide to produce an activated tyramide.

In some embodiments, the activated tyramide is directly detected. In some embodiments, the activated tyramide is detected upon the addition of a signal-detecting reagent.

In some embodiments, the signal-detecting reagent is a streptavidin-labeled fluorophore. In some embodiments, the signal-detecting reagent is a combination of a streptavidin-labeled peroxidase and a chromogenic reagent. In some embodiments, the chromogenic reagent is 3,3',5,5'-tetramethylbenzidine (TMB).

In other embodiments, the methods of the present invention are performed on a subject, already determined to express one or more oncogenic proteins, to optimize therapy, reduce toxicity, monitor the efficacy of therapeutic treatment, and/or detect adaptive non-responsiveness to therapy.

In some embodiments, the methods of the present invention are used for measuring RTK activation or phosphorylation status in the subject at risk of developing, suspected of having, or diagnosed with a solid tumor cancer, such as breast, colorectal, gastric, lung or pancreatic cancer.

In other embodiments, the methods of the present invention are used for measuring RTK dimerization status in the subject at risk of developing, suspected of having, or diagnosed with a solid tumor cancer, such as breast, colorectal, gastric, lung or pancreatic cancer.

In certain embodiments, the methods of the present invention are used measuring RTK dimerization and/or activation status in the subject who has relapsed on anti-cancer therapy, and to determine whether the tumor cells have adapted to the existing anti-cancer therapy, or whether the subject should receive PI3K inhibitor or PI3K inhibitor combination therapy.

In some embodiments, the methods of the present invention used for measuring RTK dimerization and/or activation status in the subject who has relapsed on anti-cancer therapy, and to determine whether the tumor cells have adapted to the existing anti-cancer therapy, or whether the subject should receive RTK inhibitor or RTK inhibitor combination therapy.

In another aspect, the present invention provides methods for detecting and/or quantitating (e.g. measuring) the amount of PI3K complex and the amount of activation and/or phosphorylation of a PI3K complex. The PI3K complex comprises: i) a dimerized receptor tyrosine kinase pair; ii) a PI3K p85 subunit and a PI3K p110 (e.g., α or β subunit).

In certain aspects, the assay comprises 3 antibodies:

(1) a capture antibody specific for either the PI3K p85 or the PI3K p110 subunit;

(2) a first detection antibody specific for a first member of the dimer pair, or PI3K subunit, wherein the first detection antibody is specific for a different domain than the capture antibody and wherein the PI3K subunit may be activated; and a (3) a second detection antibody specific for a second member of the dimer pair or a PI3K subunit.

In one aspect, the present invention provides methods for selecting a treatment for a subject having or suspected of having cancer, the method comprising:

(a) measuring the level of a PI3K complex activation, wherein said PI3K complex comprises i) dimerization of at least two receptor tyrosine kinases (RTKs); ii) a PI3K p85 subunit and a PI3K p110 subunit, said measuring comprises:
(i) incubating a cellular extract with one or a plurality of dilution series of capture antibodies to form a plurality of captured analytes; (ii) incubating the plurality of captured analytes with first detection antibodies comprising either a) a first or a plurality of first activation state-independent antibodies specific for one member of a dimerized receptor tyrosine kinase pair or b) a PI3K p110 subunit; and second detection antibodies comprising either a) second or a plurality of second activation state-independent antibodies specific for a) one member of a dimerized receptor tyrosine kinase pair, a PI3K p85 or a PI3K p110 subunit or b) activation state-dependent antibodies specific for a PI3K p85 subunit and/or a PI3K p110 subunit to form a plurality of detectable captured dimerized and complexed analytes, wherein the first detection antibodies are labeled with a facilitating moiety, the second detection antibodies are labeled with a first member of a signal amplification pair, and the facilitating moiety generates an oxidizing agent which channels to and reacts with the first member of the signal amplification pair; incubating the plurality of detectable captured dimerized analytes with a second member of the signal amplification pair to generate an amplified signal; and detecting the amplified signal generated from the first and second members of the signal amplification pair; and (b) selecting an anticancer drug by comparing the level of the PI3K complex activation to a reference PI3K complex activation profile wherein the reference dimerization profile is generated in the absence of the anticancer drug.

In some embodiments, the level of PI3K complex is calibrated against a standard curve generated for said PI3K complex comprising i) dimerization of at least two receptor tyrosine kinases (RTKs); ii) a PI3K p85 subunit and a PI3K p110 subunit.

In some embodiments, the cellular extract is isolated from a subject having cancer after administration of an anticancer drug. In some embodiments, the cellular extract is contacted with an anticancer drug. In some embodiments, the anticancer drug is selected from the consisting of a PI3K modulating compound, a RTK modulating compound, or a combination thereof.

In some embodiments, at least two RTKs is a member selected form the group consisting of a HER1/HER2 dimer, a HER1/HER3 dimer, a HER2/HER3 dimer, a HER2/HER2 dimer, a HER2/HER4 dimer, a p95HER2/HER3 dimer, and a p95HER2/HER2 dimer.

In some embodiments, the first activation state-independent antibodies are directly labeled with the facilitating moiety. In some embodiments, the facilitating moiety is glucose oxidase. In some embodiments, the glucose oxidase and the activation state-independent antibodies are conjugated to a sulfhydryl-activated dextran molecule. In some embodiments, the sulfhydryl-activated dextran molecule has a molecular weight of about 500 kDa.

In some embodiments, the first member of the binding pair is biotin and/or the second member of the binding pair is streptavidin.

In some embodiments, the second activation state-independent antibodies are directly labeled with the first member of the signal amplification pair.

In some embodiments, the second activation state-independent antibodies are labeled with the first member of the signal amplification pair via binding between a first member of a binding pair conjugated to the activation state-independent antibodies and a second member of the binding pair conjugated to the first member of the signal amplification pair.

In some embodiments, the capture antibodies are on a solid support, selected from the group consisting of glass, plastic, chips, pins, filters, beads, paper, membrane, fiber bundles, and combinations thereof. In some embodiments, capture antibodies are restrained on the solid support in an addressable array.

In some embodiments, the first member of the signal amplification pair is a peroxidase. In some embodiments, the peroxidase is horseradish peroxidase (HRP). In some embodiments, the second member of the signal amplification pair is a tyramide reagent. In some embodiments, the tyramide reagent is biotin-tyramide.

In some embodiments, the amplified signal is generated by peroxidase oxidization of the biotin-tyramide to produce an activated tyramide.

In some embodiments, the activated tyramide is directly detected. In some embodiments, the activated tyramide is detected upon the addition of a signal-detecting reagent.

In some embodiments, the signal-detecting reagent is a streptavidin-labeled fluorophore. In some embodiments, the signal-detecting reagent is a combination of a streptavidin-labeled peroxidase and a chromogenic reagent. In some embodiments, the chromogenic reagent is 3,3',5,5'-tetramethylbenzidine (TMB).

In one aspect, the present invention provides methods to be used to determine whether the subject should receive a PI3K inhibitor or PI3K inhibitor combination therapy.

In another aspect, the present invention provides methods used to determine whether the subject, who has relapsed on anticancer therapy, should receive a PI3K inhibitor or PI3K inhibitor combination therapy.

In another aspect, the present invention provides methods to be performed on the subject, already determined to express one or more oncogenic proteins, to optimize therapy, reduce toxicity, monitor the efficacy of therapeutic treatment, and/or detect adaptive non-responsiveness to therapy.

In some embodiments, the methods of the present invention are used for measuring PI3K activation or phosphorylation status in the subject at risk of developing, suspected of having, or diagnosed with a solid tumor cancer, such as breast, colorectal, gastric, lung or pancreatic cancer.

In some embodiments, the methods of the present invention are used for measuring PI3K complexation status in the subject at risk of developing, suspected of having, or diagnosed with a solid tumor cancer, such as breast, colorectal, gastric, lung or pancreatic cancer.

In some embodiments, the methods of the present invention are used for measuring PI3K complexation and/or activation status in the subject who has relapsed on anti-cancer therapy, and to determine whether the tumor cells have adapted to the existing anti-cancer therapy, or whether the subject should receive PI3K inhibitor or PI3K inhibitor combination therapy.

In some embodiments, the methods of the present invention are used for measuring PI3K complexation and/or activation status in the subject who has relapsed on anti-cancer therapy, and to determine whether the tumor cells have adapted to the existing anti-cancer therapy, or whether the subject should receive RTK inhibitor or RTK inhibitor combination therapy.

Other objects, features, and advantages of the present invention will be apparent to one of skill in the art from the following detailed description and figures.

BRIEF DESCRIPTION OF THE DRAWINGS

FIG. 4A shows an embodiment of a PI3K complex detectable by the methods and assays described herein. FIG. 4B shows an embodiment of a PI3K complex detectable by the methods and assays described herein. FIG. 4C illustrates the detection of PI3K complexes using a method of the present invention. PI3K complexes were detected in T47D cells (human ductal breast epithelial tumor cell line) treated with heregulin (HRG), compared to non-treated cells.

FIG. 5A shows another embodiment of a PI3K complex detectable by the methods and assays described herein. FIG. 5B shows an embodiment of a PI3K complex detectable by the methods and assays described herein.

FIG. 6 illustrates a comparison of phospho-AKT and phospho-PI3K in a pathway profiling analysis of patient with breast cancer.

FIG. 9 illustrates a high degree of correlation between the presence of phospho-HER3 and phospho-PI3K in 60 FNA samples from breast cancer patients. Regardless of the cutoff value for PI3K used in the assay, there is a correlation between phospho-HER3 and phospho-PI3K in the samples.

FIG. 10 illustrates a correlation between the presence of phospho-HER3 and phospho-AKT in breast cancer patients.

FIG. 11 also shows that activated AKT correlates with phospho-HER3 in the absence of PI3K activation.

FIG. 12 shows that phospho-HER2 is associated with activated PI3K and activated AKT in FNA samples from breast cancer patients.

FIG. 13 shows concurrent activation of phospho-HER2, phospho-PI3K and phospho-AKT in breast cancer patient samples that do not HER2 genetic mutations or amplifications.

FIG. 19 shows activation of HER3 heterodimer complexes and HER3/PI3K complexes in a pancreatic tumor sample and HDPE cells. The CEER dimer assay is performed at 10 μg, 5 μg and 2 μg using a combination of capture and multiple detection antibodies. 5 μg data is shown for all except for HER3/PI3K complex at 10 HPDE cells and tumor sample 10-494 form 1:2 and 2:3 complexes, respectively. Relative to the HPDE cells, the tumor sample has higher levels of phospho-HER3 and associates with PI3K to form a HER3/PI3K complex.

FIG. 26 illustrates IGF-1R and AKT activation in a breast cancer patient. Activated IGF-1R levels correlates with phospho-AKT levels. In addition, elevated levels of total IGF-1R also correlates with phospho-AKT.

FIG. 36 shows that HER1 (EGFR), HER2, Shc, ERK and AKT proteins are highly activated.

FIG. 39 illustrates FNA analysis of biomarkers in pathway profiling of pancreatic cancer patients with KRAS mutations.

FIG. 40 illustrates FNA analysis of biomarkers in pathway profiling of pancreatic patients with and without KRAS mutations.

FIG. 42 shows the details of the clinical study described in Example 12.

FIG. 43 shows more details of the clinical study described Example 12.

FIG. 46A illustrates the level of protein expression of components of the PI3K pathway as determined by the CEER assay. FIG. 46B shows that protein levels of HER1, HER2, HER3, cMET, IGF1R and CK are similar in the patient's breast tumor and lymph node tumor.

FIG. 47 shows that in a cohort of breast cancer patients there are statistically significant correlations between activated PI3K pathway proteins, activated PI3K mutations, and combinations thereof. There is a correlation between the level of phospho-HER2 in patients with a primary IHC HER2 score of +1 and +2 and the level of phospho-AKT as measured by CEER. In 37% of the patient profiled, the presence of phospho-HER correlates with phospho-AKT.

FIG. 48 illustrates data obtained from comprehensive disease profiling of Patient 14003-3004 in the study. The patient overexpresses HER2 and has a tumor with high HER3 and PI3K activity. The disease profile indicates that the patient may benefit from PI3K inhibitor alone or combination therapy.

FIGS. 49A-C illustrates comparative breast cancer profiling of FNA from a tumor and normal adjacent tissue. FIG. 49A shows an immunohistochemical image of a tissue section stained with an anti-pan CK antibody. The tumor cells highly express CK compared to the cells of the stroma. FIG. 49B illustrates the PI3K pathway profiles of breast cancer tumor samples and normal adjacent tissue samples. FIG. 49C depicts a graphical representation of results from CEER-FNA assays described herein.

FIGS. 50A-C shows that pathway profiling of the HER2 pathway provides more detailed data regarding total p95HER2 and activated p95HER2 expression compared to IHC for HER2 and p95HER2. FIG. 50A shows a Western blot for HER2 protein and p95HER2 protein in breast cancer aspirate samples. FIG. 50B shows that tumor samples which highly express HER2 (e.g., 3+) as measured by IHC are more likely to overexpress total p95HER2 protein and activated (phosphorylated) p95HER2 protein compared to those expressing HER2 at 2+ or 1+/0 levels which. FIG. 50C represents a graph of total p95HER2 protein expression grouped by IHC measured HER2 expression.

FIG. 51 shows that 6 FNA samples which tested positive for HER2 by CEER were from patients that expressed HER2 positive cells as determined by primary IHC.

DETAILED DESCRIPTION OF THE INVENTION

I. Introduction

Figure 1A:
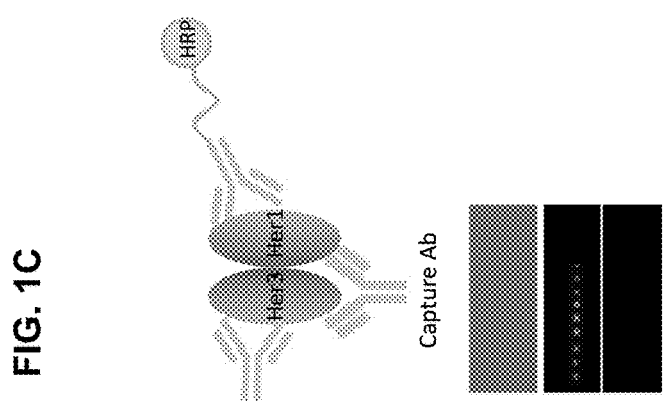
FIGS. 1A-C show one embodiment of an assay for detection of dimerization of receptor tyrosine kinases.

The PI3K signal transduction pathway is known to mediate normal physiological cellular metabolic and survival functions, however, aberrant activation of the pathway can lead to tumorigenesis or tumor metastasis. Signaling through the PI3K pathway is upregulated in many cancer cells, especially following chemotherapy. Furthermore, PI3K activation predicts therapeutic resistance to a broad range of anticancer therapy. It has also been shown that other key oncogenic pathways converge and interplay with the PI3K pathway.

One approach in developing tumor therapy is to block intracellular signaling through these pathways. Preclinical models have demonstrated that the use of PI3K pathway inhibitors can elicit dramatic anti-cancer responses in breast cancer patients with PI3K activation. Most interestingly, the presence of PIK3CA mutations failed to correlate with those patients who responded to PI3K therapy. The inventive methods are used for measuring (e.g., detecting and quantitating) PI3K pathway activation as well as other signaling pathways that converge with PI3K signaling. These methods are useful in selecting cancer patients who will be clinically sensitive to PI3K inhibitors and PI3K inhibitor-combination therapy. The continued monitoring of signal transduction pathways that are active in cancer cells as treatment progresses can provide the physician with additional information on the efficacy of treatment, prompting the physician to either continue a particular course of treatment or to switch to another line of treatment, when, for example, cancer cells have become resistant to treatment through further aberrations that activate either the same or another signal transduction pathway.

The methods herein have been used to ascertain that tumor cells can activate one or more compensatory signaling pathways in response to anticancer therapy. Without being bound by any particular theory, it is believed that tumor cells adapt to specific pathway inhibitors by activating associated signaling pathways that are not direct targets of the inhibitor. Thus, combination therapy with PI3K inhibitor may be required to achieve optimal response to treatment in some cancers. Moreover, these findings highlight the need for methods to monitor activated signaling pathways in a clinical setting.

II. Definitions

As used herein, the following terms have the meanings ascribed to them unless specified otherwise.

The term "cancer" includes any member of a class of diseases characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Examples of different types of cancer include, but are not limited to, breast cancer; lung cancer (e.g., non-small cell lung cancer); digestive and gastrointestinal cancers such as colorectal cancer, gastrointestinal stromal tumors, gastrointestinal carcinoid tumors, colon cancer, rectal cancer, anal cancer, bile duct cancer, small intestine cancer, and stomach (gastric) cancer; esophageal cancer; gallbladder cancer; liver cancer; pancreatic cancer; appendix cancer; ovarian cancer; renal cancer (e.g., renal cell carcinoma); cancer of the central nervous system; skin cancer; lymphomas; choriocarcinomas; head and neck cancers; osteogenic sarcomas; and blood cancers. As used herein, a "tumor" comprises one or more cancerous cells. In one embodiment, the breast tumor is derived from a subject with an invasive or in situ form of ductal carcinoma or lobular carcinoma. In another embodiment, the breast tumor is derived from a subject with recurrent or metastatic breast cancer.

The term "analyte" includes any molecule of interest, typically a macromolecule such as a polypeptide, whose presence, amount (expression level), activation state, and/or identity is determined. In certain instances, the analyte is a signal transduction molecule such as, e.g., a component of a HER2 (ErbB2) signaling pathway.

The term "signal transduction molecule" or "signal transducer" includes proteins and other molecules that carry out the process by which a cell converts an extracellular signal or stimulus into a response, typically involving ordered sequences of biochemical reactions inside the cell. Examples of signal transduction molecules include, but are not limited to, receptor tyrosine kinases such as EGFR (e.g., EGFR/HER1/ErbB1, HER2/Neu/ErbB2, HER3/ErbB3, HER4/ErbB4), VEGFR1/FLT1, VEGFR2/FLK1/KDR, VEGFR3/FLT4, FLT3/FLK2, PDGFR (e.g., PDGFRA, PDGFRB), c-KIT/SCFR, INSR (insulin receptor), IGF-IR, IGF-IIR, IRR (insulin receptor-related receptor), CSF-1R, FGFR 1-4, HGFR 1-2, CCK4, TRK A-C, c-MET, RON, EPHA 1-8, EPHB 1-6, AXL, MER, TYRO3, TIE 1-2, TEK, RYK, DDR 1-2, RET, c-ROS, V-cadherin, LTK (leukocyte tyrosine kinase), ALK (anaplastic lymphoma kinase), ROR 1-2, MUSK, AATYK 1-3, and RTK 106; truncated forms of receptor tyrosine kinases such as truncated HER2 receptors with missing amino-terminal extracellular domains (e.g., p95ErbB2 (p95m), p110, p95c, p95n, etc.); receptor tyrosine kinase dimers (e.g., p95HER2/HER3, p95HER2/HER2, HER2/HER2, HER2/HER3, HER1/HER2, HER2/HER3, HER2/HER4, etc.); non-receptor tyrosine kinases such as BCR-ABL, Src, Frk, Btk, Csk, Abl, Zap70, Fes/Fps, Fak, Jak, Ack, and LIMK; tyrosine kinase signaling cascade components such as AKT (e.g., AKT1, AKT2, AKT3), MEK (MAP2K1), ERK2 (MAPK1), ERK1 (MAPK3), PI3K (e.g., PIK3CA (p110), PIK3R1 (p85)), PDK1, PDK2, phosphatase and tensin homolog (PTEN), SGK3, 4E-BP1, P70S6K (e.g., p70 S6 kinase splice variant alpha I), protein tyrosine phosphatases (e.g., PTP1B, PTPN13, BDP1, etc.), RAF, PLA2, MEKK, JNKK, JNK, p38, Shc (p66), Ras (e.g., K-Ras, N-Ras, H-Ras), Rho, Rac1, Cdc42, PLC, PKC, p53, cyclin D1, STAT1, STAT3, phosphatidylinositol 4,5-bisphosphate (PIP2), phosphatidylinositol 3,4,5-trisphosphate (PIP3), mTOR, BAD, p21, p27, ROCK, IP3, TSP-1, NOS, GSK-3β, RSK 1-3, JNK, c-Jun, Rb, CREB, Ki67, and paxillin; nuclear hormone receptors such as estrogen receptor (ER), progesterone receptor (PR), androgen receptor, glucocorticoid receptor, mineralocorticoid receptor, vitamin A receptor, vitamin D receptor, retinoid receptor, thyroid hormone receptor, and orphan receptors; nuclear receptor coactivators and repressors such as amplified in breast cancer-1 (AIB1) and nuclear receptor corepressor 1 (NCOR), respectively; and combinations thereof.

The term "PI3K pathway alteration" refers to aberrant dysregulation of the PI3K signaling pathway due to PI3K gene mutations, PI3K gene amplifications and/or PTEN loss.

The terms receptor-type tyrosine kinase" or "RTK" includes any member of family of receptors each characterized as having an extracellular, a transmembrane, and an intracellular portion, while non-receptor type tyrosine kinases are wholly intracellular. The receptor family comprised of a large number of transmembrane receptors with diverse biological activity. In fact, about 20 different subfamilies of receptor-type tyrosine kinases have been identified. One tyrosine kinase subfamily, designated the HER (ErbB) subfamily, is comprised of EGFR (HER1), HER2, HER3, and HER4. Ligands of this subfamily of receptors identified so far include epithelial growth factor, TGF-alpha, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-alpha and beta receptors, CSFIR, c-kit and FLK-II.

The term "component of a HER2 signaling pathway" includes any one or more of an upstream ligand of HER2, binding partner of HER2, and/or downstream effector molecule that is modulated through HER2. Examples of HER2 signaling pathway components include, but are not limited to, heregulin, HER1/ErbB1, HER2/ErbB2, HER3/ErbB3, HER4/ErbB4, AKT (e.g., AKT1, AKT2, AKT3), MEK (MAP2K1), ERK2 (MAPK1), ERK1 (MAPK3), PI3K (e.g., PIK3CA (p110), PIK3R1 (p85)), PDK1, PDK2, PTEN, SGK3, 4E-BP1, P70S6K (e.g., splice variant alpha I), protein tyrosine phosphatases (e.g., PTP1B, PTPN13, BDP1, etc.), HER2 dimers (e.g., p95HER2/HER3, p95HER2/HER2, HER2/HER2, HER2/HER3, HER1/HER2, HER2/HER3, HER2/HER4, etc.), GSK-3β, PIP2, PIP3, p27, and combinations thereof.

The term "component of a HER3 signaling pathway" includes any one or more of an upstream ligand of HER3, binding partner of HER3, and/or downstream effector molecule that is modulated through HER3. Examples of HER3 signaling pathway components include, but are not limited to, heregulin, HER1/ErbB1, HER2/ErbB2, HER3/ErbB3, HER4/ErbB4, AKT (e.g., AKT1, AKT2, AKT3), MEK (MAP2K1), ERK2 (MAPK1), ERK1 (MAPK3), PI3K (e.g., PIK3CA (p110), PIK3R1 (p85)), PDK1, PDK2, PTEN, SGK3, 4E-BP1, P70S6K (e.g., splice variant alpha I), protein tyrosine phosphatases (e.g., PTP1B, PTPN13, BDP1, etc.), HER2 dimers (e.g., p95HER2/HER3, p95HER2/HER2, HER2/HER2, HER2/HER3, HER1/HER2, HER2/HER3, HER2/HER4, etc.), GSK-3β, PIP2, PIP3, p27, and combinations thereof.

The term "tumor adaptation" includes a process wherein cells of a tumor are exposed to anti-cancer therapy and activate signaling pathways associated with or nearby to the signaling pathway directly targeted by the therapeutic agent. Tumor cells activate associated/nearby signaling pathways as a mechanism to compensate for the blockage or inhibition brought forth by the targeted therapy.

The term "activation state" includes a particular signal transduction molecule such as a HER2 signaling pathway component in it's activated form. Similarly, the term "activation level" refers to what extent a particular signal transduction molecule such as a HER2 signaling pathway component is activated. The activation state typically corresponds to the phosphorylation, ubiquitination, and/or complexation status of one or more signal transduction molecules. Non-limiting examples of activation states (listed in parentheses) include: EGFR (EGFRvIII, phosphorylated (p-) EGFR, EGFR:Shc, ubiquitinated (u-) EGFR, p-EGFRvIII); ErbB2 (p-ErbB2, p95HER2 (truncated ErbB2), p-p95HER2, ErbB2:Shc, ErbB2:PI3K, ErbB2: EGFR, ErbB2:ErbB3, ErbB2:ErbB4); ErbB3 (p-ErbB3, ErbB3:PI3K, p-ErbB3:PI3K, ErbB3:Shc); ErbB4 (p-ErbB4, ErbB4:Shc); c-MET (p-c-MET); AKT1 (p-AKT1); AKT2 (p-AKT2); AKT3 (p-AKT3); PTEN (p-PTEN); P70S6K (p-P70S6K); MEK (p-MEK); ERK1 (p-ERK1); ERK2 (p-ERK2); PDK1 (p-PDK1); PDK2 (p-PDK2); SGK3 (p-SGK3); 4E-BP1 (p-4E-BP1); PIK3R1 (p-PIK3R1); c-KIT (p-c-KIT); ER (p-ER); IGF-1R (p-IGF-1R, IGF-1R: IRS, IRS:PI3K, p-IRS, IGF-1R:PI3K); INSR (p-INSR); FLT3 (p-FLT3); HGFR1 (p-HGFR1); HGFR2 (p-HGFR2); RET (p-RET); PDGFRA (p-PDGFRA); PDGFRB (p-PDGFRB); VEGFR1 (p-VEGFR1, VEGFR1:PLCγ, VEGFR1: Src); VEGFR2 (p-VEGFR2, VEGFR2:PLCγ, VEGFR2:Src, VEGFR2:heparin sulphate, VEGFR2:VE-cadherin); VEGFR3 (p-VEGFR3); FGFR1 (p-FGFR1); FGFR2 (p-FGFR2); FGFR3 (p-FGFR3); FGFR4 (p-FGFR4); TIE1 (p-TIE1); TIE2 (p-TIE2); EPHA (p-EPHA); EPHB (p-EPHB); GSK-3β (p-GSK-3β); NFKB (p-NFKB), IKB (p-IKB, p-P65:IKB); BAD (p-BAD, BAD:14-3-3); mTOR (p-mTOR); Rsk-1 (p-Rsk-1); Jnk (p-Jnk); P38 (p-P38); STAT3 (p-STAT3); Fak (p-Fak); Rb (p-Rb); Ki67; p53 (p-p53); CREB (p-CREB); c-Jun (p-c-Jun); c-Src (p-c-Src); and paxillin (p-paxillin).

As used herein, the term "dilution series" is intended to include a series of descending concentrations of a particular sample (e.g., cell lysate) or reagent (e.g., antibody). A dilution series is typically produced by a process of mixing a measured amount of a starting concentration of a sample or reagent with a diluent (e.g., dilution buffer) to create a lower concentration of the sample or reagent, and repeating the process enough times to obtain the desired number of serial dilutions. The sample or reagent can be serially diluted at least 2, 3, 4, 5, 6, 7, 8, 9, 10, 15, 20, 25, 30, 35, 40, 45, 50, 100, 500, or 1000-fold to produce a dilution series comprising at least 2, 3, 4, 5, 6, 7, 8, 9, 10, 11, 12, 13, 14, 15, 16, 17, 18, 19, 20, 25, 30, 35, 40, 45, or 50 descending concentrations of the sample or reagent. For example, a dilution series comprising a 2-fold serial dilution of a capture antibody reagent at a 1 mg/ml starting concentration can be produced by mixing an amount of the starting concentration of capture antibody with an equal amount of a dilution buffer to create a 0.5 mg/ml concentration of the capture antibody, and repeating the process to obtain capture antibody concentrations of 0.25 mg/ml, 0.125 mg/ml, 0.0625 mg/ml, 0.0325 mg/ml, etc.

The term "superior dynamic range" as used herein includes the ability of an assay to detect a specific analyte in as few as one cell or in as many as thousands of cells. For example, the immunoassays described herein possess superior dynamic range because they advantageously detect a particular signal transduction molecule of interest in about 1-10,000 cells (e.g., about 1, 5, 10, 25, 50, 75, 100, 250, 500, 750, 1000, 2500, 5000, 7500, or 10,000 cells) using a dilution series of capture antibody concentrations.

As used herein, the term "circulating cells" comprises extratumoral cells that have either metastasized or micrometastasized from a solid tumor. Examples of circulating cells include, but are not limited to, circulating tumor cells, cancer stem cells, and/or cells that are migrating to the tumor (e.g., circulating endothelial progenitor cells, circulating endothelial cells, circulating pro-angiogenic myeloid cells, circulating dendritic cells, etc.). Patient samples containing circulating cells can be obtained from any accessible biological fluid (e.g., whole blood, serum, plasma, sputum, bronchial lavage fluid, urine, nipple aspirate, lymph, saliva, fine needle aspirate, etc.). In certain instances, the whole blood sample is separated into a plasma or serum fraction and a cellular fraction (i.e., cell pellet). The cellular fraction typically contains red blood cells, white blood cells, and/or circulating cells of a solid tumor such as circulating tumor cells (CTCs), circulating endothelial cells (CECs), circulating endothelial progenitor cells (CEPCs), cancer stem cells (CSCs), disseminated tumor cells of the lymph node, and combinations thereof. The plasma or serum fraction usually contains, inter alia, nucleic acids (e.g., DNA, RNA) and proteins that are released by circulating cells of a solid tumor.

Circulating cells are typically isolated from a patient sample using one or more separation methods including, for example, immunomagnetic separation (see, e.g., Racila et al., *Proc. Natl. Acad. Sci. USA*, 95:4589-4594 (1998); Bilkenroth et al., *Int. J. Cancer*, 92:577-582 (2001)), the Cell-Tracks® System by Immunicon (Huntingdon Valley, Pa.), microfluidic separation (see, e.g., Mohamed et al., *IEEE Trans. Nanobiosci.*, 3:251-256 (2004); Lin et al., Abstract No. 5147, 97th AACR Annual Meeting, Washington, D.C. (2006)), FACS (see, e.g., Mancuso et al., *Blood*, 97:3658-3661 (2001)), density gradient centrifugation (see, e.g., Baker et al., *Clin. Cancer Res.*, 13:4865-4871 (2003)), and depletion methods (see, e.g., Meye et al., *Int. J Oncol.*, 21:521-530 (2002)).

The term "sample" as used herein includes any biological specimen obtained from a patient. Samples include, without limitation, whole blood, plasma, serum, red blood cells, white blood cells (e.g., peripheral blood mononuclear cells), ductal lavage fluid, nipple aspirate, lymph (e.g., disseminated tumor cells of the lymph node), bone marrow aspirate, saliva, urine, stool (i.e., feces), sputum, bronchial lavage fluid, tears, fine needle aspirate (e.g., harvested by random periareolar fine needle aspiration), any other bodily fluid, a tissue sample (e.g., tumor tissue) such as a biopsy of a tumor (e.g., needle biopsy) or a lymph node (e.g., sentinel lymph node biopsy), and cellular extracts thereof. In some embodiments, the sample is whole blood or a fractional component thereof such as plasma, serum, or a cell pellet. In preferred embodiments, the sample is obtained by isolating circulating cells of a solid tumor from whole blood or a cellular fraction thereof using any technique known in the art. In other embodiments, the sample is a formalin fixed paraffin embedded (FFPE) tumor tissue sample, e.g., from a solid tumor of the breast.

A "biopsy" refers to the process of removing a tissue sample for diagnostic or prognostic evaluation, and to the tissue specimen itself. Any biopsy technique known in the art can be applied to the methods and compositions of the present invention. The biopsy technique applied will generally depend on the tissue type to be evaluated and the size and type of the tumor (i.e., solid or suspended (i.e., blood or ascites)), among other factors. Representative biopsy techniques include excisional biopsy, incisional biopsy, needle biopsy (e.g., core needle biopsy, fine-needle aspiration biopsy, etc.), surgical biopsy, and bone marrow biopsy. Biopsy techniques are discussed, for example, in *Harrison's Principles of Internal Medicine*, Kasper, et al., eds., 16th ed., 2005, Chapter 70, and throughout Part V. One skilled in the art will appreciate that biopsy techniques can be performed to identify cancerous and/or precancerous cells in a given tissue sample.

The term "subject" or "patient" or "individual" typically includes humans, but can also include other animals such as, e.g., other primates, rodents, canines, felines, equines, ovines, porcines, and the like.

An "array" or "microarray" comprises a distinct set and/or dilution series of capture antibodies immobilized or restrained on a solid support such as, for example, glass (e.g., a glass slide), plastic, chips, pins, filters, beads (e.g., magnetic beads, polystyrene beads, etc.), paper, membrane (e.g., nylon, nitrocellulose, polyvinylidene fluoride (PVDF), etc.), fiber bundles, or any other suitable substrate. The capture antibodies are generally immobilized or restrained on the solid support via covalent or noncovalent interactions (e.g., ionic bonds, hydrophobic interactions, hydrogen bonds, Van der Waals forces, dipole-dipole bonds). In certain instances, the capture antibodies comprise capture tags which interact with capture agents bound to the solid support. The arrays used in the assays described herein typically comprise a plurality of different capture antibodies and/or capture antibody concentrations that are coupled to the surface of a solid support in different known/addressable locations.

The term "capture antibody" is intended to include an immobilized antibody which is specific for (i.e., binds, is bound by, or forms a complex with) one or more analytes of interest in a sample such as a cellular extract. In particular embodiments, the capture antibody is restrained on a solid support in an array. Suitable capture antibodies for immobilizing any of a variety of signal transduction molecules on a solid support are available from Upstate (Temecula, Calif.), Biosource (Camarillo, Calif.), Cell Signaling Technologies (Danvers, Mass.), R&D Systems (Minneapolis, Minn.), Lab Vision (Fremont, Calif.), Santa Cruz Biotechnology (Santa Cruz, Calif.), Sigma (St. Louis, Mo.), and BD Biosciences (San Jose, Calif.).

The term "detection antibody" as used herein includes an antibody comprising a detectable label which is specific for (i.e., binds, is bound by, or forms a complex with) one or more analytes of interest in a sample. The term also encompasses an antibody which is specific for one or more analytes of interest, wherein the antibody can be bound by another species that comprises a detectable label. Examples of detectable labels include, but are not limited to, biotin/streptavidin labels, nucleic acid (e.g., oligonucleotide) labels, chemically reactive labels, fluorescent labels, enzyme labels, radioactive labels, and combinations thereof. Suitable detection antibodies for detecting the activation state and/or total amount of any of a variety of signal transduction molecules are available from Upstate (Temecula, Calif.), Biosource (Camarillo, Calif.), Cell Signaling Technologies (Danvers, Mass.), R&D Systems (Minneapolis, Minn.), Lab Vision (Fremont, Calif.), Santa Cruz Biotechnology (Santa Cruz, Calif.), Sigma (St. Louis, Mo.), and BD Biosciences (San Jose, Calif.). As a non-limiting example, phospho-specific antibodies against various phosphorylated forms of signal transduction molecules such as EGFR, c-KIT, c-Src, FLK-1, PDGFRA, PDGFRB, AKT, MAPK, PTEN, Raf, and MEK are available from Santa Cruz Biotechnology.

The term "activation state-dependent antibody" includes a detection antibody which is specific for (i.e., binds, is bound by, or forms a complex with) a particular activation state of one or more analytes of interest in a sample. In preferred embodiments, the activation state-dependent antibody detects the phosphorylation, ubiquitination, and/or complexation state of one or more analytes such as one or more signal transduction molecules. In some embodiments, the phosphorylation of members of the EGFR family of receptor tyrosine kinases and/or the formation of heterodimeric complexes between EGFR family members is detected using activation state-dependent antibodies. In particular embodiments, activation state-dependent antibodies are useful for detecting one or more sites of phosphorylation in one or more of the following signal transduction molecules (phosphorylation sites correspond to the position of the amino acid in the human protein sequence): EGFR/HER1/ErbB1 (e.g., tyrosine (Y) 1068); ErbB2/HER2 (e.g., Y1248); ErbB3/HER3 (e.g., Y1289); ErbB4/HER4 (e.g., Y1284); SGK3 (e.g., threonine (T) 256 and/or serine (S) 422); 4E-BP1 (e.g., T70); ERK1 (e.g., T202 and/or Y204); ERK2 (e.g., T202); MEK (e.g., S217 and/or S221); PIK3R1 (e.g., Y688); PDK1 (e.g., S241); P70S6K (e.g., T229, T389, and/or S421); c-MET (e.g., Y1349); PTEN (e.g., S380); AKT1 (e.g., S473 and/or T308); AKT2 (e.g., S474 and/or T309); AKT3 (e.g., S472 and/or T305); GSK-3β (e.g., S9); NFKB (e.g., S536); IKB (e.g., S32); BAD (e.g., S112 and/or S136); mTOR (e.g., S2448); Rsk-1 (e.g., T357 and/or S363); Jnk (e.g., T183 and/or Y185); P38 (e.g., T180 and/or Y182); STAT3 (e.g., Y705 and/or S727); FAK (e.g., Y576); Rb (e.g., S249, T252, and/or S780); p53 (e.g., S392 and/or S20); CREB (e.g., S133); c-Jun (e.g., S63); c-Src (e.g., Y416); and paxillin (e.g., Y118).

The term "activation state-independent antibody" includes a detection antibody which is specific for (i.e., binds, is bound by, or forms a complex with) one or more analytes of interest in a sample irrespective of their activation state. For example, the activation state-independent antibody can detect both phosphorylated and unphosphorylated forms of one or more analytes such as one or more signal transduction molecules.

III. Description of the Embodiments

The present invention provides compositions and methods for detecting the status (e.g., expression and/or activation levels) of components of signal transduction pathways in tumor cells derived from tumor tissue or circulating cells of a solid tumor with a specific, multiplex, high-throughput proximity assay as described herein.

In one embodiment, the invention provides a method for detecting and/or quantitating dimerization of at least two receptor tyrosine kinases (RTKs). In another embodiment, the invention provides a method for measuring (e.g., detecting and or quantitating) the level of PI3K complex comprising a RTK dimer, a PI3K p85 regulatory subunit, and a PI3K p110 catalytic subunit.

The PI3K p85 regulatory subunit comprises any one of five variants, designated p85α (SEQ ID NO:1), p85β (SEQ ID NO:2), p55γ (SEQ ID NO:3), p150 (SEQ ID NO:4), and p101 (SEQ ID NO:5). The PI3K p110 subunit comprises any one of the variants designated p110α (SEQ ID NO:6), 11013 (SEQ ID NO:7), p110γ (SEQ ID NO:8), and p110δ (SEQ ID NO:9).

In yet another embodiment, the invention provides a method for measuring (e.g., detecting and quantitating) the level of activated PI3K in tumor cells or circulating cell from a solid tumor. In other embodiments, the invention provides methods of monitoring PI3K complexation, PI3K activation (e.g., phosphorylation), activation of downstream proteins (e.g., adaptor, effector, kinase proteins) of the PI3K pathway, and other signal transducers of pathways associated with the PI3K pathway.

The present invention provides compositions and methods for determining or predicting response of a patient's tumor to specific anticancer therapy (e.g., RTK and PI3K modulating compounds, or combinations thereof). In some instances, the methods are used to predict the clinical benefit of PI3K inhibitor therapy or PI3K inhibitor combination therapy. For instance, the measurement of elevated levels of PI3K activation or activated components in the PI3K signaling pathway in a patient's tumor cells using methods described herein, predicts that the patient can clinically benefit from PI3K inhibitor therapy or PI3K combination therapy. The present invention also provides compositions and methods for selecting appropriate therapies to down-regulate or shut down one or more deregulated signal transduction pathways. Thus, certain embodiments of the invention are used to facilitate the design of personalized therapies based on the particular molecular signature provided by the collection of total and activated signal transduction proteins in a given patient's tumor.

In one embodiment, the present invention provides methods for the measurement (e.g., detection and quantitation) of the level of expression and/or the degree of activation (e.g., phosphorylation) of PI3K and RTKs, substrates thereof, and/or other signal transduction molecules in tumor sample from a patient relapsed on anticancer therapy. As such, the present invention advantageously provides benefits to patients with solid tumors, such as breast cancer, non-small cell lung cancer, gastric cancer, pancreatic cancer and colorectal cancer who are receiving one or more targeted therapies by screening and monitoring them throughout the course of therapy and evaluating whether they should be switched to an alternative targeted therapy or combination therapy. In certain aspects, the present invention provides methods to determine whether a cancer or tumor has adapted to existing anticancer therapy. In certain instances, tumor adaptation to therapy results in activation of compensatory signaling pathways which can be detected using methods of the present invention. In other instances, determination of tumor adaption in a patient indicates that the patient's treatment should be switched to an alternative targeted therapy or a combination therapy.

In another embodiment, the present invention provides methods for selecting an anticancer drug treatment for a patient with solid tumor cancer by comparing the detection and/or quantitation of RTK dimerization and/or PI3K complexation in tumor samples either in the presence or absence of an anticancer drug. In yet another embodiment, the compositions and methods of the present invention advantageously identify patients who are resistant to anticancer therapy due to mutations in the target protein kinase, acquired resistance to therapeutic agent, adaptation by signal transduction molecules to therapy, non-compliance with the therapeutic regimen, and/or administration of a suboptimal drug dose.

In certain aspects, the methods described herein monitor and follow cancer or tumor adaptation to existing anticancer therapy. In certain instances, by following and monitoring the activation of pathway profiles using CEER techniques, it can be ascertained whether there is pathway compensation for existing therapy by for example, shunting activation and/or expression to an associated pathway. These techniques allow for evaluation of therapy efficacy. If the original pathway activation is shut down or diminished, it is important to interrogate the associated pathways to ascertain whether there is pathway compensation in another pathway. In these instances, a combination therapy regimen may be recommended, or switching therapies altogether may be recommended. For example, as illustrated in Examples 3, 4 and 6 described herein, methods of the present invention are used to monitor levels of activated PI3K, HER1, HER2, HER3, IGF-1R, AKT and/or ERK in tumor cells from patients who relapsed on anticancer therapy. In these patients' tumors, compensatory signaling pathways not directly targeted by the therapy were activated (see, FIGS. 14-17 and 25). Advantageously, using the methods herein, the pathway profiling analysis indicates that the patients can clinically benefit from PI3K inhibitor therapy or PI3K inhibitor combination therapy.

Analysis of expression of target protein or genetic mutation alone has limitations for selecting the appropriate therapy regimen with maximal clinical efficacy for a subject with cancer or suspected of having cancer. Comprehensive profiling of RTK dimerization and PI3K complexation provides insightful information on the efficacy of specific anticancer agents on their intended target proteins. The methods of the present invention also provide valuable information regarding potential drug resistance mechanisms such as activation of compensatory pathways and provides a guide to effective therapeutic treatments and regimens for patients with cancer.

IV. PI3K Signaling and Cancer

According to the present invention, the activation status of the PI3K pathway and/or RTK pathways (e.g., HER1, HER2, HER3, HER4, cMET, and IGF-1R pathways) can be quantitatively measured in tumor cells derived from a patient with solid tumor cancer, such as breast, colorectal, gastric, lung, or pancreatic cancer. The invention provides a method for simultaneous quantification of the activation level of numerous proteins of the PI3K pathway in a tumor sample.

Phosphoinositide 3-kinases (PI3Ks) have been found to play key roles in many cellular processes including cell survival, proliferation, differentiation, metabolism and motility. As major effectors downstream of receptor tyrosine kinases (RTK) and G protein coupled receptors, PI3Ks transduce signals from various growth factors and cytokines into intracellular messages by generating phospholipids, which in turn activate the serine/threonine kinase AKT and other effector pathways. Examples of other downstream effectors include, but are not limited to, RAC1, SGK, PKC, Mdm2, FKHR, NF-κB, BAD, MEK, PTEN, GSK3β, mTOR, and S6K.

When PI3Ks are activated by growth factor stimulation through RTKs (e.g., HER1, HER2, HER3 and HER4), the PI3K p85 subunit directly binds to the phosphotyrosine residues on RTKs and/or adaptor proteins. This binding relieves the intermolecular inhibition of the PI3K p110 subunit by p85 and localizes PI3K to the plasma membrane of the cell. There, PI3K catalyzes the phosphorylation of PIP2 to PIP3 which then facilitates the phosphorylation of AKT. Activated AKT phosphorylates many other proteins in associated/nearby pathways that initiate processes to enable cell survival, suppression of apoptosis and cell cycle control.

In addition to the complexity of the PI3K pathway, extensive crosstalk exists with other cellular signaling networks. These associated or nearby signaling networks include, but are not limited to, mTOR, p53, RAS and MAPK pathways. Aberrant expression and/or activation of components of the PI3K pathway, as well as the ErbB family pathways, have been reported in a number of human tumors, including breast, ovarian, gastric, lung, and colorectal cancer. In one embodiment, the methods of the present invention are used to detect the presence of dimerization, expression level and/or activation state of one or more of signal transduction molecules (e.g., a receptor tyrosine kinase such as a member of the ErbB family or a signaling pathway component such as PI3K) in a cellular extract of tumor cells such as breast, lung, pancreatic, gastric, colorectal or other cancer cells.

In some embodiments of the present invention, the method further comprises somatic mutation (e.g., allelic variant) analysis for detecting the presence of one or more rare somatic mutations in a cellular extract of tumor cells such as breast, lung, pancreatic, gastric, colorectal, or other cancer cells. Non-limiting examples of genes carrying a somatic mutation include PI3K, KRAS and BRAF. For instance, somatic mutations in the PIK3CA gene include E542K, E545D, E545K, and H1047R mutations. Methods for detecting allelic variants are disclosed in U.S. Provisional Application No. 61/525,137, and PCT/US2012/051442 the disclosures of which are hereby incorporated by reference in their entireties.

As one non-limiting example, somatic mutation (e.g., allelic variant) analysis for amplifying an allele-specific sequence can comprise: (a) hybridizing an allele-specific primer to a first nucleic acid molecule comprising a target allele; (b) hybridizing an allele-specific blocker probe to a second nucleic acid molecule comprising an alternative allele, wherein the alternative allele corresponds to the same loci as the target allele; (c) hybridizing a locus-specific detector probe to the first nucleic acid molecule; (d) hybridizing a locus-specific primer to the extension product of the allele-specific primer; and (e) PCR amplifying the target allele. In particular embodiments, the allele-specific blocker probe comprises a non-extendable blocker moiety at the 3' terminus. In other particular embodiments, both the allele-specific primer and the allele-specific blocker probe comprise a modified base at the position of the target allele and the alternative allele, respectively. See, e.g., U.S. Provisional Application No. 61/525,137, and PCT/US2012/051442 the disclosures of which are hereby incorporated by reference in their entireties.

V. Antibody Arrays

In certain aspects, the presence of dimerization, expression level and/or activation state of one or more (e.g., a plurality) of signal transduction molecules (e.g., a receptor tyrosine kinase such as HER2 or other members of the ErbB family, or a signaling pathway component such as PI3K) in a cellular extract of tumor cells such as breast, lung or other cancer cells is detected using an antibody-based array comprising a dilution series of capture antibodies restrained on a solid support. The arrays typically comprise a plurality of different capture antibodies at a range of capture antibody concentrations that are coupled to the surface of the solid support in different addressable locations.

In one particular embodiment, the present invention provides an addressable array having superior dynamic range comprising a plurality of dilution series of capture antibodies restrained on a solid support, in which the capture antibodies in each dilution series are specific for one or more analytes corresponding to a component of a signal transduction pathway and other target proteins. In various aspects, this embodiment includes arrays that comprise components of signal transduction pathways characteristic of particular tumors, e.g., signal transduction pathways active in breast cancer cells (e.g., HER pathway). Thus, the invention may be advantageously practiced wherein each signal transduction molecule or other protein of interest with a potential expression or activation defect causing cancer is represented on a single array or chip. In some aspects, the components of a given signal transduction pathway active in a particular tumor cell are arrayed in a linear sequence that corresponds to the sequence in which information is relayed through a signal transduction pathway within a cell. Examples of such arrays are described herein and disclosed in U.S. Pat. No. 8,163,499 and PCT Publication No. WO2009/108637, the disclosures of which are herein incorporated by reference in its entirety for all purposes. The capture antibodies specific for one or more components of a given signal transduction pathway active in a particular tumor cell can also be printed in a randomized fashion to minimize any surface-related artifacts.

The solid support can comprise any suitable substrate for immobilizing proteins. Examples of solid supports include, but are not limited to, glass (e.g., a glass slide), plastic, chips, pins, filters, beads, paper, membranes, fiber bundles, gels, metal, ceramics, and the like. Membranes such nylon (Biotrans™, ICN Biomedicals, Inc. (Costa Mesa, Calif.); Zeta-Probe®, Bio-Rad Laboratories (Hercules, Calif.)), nitrocellulose (Protran®, Whatman Inc. (Florham Park, N.J.)), and PVDF (Immobilon™, Millipore Corp. (Billerica, Mass.)) are suitable for use as solid supports in the arrays of the present invention. Preferably, the capture antibodies are restrained on glass slides coated with a nitrocellulose polymer, e.g., FAST® Slides, which are commercially available from Whatman Inc. (Florham Park, N.J.).

Particular aspects of the solid support which are desirable include the ability to bind large amounts of capture antibodies and the ability to bind capture antibodies with minimal denaturation. Another suitable aspect is that the solid support displays minimal "wicking" when antibody solutions containing capture antibodies are applied to the support. A solid support with minimal wicking allows small aliquots of capture antibody solution applied to the support to result in small, defined spots of immobilized capture antibody.

The capture antibodies are typically directly or indirectly (e.g., via capture tags) restrained on the solid support via covalent or noncovalent interactions (e.g., ionic bonds, hydrophobic interactions, hydrogen bonds, Van der Waals forces, dipole-dipole bonds). In some embodiments, the capture antibodies are covalently attached to the solid support using a homobifunctional or heterobifunctional crosslinker using standard crosslinking methods and conditions. Suitable crosslinkers are commercially available from vendors such as, e.g., Pierce Biotechnology (Rockford, Ill.).

Methods for generating arrays suitable for use in the present invention include, but are not limited to, any technique used to construct protein or nucleic acid arrays. In some embodiments, the capture antibodies are spotted onto an array using a microspotter, which are typically robotic printers equipped with split pins, blunt pins, or ink jet printing. Suitable robotic systems for printing the antibody arrays described herein include the PixSys 5000 robot (Cartesian Technologies; Irvine, Calif.) with ChipMaker2 split pins (TeleChem International; Sunnyvale, Calif.) as well as other robotic printers available from BioRobics (Woburn, Mass.) and Packard Instrument Co. (Meriden, Conn.). Preferably, at least 2, 3, 4, 5, or 6 replicates of each capture antibody dilution are spotted onto the array.

Another method for generating arrays suitable for use in the present invention comprises dispensing a known volume of a capture antibody dilution at each selected array position by contacting a capillary dispenser onto a solid support under conditions effective to draw a defined volume of liquid onto the support, wherein this process is repeated using selected capture antibody dilutions at each selected array position to create a complete array. The method may be practiced in forming a plurality of such arrays, where the solution-depositing step is applied to a selected position on each of a plurality of solid supports at each repeat cycle. A further description of such a method can be found, e.g., in U.S. Pat. No. 5,807,522.

In certain instances, devices for printing on paper can be used to generate the antibody arrays. For example, the desired capture antibody dilution can be loaded into the printhead of a desktop jet printer and printed onto a suitable solid support (see, e.g., Silzel et al., *Clin. Chem.*, 44:2036-2043 (1998)).

In some embodiments, the array generated on the solid support has a density of at least about 5 spots/cm$^2$, and preferably at least about 10, 20, 30, 40, 50, 60, 70, 80, 90, 100, 110, 120, 130, 140, 150, 160, 170, 180, 190, 200, 210, 220, 230, 250, 275, 300, 325, 350, 375, 400, 425, 450, 475, 500, 550, 600, 650, 700, 750, 800, 850, 900, 950, 1000, 2000, 3000, 4000, 5000, 6000, 7000, 8000 or 9000, or 10,000 spots/cm$^2$.

In certain instances, the spots on the solid support each represents a different capture antibody. In certain other instances, multiple spots on the solid support represent the same capture antibody, e.g., as a dilution series comprising a series of descending capture antibody concentrations.

Additional examples of methods for preparing and constructing antibody arrays on solid supports are described in U.S. Pat. Nos. 6,197,599, 6,777,239, 6,780,582, 6,897,073, 7,179,638, 7,192,720, and 7,771,955; U.S. Patent Publication Nos. 20060115810, 20060263837, and 20070054326; and Varnum et al., *Methods Mol. Biol.*, 264:161-172 (2004).

Methods for scanning antibody arrays are known in the art and include, without limitation, any technique used to scan protein or nucleic acid arrays. Microarray scanners suitable for use in the present invention are available from PerkinElmer (Boston, Mass.), Agilent Technologies (Palo Alto, Calif.), Applied Precision (Issaquah, Wash.), GSI Lumonics Inc. (Billerica, Mass.), and Axon Instruments (Union City, Calif.). As a non-limiting example, a GSI ScanArray3000 for fluorescence detection can be used with ImaGene software for quantitation.

A. Detection Assays for Dimerization

In one embodiment, the present invention provides an assay for detecting and/or quantitating homo- or heterodimerization of receptor tyrosine kinases including, but not limited to, HER1/HER2 dimers, HER1/HER3 dimers, HER2/HER3 dimers, HER2/HER2 dimers, HER2/HER4 dimers, p95HER2/HER3 dimers, p95HER2/HER2 dimers, and the like. A homodimer is formed by two identical molecules such as HER2/HER2 in a process called homodimerization, whereas a heterodimer is formed by two different macromolecules such as HER1/HER3 in a process called heterodimerization. In this aspect, the assay comprises 3 antibodies: (1) a capture antibody specific for one member of the dimer pair; (2) a first detection antibody specific for a first member of the dimer pair, wherein the first detection antibody is specific for a different domain than the capture antibody; and a (3) a second detection antibody specific for a second member of the dimer pair.

Certain of the CEER techniques are disclosed in U.S. Pat. No. 8,163,299, U.S. Patent Publication Nos. 20080261829, 20090035792, 20100167945, 20110071042 and 20110281748. Further details can be found, for example in WO 2010/132723 and WO 2011/008990, the disclosures of which are hereby incorporated by reference in their entireties.

Figure 1B:
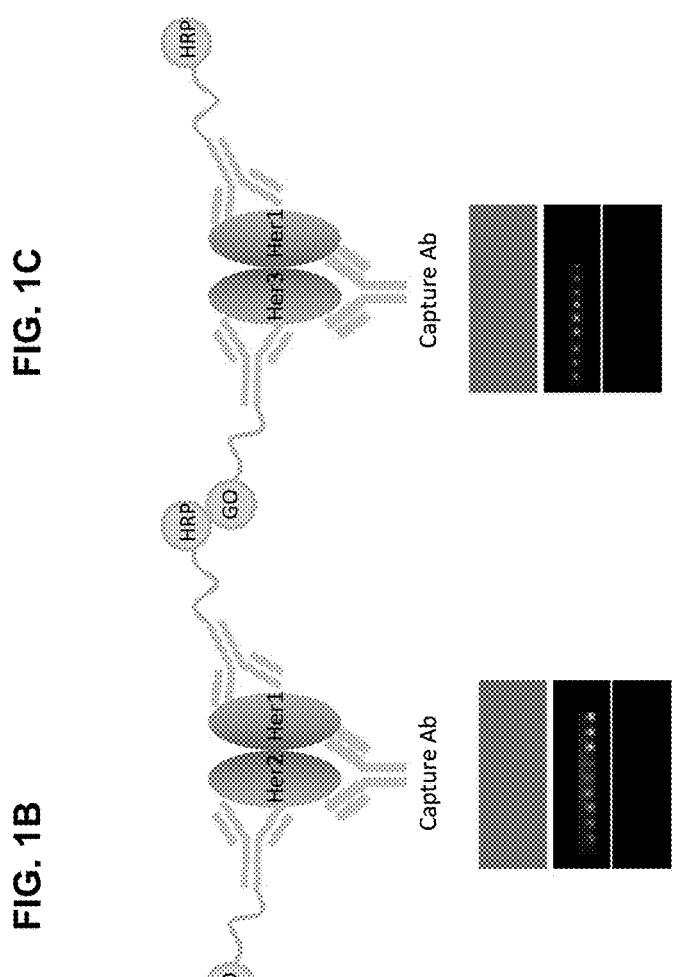
Figure 1C:
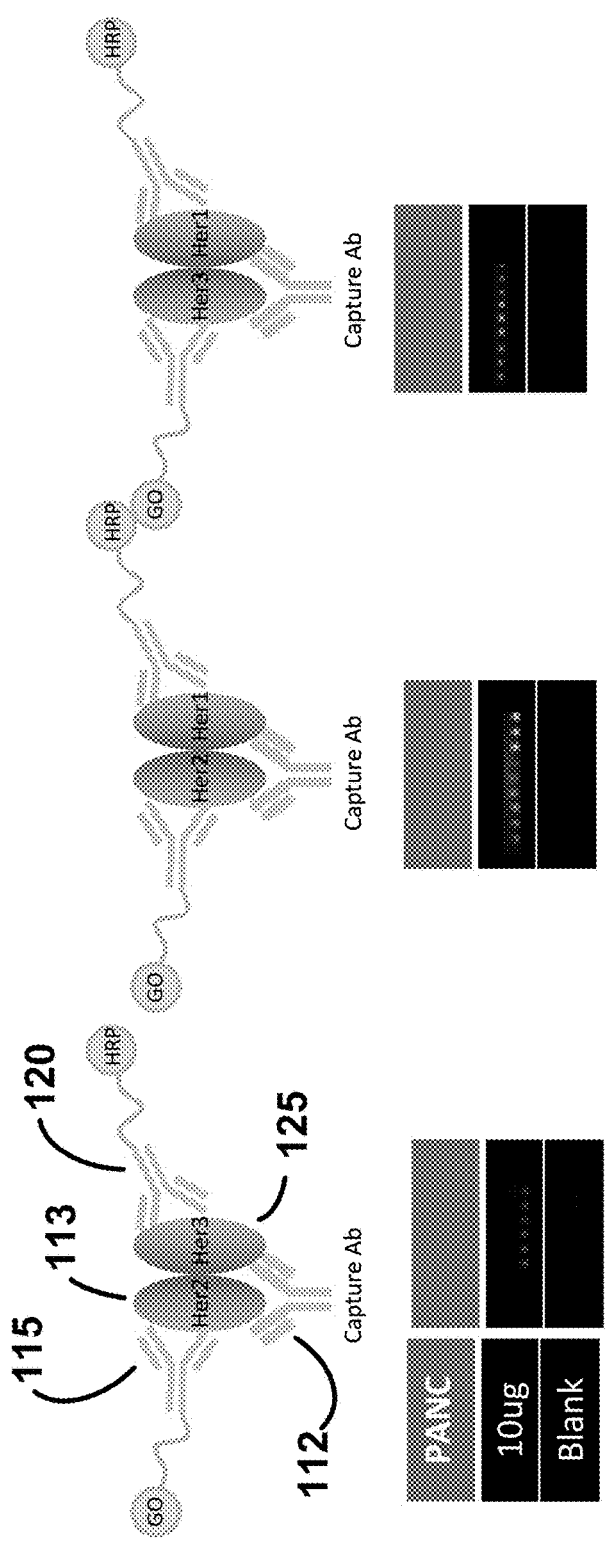

FIG. 1A-C show one embodiment of the foregoing proximity assay for detection of dimerization of receptor tyrosine kinases. As shown in FIG. 1A, a capture antibody 112 is used to capture a member of the RTK dimer, for example HER2 113. A first detection antibody 115 is then used to bind to a different portion (e.g., epitope) on HER2. A second detection 120 antibody is thereafter used to bind to the dimerized second receptor tyrosine 1kinase e.g., HER3 125. The first detection antibody comprises one or a plurality of first activation state-independent antibodies specific for one member of the dimer, whereas a second detection antibody or a plurality of second detection antibodies is specific for the other member of the dimer. The first detection antibody is labeled with a facilitating moiety e.g., glucose oxidase (GO) and the second detection antibody is labeled with a first member of a signal amplification pair e.g., horseradish peroxidase (HRP). The facilitating moiety generates an oxidizing agent e.g., hydrogen peroxide, which channels to and reacts with the first member of the signal amplification pair. Thereafter, the plurality of detectable captured analytes are incubated with a second member of the signal amplification pair e.g., tyramide or tyramide biotin to generate an amplified signal, which is then detected. Other heterodimer examples such as a HER2/HER1 dimer and a HER3/HER1 dimer are shown as FIG. 1B and FIG. 1C, respectively.

Suitable activation state-independent antibodies for measuring dimerization of receptor tyrosine kinases include any antibody that binds to an epitope on a receptor tyrosine kinase having an amino acid residue that has not been activated (e.g., phosphorylated). Activation state-independent antibodies that bind to RTKs such as members of the ErbB family, cMET, IGF-1R, and the like that are suitable for use in the present invention are commercially available from but not limited to Cell Signaling Technology (Danvers, Mass.), Thermo Scientific (Waltham, Mass.), Abcam (Cambridge, Mass.), Santa Cruz Biotechnology (Santa Cruz, Calif.), Sigma-Aldrich (St. Louis, Mo.), and EMD Millipore (Billerica, Mass.).

Suitable activation state-dependent antibodies for measuring dimerization of receptor tyrosine kinases include any antibody that binds to an epitope of a receptor tyrosine kinase having an amino acid residue that has been activated (e.g., phosphorylated). Activation state-dependent antibodies that bind to RTKs such as members of the ErbB family, cMET, IGF-1R, and the like that are suitable for use in the present invention are commercially available from but not limited to Cell Signaling Technology (Danvers, Mass.), Thermo Scientific (Waltham, Mass.), Abcam (Cambridge, Mass.), Santa Cruz Biotechnology (Santa Cruz, Calif.), Sigma-Aldrich (St. Louis, Mo.), and EMD Millipore (Billerica, Mass.).

In one embodiment, the present invention proves a method for selecting a treatment for a subject having or suspected of having cancer, the method comprises:
(a) measuring the dimerization of at least two receptor tyrosine kinases (RTKs), wherein measuring comprises: (i) incubating a cellular extract with one or a plurality of dilution series of capture antibodies to form a plurality of captured analytes; (ii) incubating the plurality of captured analytes with detection antibodies comprising a first or a plurality of first activation state-independent antibodies and a second or a plurality of second activation state-independent antibodies specific for a first member and a second member, respectively, of a dimerized pair of analytes to form a plurality of detectable captured dimerized analytes, wherein the first activation state-independent antibodies are labeled with a facilitating moiety, the second activation state-independent antibodies are labeled with a first member of a signal amplification pair, and the facilitating moiety generates an oxidizing agent which channels to and reacts with the first member of the signal amplification pair; (iii) incubating the plurality of detectable captured dimerized analytes with a second member of the signal amplification pair to generate an amplified signal; and (iv) detecting the amplified signal generated from the first and second members of the signal amplification pair; and
(b) selecting an anticancer drug by comparing the dimerization of at least two RTKs to a reference dimerization profile of the same two RTK wherein the reference dimerization profile is generated in the absence of the anticancer drug.

In some embodiments, the method further comprises calibrating the level of dimerization of at least two RTKs against a standard curve generated for the at least two RTKs.

In some embodiments, the cellular extract is isolated from a subject having cancer after administration of an anticancer drug. In some embodiments, the cellular extract is contacted with an anticancer drug. In some embodiments, the anticancer drug is selected from the consisting of a PI3K modulating compound, a RTK modulating compound, or a combination thereof.

In a preferred aspect, the amount of amplified signal is correlative to the amount of dimerized receptor tyrosine kinase.

The capture antibodies and detection antibodies are preferably selected to minimize competition between them with respect to analyte binding (i.e., both capture and detection antibodies can simultaneously bind their corresponding signal transduction molecules).

A variety of facilitating moieties are useful in the present invention. A suitable facilitating moiety for use in the present invention includes any molecule capable of generating an oxidizing agent which channels to (i.e., is directed to) and reacts with (i.e., binds, is bound by, or forms a complex with) another molecule in proximity (i.e., spatially near or close) to the facilitating moiety. Examples of facilitating moieties include, without limitation, enzymes such as glucose oxidase or any other enzyme that catalyzes an oxidation/reduction reaction involving molecular oxygen ($O_2$) as the electron acceptor, and photosensitizers such as methylene blue, rose bengal, porphyrins, squarate dyes, phthalocyanines, and the like. Non-limiting examples of oxidizing agents include hydrogen peroxide ($H_2O_2$), a singlet oxygen, and any other compound that transfers oxygen atoms or gains electrons in an oxidation/reduction reaction. Preferably, in the presence of a suitable substrate (e.g., glucose, light, etc.), the facilitating moiety (e.g., glucose oxidase, photosensitizer, etc.) generates an oxidizing agent (e.g., hydrogen peroxide ($H_2O_2$), single oxygen, etc.) which channels to and reacts with the first member of the signal amplification pair (e.g., horseradish peroxidase (HRP), hapten protected by a protecting group, an enzyme inactivated by thioether linkage to an enzyme inhibitor, etc.) when the two moieties are in proximity to each other.

Suitable signal amplification pair members include, but are not limited to, peroxidases such horseradish peroxidase (HRP), catalase, chloroperoxidase, cytochrome c peroxidase, eosinophil peroxidase, glutathione peroxidase, lactoperoxidase, myeloperoxidase, thyroid peroxidase, deiodinase, and the like. Other examples of signal amplification pair members include haptens protected by a protecting group and enzymes inactivated by thioether linkage to an enzyme inhibitor.

In one example of proximity channeling, the facilitating moiety is glucose oxidase (GO) and the first member of the signal amplification pair is horseradish peroxidase (HRP). When the GO is contacted with a substrate such as glucose, it generates an oxidizing agent (i.e., hydrogen peroxide ($H_2O_2$)). If the HRP is within channeling proximity to the GO, the $H_2O_2$ generated by the GO is channeled to and complexes with the HRP to form an HRP-$H_2O_2$ complex, which, in the presence of the second member of the signal amplification pair (e.g., a chemiluminescent substrate such as luminol or isoluminol or a fluorogenic substrate such as tyramide (e.g., biotin-tyramide), homovanillic acid, or 4-hydroxyphenyl acetic acid), generates an amplified signal. When biotin-tyramide is used as the second member of the signal amplification pair, the HRP-$H_2O_2$ complex oxidizes the tyramide to generate a reactive tyramide radical that covalently binds nearby nucleophilic residues. The activated tyramide is either directly detected or detected upon the addition of a signal-detecting reagent such as, for example, a streptavidin-labeled fluorophore or a combination of a streptavidin-labeled peroxidase and a chromogenic reagent. Examples of fluorophores suitable for use in the present invention include, but are not limited to, an Alexa Fluor® dye (e.g., Alexa Fluor® 555), fluorescein, fluorescein isothiocyanate (FITC), Oregon Green™; rhodamine, Texas red, tetrarhodamine isothiocynate (TRITC), a CyDye™ fluor (e.g., Cy2, Cy3, Cy5), and the like. The streptavidin label can be coupled directly or indirectly to the fluorophore or peroxidase using methods well-known in the art. Non-limiting examples of chromogenic reagents suitable for use in the present invention include 3,3',5,5'-tetramethylbenzidine (TMB), 3,3'-diaminobenzidine (DAB), 2,2'-azino-bis (3-ethylbenzothiazoline-6-sulfonic acid) (ABTS), 4-chloro-1-napthol (4CN), and/or porphyrinogen.

In another example of proximity channeling, the facilitating moiety is a photosensitizer and the first member of the signal amplification pair is a large molecule labeled with multiple haptens that are protected with protecting groups that prevent binding of the haptens to a specific binding partner (e.g., ligand, antibody, etc.). For example, the signal amplification pair member can be a dextran molecule labeled with protected biotin, coumarin, and/or fluorescein molecules. Suitable protecting groups include, but are not limited to, phenoxy-, analino-, olefin-, thioether-, and selenoether-protecting groups. Additional photosensitizers and protected hapten molecules suitable for use in the proximity assays of the present invention are described in U.S. Pat. No. 5,807,675. When the photosensitizer is excited with light, it generates an oxidizing agent (i.e., singlet oxygen). If the hapten molecules are within channeling proximity to the photosensitizer, the singlet oxygen generated by the photosensitizer is channeled to and reacts with thioethers on the protecting groups of the haptens to yield carbonyl groups (ketones or aldehydes) and sulphinic acid, releasing the protecting groups from the haptens. The unprotected haptens are then available to specifically bind to the second member of the signal amplification pair (e.g., a specific binding partner that can generate a detectable signal). For example, when the hapten is biotin, the specific binding partner can be an enzyme-labeled streptavidin. Exemplary enzymes include alkaline phosphatase, β-galactosidase, HRP, etc. After washing to remove unbound reagents, the detectable signal can be generated by adding a detectable (e.g., fluorescent, chemiluminescent, chromogenic, etc.) substrate of the enzyme and detected using suitable methods and instrumentation known in the art. Alternatively, the detectable signal can be amplified using tyramide signal amplification and the activated tyramide either directly detected or detected upon the addition of a signal-detecting reagent as described above.

In yet another example of proximity channeling, the facilitating moiety is a photosensitizer and the first member of the signal amplification pair is an enzyme-inhibitor complex. The enzyme and inhibitor (e.g., phosphonic acid-labeled dextran) are linked together by a cleavable linker (e.g., thioether). When the photosensitizer is excited with light, it generates an oxidizing agent (i.e., singlet oxygen). If the enzyme-inhibitor complex is within channeling proximity to the photosensitizer, the singlet oxygen generated by the photosensitizer is channeled to and reacts with the cleavable linker, releasing the inhibitor from the enzyme, thereby activating the enzyme. An enzyme substrate is added to generate a detectable signal, or alternatively, an amplification reagent is added to generate an amplified signal.

In a further example of proximity channeling, the facilitating moiety is HRP, the first member of the signal amplification pair is a protected hapten or an enzyme-inhibitor complex as described above, and the protecting groups comprise p-alkoxy phenol. The addition of phenylenediamine and $H_2O_2$ generates a reactive phenylene diimine which channels to the protected hapten or the enzyme-inhibitor complex and reacts with p-alkoxy phenol protecting groups to yield exposed haptens or a reactive enzyme. The amplified signal is generated and detected as described above (see, e.g., U.S. Pat. Nos. 5,532,138 and 5,445,944).

In one embodiment, the cellular extract comprises an extract of cells isolated from a sample. In certain instances, the sample is selected from whole blood, serum, plasma, fine needle aspirate (FNA), urine, sputum, bronchial lavage fluid, tears, nipple aspirate, lymph, saliva, and combinations thereof. In another embodiment, the sample is obtained from a patient having solid tumor cancer. Examples of such cancers include, but are not limited to, breast cancer, lung cancer (e.g., non-small cell lung carcinoma), gastric cancer, pancreatic cancer, colorectal cancer and combinations thereof.

In some instances, the cellular extract is isolated from a patient with cancer after receiving anticancer drug therapy. In certain instances, the isolated cells are in contact with an anticancer drug or a combination of anticancer drugs. In some instances, an anticancer drug includes a PI3K inhibitor or a RTK modulating compound, such as a HER1, HER2, HER3, cMET or IGF-1R inhibitor). In other instances, the isolated cells are incubated with an anticancer drug or a combination of anticancer drugs prior to growth factor stimulation. In yet other instances, the isolated cells are lysed following growth factor stimulation to produce the cellular extract.

The methods of the present invention are particularly useful for determining the RTK activation (e.g., phosphorylation) status of one or more oncogenic RTKs (e.g., HER1, HER2, HER3, p95HER2, cMET and IGF-1R) in patients at risk of developing, suspected of having, or diagnosed with a solid tumor cancer, such as breast, colorectal, gastric, lung or pancreatic cancer. In certain instances, the methods of the present invention aid, assist, or facilitate in the diagnosis and prognosis of a cancer in a subject by measuring activated (e.g., phosphorylated) RTKs (e.g., phospho-HER2 levels) to determine whether the subject expresses an activated form of one or more of the RTK family of proteins (e.g., a HER2-positive patient). In other embodiments, the methods of the present invention are performed on a subject, already determined to express one or more oncogenic proteins, to optimize therapy, reduce toxicity, monitor the efficacy of therapeutic treatment, and/or detect adaptive non-responsiveness to therapy.

In some embodiments, the methods further comprise determining the activation status of one or more effector and adaptor proteins of the RTK pathway, and/or of an associated or compensatory pathway. In some instances, the associated or compensatory pathway is deregulated upon tumor adaptation to anticancer therapy.

B. Detection Assays for a PI3K Complex

It is known for example, that HER3 activation results in PI3K activation. However, it has now been surprisingly discovered that in certain instances and under certain conditions, HER3 phosphorylation and PI3K phosphorylation occur together. Using the assays described herein, it is possible to detect and quantitate the amount of PI3K complex and the amount of activation and/or phosphorylation of a PI3K complex. The PI3K complex comprises i) a dimerized receptor tyrosine kinase pair; ii) a PI3K p85 subunit and a PI3K p110 (e.g., α or β) subunit. The assay comprises 3 antibodies: (1) a capture antibody specific for either the PI3K p85 or the PI3K p110 subunit; (2) a first detection antibody specific for a first member of the dimer pair, or PI3K subunit, wherein the first detection antibody is specific for a different domain than the capture antibody and wherein the PI3K subunit may be activated; and (3) a second detection antibody specific for a second member of the dimer pair or a PI3K subunit.

Figure 2:
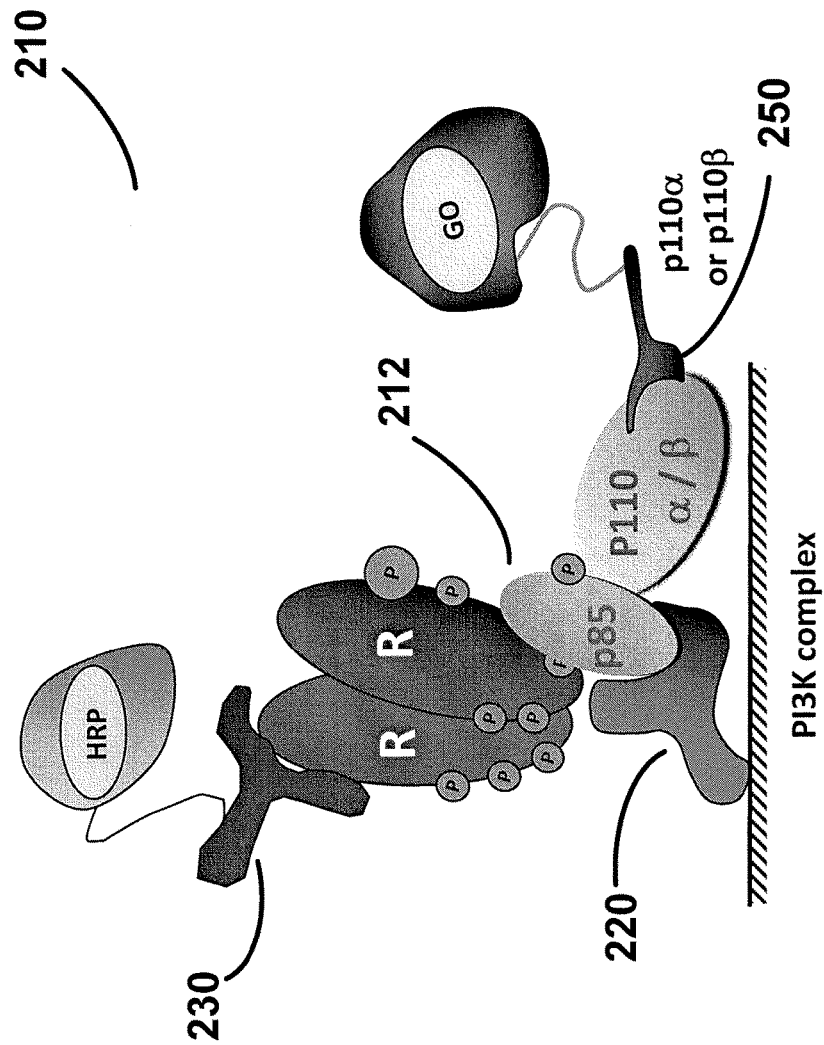
FIG. 2 shows one embodiment of a PI3K complex 210 detectable by the methods and assays described herein

FIG. 2 shows one embodiment of a PI3K complex 210 detectable by the methods and assays described herein. In this embodiment, (1) the PI3K p85 subunit 212 is bound by the capture antibody 220; (2) a first detection antibody 250 is specific for the PI3K p110 α or β subunit; and (3) a second detection antibody 230 is specific for a first member of the dimer pair.

Figure 3:
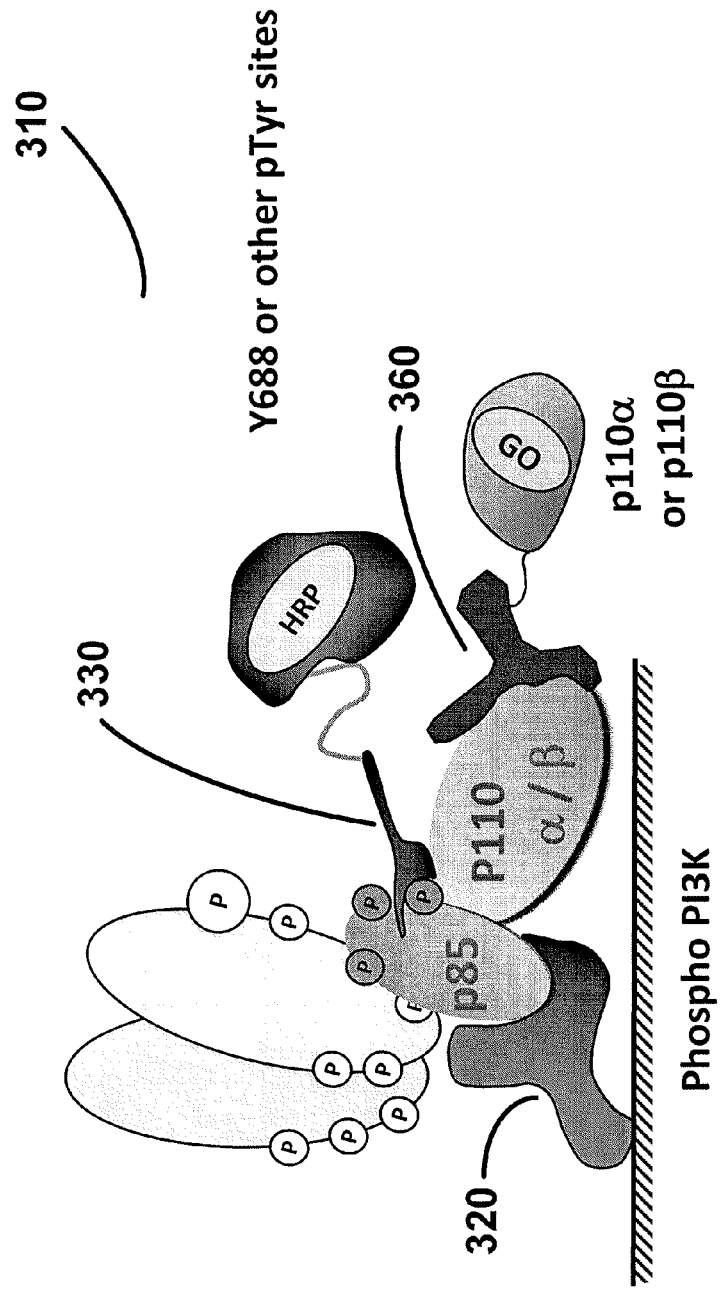
FIG. 3 shows another embodiment of a PI3K complex 310 detectable by the methods and assays described herein

FIG. 3 shows another embodiment of an activated PI3K complex 310 detectable by the methods and assays described herein. In this embodiment, (1) the PI3K p85 subunit is bound to the capture antibody 320; (2) a first detection antibody 360 is specific for the PI3K p110α or β subunit; and (3) a second detection antibody comprises an activation state-dependent antibody 330 specific for a phosphorylation site on a PI3K subunit such as p85 (e.g., Y452, Y458, Y460, Y463, Y467, Y688, Y470, or other pTyr site).

FIG. 4A shows yet another embodiment of an activated PI3K complex detectable by the methods and assays described herein. In the embodiment shown in FIG. 4A (1) the PI3K p85 subunit is bound by the capture antibody 421; (2) a first detection antibody 430 comprises an activation state-independent antibody specific for a one member of a dimerized receptor tyrosine kinase (e.g., HER1, HER2, HER3, cMET, IGF-1R and the like); and (3) a second detection antibody 450 comprises an activation state-dependent antibody specific for a phosphorylation site on a PI3K subunit such as p85 (e.g., Y452, Y458, Y460, Y463, Y467, Y688, Y470, or other pTyr site).

FIG. 4B shows still yet another embodiment of a PI3K complex detectable by the methods and assays described herein. In the embodiment shown in FIG. 4B (1) the PI3K p85 subunit is bound by the capture antibody 452; (2) a first detection antibody 471 comprises an activation state-independent antibody is specific for a one member of a dimerized receptor tyrosine kinase (e.g., HER1, HER2, HER3, cMET, IGF-1R, and the like); and (3) a second detection antibody 491 comprises an activation state-independent antibody specific for the other member of the dimerized pair.

FIG. 4C illustrates the detection of activated PI3K complexes in T47D cells (human ductal breast epithelial tumor cell line) treated with heregulin (HRG), compared to non-treated cells. In some embodiments, the detection of PI3K complexes will also correlate with the detection of activated (e.g., phosphorylated) PI3K.

FIG. 5A shows another embodiment of a PI3K complex detectable by the methods and assays described herein. In the embodiment shown in FIG. 5A (1) the PI3K p110 subunit is bound by the capture antibody 501; (2) a first detection antibody 515 comprises an activation state-independent antibody specific for a one member of a dimerized receptor tyrosine kinase (e.g., HER1, HER2, HER3, cMET, IGF-1R, and the like); and (3) a second detection antibody 525 comprises an activation state-dependent antibody specific for a phosphorylation site on a PI3K subunit such as p85 (e.g., Y452, Y458, Y460, Y463, Y467, Y688, Y470, or other pTyr site). In certain aspects, p85 capture for detecting phospho-PI3K is more sensitive than p110 capture.

FIG. 5B shows an embodiment of a PI3K complex detectable by the methods and assays described herein. In the embodiment shown in FIG. 5B (1) the PI3K p85 subunit is bound by the capture antibody 530; (2) a first detection antibody 550 comprises an activation state-independent antibody specific for one member of a dimer of a receptor tyrosine kinase (e.g., HER1, HER2, HER3, cMET, IGF-1R, and the like); and (3) a second detection antibody 562 comprises an activation state-dependent antibody specific for a phosphorylation site on a PI3K subunit such as p85 (e.g., Y452, Y458, Y460, Y463, Y467, Y688, Y470, or other pTyr site).

Suitable antibodies for measuring the level of a PI3K complex include any antibody that is specific for (i.e., recognizes, binds to, or forms a complex with) an epitope of the PI3K p110 subunit (e.g., α or β), the PI3K p85 subunit, or the dimerized receptor tyrosine kinase pair.

Suitable activation state-independent antibodies bind to an epitope of the PI3K p110 subunit, the PI3K p85 subunit or the dimerized receptor tyrosine kinase pair, wherein the epitope is free of phosphorylated amino acid residues. Such activation state-independent antibodies include PI3K p85 subunit antibodies (Cat. #4257, #4292 from Cell Signaling Technology; Cat. Nos. sc-12929, sc-56934, sc-56938, sc-71892, sc-71891, and sc-376112, sc-292114, and sc-131325 from Santa Cruz Biotechnology; Cat. Nos. ab86714, ab22653, ab40755, ab250, ab135253, ab71925, ab63040, ab90578, ab133595, ab135952, ab65261, and ab71522 from Abcam), PI3K p110 α subunit antibodies (Cat. #4249 and #4249 from Cell Signaling Technology; Cat. Nos. sc-7248, sc-7189, sc-8010, sc-7174, sc-1332, sc-1331), and PI3K p110 β subunit antibodies (Cat. #3011 from Cell Signaling Technology; Cat. Nos. sc-7248, sc-7189, sc-8010, sc-376641, sc-376412, sc-376492, sc-603, sc-7175, sc-602 from Santa Cruz Biotechnology; Cat. Nos. ab32569, ab55593, ab97322, and ab32874 from Abeam).

Suitable activation state-independent antibodies specific for dimerized RTKs include antibodies to HER1 (Cat. #2646, #2239, #2239, #2963, #3265, and #2232 from Cell Signaling Technology; Cat. Nos. sc-374607, sc-365829, sc-80543, sc-120, sc-03, sc-101, sc-373476, sc-31155, sc-71031, sc-81451 and sc-71037 from Santa Cruz Biotechnology), antibodies to HER2 (Cat. #2165, #2248, #3250 and #2242 from Cell Signaling Technology), antibodies to HER3 (Cat. #4754 from Cell Signaling Technology; Cat. Nos. sc-415, sc-7390, sc-292557, sc-81455, sc-81454, sc-71067, sc-53279, and sc-285 from Santa Cruz Biotechnology), and antibodies to HER4 (Cat. #4795 from Cell Signaling Technology; Cat. Nos. sc-31150, sc-8050, sc-81456, sc-71071, sc-71070, sc-53280, sc31151, sc-283, and sc-31149 from Santa Cruz Biotechnology).

In some embodiments, an antibody that binds to the p110 α subunit is used in the present invention. In some embodiments, an antibody that binds to the p110 β subunit is used in the present invention. Suitable activation-dependent antibodies against PI3K are described in U.S. Patent Publication No. 20080014595, the disclosure of which is hereby incorporated by reference in its entirety for all purposes. Antibodies to PI3K are also commercially available from, but not limited to, Upstate (Temecula, Calif.), Biosource (Camarillo, Calif.), Cell Signaling Technologies (Danvers, Mass.), R&D Systems (Minneapolis, Minn.), Lab Vision (Fremont, Calif.), Santa Cruz Biotechnology (Santa Cruz, Calif.), BD Biosciences (San Jose, Calif.), Thermo Scientific (Waltham, Mass.), Abcam (Cambridge, Mass.), Sigma-Aldrich (St. Louis, Mo.), and EMD Millipore (Billerica, Mass.).

For example, suitable activation state-dependent antibodies bind to an epitope on the PI3K p110 subunit or the p85 subunit, wherein the epitope has at least one phosphorylated amino acid residue (e.g., pTyr). Such activation state-dependent antibodies include a p-PI3K p85 (Tyr458)/p55 (Tyr199) antibody (Cat. #4228 from Cell Signaling Technology), a p-PI3K p85 (Tyr67) antibody (Cat. # sc-293115 from Santa Cruz Biotechnology), and a p-PI3K p85 (Tyr607) antibody (Cat. No. ab61801 from Abcam). Phospho-PI3K p85 antibodies useful in the present invention are described in U.S. Patent Publication. No. 20080014595, the disclosure of which is hereby incorporated by reference in its entirety for all purposes. Likewise, PI3K p110 antibodies useful in the present invention are described in U.S. Pat. No. 6,274,327, the disclosure of which is hereby incorporated by reference in its entirety for all purposes.

In some embodiments, antibodies specific to PI3K antigens (SEQ ID NOs: 10-12) or fragments thereof can be used in the methods for measuring PI3K complexation.

Suitable activation state-dependent antibodies for measuring dimerization of receptor tyrosine kinases include any antibody that binds to an epitope of a receptor tyrosine kinase having an amino acid residue that has been activated (e.g., phosphorylated). Activation state-dependent antibodies that bind to RTKs such as members of the ErbB family, cMET, IGF-1R, and the like that are suitable for use in the present invention are commercially available from but not limited to Upstate (Temecula, Calif.), Biosource (Camarillo, Calif.), Cell Signaling Technologies (Danvers, Mass.), R&D Systems (Minneapolis, Minn.), Lab Vision (Fremont, Calif.), Santa Cruz Biotechnology (Santa Cruz, Calif.), BD Biosciences (San Jose, Calif.), Thermo Scientific (Waltham, Mass.), Abcam (Cambridge, Mass.), Sigma-Aldrich (St. Louis, Mo.), and EMD Millipore (Billerica, Mass.).

For example, suitable activation state-dependent antibodies specific for dimerized RTKs include antibodies to HER1 (Cat. #8808, #3056, #6963, #2231, #2641, #2235, #2237, #2238, #2236, #2234, #2220, #4404, and #4407 from Cell Signaling Technology; Cat. Nos. sc-16802, sc-12351, sc-16804, sc-16803, sc-101665, sc101668, sc-101667, and sc-101669 from Santa Cruz Biotechnology), antibodies to HER2 (Cat. #2244, #2241, #6942, #2249, and #2247 from Cell Signaling Technology), antibodies to HER3 (Cat. #4561, #4787, #4791, #2842 and #8017 from Cell Signaling Technology; Cat. No. sc-135654 from Santa Cruz Biotechnology), and antibodies to HER4 (Cat. #3790 and #4757 from Cell Signaling Technology; Cat. Nos. sc-33040 and sc-81491 from Santa Cruz Biotechnology).

In one particular embodiment, the proximity assay for measuring (e., detecting and quantitating) the level of a PI3K complex, wherein the PI3K complex comprises a) a dimerized receptor tyrosine kinase pair; b) a PI3K p85 subunit and a PI3K p110 subunit, comprises:

(i) incubating a cellular extract with one or a plurality of dilution series of capture antibodies to form a plurality of captured analytes;

(ii) incubating the plurality of captured analytes with first detection antibodies comprising either a) a first or a plurality of first activation state-independent antibodies specific for one member of a dimerized receptor tyrosine kinase pair or b) a PI3K p110 subunit; and second detection antibodies comprising either a) second or a plurality of second activation state-independent antibodies specific for a) one member of a dimerized receptor tyrosine kinase pair, a PI3K p85 or a PI3K p110 subunit or b) activation state-dependent antibodies specific for a PI3K p85 subunit and/or a PI3K p110 subunit to form a plurality of detectable captured dimerized and complexed analytes, wherein the first detection antibodies are labeled with a facilitating moiety, the second detection antibodies are labeled with a first member of a signal amplification pair, and the facilitating moiety generates an oxidizing agent which channels to and reacts with the first member of the signal amplification pair;

(iii) incubating the plurality of detectable captured dimerized analytes with a second member of the signal amplification pair to generate an amplified signal; and (iv) detecting the amplified signal generated from the first and second members of the signal amplification pair.

In another embodiment, the present invention provides a method for selecting a treatment for a subject having or suspected of having cancer, the method comprising:

(a) measuring the level of a PI3K complex activation, wherein said PI3K complex comprises i) dimerization of at least two receptor tyrosine kinases (RTKs); ii) a PI3K p85 subunit and a PI3K p110 subunit, said measuring comprises: (i) incubating a cellular extract with one or a plurality of dilution series of capture antibodies to form a plurality of captured analytes; (ii) incubating the plurality of captured analytes with first detection antibodies comprising either a) a first or a plurality of first activation state-independent antibodies specific for one member of a dimerized receptor tyrosine kinase pair or b) a PI3K p110 subunit; and second detection antibodies comprising either a) second or a plurality of second activation state-independent antibodies specific for a) one member of a dimerized receptor tyrosine kinase pair, a PI3K p85 or a PI3K p110 subunit or b) activation state-dependent antibodies specific for a PI3K p85 subunit and/or a PI3K p110 subunit to form a plurality of detectable captured dimerized and complexed analytes, wherein the first detection antibodies are labeled with a facilitating moiety, the second detection antibodies are labeled with a first member of a signal amplification pair, and the facilitating moiety generates an oxidizing agent which channels to and reacts with the first member of the signal amplification pair; incubating the plurality of detectable captured dimerized analytes with a second member of the signal amplification pair to generate an amplified signal; and detecting the amplified signal generated from the first and second members of the signal amplification pair; and (b) selecting an anticancer drug by comparing the level of the PI3K complex activation to a reference PI3K complex activation profile wherein the reference complex profile is generated in the absence of the anticancer drug.

In a preferred aspect, the amount of amplified signal is correlative to the amount of PI3K complex.

In some embodiments, the level of PI3K complex is calibrated against a standard curve generated for said PI3K complex comprising i) dimerization of at least two receptor tyrosine kinases (RTKs); ii) a PI3K p85 subunit and a PI3K p110 subunit.

In some embodiments, the level of PI3K complex activation is determined by a) comparing the amount of phospho-PI3K to the total level of PI3K present in the sample, and b) establishing a ratio of activated PI3K complex to total PI3K. The level of the PI3K complex activation is determined based on the ratio. In some instances, the level of the PI3K complex activation is below a cut-off threshold, which indicates that the subject would not benefit from PI3K inhibitor treatment. In some instances, the level of the PI3K complex activation is above the cut-off threshold, which indicates that the subject would benefit from PI3K inhibitor treatment.

In some embodiments, the level of PI3K complex activation (e.g., phosphorylated PI3K complex) indicates that a PI3K inhibitor alone should be selected for the subject. In other embodiments, the level of PI3K complex activation indicates that a combination therapy comprising a PI3K inhibitor and another anticancer drug should be selected for the subject.

In some embodiments, the cellular extract is isolated from a subject having cancer after administration of an anticancer drug. In some embodiments, the cellular extract is contacted with an anticancer drug. In some embodiments, the anticancer drug is selected from the consisting of a PI3K modulating compound, a RTK modulating compound, or a combination thereof.

In some embodiments, at least two RTKs is a member selected form the group consisting of a HER1/HER2 dimer, a HER1/HER3 dimer, a HER2/HER3 dimer, a HER2/HER2 dimer, a HER2/HER4 dimer, a p95HER2/HER3 dimer, and a p95HER2/HER2 dimer.

As discussed above, in one example of proximity channeling, the facilitating moiety is glucose oxidase (GO) and the first member of the signal amplification pair is horseradish peroxidase (HRP). When the GO is contacted with a substrate such as glucose, it generates an oxidizing agent (i.e., hydrogen peroxide ($H_2O_2$)). If the HRP is within channeling proximity to the GO, the $H_2O_2$ generated by the GO is channeled to and complexes with the HRP to form an HRP-$H_2O_2$ complex, which, in the presence of the second member of the signal amplification pair (e.g., a chemiluminescent substrate such as luminol or isoluminol or a fluorogenic substrate such as tyramide (e.g., biotin-tyramide), homovanillic acid, or 4-hydroxyphenyl acetic acid), generates an amplified signal. When biotin-tyramide is used as the second member of the signal amplification pair, the HRP-$H_2O_2$ complex oxidizes the tyramide to generate a reactive tyramide radical that covalently binds nearby nucleophilic residues. The activated tyramide is either directly detected or detected upon the addition of a signal-detecting reagent such as, for example, a streptavidin-labeled fluorophore or a combination of a streptavidin-labeled peroxidase and a chromogenic reagent. Examples of fluorophores suitable for use in the present invention include, but are not limited to, an Alexa Fluor® dye (e.g., Alexa Fluor® 555), fluorescein, fluorescein isothiocyanate (FITC), Oregon Green™; rhodamine, Texas red, tetrarhodamine isothiocynate (TRITC), a CyDye™ fluor (e.g., Cy2, Cy3, Cy5), and the like. The streptavidin label can be coupled directly or indirectly to the fluorophore or peroxidase using methods well-known in the art. Non-limiting examples of chromogenic reagents suitable for use in the present invention include 3,3',5,5'-tetramethylbenzidine (TMB), 3,3'-diaminobenzidine (DAB), 2,2'-azino-bis(3-ethylbenzothiazoline-6-sulfonic acid) (ABTS), 4-chloro-1-napthol (4CN), and/or porphyrinogen.

In one embodiment, the cellular extract comprises an extract of cells isolated from a sample. In certain instances, the sample is selected from whole blood, serum, plasma, fine needle aspirate (FNA), urine, sputum, bronchial lavage fluid, tears, nipple aspirate, lymph, saliva, and combinations thereof. In another embodiment, the sample is obtained from a patient having solid tumor cancer. Examples of such cancers include, but are not limited to, breast cancer, lung cancer (e.g., non-small cell lung carcinoma), gastric cancer, pancreatic cancer, colorectal cancer and combinations thereof. In some instances, the cellular extract is isolated from a patient with cancer after receiving anticancer drug therapy. In certain instances, the isolated cells are in contact with an anticancer drug acombination of anticancer drugs. In some instances, an anticancer drug includes a PI3K inhibitor or a RTK inhibitor, such as a HER1, HER2, HER3, cMET or IGF-1R inhibitor). In other instances, the isolated cells are incubated with an anticancer drug or a combination of anticancer drugs prior to growth factor stimulation. In yet other instances, the isolated cells are lysed following growth factor stimulation to produce the cellular extract.

The methods of the present invention are particularly useful for determining the PI3K complex activation (e.g., phosphorylation) status in patients at risk of developing, suspected of having, or diagnosed with a solid tumor cancer, such as breast, colorectal, gastric, lung or pancreatic cancer. In some instances, the activation of the PI3K complex comprises one or more activated RTKs (e.g., HER1, HER2, HER3, p95HER2, cMET and IGF-1R), a PI3K p85 subunit and a PI3K p110 subunit. In certain instances, the methods of the present invention aid, assist, or facilitate in the diagnosis and prognosis of a cancer in a subject by measuring activated PI3K complexes to determine whether the subject's tumor cells express an activated PI3K complex. In other embodiments, the methods of the present invention are performed on a subject, already determined to express one or more oncogenic proteins, to optimize therapy, reduce toxicity, monitor the efficacy of therapeutic treatment, and/or detect adaptive non-responsiveness to therapy.

In some aspects, the methods further comprise determining the activation status of one or more signal transducer proteins of the PI3K pathway or of an associated and/or compensatory pathway. In some instances, the associated or compensatory pathway is deregulated upon tumor adaptation to anticancer therapy.

In another embodiment, the PI3K complex assay comprises: (1) a capture antibody specific for the p85 subunit of PI3K; (2) a detection antibody specific that binds to the activated form of an RTK or a downstream protein (e.g., adaptor protein, effector, or kinase protein); and (3) a detection antibody that recognizes to the activated form of another RTK or downstream protein. Non-limiting examples of downstream proteins (e.g., adaptor protein, effector, or kinase protein) include CK, Shc, AKT, CRKL, PDK1, MEK, FAK, PTEN, ERK/MAPK, BRAF, KRAS, PRAS40, and p70S6K.

C. Production of Antibodies

The generation and selection of antibodies not already commercially available for analyzing the expression and/or activation levels of signal transduction molecules (e.g., HER2 signaling pathway components and PI3K) in cells such as tumor cells in accordance with the present invention can be accomplished several ways. For example, one way is to express and/or purify a polypeptide of interest (i.e., antigen) using protein expression and purification methods known in the art, while another way is to synthesize the polypeptide of interest using solid phase peptide synthesis methods known in the art. See, e.g., Guide to Protein Purification, Murray P. Deutcher, ed., Meth. Enzymol., Vol. 182 (1990); Solid Phase Peptide Synthesis, Greg B. Fields, ed., Meth. Enzymol., Vol. 289 (1997); Kiso et al., Chem. Pharm. Bull., 38:1192-99 (1990); Mostafavi et al., Biomed. Pept. Proteins Nucleic Acids, 1:255-60, (1995); and Fujiwara et al., Chem. Pharm. Bull., 44:1326-31 (1996). The purified or synthesized polypeptide can then be injected, for example, into mice or rabbits, to generate polyclonal or monoclonal antibodies. One skilled in the art will recognize that many procedures are available for the production of antibodies, for example, as described in Antibodies, A Laboratory Manual, Harlow and Lane, Eds., Cold Spring Harbor Laboratory, Cold Spring Harbor, N.Y. (1988). For example, PI3K antigens such as those of SEQ ID NO: 10-12 can be used to produce antibodies suitable for use in the methods of the present invention. One skilled in the art will also appreciate that binding fragments or Fab fragments which mimic (e.g., retain the functional binding regions of) antibodies can also be prepared from genetic information by various procedures. See, e.g., Antibody Engineering: A Practical Approach, Borrebaeck, Ed., Oxford University Press, Oxford (1995); and Huse et al., J. Immunol., 149: 3914-3920 (1992).

In addition, numerous publications have reported the use of phage display technology to produce and screen libraries of polypeptides for binding to a selected target antigen (see, e.g, Cwirla et al., Proc. Natl. Acad. Sci. USA, 87:6378-6382 (1990); Devlin et al., Science, 249:404-406 (1990); Scott et al., Science, 249:386-388 (1990); and Ladner et al., U.S. Pat. No. 5,571,698). A basic concept of phage display methods is the establishment of a physical association between a polypeptide encoded by the phage DNA and a target antigen. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target antigen bind to the target antigen and these phage are enriched by affinity screening to the target antigen. The identity of polypeptides displayed from these phage can be determined from their respective genomes. Using these methods, a polypeptide identified as having a binding affinity for a desired target antigen can then be synthesized in bulk by conventional means (see, e.g., U.S. Pat. No. 6,057,098).

The antibodies that are generated by these methods can then be selected by first screening for affinity and specificity with the purified polypeptide antigen of interest and, if required, comparing the results to the affinity and specificity of the antibodies with other polypeptide antigens that are desired to be excluded from binding. The screening procedure can involve immobilization of the purified polypeptide antigens in separate wells of microtiter plates. The solution containing a potential antibody or group of antibodies is then placed into the respective microtiter wells and incubated for about 30 minutes to 2 hours. The microtiter wells are then washed and a labeled secondary antibody (e.g., an anti-mouse antibody conjugated to alkaline phosphatase if the raised antibodies are mouse antibodies) is added to the wells and incubated for about 30 minutes and then washed. Substrate is added to the wells and a color reaction will appear where antibody to the immobilized polypeptide antigen is present.

The antibodies so identified can then be further analyzed for affinity and specificity. In the development of immunoassays for a target protein, the purified target protein acts as a standard with which to judge the sensitivity and specificity of the immunoassay using the antibodies that have been selected. Because the binding affinity of various antibodies may differ, e.g., certain antibody combinations may interfere with one another sterically, assay performance of an antibody may be a more important measure than absolute affinity and specificity of that antibody.

Those skilled in the art will recognize that many approaches can be taken in producing antibodies or binding fragments and screening and selecting for affinity and specificity for the various polypeptides of interest, but these approaches do not change the scope of the present invention.

1. Polyclonal Antibodies

Polyclonal antibodies are preferably raised in animals by multiple subcutaneous (sc) or intraperitoneal (ip) injections of a polypeptide of interest and an adjuvant. It may be useful to conjugate the polypeptide of interest to a protein carrier that is immunogenic in the species to be immunized, such as, e.g., keyhole limpet hemocyanin, serum albumin, bovine thyroglobulin, or soybean trypsin inhibitor using a bifunctional or derivatizing agent. Non-limiting examples of bifunctional or derivatizing agents include maleimidobenzoyl sulfosuccinimide ester (conjugation through cysteine residues), N-hydroxysuccinimide (conjugation through lysine residues), glutaraldehyde, succinic anhydride, $SOCl_2$, and $R_1N\!=\!C\!=\!NR$, wherein R and $R_1$ are different alkyl groups.

Animals are immunized against the polypeptide of interest or an immunogenic conjugate or derivative thereof by combining, e.g., 100 µg (for rabbits) or 5 µg (for mice) of the antigen or conjugate with 3 volumes of Freund's complete adjuvant and injecting the solution intradermally at multiple sites. One month later, the animals are boosted with about ⅕ to ⅒ the original amount of polypeptide or conjugate in Freund's incomplete adjuvant by subcutaneous injection at multiple sites. Seven to fourteen days later, the animals are bled and the serum is assayed for antibody titer. Animals are typically boosted until the titer plateaus. Preferably, the animal is boosted with the conjugate of the same polypeptide, but conjugation to a different immunogenic protein and/or through a different cross-linking reagent may be used. Conjugates can also be made in recombinant cell culture as fusion proteins. In certain instances, aggregating agents such as alum can be used to enhance the immune response.

2. Monoclonal Antibodies

Monoclonal antibodies are generally obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies. For example, monoclonal antibodies can be made using the hybridoma method described by Kohler et al., Nature, 256:495 (1975) or by any recombinant DNA method known in the art (see, e.g., U.S. Pat. No. 4,816,567).

In the hybridoma method, a mouse or other appropriate host animal (e.g., hamster) is immunized as described above to elicit lymphocytes that produce or are capable of producing antibodies which specifically bind to the polypeptide of interest used for immunization. Alternatively, lymphocytes are immunized in vitro. The immunized lymphocytes are then fused with myeloma cells using a suitable fusing agent, such as polyethylene glycol, to form hybridoma cells (see, e.g., Goding, *Monoclonal Antibodies: Principles and Practice*, Academic Press, pp. 59-103 (1986)). The hybridoma cells thus prepared are seeded and grown in a suitable culture medium that preferably contains one or more substances which inhibit the growth or survival of the unfused, parental myeloma cells. For example, if the parental myeloma cells lack the enzyme hypoxanthine guanine phosphoribosyl transferase (HGPRT), the culture medium for the hybridoma cells will typically include hypoxanthine, aminopterin, and thymidine (HAT medium), which prevent the growth of HGPRT-deficient cells.

Preferred myeloma cells are those that fuse efficiently, support stable high-level production of antibody by the selected antibody-producing cells, and/or are sensitive to a medium such as HAT medium. Examples of such preferred myeloma cell lines for the production of human monoclonal antibodies include, but are not limited to, murine myeloma lines such as those derived from MOPC-21 and MPC-11 mouse tumors (available from the Salk Institute Cell Distribution Center; San Diego, Calif.), SP-2 or X63-Ag8-653 cells (available from the American Type Culture Collection; Rockville, Md.), and human myeloma or mouse-human heteromyeloma cell lines (see, e.g., Kozbor, *J. Immunol.*, 133:3001 (1984); and Brodeur et al., *Monoclonal Antibody Production Techniques and Applications*, Marcel Dekker, Inc., New York, pp. 51-63 (1987)).

The culture medium in which hybridoma cells are growing can be assayed for the production of monoclonal antibodies directed against the polypeptide of interest. Preferably, the binding specificity of monoclonal antibodies produced by hybridoma cells is determined by immunoprecipitation or by an in vitro binding assay, such as a radioimmunoassay (RIA) or an enzyme-linked immunoabsorbent assay (ELISA). The binding affinity of monoclonal antibodies can be determined using, e.g., the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (see, e.g., Goding, *Monoclonal Antibodies: Principles and Practice*, Academic Press, pp. 59-103 (1986)). Suitable culture media for this purpose include, for example, D-MEM or RPMI-1640 medium. In addition, the hybridoma cells may be grown in vivo as ascites tumors in an animal. The monoclonal antibodies secreted by the subclones can be separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody, to induce the synthesis of monoclonal antibodies in the recombinant host cells. See, e.g., Skerra et al., *Curr. Opin. Immunol.*, 5:256-262 (1993); and Pluckthun, *Immunol Rev.*, 130:151-188 (1992). The DNA can also be modified, for example, by substituting the coding sequence for human heavy chain and light chain constant domains in place of the homologous murine sequences (see, e.g., U.S. Pat. No. 4,816,567; and Morrison et al., *Proc. Natl. Acad. Sci. USA*, 81:6851 (1984)), or by covalently joining to the immunoglobulin coding sequence all or part of the coding sequence for a non-immunoglobulin polypeptide.

In a further embodiment, monoclonal antibodies or antibody fragments can be isolated from antibody phage libraries generated using the techniques described in, for example, McCafferty et al., *Nature*, 348:552-554 (1990); Clackson et al., *Nature*, 352:624-628 (1991); and Marks et al., *J. Mol. Biol.*, 222:581-597 (1991). The production of high affinity (nM range) human monoclonal antibodies by chain shuffling is described in Marks et al., *BioTechnology*, 10:779-783 (1992). The use of combinatorial infection and in vivo recombination as a strategy for constructing very large phage libraries is described in Waterhouse et al., *Nuc. Acids Res.*, 21:2265-2266 (1993). Thus, these techniques are viable alternatives to traditional monoclonal antibody hybridoma methods for the generation of monoclonal antibodies.

3. Humanized Antibodies

Methods for humanizing non-human antibodies are known in the art. Preferably, a humanized antibody has one or more amino acid residues introduced into it from a source which is non-human. These non-human amino acid residues are often referred to as "import" residues, which are typically taken from an "import" variable domain. Humanization can be essentially performed by substituting the hypervariable region sequences of a non-human antibody for the corresponding sequences of a human antibody. See, e.g., Jones et al., *Nature*, 321:522-525 (1986); Riechmann et al., *Nature*, 332:323-327 (1988); and Verhoeyen et al., *Science*, 239:1534-1536 (1988). Accordingly, such "humanized" antibodies are chimeric antibodies (see, e.g., U.S. Pat. No. 4,816,567), wherein substantially less than an intact human variable domain has been substituted by the corresponding sequence from a non-human species. In practice, humanized antibodies are typically human antibodies in which some hypervariable region residues and possibly some framework region (FR) residues are substituted by residues from analogous sites of rodent antibodies.

The choice of human variable domains, both light and heavy, to be used in making the humanized antibodies described herein is an important consideration for reducing antigenicity. According to the so-called "best-fit" method, the sequence of the variable domain of a rodent antibody is screened against the entire library of known human variable-domain sequences. The human sequence which is closest to that of the rodent is then accepted as the human FR for the humanized antibody (see, e.g., Sims et al., *J Immunol.*, 151:2296 (1993); and Chothia et al., *J. Mol. Biol.*, 196:901 (1987)). Another method uses a particular FR derived from the consensus sequence of all human antibodies of a particular subgroup of light or heavy chains. The same FR may be used for several different humanized antibodies (see, e.g., Carter et al., *Proc. Natl. Acad. Sci. USA*, 89:4285 (1992); and Presta et al., *J. Immunol.*, 151:2623 (1993)).

It is also important that antibodies be humanized with retention of high affinity for the antigen and other favorable biological properties. To achieve this goal, humanized antibodies can be prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and specifically involved in influencing antigen binding.

Various forms of humanized antibodies are contemplated in accordance with the present invention. For example, the humanized antibody can be an antibody fragment, such as a Fab fragment. Alternatively, the humanized antibody can be an intact antibody, such as an intact IgA, IgG, or IgM antibody.

4. Human Antibodies

As an alternative to humanization, human antibodies can be generated. In some embodiments, transgenic animals (e.g., mice) can be produced that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immun.*, 7:33 (1993); and U.S. Pat. Nos. 5,591,669, 5,589,369, and 5,545,807.

Alternatively, phage display technology (see, e.g., McCafferty et al., *Nature*, 348:552-553 (1990)) can be used to produce human antibodies and antibody fragments in vitro, using immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats as described in, e.g., Johnson et al., *Curr. Opin. Struct. Biol.*, 3:564-571 (1993). Several sources of V-gene segments can be used for phage display. See, e.g., Clackson et al., *Nature*, 352:624-628 (1991). A repertoire of V genes from unimmunized human donors can be constructed and antibodies to a diverse array of antigens (including self-antigens) can be isolated essentially following the techniques described in Marks et al., *J. Mol. Biol.*, 222:581-597 (1991); Griffith et al., *EMBO J.*, 12:725-734 (1993); and U.S. Pat. Nos. 5,565,332 and 5,573,905.

In certain instances, human antibodies can be generated by in vitro activated B cells as described in, e.g., U.S. Pat. Nos. 5,567,610 and 5,229,275.

5. Antibody Fragments

Various techniques have been developed for the production of antibody fragments. Traditionally, these fragments were derived via proteolytic digestion of intact antibodies (see, e.g., Morimoto et al., *J Biochem. Biophys. Meth.*, 24:107-117 (1992); and Brennan et al., *Science*, 229:81 (1985)). However, these fragments can now be produced directly using recombinant host cells. For example, the antibody fragments can be isolated from the antibody phage libraries discussed above. Alternatively, Fab'-SH fragments can be directly recovered from *E. coli* cells and chemically coupled to form $F(ab')_2$ fragments (see, e.g., Carter et al., *BioTechnology*, 10:163-167 (1992)). According to another approach, $F(ab')_2$ fragments can be isolated directly from recombinant host cell culture. Other techniques for the production of antibody fragments will be apparent to those skilled in the art. In other embodiments, the antibody of choice is a single chain Fv fragment (scFv). See, e.g., PCT Publication No. WO 93/16185; and U.S. Pat. Nos. 5,571,894 and 5,587,458. The antibody fragment may also be a linear antibody as described, e.g., in U.S. Pat. No. 5,641,870. Such linear antibody fragments may be monospecific or bispecific.

6. Bispecific Antibodies

Bispecific antibodies are antibodies that have binding specificities for at least two different epitopes. Exemplary bispecific antibodies may bind to two different epitopes of the same polypeptide of interest. Other bispecific antibodies may combine a binding site for the polypeptide of interest with binding site(s) for one or more additional antigens. Bispecific antibodies can be prepared as full-length antibodies or antibody fragments (e.g., $F(ab')_2$ bispecific antibodies).

Methods for making bispecific antibodies are known in the art. Traditional production of full-length bispecific antibodies is based on the co-expression of two immunoglobulin heavy chain-light chain pairs, where the two chains have different specificities (see, e.g., Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule is usually performed by affinity chromatography. Similar procedures are disclosed in PCT Publication No. WO 93/08829 and Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy chain constant region (CH1) containing the site necessary for light chain binding present in at least one of the fusions. DNA encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains into one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation. See, e.g., PCT Publication No. WO 94/04690 and Suresh et al., *Meth. Enzymol.*, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side-chains from the interface of the first antibody molecule are replaced with larger side chains (e.g., tyrosine or tryptophan). Compensatory "cavities" of identical or similar size to the large side-chain(s) are created on the interface of the second antibody molecule by replacing large amino acid side-chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Heteroconjugate antibodies can be made using any convenient cross-linking method. Suitable cross-linking agents and techniques are well-known in the art, and are disclosed in, e.g., U.S. Pat. No. 4,676,980.

Suitable techniques for generating bispecific antibodies from antibody fragments are also known in the art. For example, bispecific antibodies can be prepared using chemical linkage. In certain instances, bispecific antibodies can be generated by a procedure in which intact antibodies are proteolytically cleaved to generate F(ab')$_2$ fragments (see, e.g., Brennan et al., *Science,* 229:81 (1985)). These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody.

In some embodiments, Fab'-SH fragments can be directly recovered from *E. coli* and chemically coupled to form bispecific antibodies. For example, a fully humanized bispecific antibody F(ab')$_2$ molecule can be produced by the methods described in Shalaby et al., *J Exp. Med.,* 175: 217-225 (1992). Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. See, e.g., Kostelny et al., *J. Immunol.,* 148:1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA,* 90:6444-6448 (1993) has provided an alternative mechanism for making bispecific antibody fragments. The fragments comprise a heavy chain variable domain (VH) connected to a light chain variable domain (VL) by a linker which is too short to allow pairing between the two domains on the same chain. Accordingly, the VH and VL domains of one fragment are forced to pair with the complementary VL and VH domains of another fragment, thereby forming two antigen binding sites. Another strategy for making bispecific antibody fragments by the use of single-chain Fv (sFv) dimers is described in Gruber et al., *J. Immunol.,* 152:5368 (1994).

Antibodies with more than two valencies are also contemplated. For example, trispecific antibodies can be prepared. See, e.g., Tutt et al., *J. Immunol.,* 147:60 (1991).

7. Antibody Purification

When using recombinant techniques, antibodies can be produced inside an isolated host cell, in the periplasmic space of a host cell, or directly secreted from a host cell into the medium. If the antibody is produced intracellularly, the particulate debris is first removed, for example, by centrifugation or ultrafiltration. Carter et al., *BioTech.,* 10:163-167 (1992) describes a procedure for isolating antibodies which are secreted into the periplasmic space of *E. coli*. Briefly, cell paste is thawed in the presence of sodium acetate (pH 3.5), EDTA, and phenylmethylsulfonylfluoride (PMSF) for about 30 min. Cell debris can be removed by centrifugation. Where the antibody is secreted into the medium, supernatants from such expression systems are generally concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from cells can be purified using, for example, hydroxylapatite chromatography, gel electrophoresis, dialysis, and affinity chromatography. The suitability of protein A as an affinity ligand depends on the species and isotype of any immunoglobulin Fc domain that is present in the antibody. Protein A can be used to purify antibodies that are based on human γ1, γ2, or γ4 heavy chains (see, e.g., Lindmark et al., *J. Immunol. Meth.,* 62:1-13 (1983)). Protein G is recommended for all mouse isotypes and for human γ3 (see, e.g., Guss et al., *EMBO J.,* 5:1567-1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker; Phillipsburg, N.J.) is useful for purification. Other techniques for protein purification such as fractionation on an ion-exchange column, ethanol precipitation, reverse phase HPLC, chromatography on silica, chromatography on heparin SEPHAROSE™, chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25 M salt).

One of skill in the art will appreciate that any binding molecule having a function similar to an antibody, e.g., a binding molecule or binding partner which is specific for one or more analytes of interest in a sample, can also be used in the methods and compositions of the present invention. Examples of suitable antibody-like molecules include, but are not limited to, domain antibodies, unibodies, nanobodies, shark antigen reactive proteins, avimers, adnectins, anticalms, affinity ligands, phylomers, aptamers, affibodies, trinectins, and the like.

D. Methods of Administration

According to the methods of the invention, the anticancer drugs described herein are administered to a subject by any convenient means known in the art. The methods of the invention can be used to determine, predict, identify, and/or monitor the response of a tumor (e.g., a primary or metastatic breast tumor) to treatment with one or more anticancer drugs. The methods of the invention can also be used to select one or more suitable anticancer drugs for the treatment of a tumor (e.g., a primary or metastatic breast tumor) in a subject. One of skill in the art will appreciate that the anticancer drug(s) can be administered alone or as part of a combined therapeutic approach with conventional chemotherapy, radiotherapy, hormonal therapy, immunotherapy, and/or surgery.

In certain embodiments, the anticancer drug comprises an anti-signaling agent (i.e., a cytostatic drug) such as a monoclonal antibody or a tyrosine kinase inhibitor; an anti-proliferative agent; a chemotherapeutic agent (i.e., a cytotoxic drug); a hormonal therapeutic agent; a radiotherapeutic agent; a vaccine; and/or any other compound with the ability to reduce or abrogate the uncontrolled growth of aberrant cells such as cancerous cells. In some embodiments, the subject is treated with one or more anti-signaling agents, anti-proliferative agents, and/or hormonal therapeutic agents in combination with at least one chemotherapeutic agent. Exemplary monoclonal antibodies, tyrosine kinase inhibitors, anti-proliferative agents, chemotherapeutic agents, hormonal therapeutic agents, radiotherapeutic agents, and vaccines are described herein.

In particular embodiments, the anticancer drug comprises one or more compounds that modulate HER2 activity including monoclonal antibodies, tyrosine kinase inhibitors, and combinations thereof. Non-limiting examples of HER2-modulating compounds include monoclonal antibodies such as trastuzumab (Herceptin®), trastuzumab-DM1, ertumaxomab and pertuzumab (2C4; Omnitarg™); small molecule tyrosine kinase inhibitors such as gefitinib (Iressa®), erlotinib (Tarceva®), pilitinib, CP-654577, CP-724714, canertinib (CI 1033), HKI-272, lapatinib (GW-572016; Tykerb®), PKI-166, AEE788, BMS-599626, HKI-357, BIBW 2992, ARRY-334543, JNJ-26483327, and JNJ-26483327; and combinations thereof. In certain embodiments, HER2-modulating compounds can be used in combination with one or more other anticancer drugs described herein or known to one of skill in the art.

In other embodiments, the anticancer drug comprises one of more compounds that modulate activity of HER3 and other ErbB family members including monoclonal antibodies, tyrosine kinase inhibitors, and combinations thereof. Non-limiting examples of these compounds include monoclonal antibodies such as MM-121, AMG-888 (U3-1287), trastuzumab (Herceptin®), pertuzumab (2C4; Omnitarg™), cetuximab (Erbitux®); small molecule tyrosine kinase inhibitors such as gefitinib (Iressa®), erlotinib (Tarceva®), canertinib (CI 1033), lapatinib (GW-572016; Tykerb®), MP-470, AZD8931, PF00299804; and combinations thereof. In some embodiments, RTK modulating compounds include HER1-, HER2- and HER3-modulating compounds, cMET modulating compounds and IGF-1R modulating compounds. In certain embodiments, HER1-, HER2- and HER3-modulating compounds can be used in combination with one or more other anticancer drugs described herein or known to one of skill in the art.

In other embodiments, the anticancer drug comprises one of more compounds that modulate PI3K activity including monoclonal antibodies, inhibitors, and combinations thereof. Non-limiting examples of these compounds include inhibitors such as SF1126 (Semaphore Pharmaceuticals), XL147 (Exelixis), XL765 (Exelixis), NVP-BEZ235 (Novartis), NVP-BGT226 (Novartis), NVP-BKM120 (Novartis), GDC-0941 (Genentech/Piramed Pharma), PX-866 (ProIX Pharmaceuticals), GSK1059615 (GlaxoSithKline), CAL-101 (Calistoga Pharmaceuticals), and combinations thereof.

Examples of anti-signaling agents suitable for use in the present invention include, without limitation, monoclonal antibodies such as trastuzumab (Herceptin®), pertuzumab (2C4; Omnitarg™), alemtuzumab (Campath®), bevacizumab (Avastin), cetuximab (Erbitux®), gemtuzumab (Mylotarg®), panitumumab (Vectibix™), rituximab (Rituxan®), and tositumomab (BEXXAR®); tyrosine kinase inhibitors such as gefitinib (Iressa®), sunitinib (Sutent®), erlotinib (Tarceva®), lapatinib (GW-572016; Tykerb®), canertinib (CI 1033), semaxinib (SU5416), vatalanib (PTK787/ZK222584), sorafenib (BAY 43-9006; Nexavar), imatinib mesylate (Gleevec®), leflunomide (SU101), vandetanib (ZACTIMA™; ZD6474), pilitinib, CP-654577, CP-724714, HKI-272, PKI-166, AEE788, BMS-599626, HKI-357, BIBW 2992, ARRY-334543, JNJ-26483327, and JNJ-26483327; and combinations thereof.

Exemplary anti-proliferative agents include mTOR inhibitors such as sirolimus (rapamycin), temsirolimus (CCI-779), and everolimus (RAD001); AKT inhibitors such as 1L6-hydroxymethyl-chiro-inositol-2-(R)-2-O-methyl-3-O-octadecyl-sn-glycerocarbonate, 9-methoxy-2-methylellipticinium acetate, 1,3-dihydro-1-(1-((4-(6-phenyl-1H-imidazo[4,5-g]quinoxalin-7-yl)phenyl)methyl)-4-piperidinyl)-2H-benzimidazol-2-one, 10-(4'-(N-diethylamino)butyl)-2-chlorophenoxazine, 3-formylchromone thiosemicarbazone ($Cu(II)Cl_2$ complex), API-2, a 15-mer peptide derived from amino acids 10-24 of the proto-oncogene TCL1 (Hiromura et al., *J. Biol. Chem.*, 279:53407-53418 (2004), KP372-1, and the compounds described in Kozikowski et al., *J. Am. Chem. Soc.*, 125:1144-1145 (2003) and Kau et al., *Cancer Cell*, 4:463-476 (2003); and combinations thereof.

Non-limiting examples of chemotherapeutic agents include platinum-based drugs (e.g., oxaliplatin, cisplatin, carboplatin, spiroplatin, iproplatin, satraplatin, etc.), alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, 6-mercaptopurine, methotrexate, leucovorin, capecitabine, cytarabine, floxuridine, fludarabine, gemcitabine (Gemzar®), pemetrexed (ALIMTA®), raltitrexed, etc.), plant alkaloids (e.g., vincristine, vinblastine, vinorelbine, vindesine, podophyllotoxin, paclitaxel (Taxol®), docetaxel (Taxotere®), etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), pharmaceutically acceptable salts thereof, stereoisomers thereof, derivatives thereof, analogs thereof, and combinations thereof.

Examples of hormonal therapeutic agents include, without limitation, aromatase inhibitors (e.g., aminoglutethimide, anastrozole (Arimidex®), letrozole (Femara®), vorozole, exemestane (Aromasin®), 4-androstene-3,6,17-trione (6-OXO), 1,4,6-androstatrien-3,17-dione (ATD), formestane (Lentaron®), etc.), selective estrogen receptor modulators (e.g., bazedoxifene, clomifene, fulvestrant, lasofoxifene, raloxifene, tamoxifen, toremifene, etc.), steroids (e.g., dexamethasone), finasteride, and gonadotropin-releasing hormone agonists (GnRH) such as goserelin, pharmaceutically acceptable salts thereof, stereoisomers thereof, derivatives thereof, analogs thereof, and combinations thereof.

Non-limiting examples of cancer vaccines useful in the present invention include ANYARA from Active Biotech, DCVax-LB from Northwest Biotherapeutics, EP-2101 from IDM Pharma, GV1001 from Pharmexa, IO-2055 from Idera Pharmaceuticals, INGN 225 from Introgen Therapeutics and Stimuvax from Biomira/Merck.

Examples of radiotherapeutic agents include, but are not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

In some embodiments, the anticancer drugs described herein can be co-administered with conventional immunotherapeutic agents including, but not limited to, immunostimulants (e.g., *Bacillus* Calmette-Guérin (BCG), levamisole, interleukin-2, alpha-interferon, etc.), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., anti-CD20 monoclonal antibody conjugated to $^{111}$In, $^{90}$Y, or $^{131}$I, etc.).

Anticancer drugs can be administered with a suitable pharmaceutical excipient as necessary and can be carried out via any of the accepted modes of administration. Thus, administration can be, for example, oral, buccal, sublingual, gingival, palatal, intravenous, topical, subcutaneous, transcutaneous, transdermal, intramuscular, intra joint, parenteral, intra-arteriole, intradermal, intraventricular, intracranial, intraperitoneal, intravesical, intrathecal, intralesional, intranasal, rectal, vaginal, or by inhalation. By "co-administer" it is meant that an anticancer drug is administered at the same time, just prior to, or just after the administration of a second drug (e.g., another anticancer drug, a drug useful for reducing the side-effects associated with anticancer drug therapy, a radiotherapeutic agent, a hormonal therapeutic agent, an immunotherapeutic agent, etc.).

A therapeutically effective amount of an anticancer drug may be administered repeatedly, e.g., at least 2, 3, 4, 5, 6, 7, 8, or more times, or the dose may be administered by continuous infusion. The dose may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages.

As used herein, the term "unit dosage form" refers to physically discrete units suitable as unitary dosages for human subjects and other mammals, each unit containing a predetermined quantity of an anticancer drug calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the anticancer drug.

Methods for preparing such dosage forms are known to those skilled in the art (see, e.g., REMINGTON'S PHARMACEUTICAL SCIENCES, 18TH ED., Mack Publishing Co., Easton, Pa. (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., REMINGTON'S PHARMACEUTICAL SCIENCES, supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the therapeutically effective dose takes the form of a pill, tablet, or capsule, and thus, the dosage form can contain, along with an anticancer drug, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. An anticancer drug can also be formulated into a suppository disposed, for example, in a polyethylene glycol (PEG) carrier.

Liquid dosage forms can be prepared by dissolving or dispersing an anticancer drug and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. An anticancer drug can also be formulated into a retention enema.

For topical administration, the therapeutically effective dose can be in the form of emulsions, lotions, gels, foams, creams, jellies, solutions, suspensions, ointments, and transdermal patches. For administration by inhalation, an anticancer drug can be delivered as a dry powder or in liquid form via a nebulizer. For parenteral administration, the therapeutically effective dose can be in the form of sterile injectable solutions and sterile packaged powders. Preferably, injectable solutions are formulated at a pH of from about 4.5 to about 7.5.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to a subject.

A subject can also be monitored at periodic time intervals to assess the efficacy of a certain therapeutic regimen. For example, the activation states of certain signal transduction molecules may change based on the therapeutic effect of treatment with one or more of the anticancer drugs described herein. The subject can be monitored to assess response and understand the effects of certain drugs or treatments in an individualized approach. Additionally, subjects who initially respond to a specific anticancer drug or combination of anticancer drugs may become refractory to the drug or drug combination, indicating that these subjects have developed acquired drug resistance. These subjects can be discontinued on their current therapy and an alternative treatment prescribed in accordance with the methods of the present invention.

In certain aspects, the methods described herein can be used in conjunction with panels of gene expression markers that predict the likelihood of breast cancer prognosis and/or recurrence in various populations of women with for example, node-negative disease. These gene panels can be useful for identifying women who are unlikely to experience recurrence and, thus, unlikely to benefit from adjuvant chemotherapy. The expression panels can be used to identify women who can safely avoid adjuvant chemotherapy, without negatively affecting disease-free and overall survival outcomes. Suitable systems include, but are not limited to, Oncotype DX™, which is a 21-gene panel from Genomic Health, Inc.; MammaPrint,® which is a 70-gene panel from Agendia; and a 76-gene panel from Veridex.

In addition, in certain other aspects, the methods described herein can be used in conjunction with panels of gene expression markers that identify the original tumors for cancers of unknown primary (CUP). These gene panels can be useful in identifying women with metastatic cancer who would benefit from therapy consistent with that given to women diagnosed initially with breast cancer. Suitable systems include, but are not limited to, the Aviara CancerTYPE ID assay, an RT-PCR-based expression assay that measures 92 genes to identify the primary site of origin for 39 tumor types; and the Pathwork® Tissue of Origin Test, which measures the expression of more than 1600 genes on a microarray and compares a tumor's gene expression "signature" against those of 15 known tissue types."

VI. Examples

The following examples are offered to illustrate, but not to limit, the claimed invention.

Example 1

Quantitative Analysis of PI3K Activation for Selecting Patients for PI3K-Modulating Compounds This example demonstrates the presence of activated (phosphorylated) PI3K complex correlates with the presence of activated PI3K complex pathway components, including, as but not limited to AKT, mTOR and S6K. This example illustrates that in certain instances, breast cancer patients with elevated levels of PI3K activation also express activated (phosphorylated) AKT. Of the 21 patients with activated PI3K, 19 also had elevated levels of phospho-AKT. This supports the discovery that phospho-AKT acts downstream of PI3K and that activation of PI3K can result in activation of AKT. The high degree of correlation (p-value=0.0222; FIG. 6) between PI3K activation and phosphorylated AKT in breast cancer patient samples confirms that PI3K pathway activation is biologically relevant to tumorogenesis.

Pathway profiling analysis was perform on 60 FNA samples collected from breast cancer patients. A multiplexed immunoarray CEER (Collaborative Enzyme Enhanced Reactive-immunoassay) platform was utilized to determine the levels of pathway protein expression and phosphorylation. DNA was extracted from the samples and analyzed for panels of somatic mutations. Activated pathways detected include HER1, HER2, HER3, IGF-1R, cMET, PI3K and associated downstream proteins.

Figure 7:
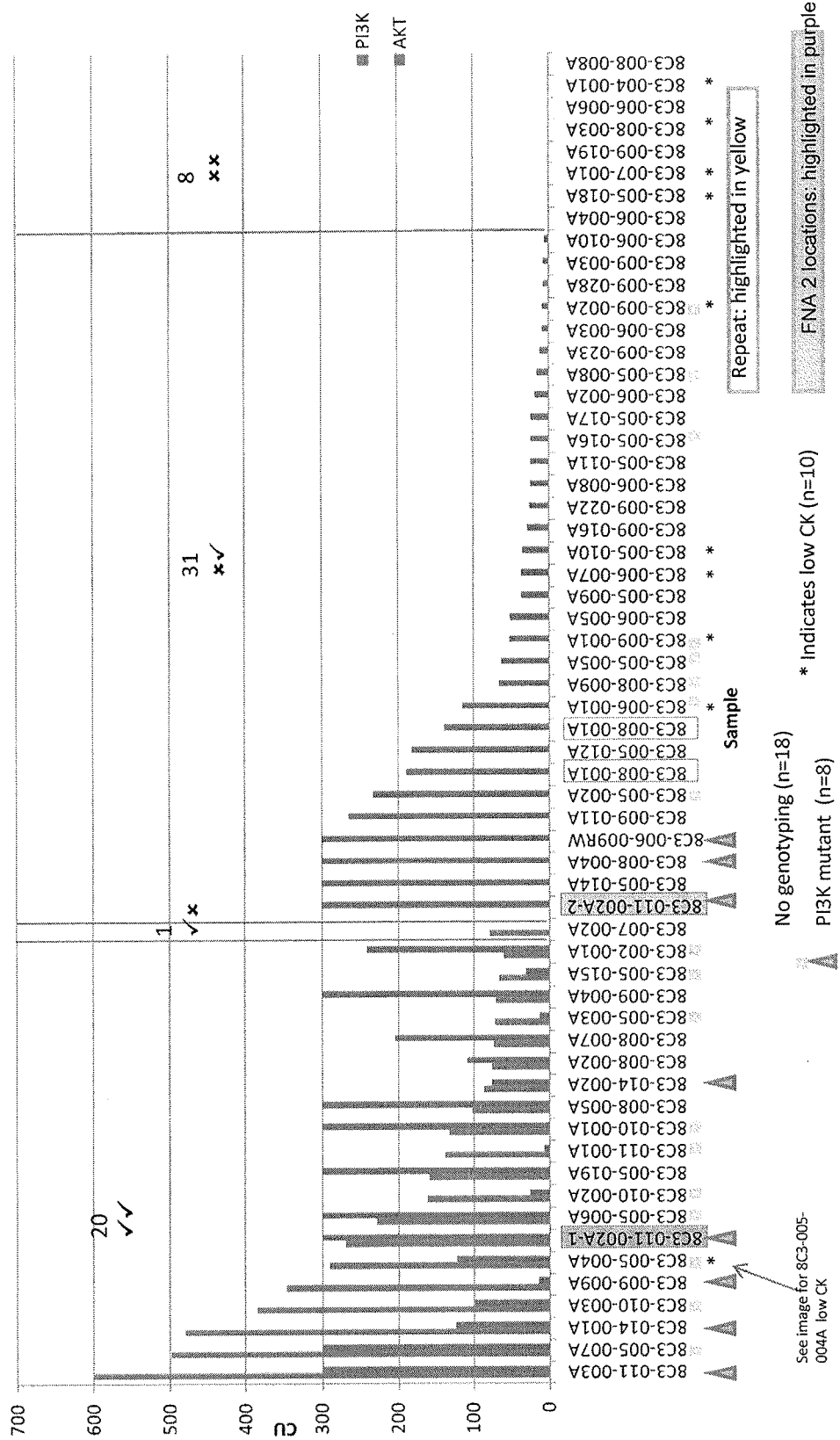
FIG. 7 illustrates that the presence of phospho-PI3K correlates with phospho-AKT in 60 FNA samples from patients with breast cancer. Activated AKT was detected in patients without PI3KCA mutations.
Figure 8:
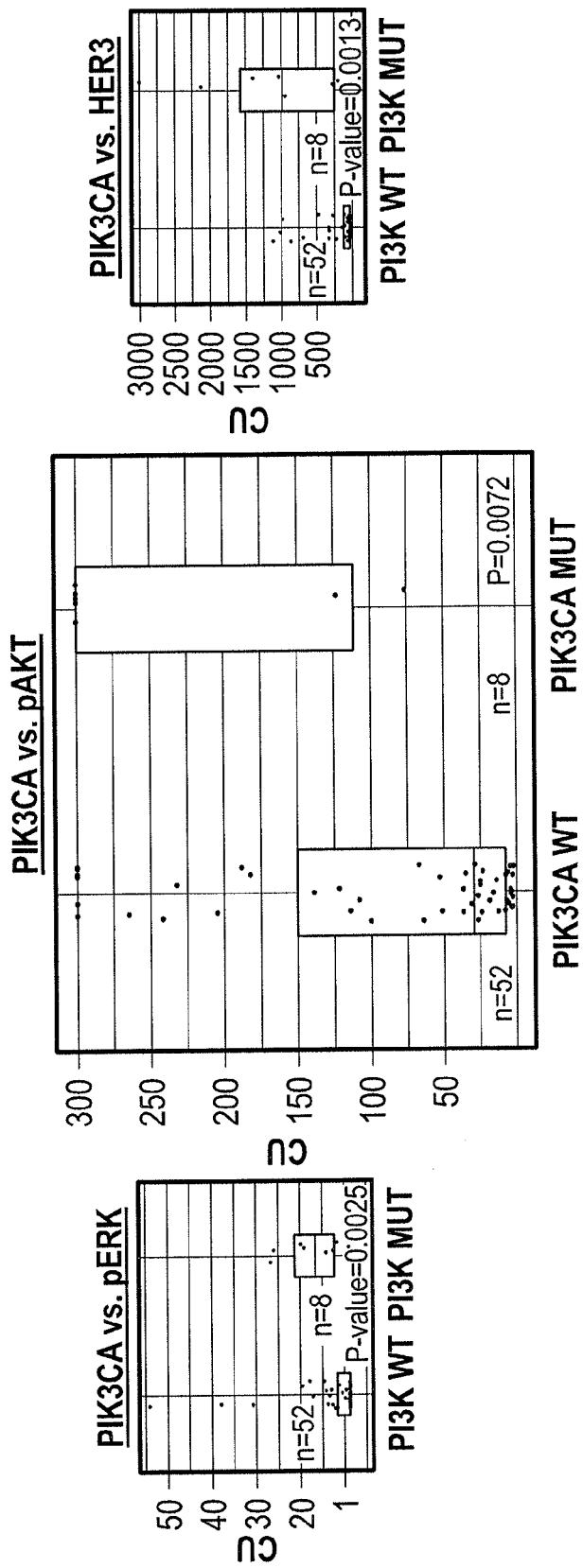
FIG. 8 illustrates one embodiment of the correlation between AKT and PI3K. The graphs show that activated AKT (pAKT) does not correlate with the presence of PI3KCA somatic mutations.

This example shows that only 5 out of 21 patients with PI3K activation carried PI3KCA mutations. And that in most breast cancer patients, activated (phosphorylated) AKT corresponds with PI3KCA wild-type status. While there is a correlation between PI3KCA mutations and responsiveness to PI3K inhibitors, this example illustrates that cancer patients without PI3K pathway alteration can also benefit from PI3K inhibitor therapy. FIG. 6 illustrates a comparison of phospho-AKT and phospho-PI3K in pathway profiling analysis of patient with breast cancer. FIG. 7 illustrates that the presence of phospho-PI3K correlates with phospho-AKT in 60 FNA samples from patients with breast cancer. Activated AKT was detected in patients without PI3KCA mutations. FIG. 8 illustrates that activated AKT does not correlate with PI3KCA somatic mutations.

Example 2

Quantitative Analysis of PI3K Activation and ErbB Family Receptor Tyrosine Kinase (RTK) Activation in FNA Samples from Breast Cancer Patients This example illustrates an analysis of ErbB activation and dimer formation along with PI3K pathway activation in breast cancer patients. In particular, this example shows that an increased level of activated phosphorylated ErbB, such as phosphorylated HER2 and phosphorylated HER3, is associated with increased levels of p-AKT and p-PI3K. In addition, this example shows that patients with increased levels of ErbB activation and dimerization can benefit from treatments with PI3K inhibitors. By detecting the presence or absence of any changes in activated HER2, HER3, PI3K, and/or AKT levels, the clinical sensitivity to PI3K inhibitors can be assessed.

Pathway analysis was perform on 60 FNA samples collected from breast cancer patients. A multiplexed immunoarray CEER (Collaborative Enzyme Enhanced Reactive-immunoassay) platform was utilized to determine the levels of pathway protein expression and phosphorylation. DNA was extracted from the samples and analyzed for panels of somatic mutations. Activated pathways detected include HER1, HER2, HER3, IGF-1R, cMET, PI3K and associated downstream proteins (e.g., adaptor and effector proteins).

Figure 11:
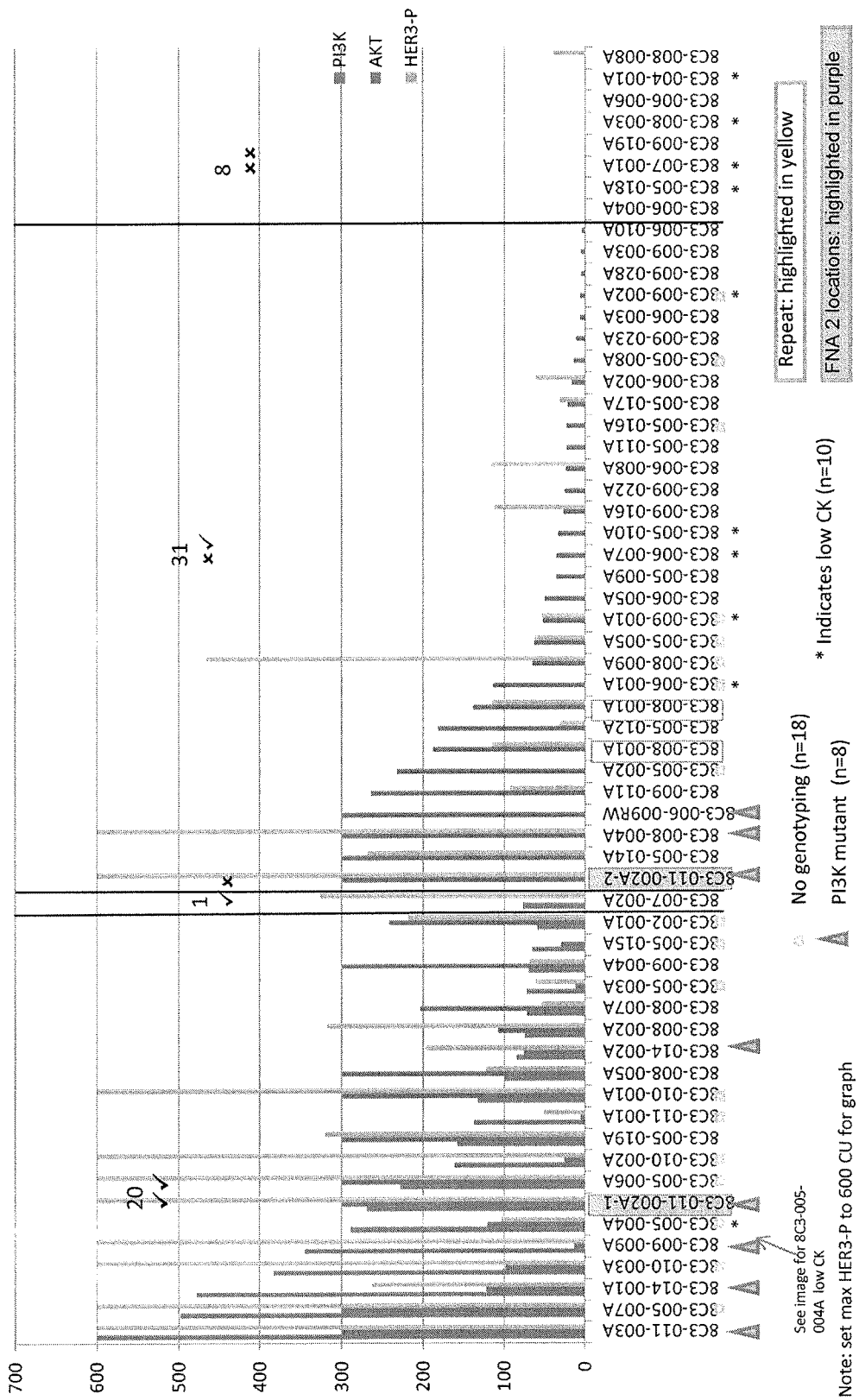
FIG. 11 shows that activated PI3K is associated with activated AKT and phospho-HER3.

This example illustrates a high degree of correlation among activated HER2, HER3, PI3K and AKT in 60 FNA samples from breast cancer patients. In particular, phospho-HER3 is activated in 20 out of 21 patients who have activated phospho-PI3K (p=0.00001, FIG. 9). This example also shows that patients with ErbB activation (i.e., increased levels of HER3:PI3K complex, phospho-HER3, total HER3, HER2/HER3 heterodimer, HER1/HER3 heterodimer, HER4/HER3 heterodimer in the presence of Heregulin (HRG) or TGFα) can benefit from PI3K inhibitor treatment. FIG. 9 illustrates a high degree of correlation between the presence of phospho-HER3 and phospho-PI3K in 60 FNA samples from breast cancer patients. Regardless of the cutoff value for PI3K used in the assay, there is a correlation between phospho-HER3 and phospho-PI3K in the samples. FIG. 10 illustrates a correlation between the presence of phospho-HER3 and phospho-AKT in breast cancer patients. FIG. 11 shows that activated PI3K is associated with activated AKT and phospho-HER3. FIG. 6 also shows that activated AKT correlates with phospho-HER3 in the absence of PI3K activation. FIG. 12 shows that phospho-HER2 is associated with activated PI3K and activated AKT in FNA samples from breast cancer patients. FIG. 13 shows concurrent activation of phospho-HER2, phospho-PI3K and phospho-AKT in breast cancer patient samples that do not have HER2 genetic mutations or amplifications.

Example 3

Quantitative Analysis of PI3K Activation and HER3 Activation in Patients Relapsed on Herceptin Combination Therapy A comprehensive analysis of key signature receptor tyrosine kinases including HER1, HER2, p95HER2, HER3, cMET, IGF-1R, and downstream kinases and adapter proteins including PI3K, Shc, AKT and ERK, in fine needle aspirate (FNA) samples collected from metastatic sites of breast cancer (BCA) patients who have relapsed on anticancer therapy is reported herein.

In this study CEER-FNA pathway profiling analysis was performed on an endoscopic ultrasound (EUS) guided liver biopsy of a breast cancer patient relapsed on Herceptin combination therapy. Elevated levels of the activated forms of HER1, HER2, HER3, p95, PI3K, AKT, ERK/MAPK, and Shc proteins in the sample were detected. The pathway activation profile suggests that the patient may be clinically sensitive to a combination treatment comprising a pan-HER inhibitor and a PI3K inhibitor.

In another study CEER-FNA pathway profiling analysis was performed on a biopsy from the axilar node of a breast cancer patient relapsed on Herceptin combination therapy. Somatic mutational analysis shows that the patient has a H1047R PIK3CA mutation. Elevated levels of the activated forms of HER1, HER2, HER3, cMET, Shc, ERK/MAPK, PI3K and AKT proteins were detected. The pathway activation profile suggests that the patient may be responsive to PI3K inhibitor combination therapy.

Figure 14:
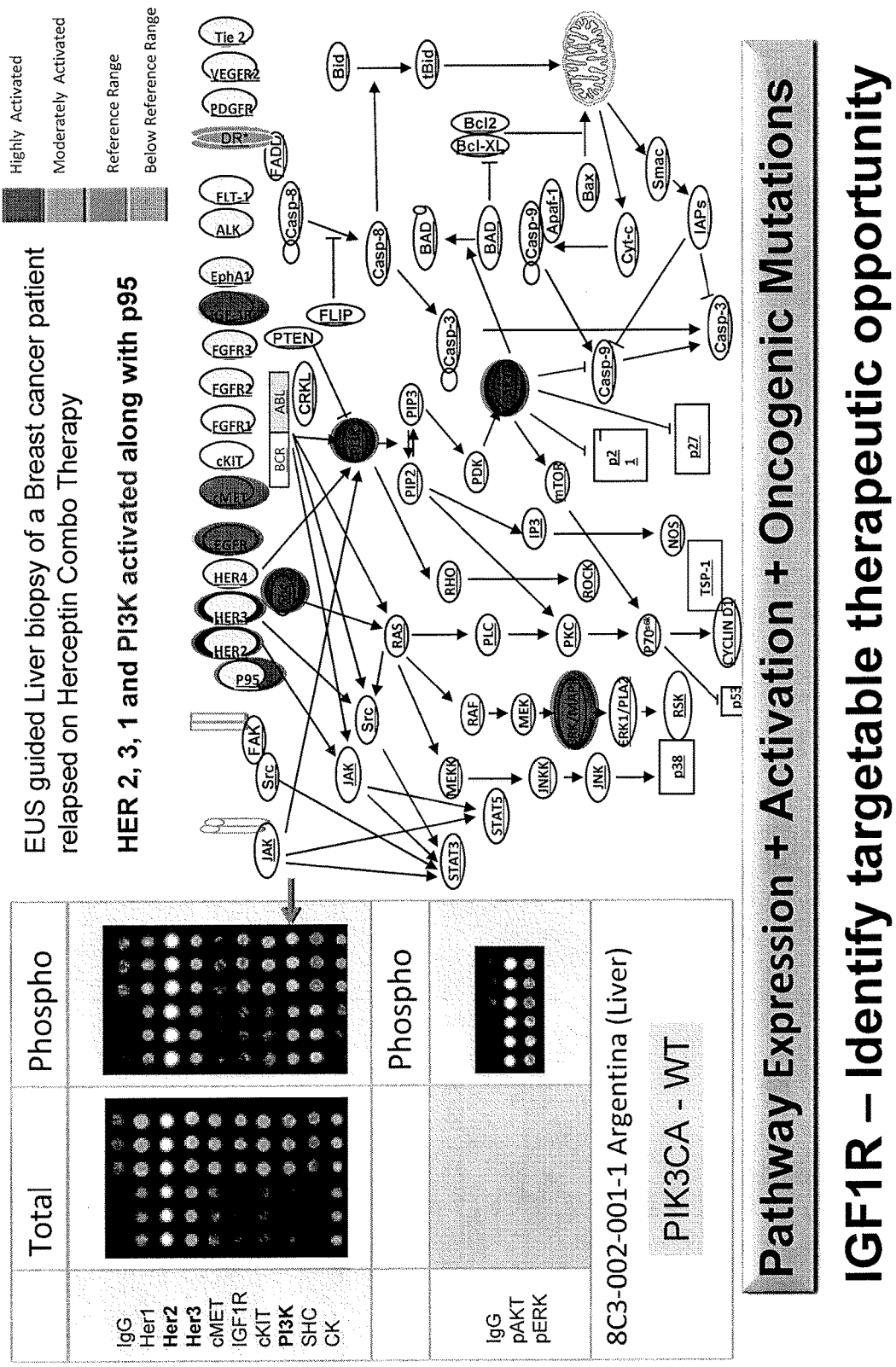
FIG. 14 shows activated HER1, HER2, HER3, p95, ERK, Shc, PI3K, AKT and ERK proteins in a sample from a breast cancer patient who relapsed on Herceptin combination therapy.
Figure 15:
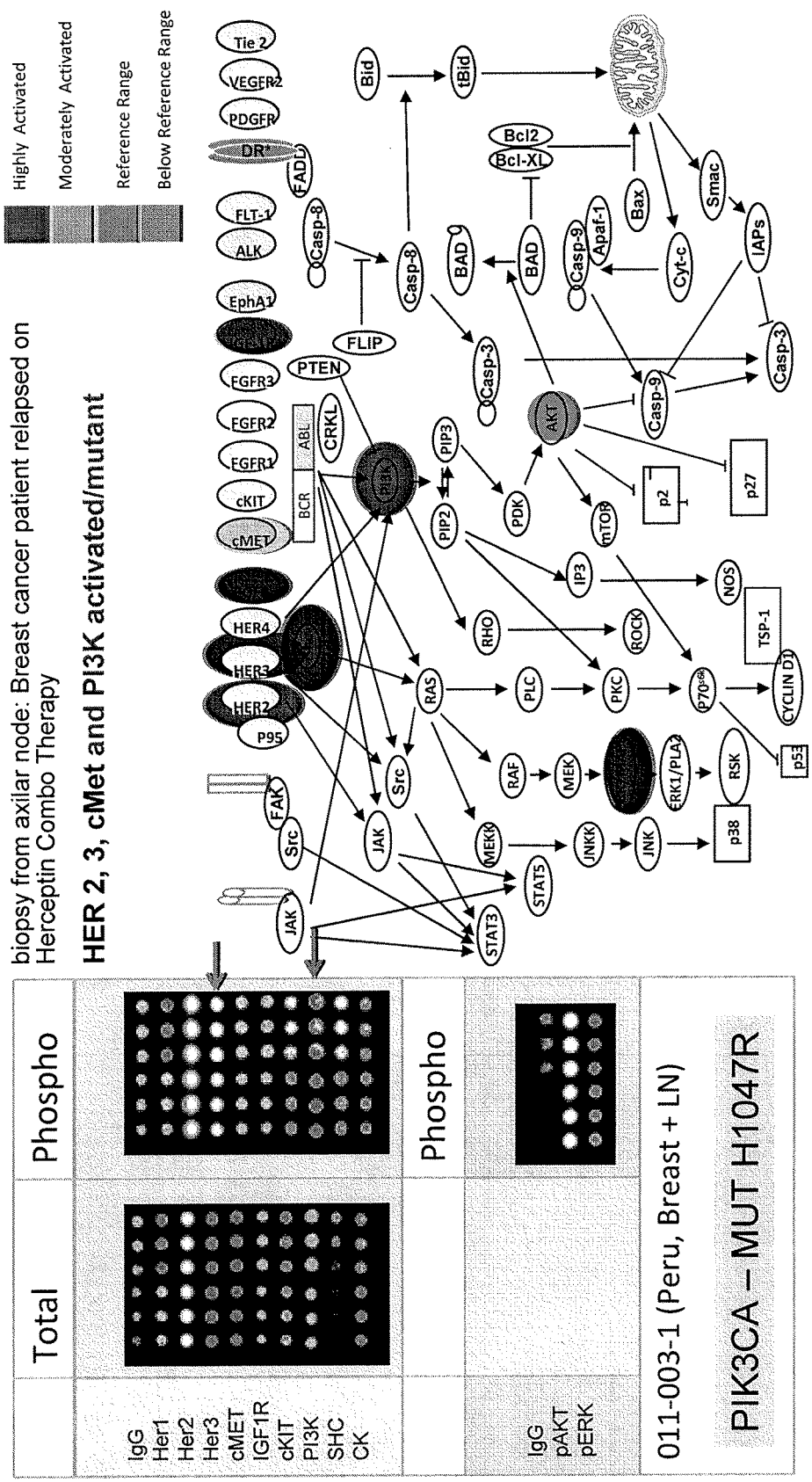
FIG. 15 shows activated HER2, HER3, cMet, ERK, PI3K, and AKT proteins in a sample from a breast cancer patient with a H1047R PIK3CA somatic mutation who relapsed on Herceptin combination therapy.

This example also suggests that patients with ErbB activation (i.e., increased levels of HER3:PI3K complex, phospho-HER3, total HER3, HER2/HER3 heterodimer, HER1/HER3 heterodimer, HER4/HER3 heterodimer, Heregulin (HRG) or TGFα) may benefit from combination treatment. In one embodiment, a patient with solid tumor cancer who has an elevated level of HER3/PI3K complex may benefit from a treatment regimen comprising PI3K inhibitor and anti-HER3 antibody therapy. In another embodiment, a solid tumor cancer patient who has elevated levels of HER2/HER3 heterodimer may be clinically sensitive to a combination treatment of PI3K inhibitor and either Pertuzamab or an anti-HER2 antibody or a TKI). FIG. 14 shows activated HER1, HER2, HER3, p95, ERK, Shc, PI3K, AKT and ERK proteins in a sample from a breast cancer patient who relapsed on Herceptin combination therapy. FIG. 15 shows activated HER2, HER3, cMet, ERK, PI3K, and AKT proteins in a sample from a breast cancer patient with a H1047R PIK3CA somatic mutation who relapsed on Herceptin combination therapy.

Example 4

Pathway Activation Profiling of Tumor Samples Exposed to Anti-Cancer Therapy

Figure 16:
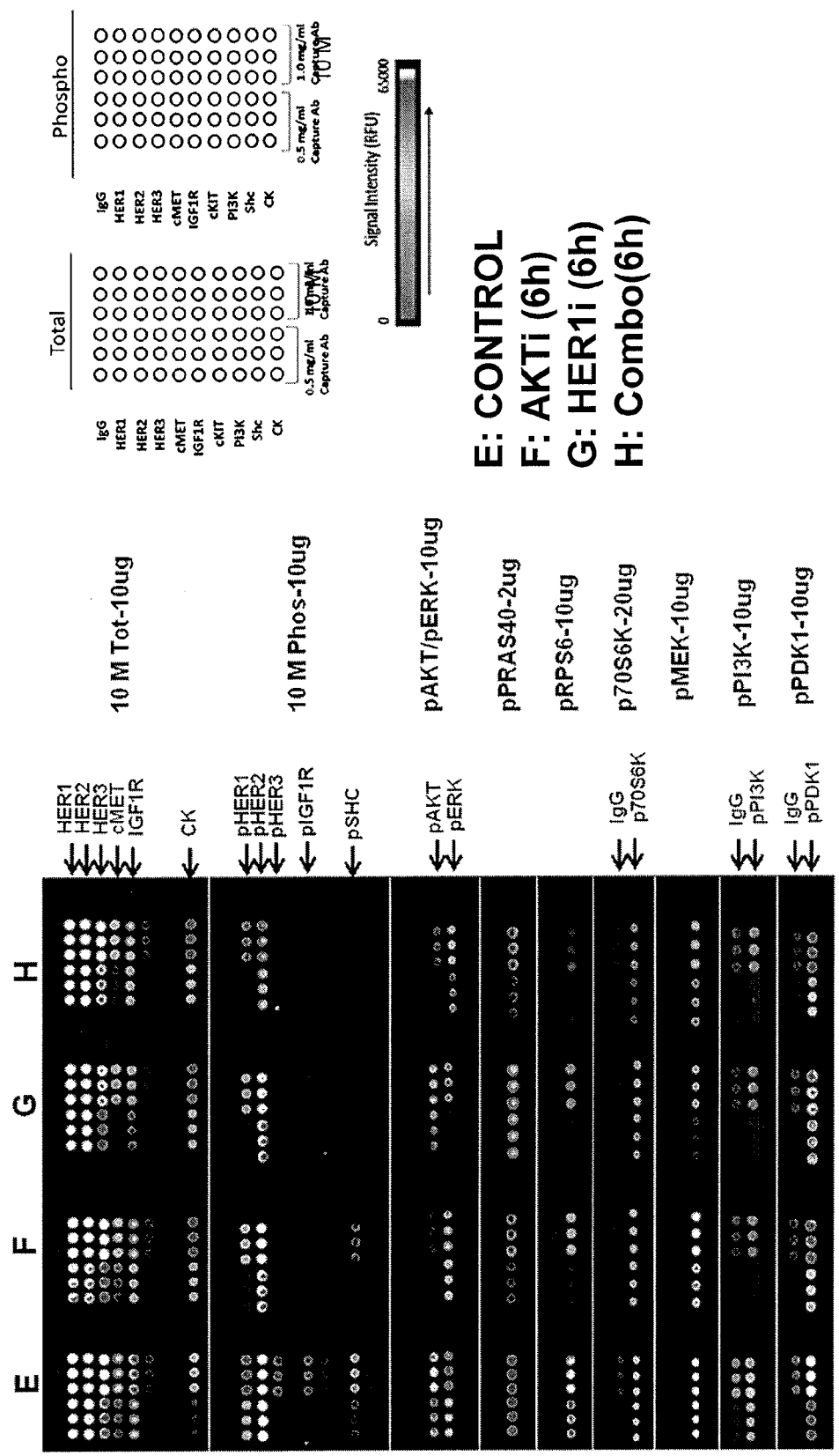
FIG. 16 shows CEER-FNA analysis of PI3K pathway activation in NSCLC tumor cell samples after treatment with an AKT inhibitor, a HER1 inhibitor or combination therapy.
Figure 17:
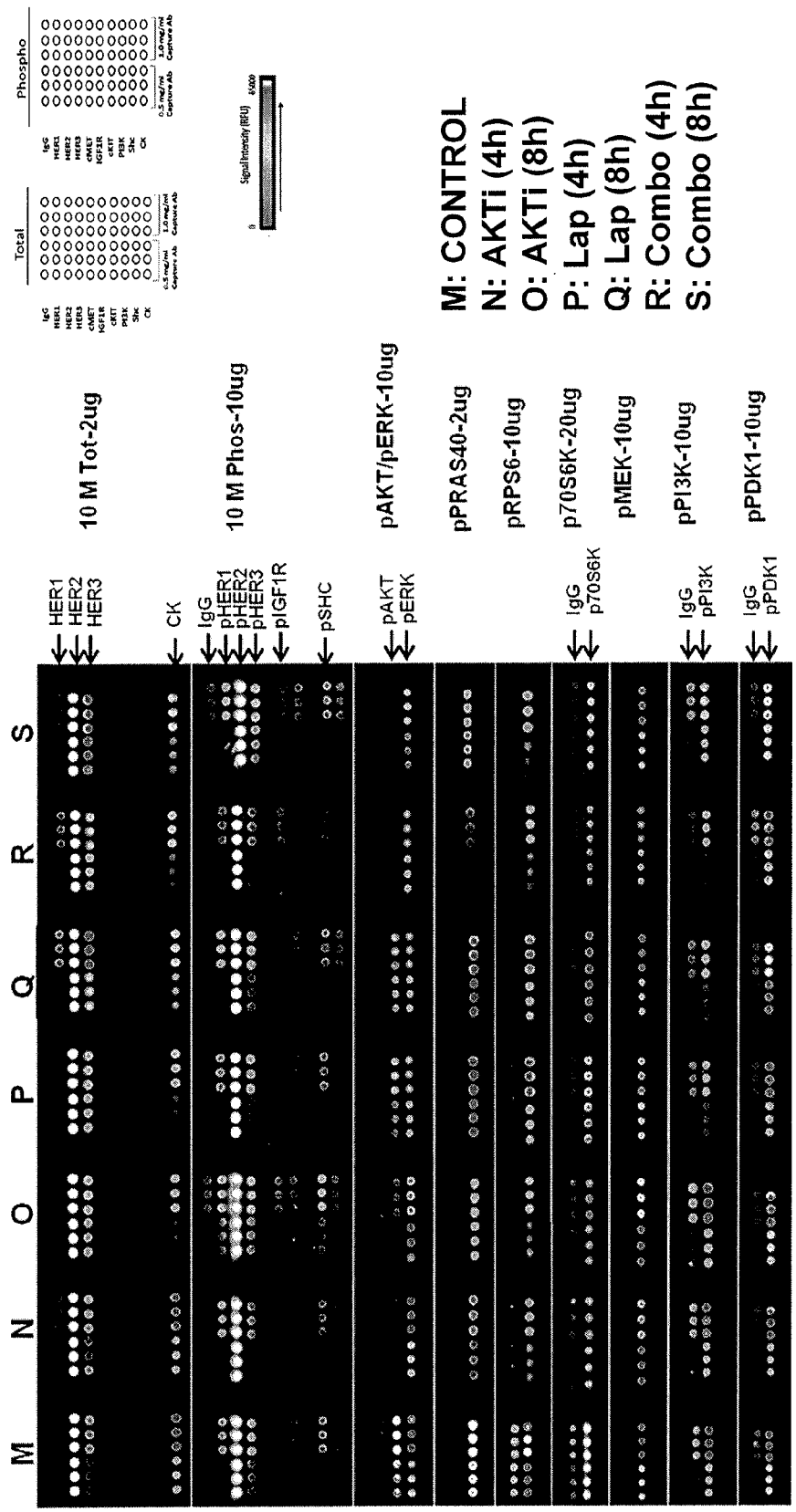
FIG. 17 illustrates CEER-FNA analysis of biomarkers in pathway profiling of breast cancer cell samples after treatment with an AKT inhibitor, Lapatinib (a tyrosine kinase inhibitor) or combination therapy.

This example demonstrates the detection of total and activated (phosphorylated) levels of RTK pathways and downstream kinases, effector and adaptor proteins in tumor cell samples as determined by a CEER assay platform. Higher levels of phosphorylated PI3K, AKT, ERK (downstream effector targets), as well as activated HER1, HER2, HER3 and IGF1R (which are also known as PI3K membrane recruiter proteins) were detected. In some embodiments, the non-small cell lung carcinoma tumor cell samples are exposed to AKT inhibitor and/or HER1 inhibitor therapy. Higher levels of phosphorylated PI3K, AKT, ERK (downstream effector targets), as well as activated HER1, HER2, HER3 and IGF-1R (which are also known as PI3K membrane recruiter proteins) were detected. The breast cancer tumor samples were exposed to AKT inhibitor and/or Lapatinib (a tyrosine kinase inhibitor). This example illustrates that cancer cells can adapt to therapeutic pressure due to drug therapy. It also shows that PI3K inhibitor therapy in combination with ErbB modulating compounds (i.e., anti-HER2 antibody, such as Pertuzamab, anti-HER3 antibody, and tyrosine kinase inhibitor) can benefit patients who are no longer responsive to ErbB modulating compounds alone. FIG. 16 shows CEER-FNA analysis of PI3K pathway activation in NSCLC tumor cell samples after treatment with an AKT inhibitor, a HER1 inhibitor or combination therapy. FIG. 17 illustrates CEER-FNA analysis of biomarkers in pathway profiling of breast cancer cell samples after treatment with an AKT inhibitor, Lapatinib (a tyrosine kinase inhibitor) or combination therapy.

Example 5

Novel Proximity Based Complex Assays to Measure HER Activation and Dimerization

This example illustrates novel proximity dimerization and complexation assays capable of specifically detecting activation events in signal transduction complexes with sensitivity at a single cell level. The assays comprising a CEER platform, are extremely useful in dealing with a limited amount of sample and advantageously provide expression/activation profiling of kinases and other signal transduction pathway molecules on collected circulating tumor cells and metastatic FNA tumor samples.

In one embodiment, the novel proximity based dimer assay is able to detect ErbB heterodimer complexes in patient tumor samples. It also can detect these complexes in cancer cells exposed to anticancer drugs and/or pathway activating ligands, such as, but not limited to HRG and EGF.

In another embodiment, the novel proximity based complex assay detects HER3/PI3K complexes in pancreatic cancer tumor samples.

This example illustrates that three antibodies used in the proximity assay can comprise: (1) a capture antibody specific for one member of the dimer pair; (2) a first detection antibody specific for a first member of the dimer pair, wherein the first detection antibody is specific for a different domain than the capture antibody; and a (3) a second detection antibody specific for a second member of the dimer pair. In some embodiments, the novel proximity based dimer assay is used to detect and quantitate homo- or heterodimerization of receptor tyrosine kinases including, but not limited to, HER1/HER2 dimers, HER1/HER3 dimers, HER2/HER3 dimers, HER2/HER2 dimers, HER2/HER4 dimers, p95HER2/HER3 dimers, p95HER2/HER2 dimers, and the like.

Figure 18:
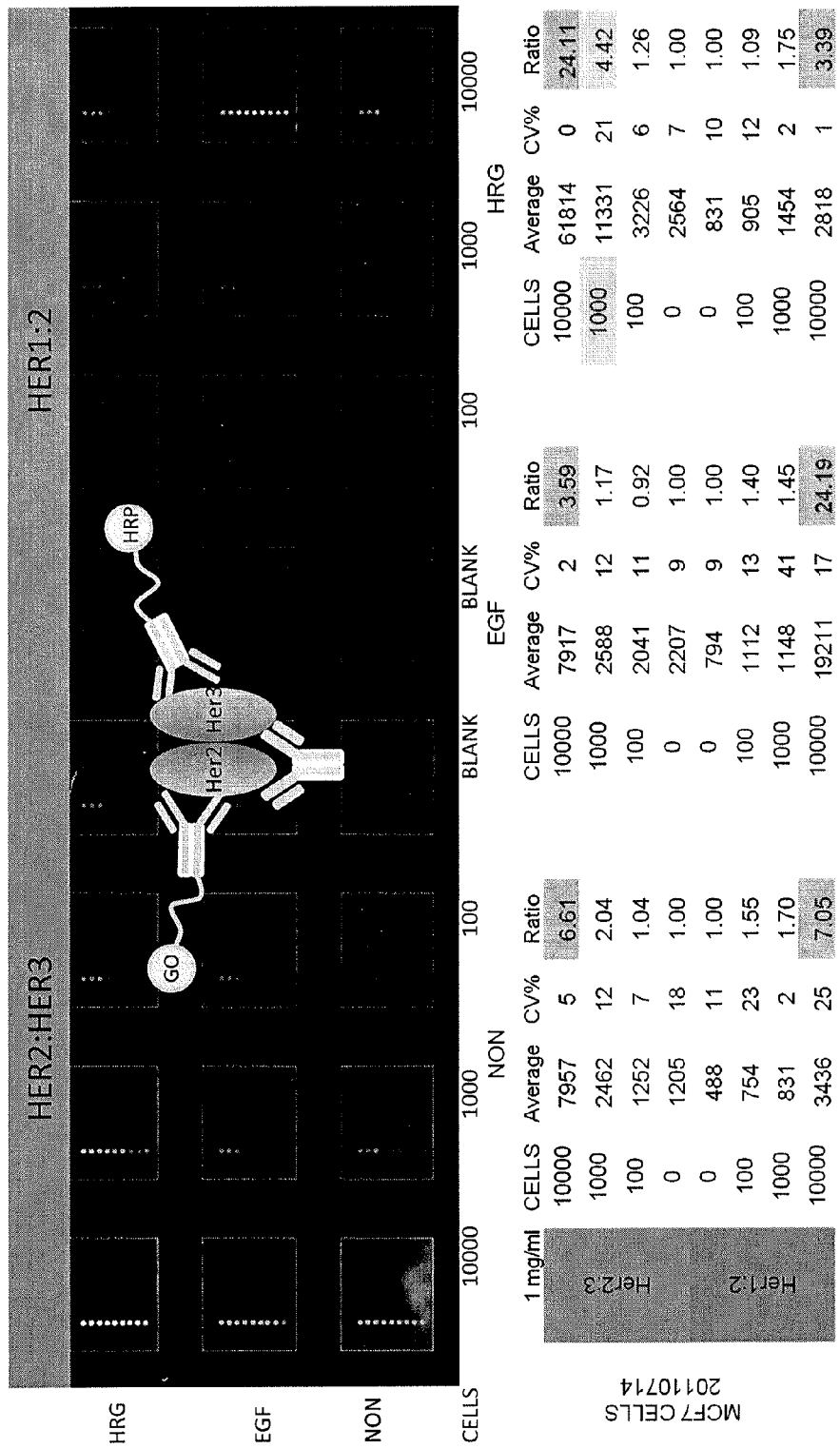
FIG. 18 shows raw data of HER1/2 and HER2/3 heterocomplexes on MCF7 cells detected using a novel proximity based dimer assay.
Figure 20:
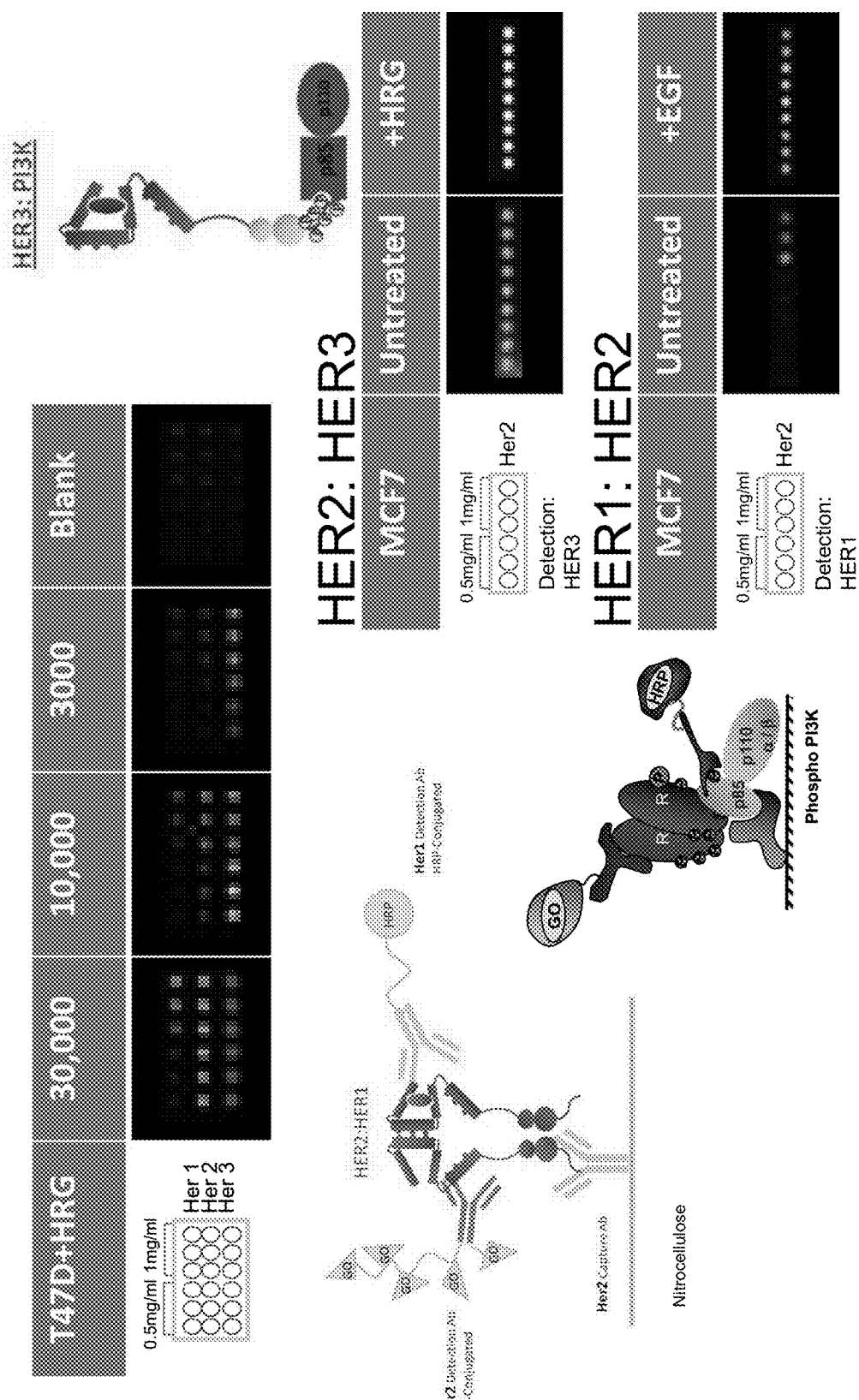
FIG. 20 shows activation of HER2 heterodimers and PI3K in response to HRG or EGF in MCF7 cells (a human breast adenocarcinoma cell line).

In an embodiment, the PI3K complex assay comprises: (1) a capture antibody specific for the p85 subunit of PI3K; (2) a detection antibody specific that binds to the activated form of an RTK or an adaptor protein; and (3) a detection antibody that recognizes the activated form of the p85 subunit of PI3K. In another embodiment, the PI3K complex assay comprises: (1) a capture antibody specific for the p85 subunit of PI3K; (2) a detection antibody specific that binds to the activated form of an RTK or an adaptor protein; and (3) a detection antibody that recognizes to the activated form of another RTK or adaptor protein. In another embodiment, the PI3K complex assay comprises: (1) a capture antibody specific for the p110 subunit of PI3K; (2) a detection antibody specific that binds to the activated form of an RTK or an adaptor protein; and (3) a detection antibody that recognizes the activated form of the p85 subunit of PI3K. In yet another embodiment, the PI3K complex assay comprises: (1) a capture antibody specific for the p85 subunit of PI3K; (2) a detection antibody specific that binds to the activated form of an RTK or an adaptor protein; and (3) a detection antibody that recognizes the activated form of the p110 subunit of PI3K. In an embodiment, the PI3K complex assay comprises: (1) a capture antibody specific for the p85 subunit of PI3K; (2) a detection antibody specific that binds to the activated form of the p85 subunit of PI3K; and (3) a detection antibody that recognizes the activated form of the p110 subunit of PI3K. FIG. 18 shows raw data of HER1/2 and HER2/3 heterocomplexes on MCF7 cells detected using a novel proximity based dimer assay. FIG. 19 shows activation of HER3 heterodimer complexes and HER3/PI3K complexes in a pancreatic tumor sample and HDPE cells. The CEER dimer assay is performed at 10 µg, 5 µg and 2 µg using a combination of capture and multiple detection antibodies. 5 µg data is shown for all except for HER3/PI3K complex at 10 µg. HPDE cells and tumor sample 10-494 form 1:2 and 2:3 complexes, respectively. Relative to the HPDE cells, the tumor sample has higher levels of phosopho-HER3 and associates with PI3K to form a HER3/PI3K complex. FIG. 20 shows activation of HER2 heterodimers and PI3K in response to HRG or EGF in MCF7 cells (a human breast adenocarcinoma cell line).

Example 6

Detection of RTK and PI3K Pathway Activation in FNA from Breast Cancer Patients

Figure 21:
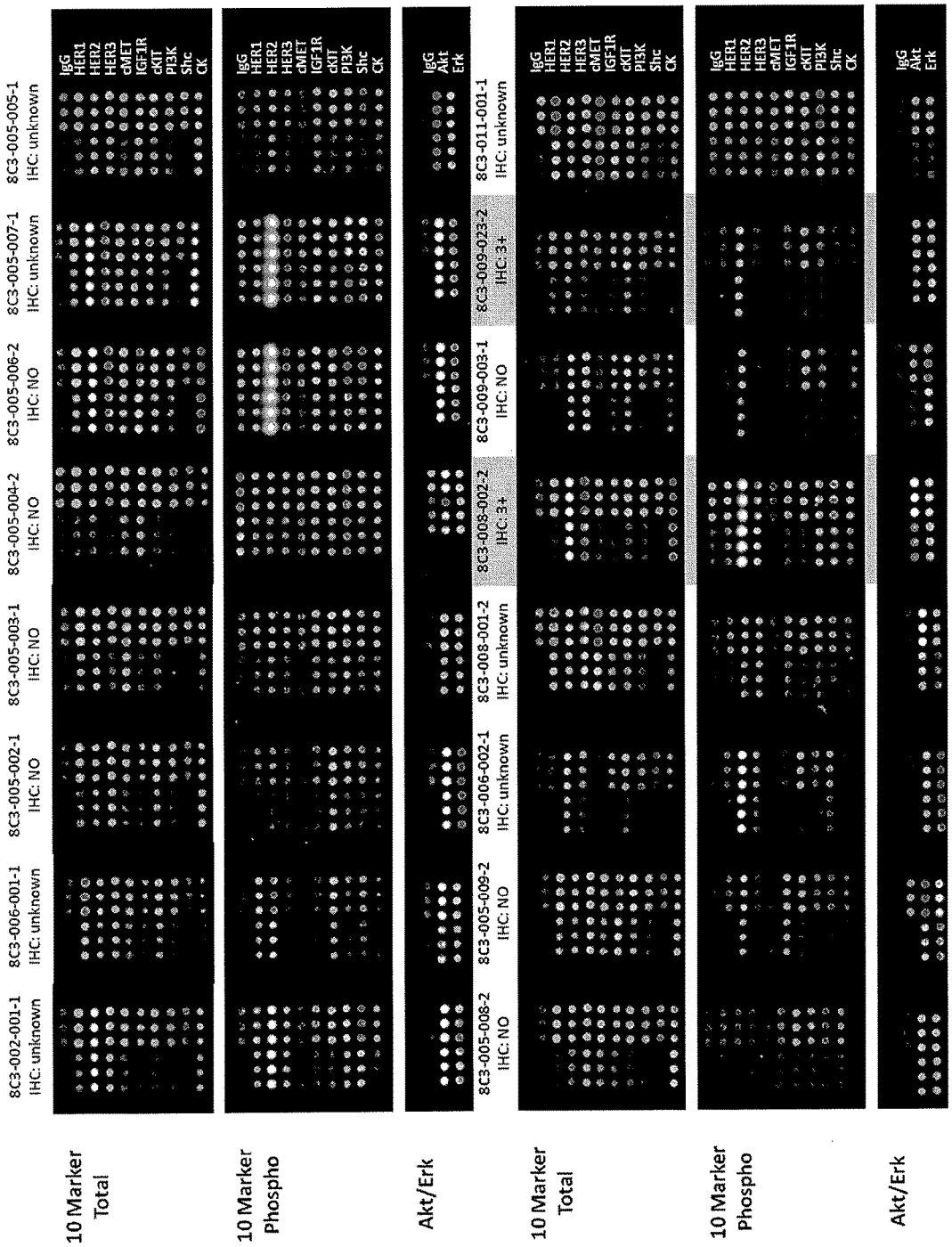
FIG. 21 illustrates raw data from CEER-FNA pathway analysis of breast cancer patients.
Figure 22:
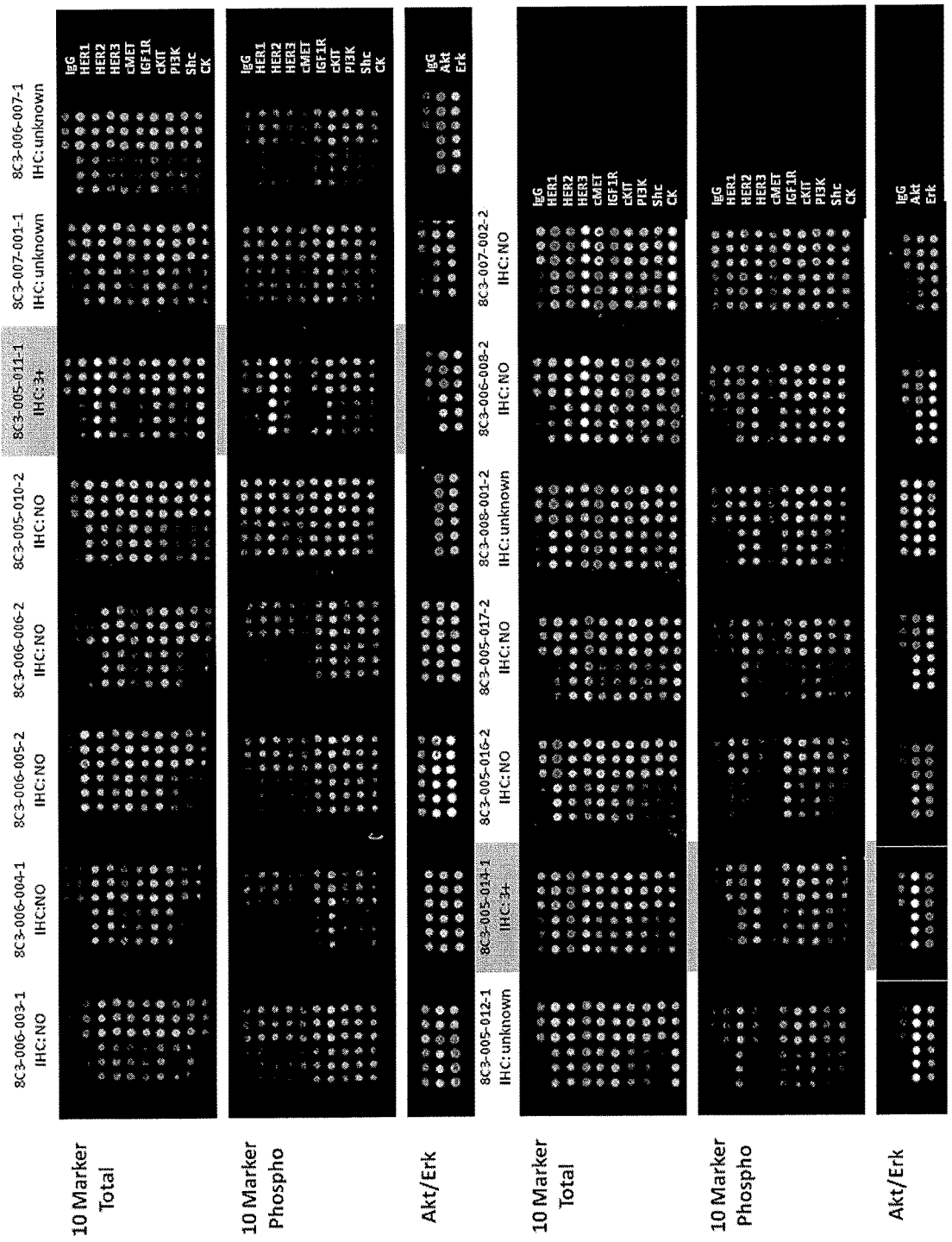
FIG. 22 illustrates CEER-FNA pathway analysis of more breast cancer patients.
Figure 23:
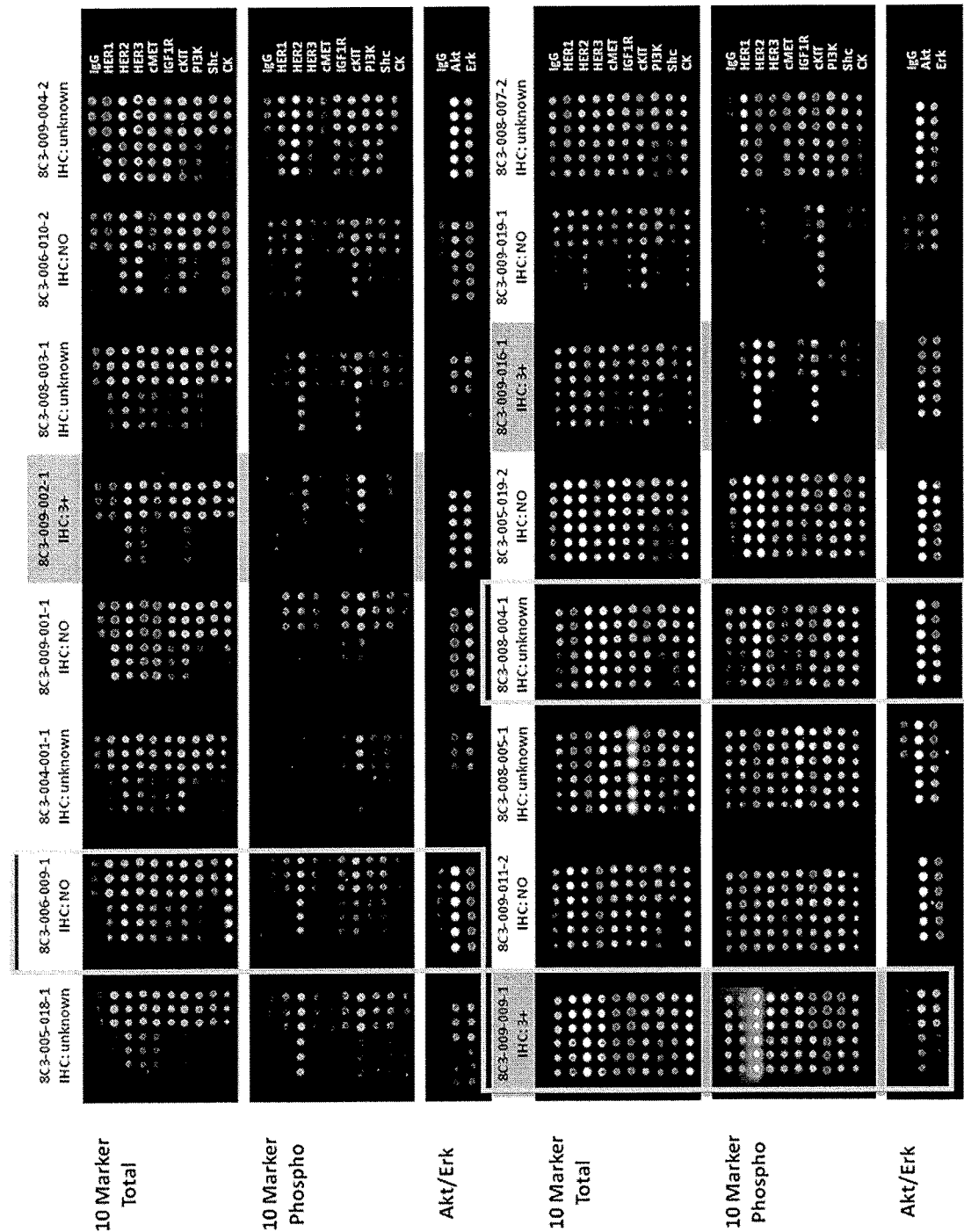
FIG. 23 illustrates from CEER-FNA pathway analysis of yet more breast cancer patients.
Figure 24:
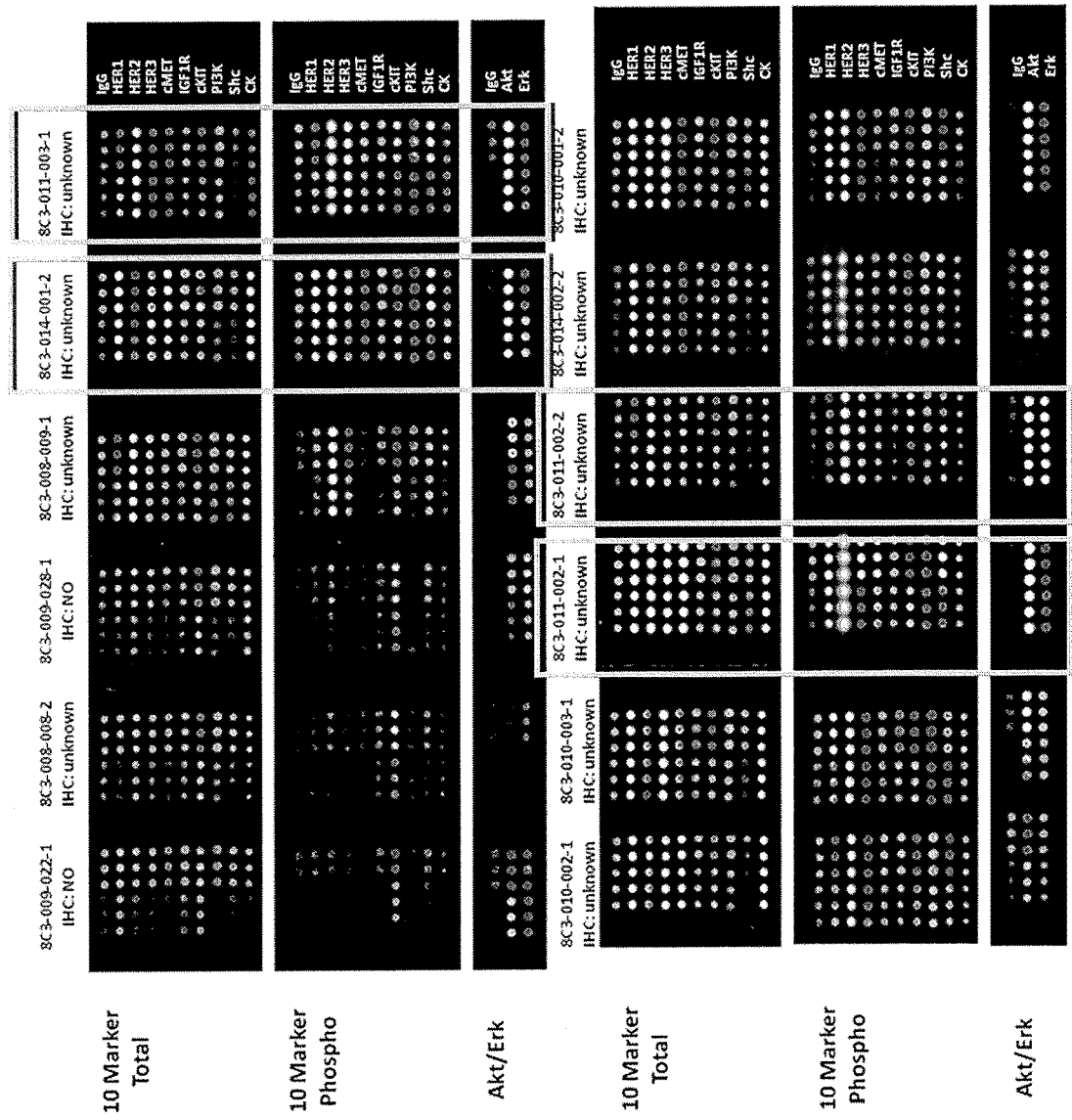
FIG. 24 illustrates CEER-FNA pathway analysis of breast cancer patients.

This example illustrates CEER-FNA pathway analysis of 59 breast cancer patients. The incidence of RTK pathway activation as well as downstream effector and adaptor proteins were assessed, as measured by the CEER assay, in a group of breast cancer patients with solid tumors. High levels of phosphorylated HER2, HER3, PI3K and AKT were detected in several samples. This example illustrates that PI3K inhibitor therapy in combination with ErbB modulating compounds (i.e., anti-HER2 antibody, such as Pertuzamab, anti-HER3 antibody, and tyrosine kinase inhibitor) can benefit patients with this pathway profile. CEER-FNA pathway analysis of solid tumor patients provides valuable clinical information to assist clinicians in assessing the disease treatment options for each patient according to the pathway activation profile. FIG. 21 illustrates CEER-FNA pathway analysis of breast cancer patients. FIG. 22 illustrates CEER-FNA pathway analysis of more breast cancer patients. FIG. 23 illustrates from CEER-FNA pathway analysis of yet more breast cancer patients. FIG. 24 illustrates CEER-FNA pathway analysis of breast cancer patients.

Example 7

Quantitative Analysis of PI3K and IGF-1R Activation in Breast Cancer Patients

Figure 25:
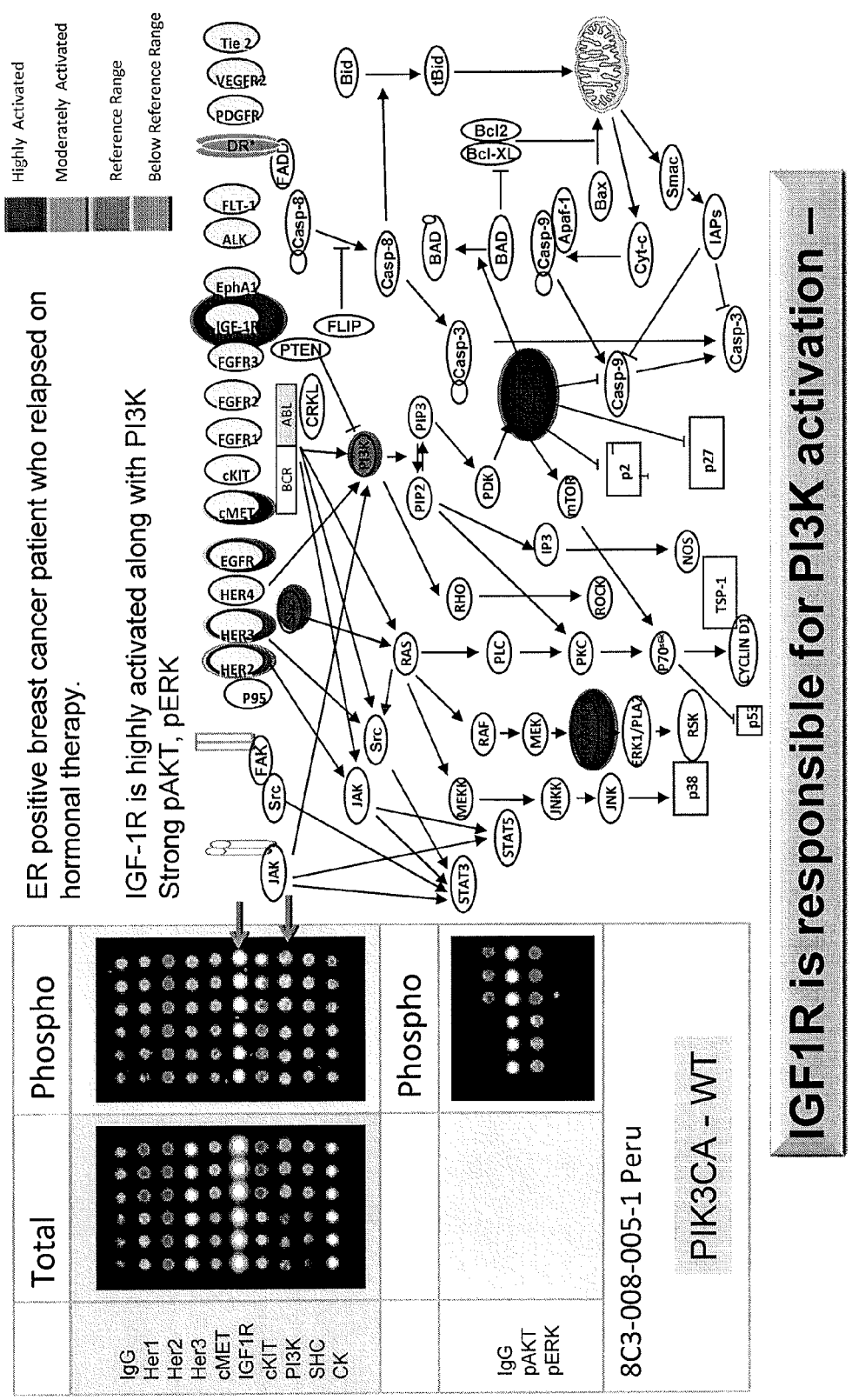
FIG. 25 illustrates IGF-1R, PI3K, AKT and ERK activation in a breast cancer patient.

This example illustrates a comprehensive analysis of key signature receptor tyrosine kinases including HER1, HER2, p95HER2, HER3, cMET, IGF1R, and downstream kinases and adapter proteins including PI3K, Shc, AKT and ERK, in FNA samples collected from a breast cancer patient who have relapsed on hormonal therapy. We detected elevated levels of the activated IGF-1R, PI3K AKT and ERK/MAPK proteins. Notably, PI3K activation in the patient was not due to PIK3CA mutation. Surprisingly, the existing therapy (e.g., hormonal therapy) activated compensatory pathways associated with the hormonal pathway shut down by the therapy, but not directly targeted by it. The pathway activation profile suggests that the patient may clinically benefit from a combination treatment comprising an IGF-1R inhibitor and a PI3K inhibitor. The pathway profile also suggests that therapeutic agent that targets the IGF-1R pathway may be effective in treating ER positive breast cancer patients. FIG. 25 illustrates IGF-1R, PI3K, AKT and ERK activation in a breast cancer patient. FIG. 26 illustrates IGF-1R and AKT activation in a breast cancer patient. Activated IGF-1R levels correlates with phospho-AKT levels. In addition, elevated levels of total IGF-1R also correlates with phospho-AKT.

Example 8

Quantitative Analysis of PI3K Activation Along with IGF-1R or cMet Activation in Non-Small Cell Lung Carcinoma Patients This example illustrates a comprehensive analysis of key signature receptor tyrosine kinases including HER1, HER2, p95HER2, HER3, cMET, IGF-1R, and downstream kinases and adapter proteins including PI3K, Shc, AKT and ERK, in FNA samples collected from NSCLC patients prior to anti-cancer treatment. In one particular embodiment, the present method enables the detection and measurement of expression levels of a plurality of oncogenic proteins (e.g., FGFR1, FGFR2, IGF-1R, cMET, HER1, HER2, HER3, VEGFR2, PI3K, SHC, FAK, CRKL) and) as well as expression levels of their activated (e.g., phosphorylated) forms in a biological sample harvested from patient tumor tissue. In certain instances, tumor samples from NSCLC patients have a KRAS mutation (e.g., G12C, G12D, G12R, G12S, G12V, G13C and G13R).

Figure 27:
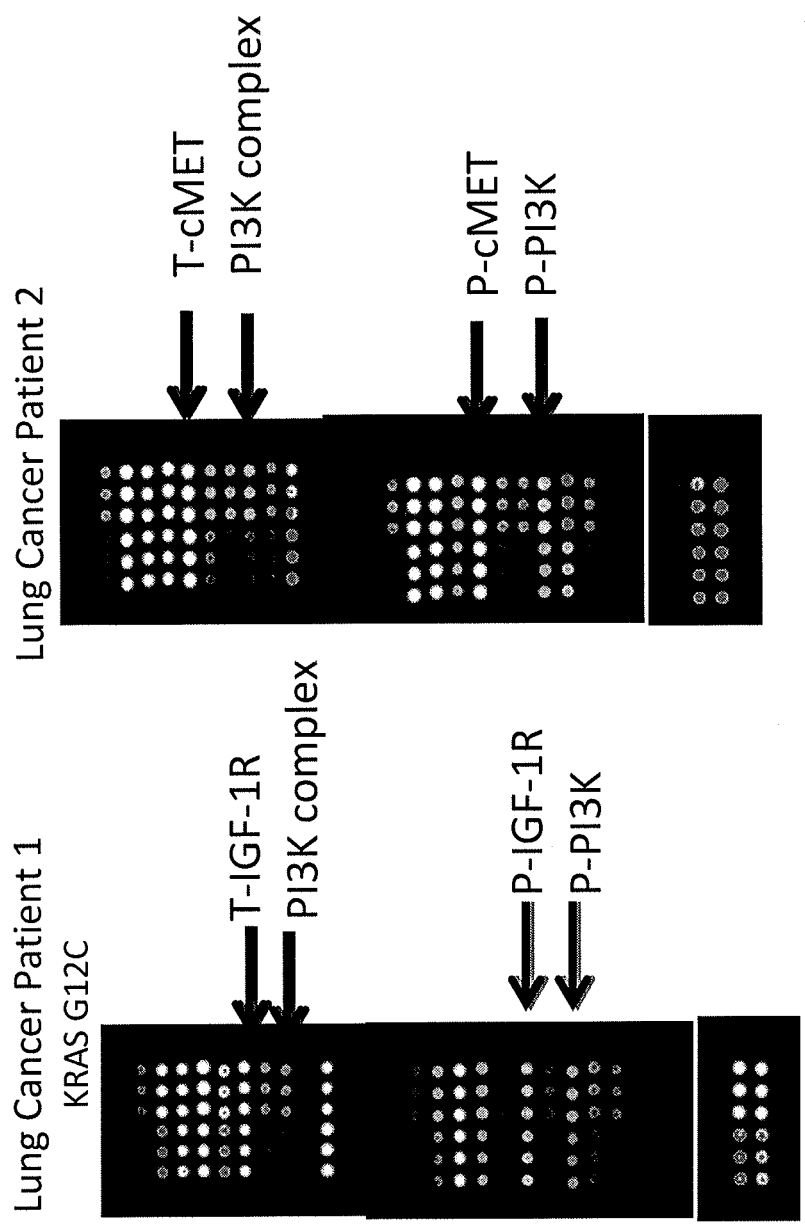
FIG. 27 illustrates PI3K activation along with IGF-1R or cMET activation in a NSCLC patients. Tumor sample from patient 1 with G12C KRAS mutation has high levels of total and phosphorylated IGF-1R along with high levels of PI3K complex and phospho-PI3K. The pathway profiling analysis also shows that tumor sample from patient 2 also expresses high levels of total and phosphorylated IGF-1R, PI3K complex and phospho-PI3K.
Figure 28:
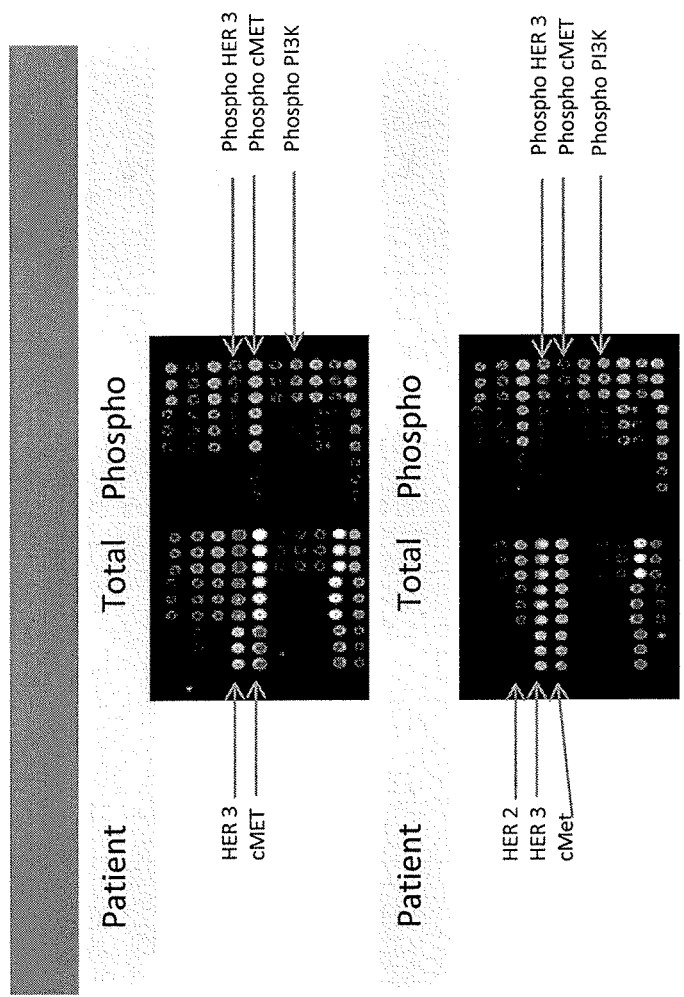
FIG. 28 illustrates that PI3K activation along with HER3 and/or cMET activation are detected in a lung cancer patient.
Figure 29:
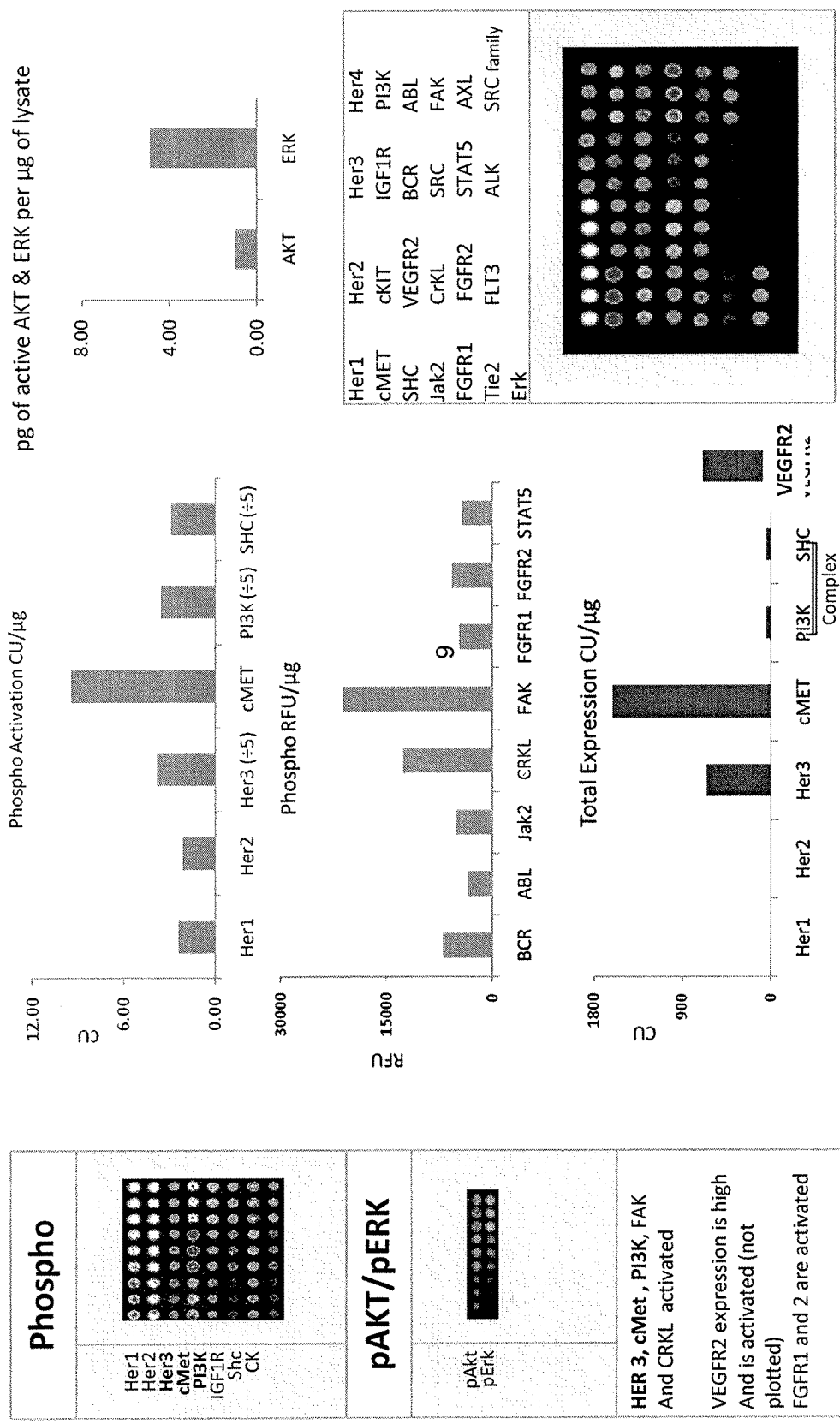
FIG. 29 illustrates concurrent activation of HER3, cMET and PI3K in a NSCLC patient with a G12C KRAS mutation. Other activated downstream effector proteins (e.g. FAK, and CRKL) were detected. VEGFR2 expression was high and both FGFR1 and FGFR2 were activated in the sample. The pathway analysis profiling was performed on the tumor sample prior to treatment.
Figure 30:
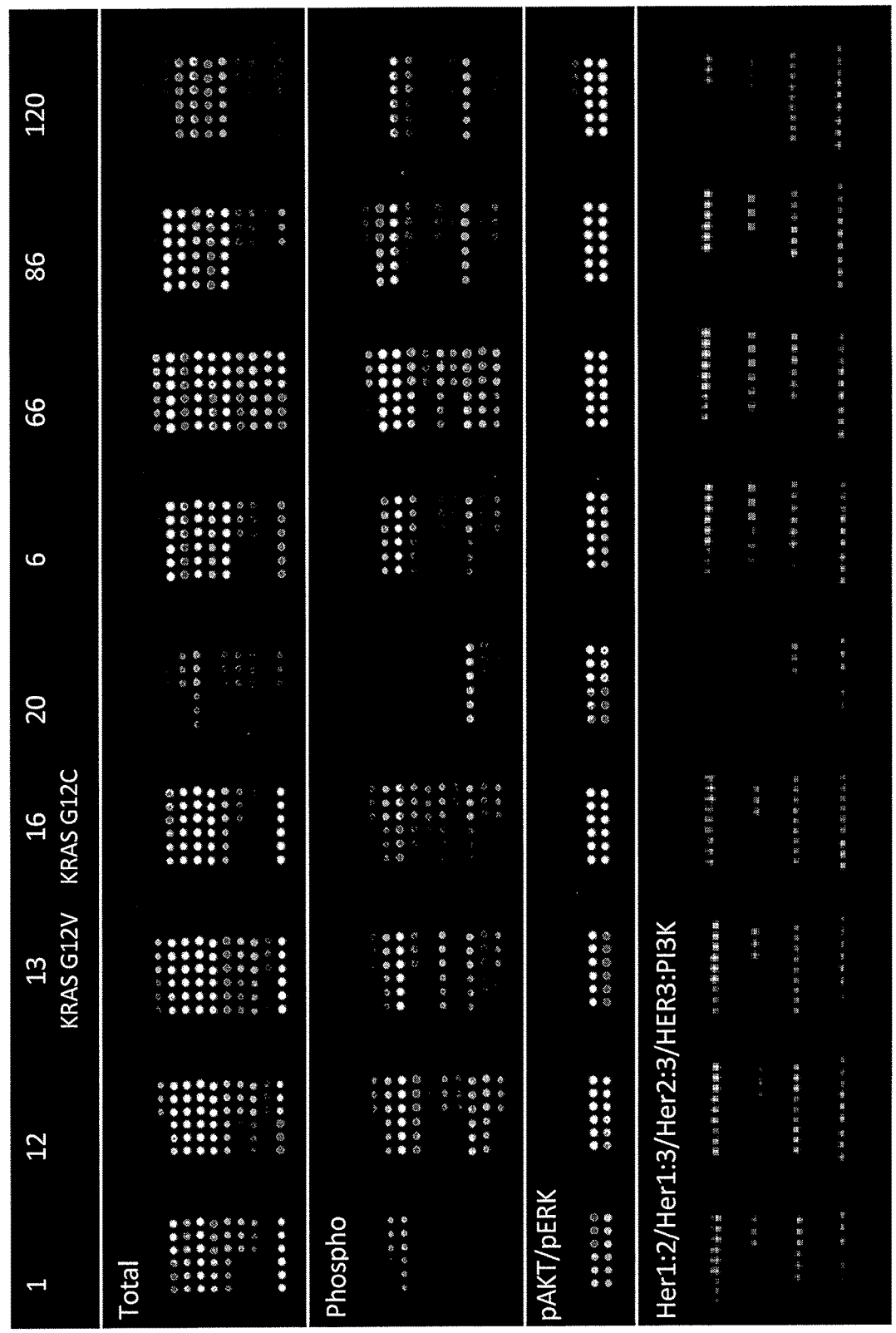
FIG. 30 shows a "heat map" of PI3K activation and HER heterodimers in NSCLC patients. ErbB dimerization and PI3K pathway activation were detected the tumor samples.
Figure 31:
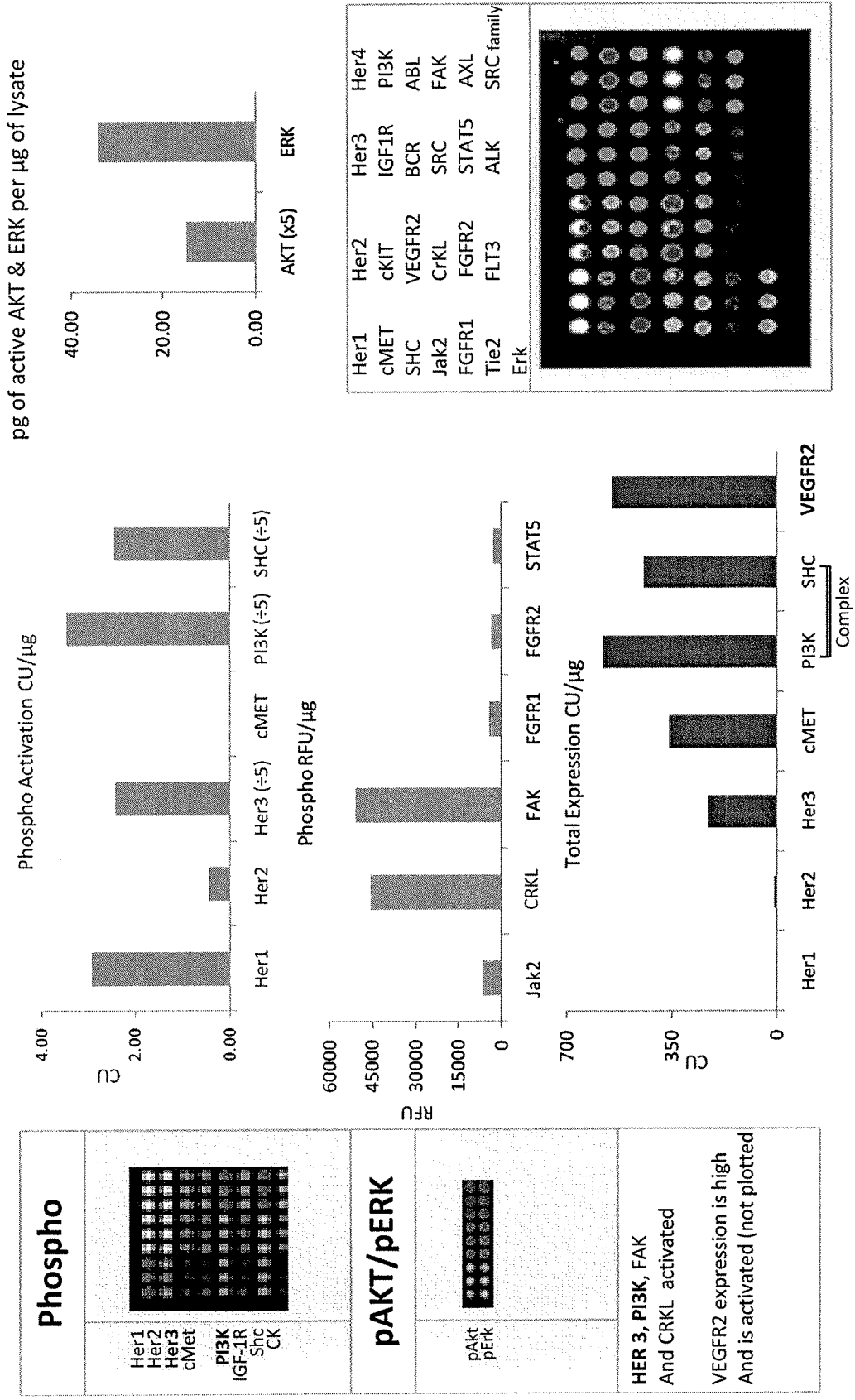
FIG. 31 illustrates concurrent activation of HER3 and PI3K in a tumor sample without KRAS and EGFR somatic mutations from a NSCLC patient. Levels of activated CRKL, FAK and Shc were also detected. Total VEGFR2 expression was high as well.

The method described herein was used to perform PI3K activation profiling of tumor samples from lung cancer patients. Elevated levels of PI3K and AKT activation along with HER1/2, HER1/3, HER2/3 and HER3/PI3K complexation were detected. Interestingly, activation of the ERK was also seen. FIG. 27 illustrates PI3K activation along with IGF-1R or cMET activation in NSCLC patients. Tumor sample from patient 1 with G12C KRAS mutation has high levels of total and phosphorylated IGF-1R along with high levels of PI3K complex and phospho-PI3K. The pathway profiling analysis also shows that tumor sample from patient 2 also expresses high levels of total and phosphorylated IGF-1R, PI3K complex and phospho-PI3K. FIG. 28 illustrates that PI3K activation along with HER3 and/or cMET activation are detected in a lung cancer patient. FIG. 29 illustrates concurrent activation of HER3, cMET and PI3K in a NSCLC patient with a G12C KRAS mutation. Other activated downstream effector proteins (e.g. FAK, and CRKL) were detected. VEGFR2 expression was high and both FGFR1 and FGFR2 were activated in the sample. The pathway analysis profiling was performed on the tumor sample prior to treatment. FIG. 30 shows a "heat map" of PI3K activation and HER heterodimers in NSCLC patients. ErbB dimerization and PI3K pathway activation were detected the tumor samples. FIG. 31 illustrates concurrent activation of HER3 and PI3K in a tumor sample without KRAS and EGFR somatic mutations from a NSCLC patient. Levels of activated CRKL, FAK and Shc were also detected. Total VEGFR2 expression was high as well.

Example 9

Quantitation of ErbB Family Receptor Tyrosine Kinases Activation and PI3K Activation in Gastric Cancer Patients This example illustrates a comprehensive analysis of key signature receptor tyrosine kinases including HER1, HER2, HER3, cMET, IGF-1R, cKIT and downstream effector proteins including PI3K, Shc, AKT and ERK, in FNA samples collected from gastric cancer patients. In one particular embodiment, high levels of ErbB family RTK activation and dimer formation was detected in several tumor samples. In some sample, cMET activation correlated to phospho-HER1 levels.

Figure 32:
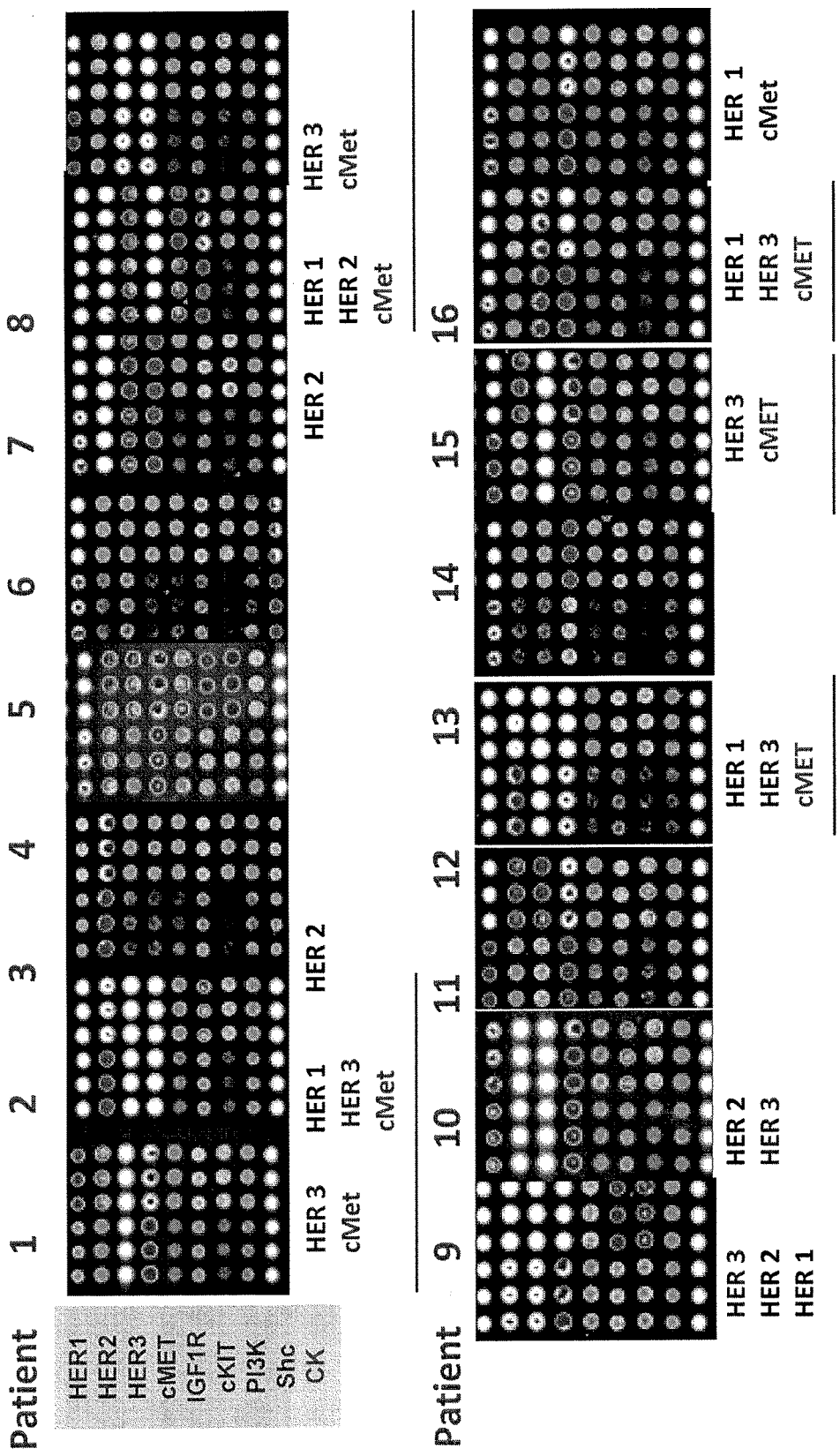
FIG. 32 illustrates the presence of phospho-HER3 in gastric cancer patient samples. In some samples, activated HER3 correlated with the presence of activated cMET. Activated ErbB receptors were detected in several gastric tumor samples.
Figure 33:
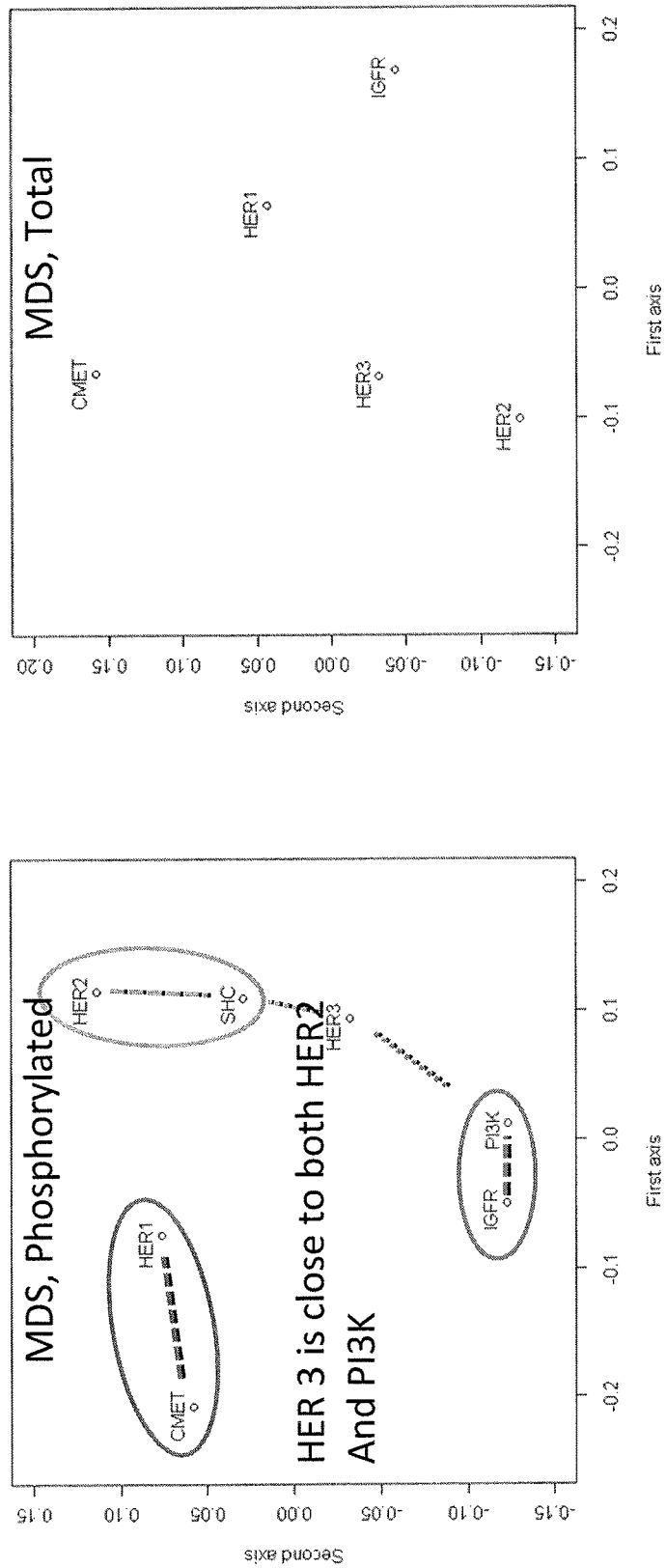
FIG. 33 shows a MultiDimensional Scaling (MDS) graph that displays the concordance of phosphorylated pathway markers.
Figure 34:
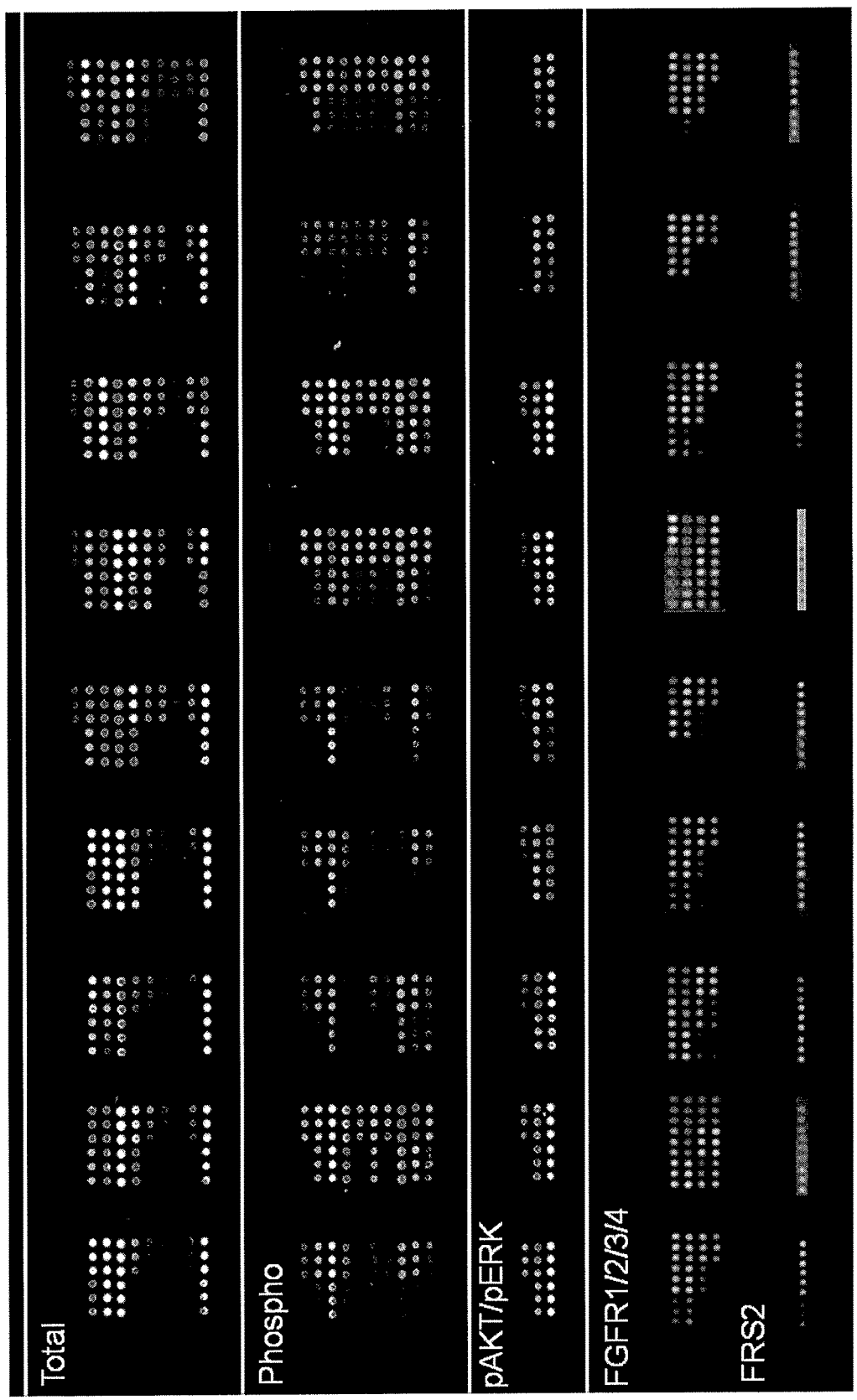
FIG. 34 illustrates a comparison of phospho-PI3K and phospho-AKT/ERK in pathway profiling analysis of patients with gastric cancer. Activation of the FGFR family including FGFR1, FGFR2, FGFR3, and FGFR4 were detected in some of the samples.

Marker grouping analysis was performed to evaluate the concordance or correlation between predictive biomarkers for solid tumor cancer. Using Multi Dimensional Scaling which is similar to Principal Component Analysis, it was determined that phosphorylated forms of cMET and HER1 have a high degree of concordance in tumor samples from gastric cancer patients. A concordance was also present between HER2 and Shc, as well as IGF-1R and PI3K in these samples. Interestingly, HER3 has a close relationship to both HER2 and PI3K. This supports the notion that detection of an activated PI3K complex comprising HER2, HER3 and PI3K can be used to determine the disease status or pathway profile of gastric tumor samples. FIG. 32 illustrates the presence of phospho-HER3 in gastric cancer patient samples. In some samples, activated HER3 correlated with the presence of activated cMET. Activated ErbB receptors were detected in several gastric tumor samples. FIG. 33 shows a MultiDimensional Scaling (MDS) graph that displays the concordance of phosphorylated pathway markers. FIG. 34 illustrates a comparison of phospho-PI3K and phospho-AKT/ERK in pathway profiling analysis of patients with gastric cancer. Activation of the FGFR family including FGFR1, FGFR2, FGFR3, and FGFR4 were detected in some of the samples.

Example 10

Figure 35:
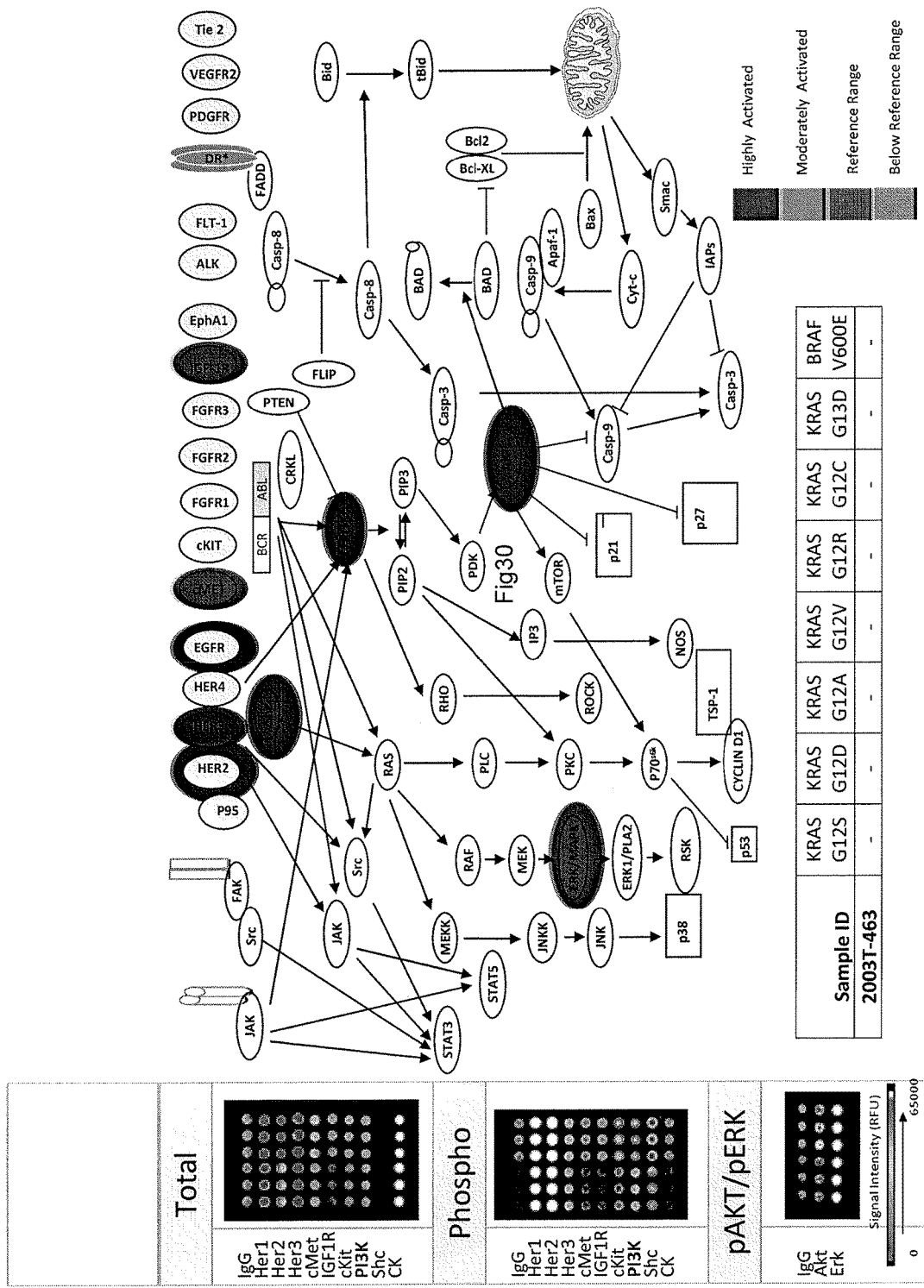
FIG. 35 illustrates PI3K pathway activation and HER pathway activation in a patient with colorectal cancer prior to therapy.
Figure 36:
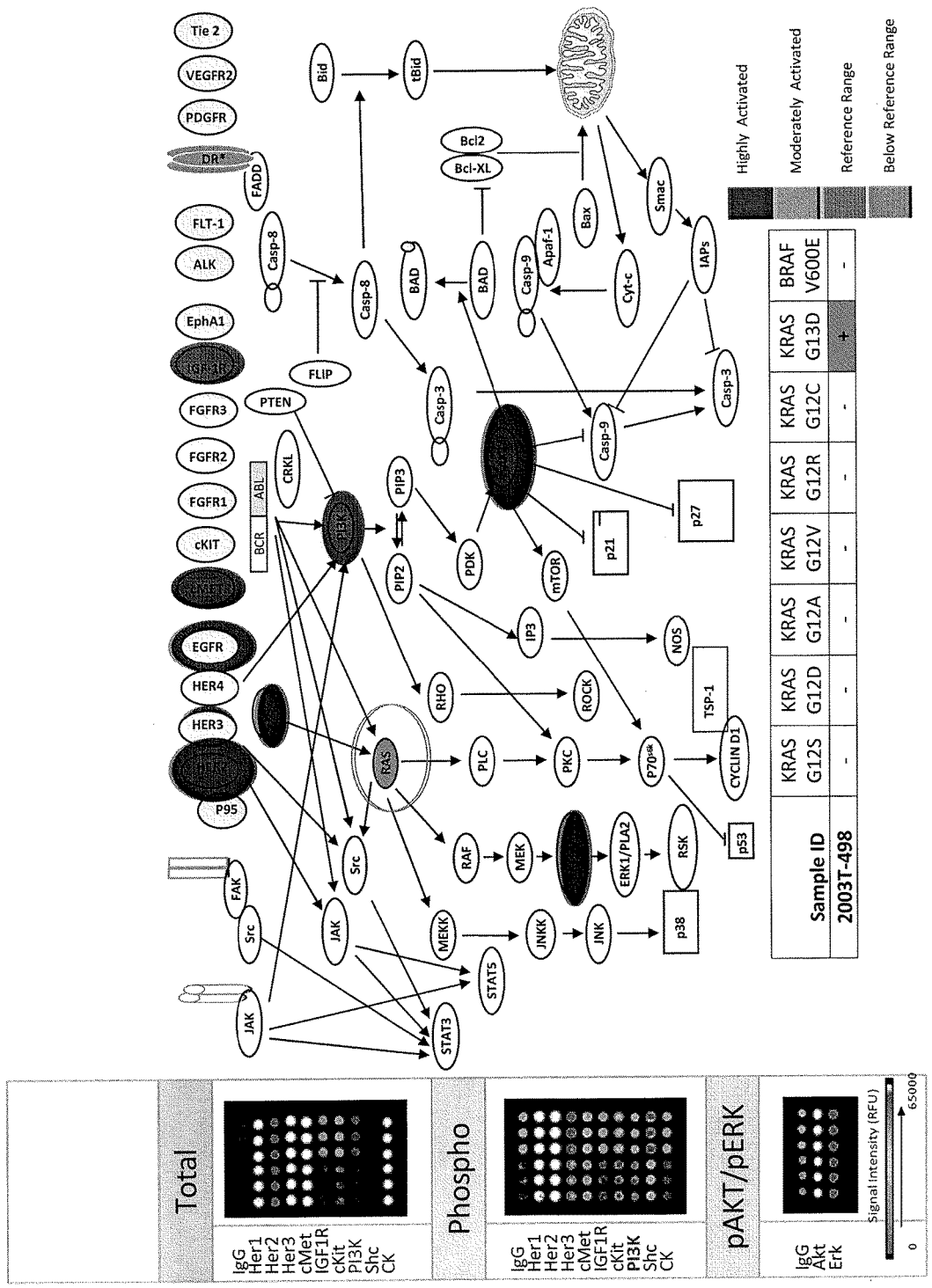
FIG. 36 illustrates PI3K pathway activation and HER pathway activation in a sample with a G13D KRAS mutation taken from colorectal cancer patient a prior to therapy.
Figure 37:
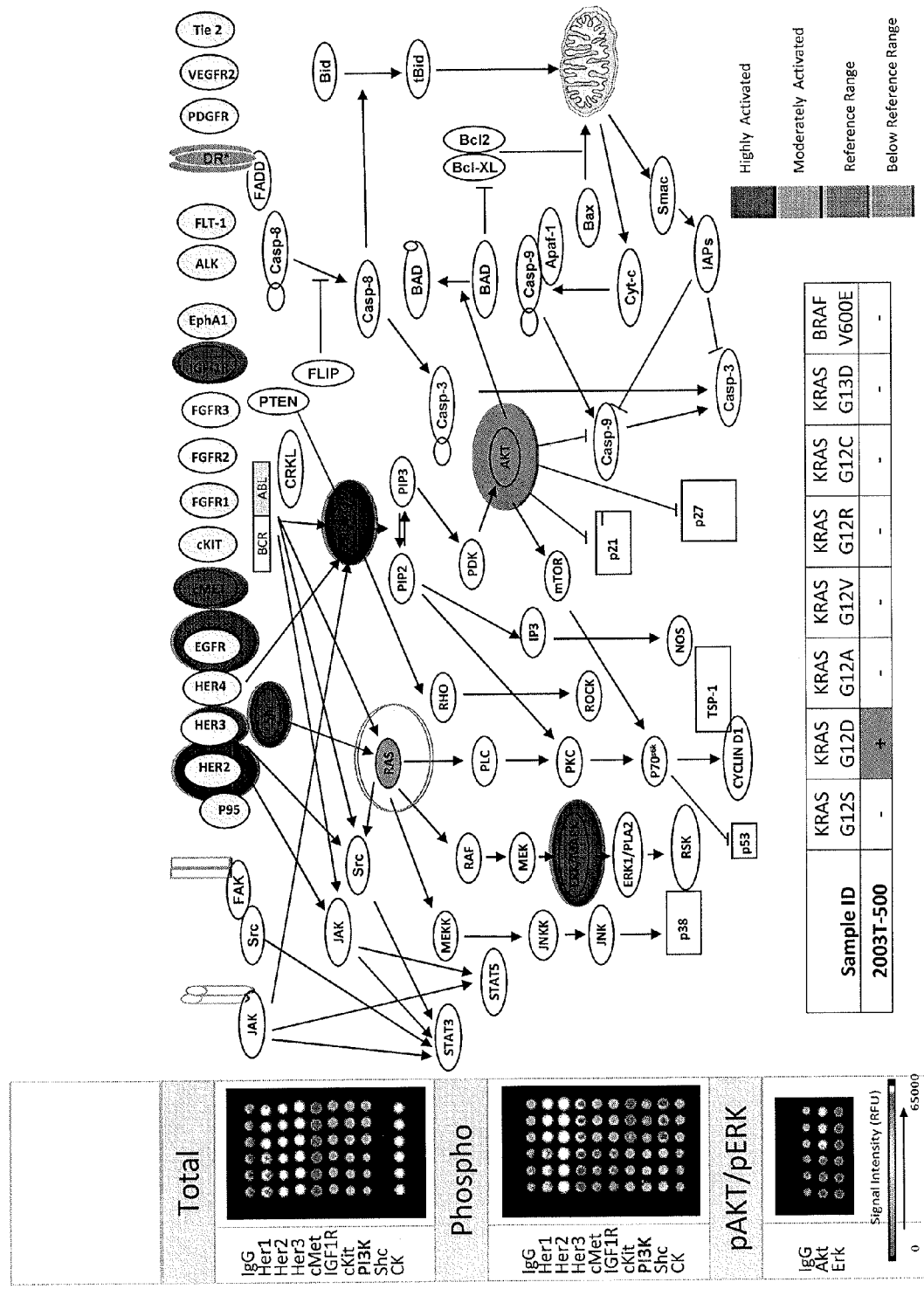
FIG. 37 illustrates PI3K pathway activation and HER pathway activation in a colorectal cancer patient with a G12D KRAS mutation prior to therapy.
Figure 38:
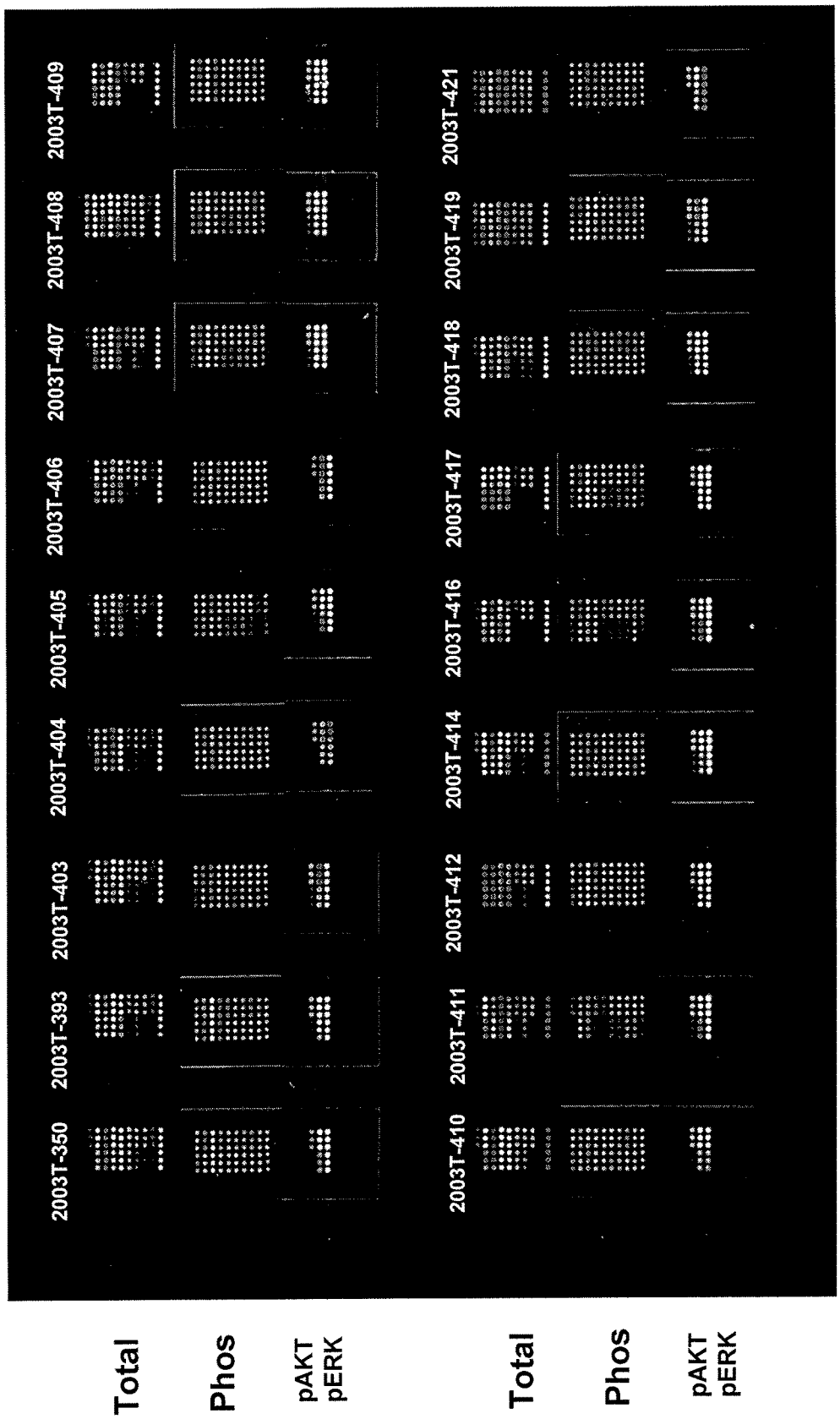
FIG. 38 illustrates FNA analysis of biomarkers in pathway profiling of samples from patients with colorectal cancer.

Detection of PI3K Pathway Activation from Solid Tumor Samples from Colorectal Cancer Patients Prior to Therapy This example illustrates a comprehensive analysis of key signature receptor tyrosine kinases including HER1, HER2, HER3, cMET, IGF-1R, cKIT and downstream effector proteins including PI3K, Shc, AKT and ERK, in FNA samples collected from colorectal cancer patients. In one embodiment, the tumor sample has a G13D KRAS mutation. In another embodiment, the tumor sample expresses wild-type KRAS gene. FIG. 35 illustrates PI3K pathway activation and HER pathway activation in a patient with colorectal cancer prior to therapy. FIG. 36 illustrates PI3K pathway activation and HER pathway activation in a sample with a G13D KRAS mutation taken from colorectal cancer patient a prior to therapy. FIG. 36 shows that HER1 (EGFR), HER2, Shc, ERK and AKT proteins are highly activated. FIG. 37 illustrates PI3K pathway activation and HER pathway activation in a colorectal cancer patient with a G12D KRAS mutation prior to therapy. FIG. 38 illustrates FNA analysis of biomarkers in pathway profiling of samples from patients with colorectal cancer.

Example 11

Figure 39:
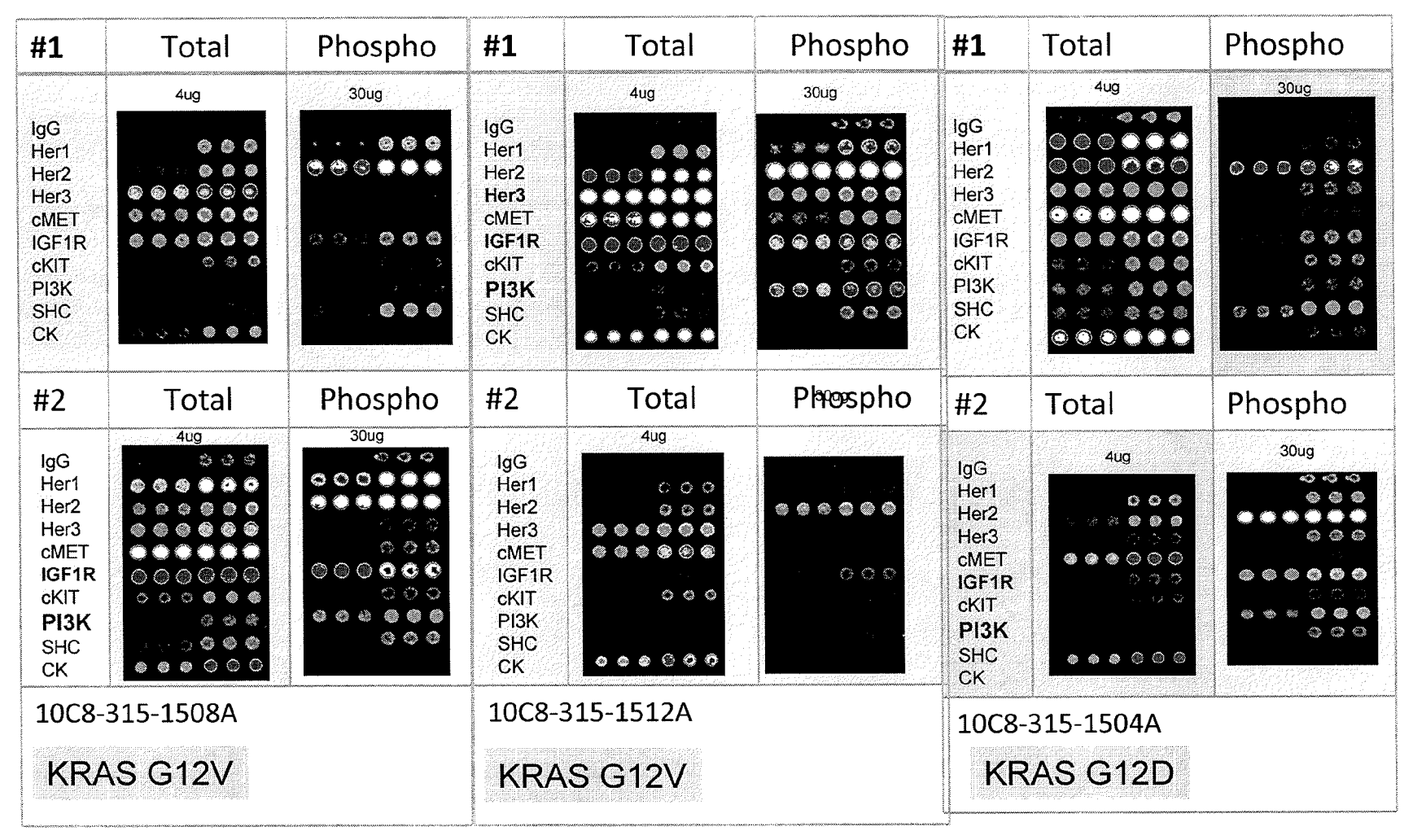
Figure 40:
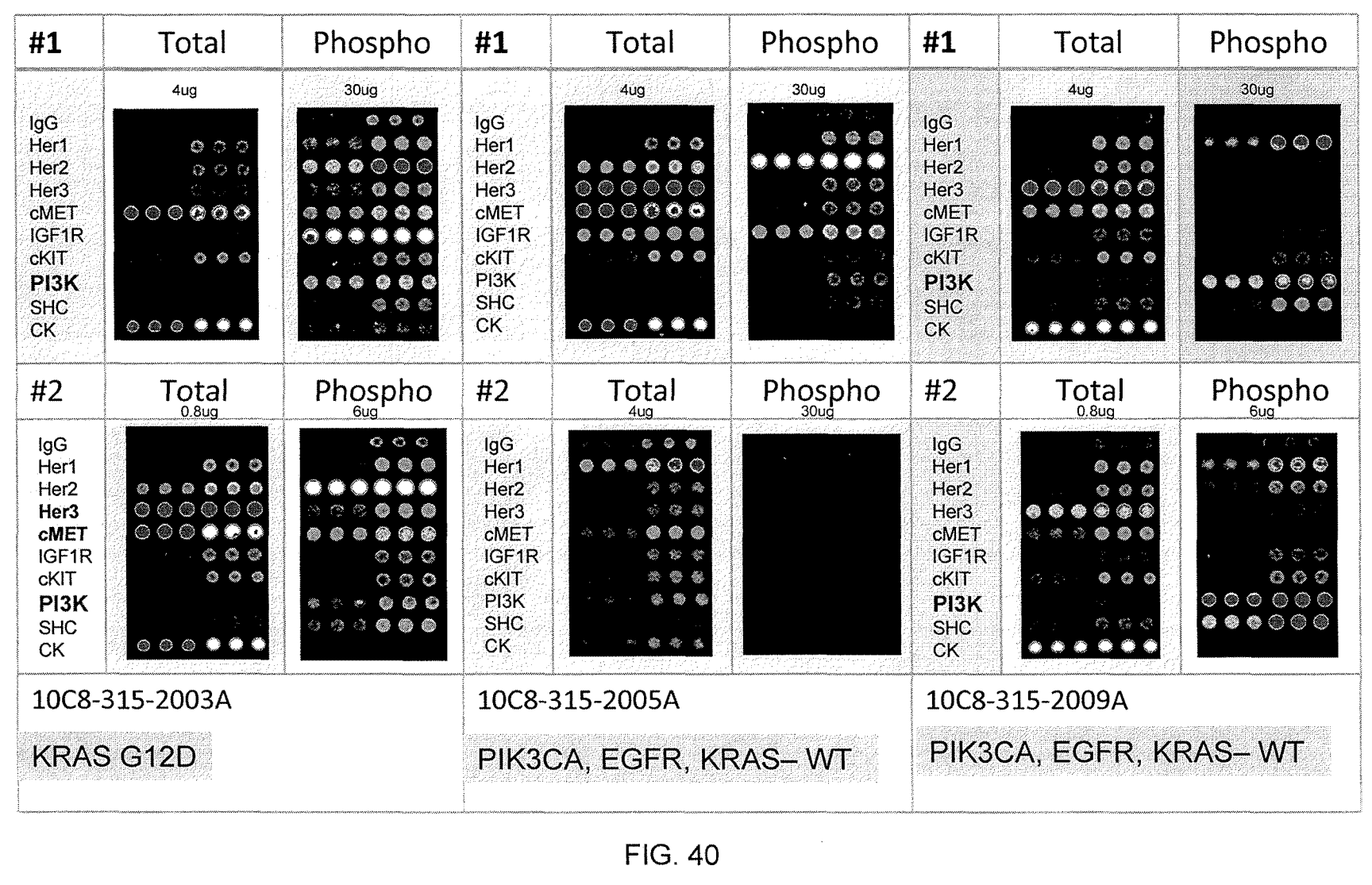

Method of Detecting PI3K Pathway Activation from Solid Tumors of Pancreatic Cancer Patients Analysis of expression of target protein or mutation alone has limitations for selecting the right therapy regimen with maximal clinical efficacy. A comprehensive functional analysis of pathway proteins including their level of expression and phosphorylation is critical in developing clinical strategies focused on the most effective targeted drug combination. A pathway profiling analysis was conducted on key receptor tyrosine kinases including HER1, HER2, p95HER2, HER3, cMET, IGF-1R, and downstream effector proteins including PI3K, Shc, AKT and ERK, in FNA samples collected from pancreatic cancer patients. Surprisingly, concurrent activation of PI3K along with HER3, IGF-1R and/or cMET in the patient samples. PIK3CA mutations and KRAS mutations (e.g., G12V or G12D) were found in this cohort. FIG. 39 illustrates FNA analysis of biomarkers in pathway profiling of pancreatic cancer patients with KRAS mutations. FIG. 40 illustrates FNA analysis of biomarkers in pathway profiling of pancreatic patients with and without KRAS mutations.

Example 12

Figure 41A:
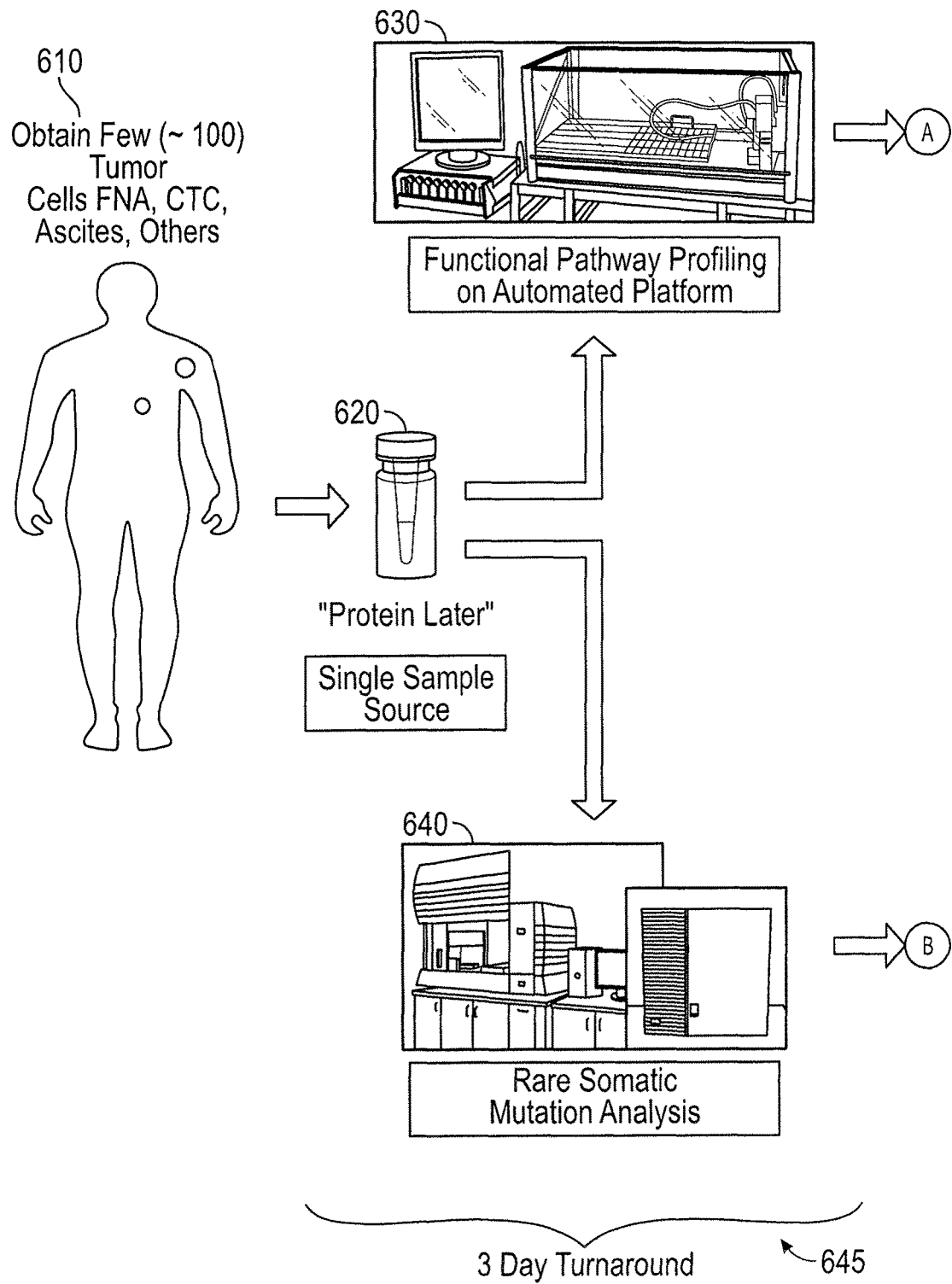
FIGS. 41A-B. show a schematic of an exemplary method of comprehensive disease profiling using a combination of nucleic acid and function protein analysis.
Figure 41B:
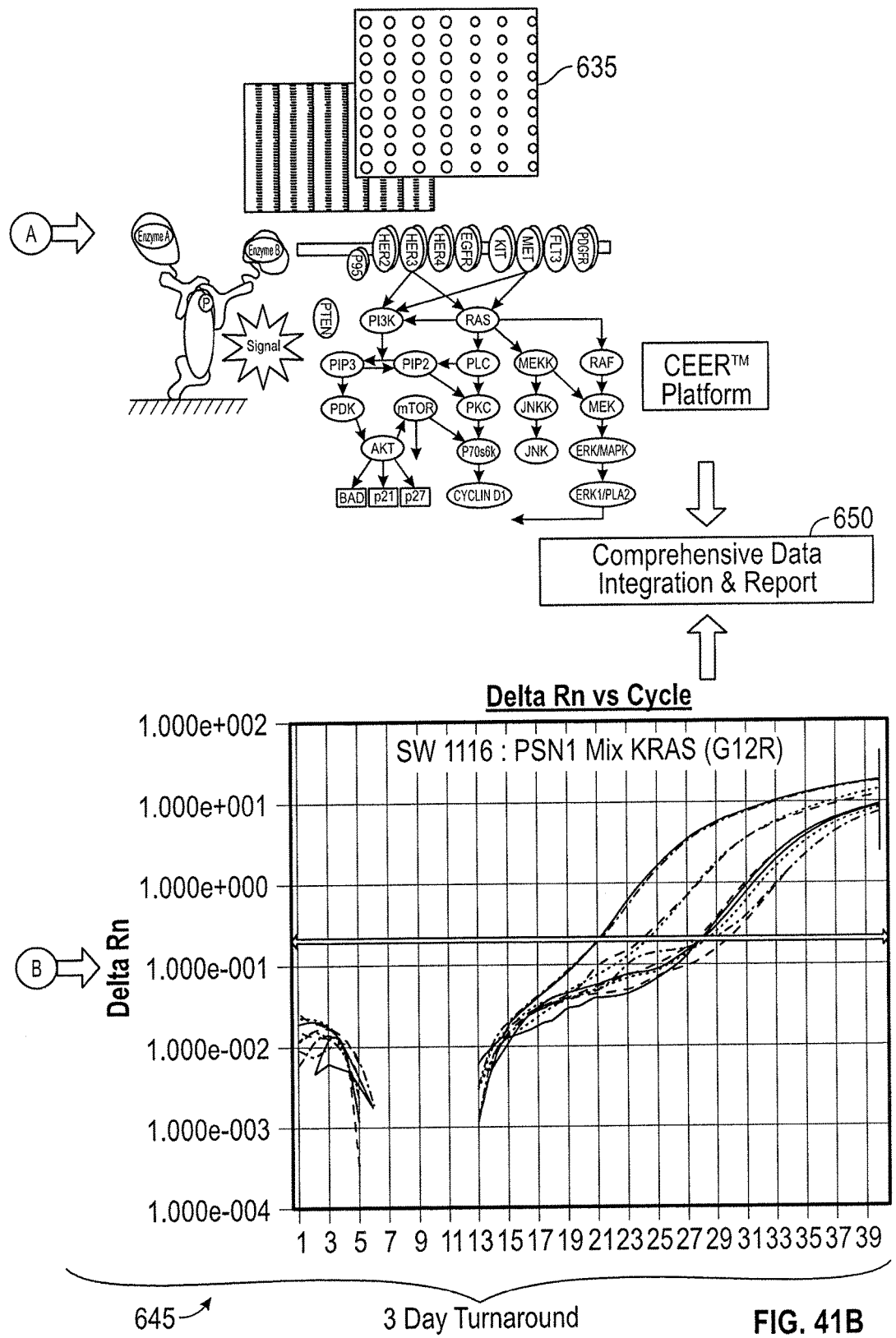

Comprehensive Disease Profiling of Breast Cancer Patients Using Combined Nucleic Acid and Functional Protein Analysis This example illustrates a method of comprehensive disease profiling using a combination of nucleic acid and functional protein analysis. FIGS. 41A-B show a schematic of an exemplary method. The method of the present invention uses as few as about 100 cells obtained from a patient (610). In some embodiments, the sample is from a fine needle aspirate (FNA), circulating tumor cells (CTC), ascites, an endoscopic ultrasound guided biopsy, or other cells harvested from a patient. The harvested patient sample represents the single sample source (620) and can be stored and shipped by methods described in International Patent Publication No. WO2011/008149, which is herein incorporated by reference. An aliquot of the sample can be analyzed using methods for determining the functional pathway profile on an automated platform (630), such as the CEER platform (635). Another aliquot of the sample can be analyzed using methods for determining the presence of rare somatic mutations (640). Non-limiting examples of methods of detecting somatic mutations include allelic variant quantitation and SNP genotyping (645). The methods of the present invention integrate data obtained from functional pathway profiling and somatic mutation analysis to provide a comprehensive disease profile (650). In some embodiments, the disease profile can be presented as a report.

The example describes results from a multi-national and multi-center study of combined CEER-FNA pathway profiling and somatic mutation analysis of breast cancer patients. The details of the study are shown in FIGS. 42 and 43. Tissues from patients were screened for HER2 overexpression by primary immunohistochemistry (IHC) and/or fluorescence in situ hybridization (FISH). Patients undergoing disease relapse and are diagnosed with Stage IIIB or IV breast cancer (124 patients) were enrolled in the study. FNA samples were collected from various and/or multiple metastatic sites from each patient. Non-limiting examples of metastatic sites include liver, bone, axilar and other lymph nodes, lung, skin, chest wall, brain and sternal mass. In some embodiments, FNA was collected in 100 of ProteinLater (Prometheus Laboratories; San Diego, Calif.) with a 23 gauge needle, and stored and shipped at ambient temperature. In other embodiments, the patient's FNA sample was collected in 100 µl of ProteinLater by endoscopic ultrasound (EUS) guided biopsy, and stored and shipped at ambient temperature.

This example describes the interim analysis performed on 58 patients for multiple pathway proteins such as, HER1, HER2, p95HER2, HER3, cMET, IGF-1R, CK, SHC, AKT, ERK and PI3K, and somatic mutations in genes such as PIK3CA, KRAS and BRAF. The CEER assay can be used to detect levels of total protein and/or activated (phosphorylated) protein of signaling pathways (e.g., RTK and PI3K pathways). The profile of RTKs and downstream signaling proteins was obtained for 100% (58 out of 58 patients) of the FNA lysates tested. This is much greater than the ~70% success rate achieved for RNA-based analysis. In some embodiments, 4-8 µl of about 100 µl of the FNA lysate is sufficient for the pathway profiling analysis. The proteins in the FNA lysate are well-preserved for both functional pathway profiling and genotyping screening. In particular, phosphorylated sites are maintained on proteins. Thus, a single sample source can be used for both mutation and pathway profiling to establish a comprehensive disease profile.

Figure 44:
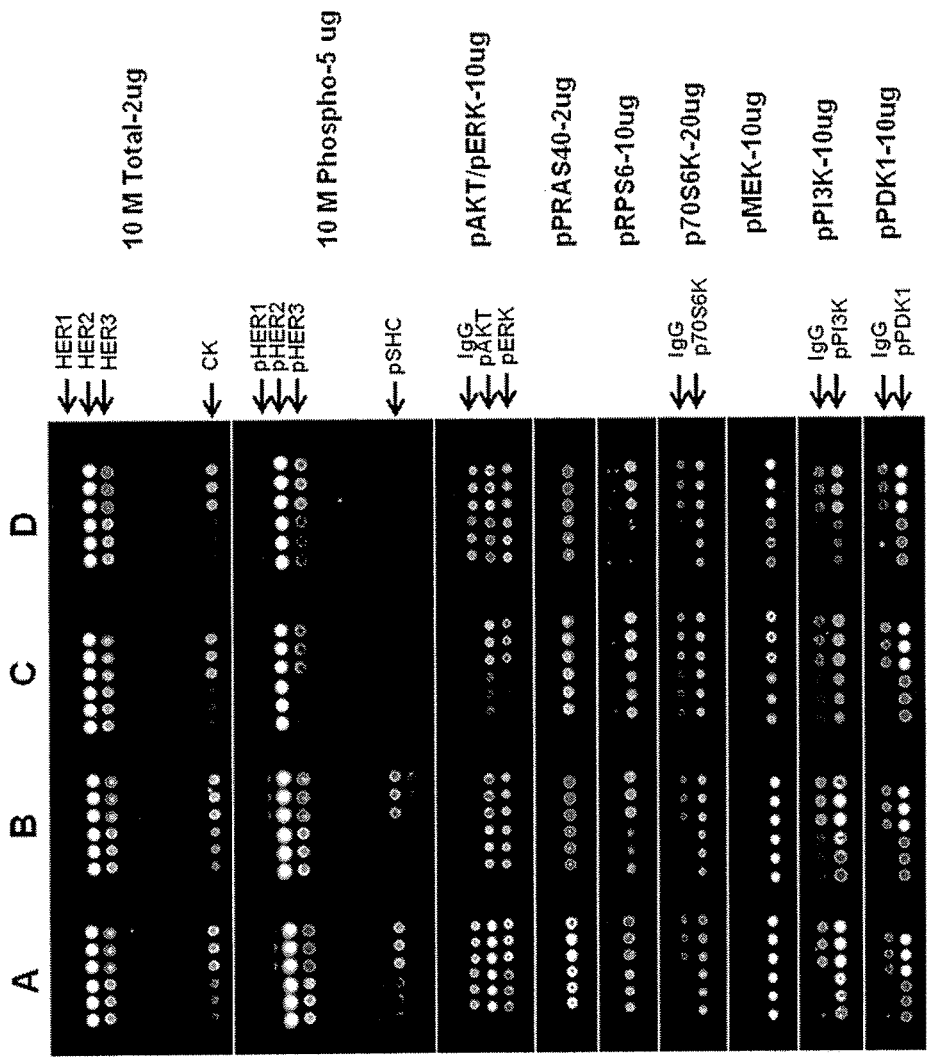
FIG. 44 illustrates activated (phosphorylated) PI3K pathway profiling of breast cancer aspirate from samples (e.g., Panels A, B, C and D) exposed to HER1 inhibitor.

In some embodiments, pathway profiling can be performed on breast cancer aspirate from a patient receiving anti-cancer therapeutic agents. FIG. 44 illustrates the use of PI3K pathway profiling of breast cancer aspirate from a sample exposed to HER1 inhibitor.

Figure 45:
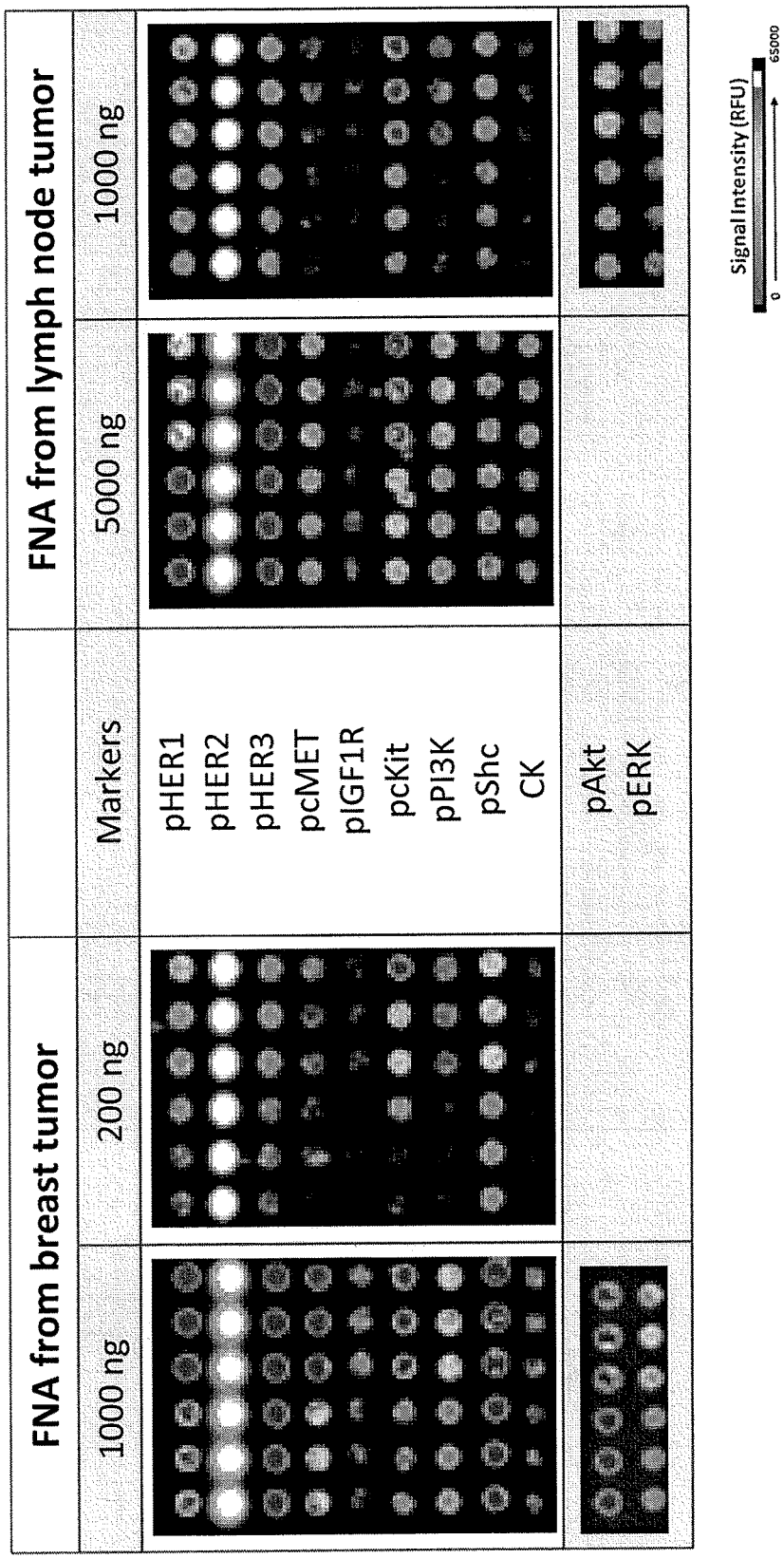
FIG. 45 illustrates activated (phosphorylated) PI3K pathway profiles from FNA of a breast tumor and FNA of a lymph node tumor.

In some embodiments, the methods of the present invention include determining and comparing a signaling pathway and somatic mutation profiles of a patient's primary tumor and secondary tumor from a minimal amount of sample. FIG. 45 illustrates the activated (phosphorylated) PI3K pathway profiles of FNA from a breast tumor and FNA from a lymph node tumor. The FNA samples were obtained using a 23 or 25 gauge needle for either the lymph node or the axilar region. In other instances, the samples were EUS-FNA. FIG. 46A illustrates the level of protein expression of components of the PI3K pathway as determined by the CEER assay. FIG. 46B shows that protein levels of HER1, HER2, HER3, cMET, IGF1R and CK are similar in the patient's breast tumor and lymph node tumor.

In some embodiments, the methods of the present invention can be used to analyze signaling pathway profiles in a patient cohort and establish a correlation between a plurality of biomarkers and disease profiles. In some instances, comprehensive disease profiling of a breast cancer patient can be performed to determine whether the patient would benefit from a treatment comprising a PI3K inhibitor. FIG. 47 shows that in a cohort of breast cancer patients in the study there are statistically significant correlations between activated PI3K pathway proteins, activated PI3K mutations, and combinations thereof. FIG. 48 illustrates the data obtained from comprehensive disease profiling of Patient 14003-3004 in the interim analysis of the study. It was determined using the methods described herein that the patient overexpressed HER2 and has a breast cancer tumor with high HER3 and PI3K activity. The disease profile indicates that the patient can benefit from PI3K inhibitor therapy.

In some embodiments, the methods of the present invention can be used to compare the pathway profile of a tumor and a normal adjacent tissue (NAT). FIG. 49A shows an immunohistochemical image of tissue stained with an anti-pan CK antibody. The tumor cells are positive for CK, while the normal adjacent tissue does not express CK. FIG. 49B illustrates the PI3K pathway profiles of breast cancer tumor samples and normal adjacent tissue samples. FIG. 49C shows results from CEER-FNA assays described herein. The graph shows that pathway profile of tumor samples is different compared to that of normal adjacent tissue. In particular, HER2, HER3, IGF-1R and CK are overexpressed in tumors compared to normal adjacent tissue.

The methods of the present invention can be used to demonstrate that in a breast cancer FNA sample the prevalence of HER2 protein as measured by immunohistochemistry (IHC) correlates with the increased levels of both total p95HER2 protein and phospho-p95HER2 protein as determined by CEER assay. FIG. 50A shows a Western blot for HER2 protein and p95HER2 protein in breast cancer aspirate samples. FIG. 50B shows that tumor samples which highly express HER2 (e.g., 3+) as measured by IHC are more likely to overexpress total p95HER2 protein and activated (phosphorylated) p95HER2 protein compared to those expressing HER2 at 2+ or 1+/0 levels. FIG. 50C represents a graph of total p95HER2 protein expression grouped by IHC measured HER2 expression.

The interim analysis of the study also showed a high concordance (100%) for IHC HER2 (e.g., 3+) samples with CEER. FIG. 51 shows that 6 FNA samples which tested positive for HER2 by CEER were from patients that expressed HER2 positive cells as determined by primary IHC. There was also a 90.5% concordance for IHC HER2 negative tumors with CEER. Notably, 8 patient samples had PI3KCA somatic mutations.

Figure 52:
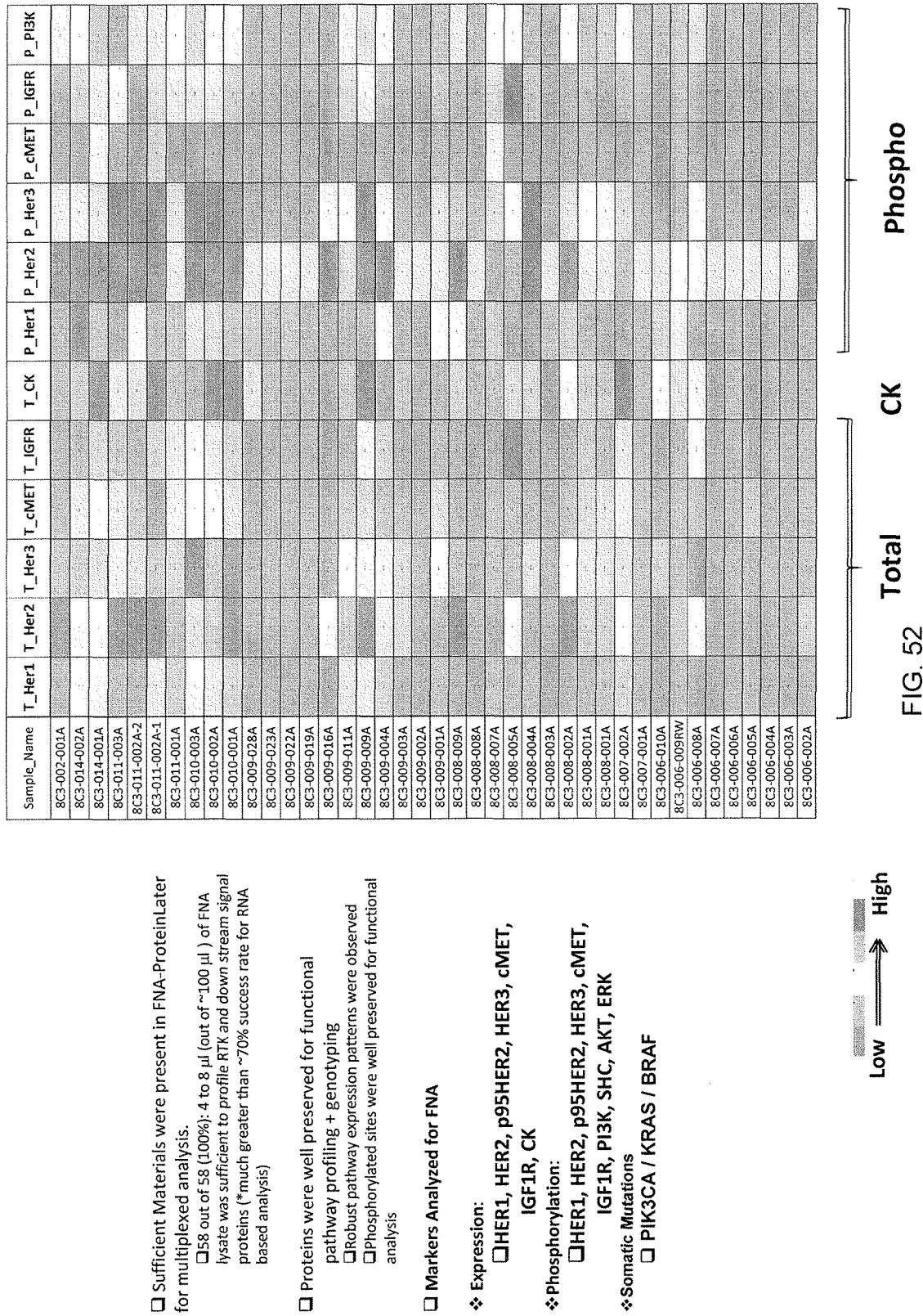
FIG. 52 illustrates a non-limiting example of a comprehensive pathway analysis of the present invention using a combination of functional pathway profiling and genotyping. In particular, FNA samples were analyzed to detect total and activated (i.e., phosphorylated) signaling pathway components (e.g., HER1, HER2, p95HER2, HER3, cMET, IGF-1R, CK, PI3K, SHC, AKT, and/or ERK) by CEER assay and to detect somatic mutations in genes such as PIK3CA, KRAS, and/or BRAF.

The methods of the present invention can be used to determine a comprehensive disease profile for breast cancer patients. FIG. 52 illustrates data from the comprehensive pathway analysis described herein using a combination of functional pathway profiling and genotyping. FNA samples were analyzed to detect total and activated (i.e., phosphorylated) signaling pathway components (e.g., HER1, HER2, p95HER2, HER3, cMET, IGF-1R, CK, PI3K, SHC, AKT, and/or ERK) by CEER assay and to detect somatic mutations in genes such as PIK3CA, KRAS, and/or BRAF.

Example 13

Detection of HER2 Expression and Phosphorylation in Breast Cancer CTC Samples by CEER This example illustrates the use of the methods of the invention for monitoring and quantitating the levels of activated and/or total HER2 protein in a multiplexed immuno-microarray platform, such as the CEER platform.

Survival rates of metastatic breast cancers are considerably low. Tumor cells at the primary site often do not reflect the profile of the tumor cell population in recurrent disease. Evaluating circulating tumor cells (CTCs) in the peripheral blood of patients offers a non-invasive method of monitoring disease. Identification and evaluation of reliable molecular markers within CTCs from patients with recurrent disease can further improve breast cancer survival.

The Collaborative Enzyme Enhanced Reactive-immunoassay (CEER) technology utilizes the formation of a unique immuno-complex requiring co-localization of two detector antibodies in proximity to capture antibodies immobilized on an immuno-array. The collaboration between two channeling-enzymes conjugated on two detection antibodies in proximity, enables the profiling of the target proteins with extreme sensitivity and specificity.

In this study CEER was utilized to analyze the levels of activated and/or total HER2 protein in CTCs isolated from 76 breast cancer patients at stages III to IV with HER2 negative primary disease. Approximately 25% of the HER2 negative BCA patients in this cohort showed varying levels of HER2 activation (phosphorylation) in CTCs isolated from the recurrent disease. About 8% of the patients who determined to have HER2 activation also showed significant over-expression of total HER2 protein.

The results show that HER2 activation takes place in the presence or absence of HER2 over-expression. In some instances, HER2 activation can occur from formation of either HER2 heterodimers (e.g., p95HER2/HER2, HER1/HER2, HER2/HER3, HER2/HER4, etc.) and thus, levels of total HER2 proteins are not elevated. In other instances, HER2 activation can occur from HER2 over-expression and formation HER2 homodimers (e.g., HER2/HER2). The results show that detecting levels of activated and total HER2 protein provide an improved method of monitoring disease in breast cancer patients with recurrent disease.

Since HER2 profiles can vary been a primary tumor and recurrent disease in a patient, there is an urgent need for routine monitoring of HER2 status in CTCs in metastatic breast cancer patients. In addition, monitoring the incidence of HER2 alterations in CTCs using CEER can also aid in the selection of effective treatment regimens for BCA patients with relapsed disease. Furthermore, CEER can be used for profiling other druggable target proteins and guiding the development of effective clinical therapies.

Example 14

Pathway Activation and Somatic Mutation Analysis in Fine Needle Aspirates can Identify Candidate Drugs for Effective Treatment of Breast Cancer This example illustrates a comprehensive genetic and molecular analysis of fine needle aspirates (FNA) samples collected from metastatic sites of 58 breast cancer (BCA) patients. This example illustrates using the methods of the invention, such as performing CEER-FNA pathway analysis to assess RTK pathway activation and oncogenic somatic mutation profiling. In particular, this example illustrates that the methods of the present invention can be used to develop a disease profile from a limited amount of patient sample.

In this study, CEER-FNA pathway analysis included interrogation of key receptor tyrosine kinases and their downstream signaling molecules including HER1, HER2, p95HER2, HER3, cMET, IGF-1R, PI3K, Shc, AKT and ERK, as well as somatic mutational profiling of oncogenic genes (e.g., PI3KCA, KRAS, BRAF, and EGFR). A multiplexed immuno-array CEER (Collaborative Enzyme Enhanced Reactive-immunoassay) platform was utilized to determine the levels of pathway protein expression and activation (e.g., phosphorylation). All FNA samples provided sufficient materials for the combined analysis of multiplexed pathway expression/activation and somatic mutation analysis.

For the unblinded samples, all FNA from metastatic sites (mFNA) collected from HER2 positive primary tumors as by determined by IHC were confirmed to be HER2 positive by CEER analysis. Over-expression of HER2 was found in 10% of mFNAs collected from breast cancer patients with HER2 negative primary tumors. PIK3CA mutations were found in 20% of the samples in this cohort. Statistically significant higher levels of phosphorylated AKT, ERK as well as HER1, HER2, HER3 and IGF-1R were found in mFNAs also carrying PIK3CA mutations. A significant number of PIK3CA wild-type patients also showed robust pathway signatures indicating pathway activation. The results of the study show that evaluation of biomarkers in breast cancer patients should include both pathway proteins as well as mutation analysis.

Comprehensive disease profiling can provide insightful information on the efficacy of specific agents on their intended target proteins. The multiplexed pathway analysis of the present invention can also provide valuable information regarding potential drug resistance mechanisms. Furthermore, the combined mutational and pathway activation profiling described herein can help guide therapeutic strategies in a clinical setting.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

INFORMAL SEQUENCE LISTING

```
<160> NUMBER OF SEQ ID NOS:
<210> SEQ ID NO 1
<211> LENGTH: 724
<212> TYPE: prt
<213> ORGANISM Homo sapiens
<223> OTHER INFORMATION: PI3K p85α

<400> SEQUENCE: 1
MSAEGYQYRALYDYKKEREEDIDLHLGDILTVNKGSLVALGFSDGQEARPEEIGWLNGYN
ETTGERGDFPGTYVEYIGRKKISPPTPKPRPPRPLPVAPGSSKTEADVEQQALTLPDLAE
QFAPPDIAPPLLIKLVEAIEKKGLECSTLYRTQSSSNLAELRQLLDCDTPSVDLEMIDVH
VLADAFKRYLLDLPNPVIPAAVYSEMISLAPEVQSSEEYIQLLKKLIRSPSIPHQYWLTL
QYLLKHFFKLSQTSSKNLLNARVLSEIFSPMLFRFSAASSDNTENLIKVIEILISTEWNE
RQPAPALPPKPPKPTTVANNGMNNNMSLQDAEWYWGDISREEVNEKLRDTADGTFLVRDA
```

| INFORMAL SEQUENCE LISTING |
| --- |

STKMHGDYTLTLRKGGNNKLIKIFHRDGKYGFSDPLTFSSVVELINHYRNESLAQYNPKL
DVKLLYPVSKYQQDQVVKEDNIEAVGKKLHEYNTQFQEKSREYDRLYEEYTRTSQEIQMK
RTATEAFNETIKIFEEQCQTQERYSKEYIEKFKREGNEKEIQRIMHNYDKLKSRISETID
SRRRLEEDLKKQAAEYREIDKRMNSIKPDLIQLRKTRDQYLMWLTQKGVRQKKLNEWLGN
ENTEDQYSLVEDDEDLPHHDEKTWNVGSSNRNKAENLLRGKRDGTFLVRESSKQGCYACS
VVVDGEVKHCVINKTATGYGFAEPYNLYSSLKELVLHYQHTSLVQHNDSLNVTLAYPVYA
QQRR

<210> SEQ ID NO 2
<211> LENGTH: 728
<212> TYPE: prt
<213> ORGANISM Homo sapiens
<223> OTHER INFORMATION: PI3K p85β

<400> SEQUENCE: 2
MAGPEGFQYRALYPFRRERPEDLELLPGDVLVVSRAALQALGVAEGGERCPQSVGWMPGL
NERTRQRGDFPGTYVEFLGPVALARPGPRPRGPRPLPARPRDGAPEPGLTLPDLPEQFSP
PDVAPPLLVKLVEATERTGLDSESHYRPELPAPRTDWSLSDVDQWDTAALADGIKSFLLA
LPAPLVTPEASAEARRALREAAGPVGPALEPPTLPLHRALTLRFLLQHLGRVASRAPALG
PAVRALGATFGPLLLRAPPPPSSPPPGGAPDGSEPSPDFPALLVEKLLQEHLEEQEVAPP
ALPPKPPKAKPASTVLANGGSPPSLQDAEWYWGDISREEVNEKLRDTPDGTFLVRDASSK
IQGEYTLTLRKGGNNKLIKVFHRDGHYGFSEPLTFCSVVDLINHYRHESLAQYNAKLDTR
LLYPVSKYQQDQIVKEDSVEAVGAQLKVYHQQYQDKSREYDQLYEEYTRTSQELQMKRTA
IEAFNETIKIFEEQGQTQEKCSKEYLERFRREGNEKEMQRILLNSERLKSRIAEIHESRT
KLEQQLRAQASDNREIDKRMNSLKPDLMQLRKIRDQYLVWLTQKGARQKKINEWLGIKNE
TEDQYALMEDEDDLPHHEERTWYVGKINRTQAEEMLSGKRDGTFLIRESSQRGCYACSVV
VDGDTKHCVIYRTATGFGFAEPYNLYGSLKELVLHYQHASLVQHNDALTVTLAHPVRAPG
PGPPPAAR

<210> SEQ ID NO 3
<211> LENGTH: 461
<212> TYPE: PRT
<213> ORGANISM Homo sapiens
<223> OTHER INFORMATION: PI3K p55γ

<400> SEQUENCE: 3
MYNTVWSMDRDDADWREVMMPYSTELIFYIEMDPPALPPKPPKPMTSAVPNGMKDSSVSL
QDAEWYWGDISREEVNDKLRDMPDGTFLVRDASTKMQGDYTLTLRKGGNNKLIKIYHRDG
KYGFSDPLTFNSVVELINHYHHESLAQYNPKLDVKLMYPVSRYQQDQLVKEDNIDAVGKK
LQEYHSQYQEKSKEYDRLYEEYTRTSQEIQMKRTAIEAFNETIKIFEEQCHTQEQHSKEY
IERFRREGNEKEIERIMMNYDKLKSRLGEIHDSKMRLEQDLKNQALDNREIDKKMNSIKP
DLIQLRKIRDQHLVWLNHKGVRQKRLNVWLGIKNEDADENYFINEEDENLPHYDEKTWFV
EDINRVQAEDLLYGKPDGAFLIRESSKKGCYACSVVADGEVKHCVIYSTARGYGFAEPYN
LYSSLKELVLHYQQTSLVQHNDSLNVRLAYPVHAQMPSLCR

<210> SEQ ID NO 4
<211> LENGTH: 1358
<212> TYPE: PRT
<213> ORGANISM Homo sapiens
<223> OTHER INFORMATION: PI3K p150

<400> SEQUENCE: 4
MGNQLAGIAPSQILSVESYFSDIHDFEYDKSLGSTRFFKVARAKHREGLVVVKVFAIQDP
TLPLTSYKQELEELKIRLNSAQNCLPFQKASEKASEKAAMLFRQYVRDNLYDRISTRPFL
NNIEKRWIAFQILTAVDQAHKSGVRHGDIKTENVMVTSWNWVLLTDFASFKPTYLPEDNP
ADFNYFFDTSRRRTCYIAPERFVDGGMFATELEYMRDPSTPLVDLNSNQRTRGELKRAMD
IFSAGCVIAELFTEGVPLFDLSQLLAYRNGHFFPEQVLNKIEDHSIRELVTQMIHREPDK
RLEAEDYLKQQRGNAFPEIFYTELQPYMAQFAKETELSADERILVIRKDLGNIIHNLCGH
DLPEKAEGEPKENGLVILVSVITSCLQTLKYCDSKLAALELILHLAPRLSVEILLDRITP
YLLHFSNDSVPRVRAEALRTLTKVLALVKEVPRNDINIYPEYILPGIAHLAQDDATIVRL
AYAENIALLAETALRFLELVQLKNLNMENDPNNEEIDEVTHPNGNYDTELQALHEMVQQK
VVTLLSDPENIVKQTLMENGITRLCVFFGRQKANDVLLSHMITFLNDKNDWHLRGAFFDS
IVGVAAYVGWQSSSILKPLLQQGLSDAEEFVIVKALYALTCMCQLGLLQKPHVYEFASDI
APFLCHPNLWIRYGAVGFITVVARQISTADVYCKLMPYLDPYITQPIIQIERKLVLLSVL
KEPVSRSIFDYALRSKDITSLFRHLHMRQKKRNGSLPDCPPPEDPAIAQLLKKLLSQGMT
EEEEDKLLALKDFMMKSNKAKANIVDQSHLHDSSQKGVIDLAALGITGRQVDLVKTKQEP
DDKRARKHVKQDSNVNEEWKSMFGSLDPPNMPQALPKGSDQEVIQTGKPPRSESSAGICV
PLSTSSQVPEVTTVQNKKPVIPVLSSTILPSTYQIRITTCKTELQQLIQQKREQCNAERI
AKQMMENAEWESKPPPPGWRPKGLLVAHLHEHKSAVNRIRVSDEHSLFATCSNDGTVKIW
NSQKMEGKTTTTRSILTYSRIGGRVKILTFCQGSHYLAIASDNGAVQLLGIEASKLPKSP
KIHPLQSRILDQKEDGCVVDMHHFNSGAQSVLAYATVNGSLVGWDLRSSSNAWTLKHDLK
SGLITSFAVDIHQCWLCIGTSSGTMACWDMRFQLPISSHCHPSRARIRRLSMHPLYQSWV
IAAVQGNNEVSMWDMETGDRRFTLWASSAPPLSELQPSPHSVHGIYCSPADGNPILLTAG
SDMKIRFWDLAYPERSYVVAGSTSSPSVSYYRKIIEGTEVVQEIQNKQKVGPSDDTPRRG
PESLPVGHHDIITDVATFQTTQGFIVTASRDGIVKVWK

-continued

INFORMAL SEQUENCE LISTING

<210> SEQ ID NO 5
<211> LENGTH: 880
<212> TYPE: PRT
<213> ORGANISM Homo sapiens
<223> OTHER INFORMATION: PI3K p101

<400> SEQUENCE: 5
MQPGATTCTEDRIQHALERCLHGLSLSRRSTSWSAGLCLNCWSLQELVSRDPGHFLILLE
QILQKTREVQEKGTYDLLTPLALLFYSTVLCTPHFPPDSDLLLKAASTYHRFLTWPVPYC
SICQELLTFIDAELKAPGISYQRLVRAEQGLPIRSHRSSTVTVLLLNPVEVQAEFLAVAN
KLSTPGHSPHSAYTTLLLHAFQATFGAHCDVPGLHCRLQAKTLAELEDIFTETAEAQELA
SGIGDAAEARRWLRTKLQAVGEKAGFPGVLDTAKPGKLHTIPIPVARCYTYSWSQDSFDI
LQEILLKEQELLQPGILGDDEEEEEEEEEVEEDLETDGHCAERDSLLSTSSLASHDSTLS
LASSQASGPALSRHLLTSFVSGLSDGMDSGYVEDSEESSSEWPWRRGSQERRGHRRPGQK
FIRIYKLFKSTSQLVLRRDSRSLEGSSDTALPLRRAGSLCSPLDEPVSPPSRAQRSRSLP
QPKLGTQLPSWLLAPASRPQRRRPFLSGDEDPKASTLRVVVFGSDRISGKVARAYSNLRR
LENNRPLLTRFFKLQFFYVPVKRSHGTSPGACPPPRSQTPSPPTDSPRHASPGELGTTPW
EESTNDISHYLGMLDPWYERNVLGLMHLPPEVLCQQSLKAEAQALEGSPTQLPILADMLL
YYCRFAARPVLLQVYQTELTFITGEKTTEIFIHSLELGHSAATRAIKASGPGSKRLGIDG
DREAVPLTLQIIYSKGAISGRSRWSNLEKVCTSVNLNKACRKQEELDSSMEALTLNLTEV
VKRQNSKSKKGFNQISTSQIKVDKVQIIGSNSCPFAVCLDQDERKILQSVVRCEVSPCYK
PEKSDLSSPPQTPPDLPAQAAPDLCSLLCLPIMTFSGALP

<210> SEQ ID NO 6
<211> LENGTH: 1068
<212> TYPE: PRT
<213> ORGANISM Homo sapiens
<223> OTHER INFORMATION: PI3K p110α

<400> SEQUENCE: 6
MPPRPSSGELWGIHLMPPRILVECLLPNGMIVTLECLREATLITIKHELFKEARKYPLHQ
LLQDESSYIFVSVTQEAEREEFFDETRRLCDLRLFQPFLKVIEPVGNREEKILNREIGFA
IGMPVCEFDMVKDPEVQDFRRNILNVCKEAVDLRDLNSPHSRAMYVYPPNVESSPELPKH
IYNKLDKGQIIVVIWVIVSPNNDKQKYTLKINHDCVPEQVIAEAIRKKTRSMLLSSEQLK
LCVLEYQGKYILKVCGCDEYFLEKYPLSQYKYIRSCIMLGRMPNLMLMAKESLYSQLPMD
CFTMPSYSRRISTATPYMNGETSTKSLWVINSALRIKILCATYVNVNIRDIDKIYVRTGI
YHGGEPLCDNVNTQRVPCSNPRWNEWLNYDIYIPDLPRAARLCLSICSVKGRKGAKEEHC
PLAWGNINLFDYTDTLVSGKMALNLWPVPHGLEDLLNPIGVTGSNPNKETPCLELEFDWF
SSVVKFPDMSVIEEHANWSVSREAGFSYSHAGLSNRLARDNELRENDKEQLKAISTRDPL
SEITEQEKDFLWSHRHYCVTIPEILPKLLLSVKWNSRDEVAQMYCLVKDWPPIKPEQAME
LLDCNYPDPMVRGFAVRCLEKYLTDDKLSQYLIQLVQVLKYEQYLDNLLVRFLLKKALTN
QRIGHFFFWHLKSEMHNKTVSQRFGLLLESYCRACGMYLKHLNRQVEAMEKLINLTDILK
QEKKDETQKVQMKFLVEQMRRPDFMDALQGFLSPLNPAHQLGNLRLEECRIMSSAKRPLW
LNWENPDIMSELLFQNNEIIFKNGDDLRQDMLTLQIIRIMENIWQNQGLDLRMLPYGCLS
IGDCVGLIEVVRNSHTIMQIQCKGGLKGALQFNSHTLHQWLKDKNKGEIYDAAIDLFTRS
CAGYCVATFILGIGDRHNSNIMVKDDGQLFHIDFGHFLDHKKKKFGYKRERVPFVLTQDF
LIVISKGAQECTKTREFERFQEMCYKAYLAIRQHANLFINLFSMMLGSGMPELQSFDDIA
YIRKTLALDKTEQEALEYFMKQMNDAHHGGWTTKMDWIFHTIKQHALN

<210> SEQ ID NO 7
<211> LENGTH: 1070
<212> TYPE: PRT
<213> ORGANISM Homo sapiens
<223> OTHER INFORMATION: PI3K p110β

<400> SEQUENCE: 7
MCFSFIMPPAMADILDIWAVDSQIASDGSIPVDFLLPTGIYIQLEVPREATISYIKQMLW
KQVHNYPMFNLLMDIDSYMFACVNQTAVYEELEDETRRLCDVRPFLPVLKLVTRSCDPGE
KLDSKIGVLIGKGLHEFDSLKDPEVNEFRRKMRKFSEEKILSLVGLSWMDWLKQTYPPEH
EPSIPENLEDKLYGGKLIVAVHFENCQDVFSFQVSPNMNPIKVNELAIQKRLTIHGKEDE
VSPYDYVLQVSGRVEYVFGDHPLIQFQYIRNCVMNRALPHFILVECCKIKKMYEQEMIAI
EAAINRNSSNLPLPLPPKKTRIISHVWENNNPFQIVLVKGNKLNTEETVKVHVRAGLFHG
TELLCKTIVSSEVSGKNDHIWNEPLEFDINICDLPRMARLCFAVYAVLDKVKTKKSTKTI
NPSKYQTIRKAGKVHYPVAWVNTMVFDFKGQLRTGDIILHSWSSFPDELEEMLNPMGTVQ
TNPYTENATALHVKFPENKKQPYYYPPFDKIIEKAAEIASSDSANVSSRGGKKFLPVLKE
ILDRDPLSQLCENEMDLIWTLRQDCREIFPQSLPKLLLSIKWNKLEDVAQLQALLQIWPK
LPPREALELLDFNYPDQYVREYAVGCLRQMSDEELSQYLLQLVQVLKYEPFLDCALSRFL
LERALGNRRIGQFLFWHLRSEVHIPAVSVQFGVILEAYCRGSVGHMKVLSKQVEALNKLK
TLNSLIKLNAVKLNRAKGKEAMHTCLKQSAYREALSDLQSPLNPCVILSELYVEKCKYMD
SKMKPLWLVYNNKVFGEDSVGVIFKNGDDLRQDMLTLQMLRLMDLLWKEAGLDLRMLPYG
CLATGDRSGLIEVVSTSETIADIQLNSSNVAAAAAFNKDALLNWLKEYNSGDDLDRAIEE
FTLSCAGYCVASYVLGIGDRHSDNIMVKKTGQLFHIDFGHILGNFKSKFGIKRERVPFIL
TYDFIHVIQQGKTGNTEKFGRFRQCCEDAYLILRRHGNLFITLFALMLTAGLPELTSVKD
IQYLKDSLALGKSEEEALKQFKQKFDEALRESWTTKVNWMAHTVRKDYRS

INFORMAL SEQUENCE LISTING

<210> SEQ ID NO 8
<211> LENGTH: 1102
<212> TYPE: PRT
<213> ORGANISM Homo sapiens
<223> OTHER INFORMATION: PI3K p110γ

<400> SEQUENCE: 8
MELENYKQPVVLREDNCRRRRMKPRSAAASLSSMELIPIEFVLPTSQRKCKSPETALLH
VAGHGNVEQMKAQVWLRALETSVAADFYHRLGPHHFLLLYQKKGQWYEIYDKYQVVQTLD
CLRYWKATHRSPGQIHLVQRHPPSEESQAFQRQLTALIGYDVTDVSNVHDDELEFTRRGL
VTPRMAEVASRDPKLYAMHPWVTSKPLPEYLWKKIANNCIFIVIHRSTTSQTIKVSPDDT
PGAILQSFFTKMAKKKSLMDIPESQSEQDFVLRVCGRDEYLVGETPIKNFQWVRHCLKNG
EEIHVVLDTPPDPALDEVRKEEWPLVDDCTGVTGYHEQLTIHGKDHESVFTVSLWDCDRK
FRVKIRGIDIPVLPRNTDLTVFVEANIQHGQQVLCQRRTSPKPFTEEVLWNVWLEFSIKI
KDLPKGALLNLQIYCGKAPALSSKASAESPSSESKGKVQLLYYVNLLLIDHRFLLRRGEY
VLHMWQISGKGEDQGSFNADKLTSATNPDKENSMSISILLDNYCHPIALPKHQPTPDPEG
DRVRAEMPNQLRKQLEAIIATDPLNPLTAEDKELLWHFRYESLKHPKAYPKLFSSVKWGQ
QEIVAKTYQLLARREVWDQSALDVGLTMQLLDCNFSDENVRAIAVQKLESLEDDDVLHYL
LQLVQAVKFEPYHDSALARFLLKRGLRNKRIGHFLFWFLRSEIAQSRHYQQRFAVILEAY
LRGCGTAMLHDFTQQVQVIEMLQKVTLDIKSLSAEKYDVSSQVISQLKQKLENLQNSQLP
ESFRVPYDPGLKAGALAIEKCKVMASKKKPLWLEFKCADPTALSNETIGIIFKHGDDLRQ
DMLILQILRIMESIWETESLDLCLLPYGCISTGDKIGMIEIVKDATTIAKIQQSTVGNTG
APKDEVLNHWLKEKSPTEEKFQAAVERFVYSCAGYCVATFVLGIGDRHNDNIMITETGNL
FHIDFGHILGNYKSFLGINKERVPFVLTPDFLFVMGTSGKKTSPHFQKFQDICVKAYLAL
RHHTNLLIILFSMMLMTGMPQLTSKEDIEYIRDALTVGKNEEDAKKYFLDQIEVCRDKGW
TVQFNWFLHLVLGIKQGEKHSA

<210> SEQ ID NO 9
<211> LENGTH: 1044
<212> TYPE: PRT
<213> ORGANISM Homo sapiens
<223> OTHER INFORMATION: PI3K p110δ

<400> SEQUENCE: 9
MPPGVDCPMEFWTKEENQSVVVDFLLPTGVYLNFPVSRNANLSTIKQLLWHRAQYEPLFH
MLSGPEAYVFTCINQTAEQQELEDEQRRLCDVQPFLPVLRLVAREGDRVKKLINSQISLL
IGKGLHEFDSLCDPEVNDFRAKMCQFCEEAAARRQQLGWEAWLQYSFPLQLEPSAQTWGP
GTLRLPNRALLVNVKFEGSEESFTFQVSTKDVPLALMACALRKKATVFRQPLVEQPEDYT
LQVNGRHEYLYGSYPLCQFQYICSCLHSGLTPHLTMVHSSSILAMRDEQSNPAPQVQKPR
AKPPPIPAKKPSSVSLWSLEQPFRIELIQGSKVNADERMKLVVQAGLFHGNEMLCKTVSS
SEVSVCSEPVWKQRLEFDINICDLPRMARLCFALYAVIEKAKKARSTKKKSKKADCPIAW
ANLMLFDYKDQLKTGERCLYMWPSVPDEKGELLNPTGTVRSNPNTDSAAALLICLPEVAP
HPVYYPALEKILELGRHSECVHVTEEEQLQLREILERRGSGELYEHEKDLVWKLRHEVQE
HFPEALARLLLVTKWNKHEDVAQMLYLLCSWPELPVLSALELLDFSFPDCHVGSFAIKSL
RKLTDDELFQYLLQLVQVLKYESYLDCELTKFLLDRALANRKIGHFLFWHLRSEMHVPSV
ALRFGLILEAYCRGSTHHMKVLMKQGEALSKLKALNDFVKLSSQKTPKPQTKELMHLCMR
QEAYLEALSHLQSPLDPSTLLAEVCVEQCTFMDSKMKPLWIMYSNEEAGSGGSVGIIFKN
GDDLRQDMLTLQMIQLMDVLWKQEGLDLRMTPYGCLPTGDRTGLIEVVLRSDTIANIQLN
KSNMAATAAFNKDALLNWLKSKNPGEALDRAIEEFTLSCAGYCVATYVLGIGDRHSDNIM
IRESGQLFHIDFGHFLGNFKTKFGINRERVPFILTYDEVHVIQQGKTNNSEKFERFRGYC
ERAYTILRRHGLLFLHLFALMRAAGLPELSCSKDIQYLKDSLALGKTEEEALKHFRVKFN
EALRESWKTKVNWLAHNVSKDNRQ

<210> SEQ ID NO 10
<211> LENGTH: 17
<212> TYPE: PRT
<213> ORGANISM Homo sapiens
<220> FEATURE:
<221> NAME/KEY: MOD_RES
<222> (10) . . . (10)
<223> OTHER INFORMATION: PHOSPHORYLATION; tyrosine at position 10 is phosphorylated

<400> SEQUENCE: 10
CGFAEPYNLYSSLKEKV

<210> SEQ ID NO 11
<211> LENGTH: 15
<212> TYPE: PRT
<213> ORGANISM Homo sapiens
<220> FEATURE:
<221> NAME/KEY: MOD_RES
<222> (9) . . . (9)
<223> OTHER INFORMATION: PHOSPHORYLATION; tyrosine at position 9 is phosphorylated

INFORMAL SEQUENCE LISTING

<400> SEQUENCE: 11
CSKEYDRLYEEYTRT

<210> SEQ ID NO 12
<211> LENGTH: 128
<212> TYPE: PRT
<213> ORGANISM Homo sapiens
<223> OTHER INFORMATION: PI3K p110 antigen
<400> SEQUENCE: 12
MPPRPSSGELWGIHLMPPRILVECLLPNGMIVTLECLREA
TLVTIKHELFKEARKYPLHQLLQDESSYIFVSVTQEAERE
EFFDETRRLCDLRLFQPFLKVIEPVGNREEKLNREIGFAI
GMPVCE

SEQUENCE LISTING

<160> NUMBER OF SEQ ID NOS: 12

<210> SEQ ID NO 1
<211> LENGTH: 724
<212> TYPE: PRT
<213> ORGANISM: Homo sapiens
<220> FEATURE:
<223> OTHER INFORMATION: phosphatidylinositol 3-kinase (PI3K) regulatory subunit p85alpha

<400> SEQUENCE: 1

```
Met Ser Ala Glu Gly Tyr Gln Tyr Arg Ala Leu Tyr Asp Tyr Lys Lys
  1               5                  10                  15

Glu Arg Glu Glu Asp Ile Asp Leu His Leu Gly Asp Ile Leu Thr Val
             20                  25                  30

Asn Lys Gly Ser Leu Val Ala Leu Gly Phe Ser Asp Gly Gln Glu Ala
         35                  40                  45

Arg Pro Glu Glu Ile Gly Trp Leu Asn Gly Tyr Asn Glu Thr Thr Gly
     50                  55                  60

Glu Arg Gly Asp Phe Pro Gly Thr Tyr Val Glu Tyr Ile Gly Arg Lys
 65                  70                  75                  80

Lys Ile Ser Pro Pro Thr Pro Lys Pro Arg Pro Pro Arg Pro Leu Pro
                 85                  90                  95

Val Ala Pro Gly Ser Ser Lys Thr Glu Ala Asp Val Glu Gln Gln Ala
            100                 105                 110

Leu Thr Leu Pro Asp Leu Ala Glu Gln Phe Ala Pro Pro Asp Ile Ala
        115                 120                 125

Pro Pro Leu Leu Ile Lys Leu Val Glu Ala Ile Glu Lys Lys Gly Leu
    130                 135                 140

Glu Cys Ser Thr Leu Tyr Arg Thr Gln Ser Ser Ser Asn Leu Ala Glu
145                 150                 155                 160

Leu Arg Gln Leu Leu Asp Cys Asp Thr Pro Ser Val Asp Leu Glu Met
                165                 170                 175

Ile Asp Val His Val Leu Ala Asp Ala Phe Lys Arg Tyr Leu Leu Asp
            180                 185                 190

Leu Pro Asn Pro Val Ile Pro Ala Ala Val Tyr Ser Glu Met Ile Ser
        195                 200                 205

Leu Ala Pro Glu Val Gln Ser Ser Glu Glu Tyr Ile Gln Leu Leu Lys
    210                 215                 220

Lys Leu Ile Arg Ser Pro Ser Ile Pro His Gln Tyr Trp Leu Thr Leu
225                 230                 235                 240
```

```
Gln Tyr Leu Leu Lys His Phe Phe Lys Leu Ser Gln Thr Ser Ser Lys
                245                 250                 255

Asn Leu Leu Asn Ala Arg Val Leu Ser Glu Ile Phe Ser Pro Met Leu
                260                 265                 270

Phe Arg Phe Ser Ala Ala Ser Ser Asp Asn Thr Glu Asn Leu Ile Lys
            275                 280                 285

Val Ile Glu Ile Leu Ile Ser Thr Glu Trp Asn Glu Arg Gln Pro Ala
        290                 295                 300

Pro Ala Leu Pro Pro Lys Pro Pro Lys Pro Thr Thr Val Ala Asn Asn
305                 310                 315                 320

Gly Met Asn Asn Asn Met Ser Leu Gln Asp Ala Glu Trp Tyr Trp Gly
                325                 330                 335

Asp Ile Ser Arg Glu Glu Val Asn Glu Lys Leu Arg Asp Thr Ala Asp
                340                 345                 350

Gly Thr Phe Leu Val Arg Asp Ala Ser Thr Lys Met His Gly Asp Tyr
            355                 360                 365

Thr Leu Thr Leu Arg Lys Gly Gly Asn Asn Lys Leu Ile Lys Ile Phe
        370                 375                 380

His Arg Asp Gly Lys Tyr Gly Phe Ser Asp Pro Leu Thr Phe Ser Ser
385                 390                 395                 400

Val Val Glu Leu Ile Asn His Tyr Arg Asn Glu Ser Leu Ala Gln Tyr
                405                 410                 415

Asn Pro Lys Leu Asp Val Lys Leu Leu Tyr Pro Val Ser Lys Tyr Gln
                420                 425                 430

Gln Asp Gln Val Val Lys Glu Asp Asn Ile Glu Ala Val Gly Lys Lys
            435                 440                 445

Leu His Glu Tyr Asn Thr Gln Phe Gln Glu Lys Ser Arg Glu Tyr Asp
        450                 455                 460

Arg Leu Tyr Glu Glu Tyr Thr Arg Thr Ser Gln Glu Ile Gln Met Lys
465                 470                 475                 480

Arg Thr Ala Ile Glu Ala Phe Asn Glu Thr Ile Lys Ile Phe Glu Glu
                485                 490                 495

Gln Cys Gln Thr Gln Glu Arg Tyr Ser Lys Glu Tyr Ile Glu Lys Phe
                500                 505                 510

Lys Arg Glu Gly Asn Glu Lys Glu Ile Gln Arg Ile Met His Asn Tyr
            515                 520                 525

Asp Lys Leu Lys Ser Arg Ile Ser Glu Ile Ile Asp Ser Arg Arg Arg
        530                 535                 540

Leu Glu Glu Asp Leu Lys Lys Gln Ala Ala Glu Tyr Arg Glu Ile Asp
545                 550                 555                 560

Lys Arg Met Asn Ser Ile Lys Pro Asp Leu Ile Gln Leu Arg Lys Thr
                565                 570                 575

Arg Asp Gln Tyr Leu Met Trp Leu Thr Gln Lys Gly Val Arg Gln Lys
            580                 585                 590

Lys Leu Asn Glu Trp Leu Gly Asn Glu Asn Thr Glu Asp Gln Tyr Ser
        595                 600                 605

Leu Val Glu Asp Asp Glu Asp Leu Pro His His Asp Glu Lys Thr Trp
610                 615                 620

Asn Val Gly Ser Ser Asn Arg Asn Lys Ala Glu Asn Leu Leu Arg Gly
625                 630                 635                 640

Lys Arg Asp Gly Thr Phe Leu Val Arg Glu Ser Ser Lys Gln Gly Cys
                645                 650                 655
```

```
Tyr Ala Cys Ser Val Val Asp Gly Glu Val Lys His Cys Val Ile
            660                 665                 670

Asn Lys Thr Ala Thr Gly Tyr Gly Phe Ala Glu Pro Tyr Asn Leu Tyr
        675                 680                 685

Ser Ser Leu Lys Glu Leu Val Leu His Tyr Gln His Thr Ser Leu Val
    690                 695                 700

Gln His Asn Asp Ser Leu Asn Val Thr Leu Ala Tyr Pro Val Tyr Ala
705                 710                 715                 720

Gln Gln Arg Arg

<210> SEQ ID NO 2
<211> LENGTH: 728
<212> TYPE: PRT
<213> ORGANISM: Homo sapiens
<220> FEATURE:
<223> OTHER INFORMATION: phosphatidylinositol 3-kinase (PI3K) regulatory
      subunit p85beta

<400> SEQUENCE: 2

Met Ala Gly Pro Glu Gly Phe Gln Tyr Arg Ala Leu Tyr Pro Phe Arg
1               5                   10                  15

Arg Glu Arg Pro Glu Asp Leu Glu Leu Leu Pro Gly Asp Val Leu Val
            20                  25                  30

Val Ser Arg Ala Ala Leu Gln Ala Leu Gly Val Ala Glu Gly Gly Glu
        35                  40                  45

Arg Cys Pro Gln Ser Val Gly Trp Met Pro Gly Leu Asn Glu Arg Thr
    50                  55                  60

Arg Gln Arg Gly Asp Phe Pro Gly Thr Tyr Val Glu Phe Leu Gly Pro
65                  70                  75                  80

Val Ala Leu Ala Arg Pro Gly Pro Arg Pro Arg Gly Pro Arg Pro Leu
                85                  90                  95

Pro Ala Arg Pro Arg Asp Gly Ala Pro Glu Pro Gly Leu Thr Leu Pro
            100                 105                 110

Asp Leu Pro Glu Gln Phe Ser Pro Pro Asp Val Ala Pro Pro Leu Leu
        115                 120                 125

Val Lys Leu Val Glu Ala Ile Glu Arg Thr Gly Leu Asp Ser Glu Ser
    130                 135                 140

His Tyr Arg Pro Glu Leu Pro Ala Pro Arg Thr Asp Trp Ser Leu Ser
145                 150                 155                 160

Asp Val Asp Gln Trp Asp Thr Ala Ala Leu Ala Asp Gly Ile Lys Ser
                165                 170                 175

Phe Leu Leu Ala Leu Pro Ala Pro Leu Val Thr Pro Glu Ala Ser Ala
            180                 185                 190

Glu Ala Arg Arg Ala Leu Arg Glu Ala Ala Gly Pro Val Gly Pro Ala
        195                 200                 205

Leu Glu Pro Pro Thr Leu Pro Leu His Arg Ala Leu Thr Leu Arg Phe
    210                 215                 220

Leu Leu Gln His Leu Gly Arg Val Ala Ser Arg Ala Pro Ala Leu Gly
225                 230                 235                 240

Pro Ala Val Arg Ala Leu Gly Ala Thr Phe Gly Pro Leu Leu Leu Arg
                245                 250                 255

Ala Pro Pro Pro Ser Ser Pro Pro Gly Gly Ala Pro Asp Gly
            260                 265                 270

Ser Glu Pro Ser Pro Asp Phe Pro Ala Leu Leu Val Glu Lys Leu Leu
        275                 280                 285
```

```
Gln Glu His Leu Glu Glu Gln Glu Val Ala Pro Pro Ala Leu Pro Pro
    290                 295                 300
Lys Pro Pro Lys Ala Lys Pro Ala Ser Thr Val Leu Ala Asn Gly Gly
305                 310                 315                 320
Ser Pro Pro Ser Leu Gln Asp Ala Glu Trp Tyr Trp Gly Asp Ile Ser
                325                 330                 335
Arg Glu Glu Val Asn Glu Lys Leu Arg Asp Thr Pro Asp Gly Thr Phe
            340                 345                 350
Leu Val Arg Asp Ala Ser Ser Lys Ile Gln Gly Glu Tyr Thr Leu Thr
        355                 360                 365
Leu Arg Lys Gly Gly Asn Asn Lys Leu Ile Lys Val Phe His Arg Asp
    370                 375                 380
Gly His Tyr Gly Phe Ser Glu Pro Leu Thr Phe Cys Ser Val Val Asp
385                 390                 395                 400
Leu Ile Asn His Tyr Arg His Glu Ser Leu Ala Gln Tyr Asn Ala Lys
                405                 410                 415
Leu Asp Thr Arg Leu Leu Tyr Pro Val Ser Lys Tyr Gln Gln Asp Gln
            420                 425                 430
Ile Val Lys Glu Asp Ser Val Glu Ala Val Gly Ala Gln Leu Lys Val
        435                 440                 445
Tyr His Gln Gln Tyr Gln Asp Lys Ser Arg Glu Tyr Asp Gln Leu Tyr
    450                 455                 460
Glu Glu Tyr Thr Arg Thr Ser Gln Glu Leu Gln Met Lys Arg Thr Ala
465                 470                 475                 480
Ile Glu Ala Phe Asn Glu Thr Ile Lys Ile Phe Glu Glu Gln Gly Gln
                485                 490                 495
Thr Gln Glu Lys Cys Ser Lys Glu Tyr Leu Glu Arg Phe Arg Arg Glu
            500                 505                 510
Gly Asn Glu Lys Glu Met Gln Arg Ile Leu Leu Asn Ser Glu Arg Leu
        515                 520                 525
Lys Ser Arg Ile Ala Glu Ile His Glu Ser Arg Thr Lys Leu Glu Gln
    530                 535                 540
Gln Leu Arg Ala Gln Ala Ser Asp Asn Arg Glu Ile Asp Lys Arg Met
545                 550                 555                 560
Asn Ser Leu Lys Pro Asp Leu Met Gln Leu Arg Lys Ile Arg Asp Gln
                565                 570                 575
Tyr Leu Val Trp Leu Thr Gln Lys Gly Ala Arg Gln Lys Lys Ile Asn
            580                 585                 590
Glu Trp Leu Gly Ile Lys Asn Glu Thr Glu Asp Gln Tyr Ala Leu Met
        595                 600                 605
Glu Asp Glu Asp Asp Leu Pro His His Glu Glu Arg Thr Trp Tyr Val
    610                 615                 620
Gly Lys Ile Asn Arg Thr Gln Ala Glu Glu Met Leu Ser Gly Lys Arg
625                 630                 635                 640
Asp Gly Thr Phe Leu Ile Arg Glu Ser Ser Gln Arg Gly Cys Tyr Ala
                645                 650                 655
Cys Ser Val Val Asp Gly Asp Thr Lys His Cys Val Ile Tyr Arg
            660                 665                 670
Thr Ala Thr Gly Phe Gly Phe Ala Glu Pro Tyr Asn Leu Tyr Gly Ser
        675                 680                 685
Leu Lys Glu Leu Val Leu His Tyr Gln His Ala Ser Leu Val Gln His
    690                 695                 700
Asn Asp Ala Leu Thr Val Thr Leu Ala His Pro Val Arg Ala Pro Gly
```

Pro Gly Pro Pro Pro Ala Ala Arg
                725

<210> SEQ ID NO 3
<211> LENGTH: 461
<212> TYPE: PRT
<213> ORGANISM: Homo sapiens
<220> FEATURE:
<223> OTHER INFORMATION: phosphatidylinositol 3-kinase (PI3K) p55gamma

<400> SEQUENCE: 3

Met Tyr Asn Thr Val Trp Ser Met Asp Arg Asp Asp Ala Asp Trp Arg
 1               5                  10                  15

Glu Val Met Met Pro Tyr Ser Thr Glu Leu Ile Phe Tyr Ile Glu Met
            20                  25                  30

Asp Pro Pro Ala Leu Pro Pro Lys Pro Pro Lys Pro Met Thr Ser Ala
        35                  40                  45

Val Pro Asn Gly Met Lys Asp Ser Ser Val Ser Leu Gln Asp Ala Glu
    50                  55                  60

Trp Tyr Trp Gly Asp Ile Ser Arg Glu Glu Val Asn Asp Lys Leu Arg
65                  70                  75                  80

Asp Met Pro Asp Gly Thr Phe Leu Val Arg Asp Ala Ser Thr Lys Met
                85                  90                  95

Gln Gly Asp Tyr Thr Leu Thr Leu Arg Lys Gly Gly Asn Asn Lys Leu
            100                 105                 110

Ile Lys Ile Tyr His Arg Asp Gly Lys Tyr Gly Phe Ser Asp Pro Leu
        115                 120                 125

Thr Phe Asn Ser Val Val Glu Leu Ile Asn His Tyr His His Glu Ser
130                 135                 140

Leu Ala Gln Tyr Asn Pro Lys Leu Asp Val Lys Leu Met Tyr Pro Val
145                 150                 155                 160

Ser Arg Tyr Gln Gln Asp Gln Leu Val Lys Glu Asp Asn Ile Asp Ala
                165                 170                 175

Val Gly Lys Lys Leu Gln Glu Tyr His Ser Gln Tyr Gln Glu Lys Ser
            180                 185                 190

Lys Glu Tyr Asp Arg Leu Tyr Glu Glu Tyr Thr Arg Thr Ser Gln Glu
        195                 200                 205

Ile Gln Met Lys Arg Thr Ala Ile Glu Ala Phe Asn Glu Thr Ile Lys
    210                 215                 220

Ile Phe Glu Glu Gln Cys His Thr Gln Glu Gln His Ser Lys Glu Tyr
225                 230                 235                 240

Ile Glu Arg Phe Arg Arg Glu Gly Asn Glu Lys Glu Ile Glu Arg Ile
                245                 250                 255

Met Met Asn Tyr Asp Lys Leu Lys Ser Arg Leu Gly Glu Ile His Asp
            260                 265                 270

Ser Lys Met Arg Leu Glu Gln Asp Leu Lys Asn Gln Ala Leu Asp Asn
        275                 280                 285

Arg Glu Ile Asp Lys Lys Met Asn Ser Ile Lys Pro Asp Leu Ile Gln
    290                 295                 300

Leu Arg Lys Ile Arg Asp Gln His Leu Val Trp Leu Asn His Lys Gly
305                 310                 315                 320

Val Arg Gln Lys Arg Leu Asn Val Trp Leu Gly Ile Lys Asn Glu Asp
                325                 330                 335

Ala Asp Glu Asn Tyr Phe Ile Asn Glu Glu Asp Glu Asn Leu Pro His

```
                  340                 345                 350
Tyr Asp Glu Lys Thr Trp Phe Val Glu Asp Ile Asn Arg Val Gln Ala
            355                 360                 365

Glu Asp Leu Leu Tyr Gly Lys Pro Asp Gly Ala Phe Leu Ile Arg Glu
        370                 375                 380

Ser Ser Lys Lys Gly Cys Tyr Ala Cys Ser Val Val Ala Asp Gly Glu
385                 390                 395                 400

Val Lys His Cys Val Ile Tyr Ser Thr Ala Arg Gly Tyr Gly Phe Ala
                405                 410                 415

Glu Pro Tyr Asn Leu Tyr Ser Ser Leu Lys Glu Leu Val Leu His Tyr
            420                 425                 430

Gln Gln Thr Ser Leu Val Gln His Asn Asp Ser Leu Asn Val Arg Leu
        435                 440                 445

Ala Tyr Pro Val His Ala Gln Met Pro Ser Leu Cys Arg
    450                 455                 460

<210> SEQ ID NO 4
<211> LENGTH: 1358
<212> TYPE: PRT
<213> ORGANISM: Homo sapiens
<220> FEATURE:
<223> OTHER INFORMATION: phosphatidylinositol 3-kinase (PI3K) p150

<400> SEQUENCE: 4

Met Gly Asn Gln Leu Ala Gly Ile Ala Pro Ser Gln Ile Leu Ser Val
1               5                   10                  15

Glu Ser Tyr Phe Ser Asp Ile His Asp Phe Glu Tyr Asp Lys Ser Leu
            20                  25                  30

Gly Ser Thr Arg Phe Phe Lys Val Ala Arg Ala Lys His Arg Glu Gly
        35                  40                  45

Leu Val Val Lys Val Phe Ala Ile Gln Asp Pro Thr Leu Pro Leu
    50                  55                  60

Thr Ser Tyr Lys Gln Glu Leu Glu Glu Leu Lys Ile Arg Leu Asn Ser
65                  70                  75                  80

Ala Gln Asn Cys Leu Pro Phe Gln Lys Ala Ser Glu Lys Ala Ser Glu
                85                  90                  95

Lys Ala Ala Met Leu Phe Arg Gln Tyr Val Arg Asp Asn Leu Tyr Asp
            100                 105                 110

Arg Ile Ser Thr Arg Pro Phe Leu Asn Asn Ile Glu Lys Arg Trp Ile
        115                 120                 125

Ala Phe Gln Ile Leu Thr Ala Val Asp Gln Ala His Lys Ser Gly Val
    130                 135                 140

Arg His Gly Asp Ile Lys Thr Glu Asn Val Met Val Thr Ser Trp Asn
145                 150                 155                 160

Trp Val Leu Leu Thr Asp Phe Ala Ser Phe Lys Pro Thr Tyr Leu Pro
                165                 170                 175

Glu Asp Asn Pro Ala Asp Phe Asn Tyr Phe Asp Thr Ser Arg Arg
            180                 185                 190

Arg Thr Cys Tyr Ile Ala Pro Glu Arg Phe Val Asp Gly Gly Met Phe
        195                 200                 205

Ala Thr Glu Leu Glu Tyr Met Arg Asp Pro Ser Thr Pro Leu Val Asp
    210                 215                 220

Leu Asn Ser Asn Gln Arg Thr Arg Gly Glu Leu Lys Arg Ala Met Asp
225                 230                 235                 240

Ile Phe Ser Ala Gly Cys Val Ile Ala Glu Leu Phe Thr Glu Gly Val
```

```
            245                 250                 255
Pro Leu Phe Asp Leu Ser Gln Leu Leu Ala Tyr Arg Asn Gly His Phe
            260                 265                 270

Phe Pro Glu Gln Val Leu Asn Lys Ile Glu Asp His Ser Ile Arg Glu
        275                 280                 285

Leu Val Thr Gln Met Ile His Arg Glu Pro Asp Lys Arg Leu Glu Ala
    290                 295                 300

Glu Asp Tyr Leu Lys Gln Arg Gly Asn Ala Phe Pro Glu Ile Phe
305                 310                 315                 320

Tyr Thr Phe Leu Gln Pro Tyr Met Ala Gln Phe Ala Lys Glu Thr Phe
                325                 330                 335

Leu Ser Ala Asp Glu Arg Ile Leu Val Ile Arg Lys Asp Leu Gly Asn
            340                 345                 350

Ile Ile His Asn Leu Cys Gly His Asp Leu Pro Glu Lys Ala Glu Gly
                355                 360                 365

Glu Pro Lys Glu Asn Gly Leu Val Ile Leu Val Ser Val Ile Thr Ser
    370                 375                 380

Cys Leu Gln Thr Leu Lys Tyr Cys Asp Ser Lys Leu Ala Ala Leu Glu
385                 390                 395                 400

Leu Ile Leu His Leu Ala Pro Arg Leu Ser Val Glu Ile Leu Leu Asp
                405                 410                 415

Arg Ile Thr Pro Tyr Leu Leu His Phe Ser Asn Asp Ser Val Pro Arg
                420                 425                 430

Val Arg Ala Glu Ala Leu Arg Thr Leu Thr Lys Val Leu Ala Leu Val
        435                 440                 445

Lys Glu Val Pro Arg Asn Asp Ile Asn Ile Tyr Pro Glu Tyr Ile Leu
    450                 455                 460

Pro Gly Ile Ala His Leu Ala Gln Asp Ala Thr Ile Val Arg Leu
465                 470                 475                 480

Ala Tyr Ala Glu Asn Ile Ala Leu Leu Ala Glu Thr Ala Leu Arg Phe
                485                 490                 495

Leu Glu Leu Val Gln Leu Lys Asn Leu Asn Met Glu Asn Asp Pro Asn
            500                 505                 510

Asn Glu Glu Ile Asp Glu Val Thr His Pro Asn Gly Asn Tyr Asp Thr
        515                 520                 525

Glu Leu Gln Ala Leu His Glu Met Val Gln Gln Lys Val Val Thr Leu
    530                 535                 540

Leu Ser Asp Pro Glu Asn Ile Val Lys Gln Thr Leu Met Glu Asn Gly
545                 550                 555                 560

Ile Thr Arg Leu Cys Val Phe Phe Gly Arg Gln Lys Ala Asn Asp Val
                565                 570                 575

Leu Leu Ser His Met Ile Thr Phe Asn Asp Lys Asn Asp Trp His
            580                 585                 590

Leu Arg Gly Ala Phe Phe Asp Ser Ile Gly Val Ala Ala Tyr Val
        595                 600                 605

Gly Trp Gln Ser Ser Ser Ile Leu Lys Pro Leu Leu Gln Gln Gly Leu
    610                 615                 620

Ser Asp Ala Glu Glu Phe Val Ile Val Lys Ala Leu Tyr Ala Leu Thr
625                 630                 635                 640

Cys Met Cys Gln Leu Gly Leu Leu Gln Lys Pro His Val Tyr Glu Phe
                645                 650                 655

Ala Ser Asp Ile Ala Pro Phe Leu Cys His Pro Asn Leu Trp Ile Arg
            660                 665                 670
```

-continued

```
Tyr Gly Ala Val Gly Phe Ile Thr Val Val Ala Arg Gln Ile Ser Thr
            675                 680                 685
Ala Asp Val Tyr Cys Lys Leu Met Pro Tyr Leu Asp Pro Tyr Ile Thr
690                 695                 700
Gln Pro Ile Ile Gln Ile Glu Arg Lys Leu Val Leu Leu Ser Val Leu
705                 710                 715                 720
Lys Glu Pro Val Ser Arg Ser Ile Phe Asp Tyr Ala Leu Arg Ser Lys
                725                 730                 735
Asp Ile Thr Ser Leu Phe Arg His Leu His Met Arg Gln Lys Lys Arg
                740                 745                 750
Asn Gly Ser Leu Pro Asp Cys Pro Pro Glu Asp Pro Ala Ile Ala
                755                 760                 765
Gln Leu Leu Lys Lys Leu Leu Ser Gln Gly Met Thr Glu Glu Glu Glu
770                 775                 780
Asp Lys Leu Leu Ala Leu Lys Asp Phe Met Met Lys Ser Asn Lys Ala
785                 790                 795                 800
Lys Ala Asn Ile Val Asp Gln Ser His Leu His Asp Ser Ser Gln Lys
                805                 810                 815
Gly Val Ile Asp Leu Ala Ala Leu Gly Ile Thr Gly Arg Gln Val Asp
                820                 825                 830
Leu Val Lys Thr Lys Gln Glu Pro Asp Asp Lys Arg Ala Arg Lys His
                835                 840                 845
Val Lys Gln Asp Ser Asn Val Asn Glu Glu Trp Lys Ser Met Phe Gly
850                 855                 860
Ser Leu Asp Pro Pro Asn Met Pro Gln Ala Leu Pro Lys Gly Ser Asp
865                 870                 875                 880
Gln Glu Val Ile Gln Thr Gly Lys Pro Arg Ser Glu Ser Ser Ala
                885                 890                 895
Gly Ile Cys Val Pro Leu Ser Thr Ser Ser Gln Val Pro Glu Val Thr
                900                 905                 910
Thr Val Gln Asn Lys Lys Pro Val Ile Pro Val Leu Ser Ser Thr Ile
                915                 920                 925
Leu Pro Ser Thr Tyr Gln Ile Arg Ile Thr Thr Cys Lys Thr Glu Leu
            930                 935                 940
Gln Gln Leu Ile Gln Gln Lys Arg Glu Gln Cys Asn Ala Glu Arg Ile
945                 950                 955                 960
Ala Lys Gln Met Met Glu Asn Ala Glu Trp Glu Ser Lys Pro Pro Pro
                965                 970                 975
Pro Gly Trp Arg Pro Lys Gly Leu Leu Val Ala His Leu Glu His
            980                 985                 990
Lys Ser Ala Val Asn Arg Ile Arg Val Ser Asp Glu His Ser Leu Phe
                995                 1000                1005
Ala Thr Cys Ser Asn Asp Gly Thr Val Lys Ile Trp Asn Ser Gln Lys
            1010                1015                1020
Met Glu Gly Lys Thr Thr Thr Arg Ser Ile Leu Thr Tyr Ser Arg
1025                1030                1035                1040
Ile Gly Gly Arg Val Lys Thr Leu Thr Phe Cys Gln Gly Ser His Tyr
                1045                1050                1055
Leu Ala Ile Ala Ser Asp Asn Gly Ala Val Gln Leu Leu Gly Ile Glu
            1060                1065                1070
Ala Ser Lys Leu Pro Lys Ser Pro Lys Ile His Pro Leu Gln Ser Arg
            1075                1080                1085
```

```
Ile Leu Asp Gln Lys Glu Asp Gly Cys Val Val Asp Met His His Phe
    1090                1095                1100

Asn Ser Gly Ala Gln Ser Val Leu Ala Tyr Ala Thr Val Asn Gly Ser
1105                1110                1115                1120

Leu Val Gly Trp Asp Leu Arg Ser Ser Asn Ala Trp Thr Leu Lys
            1125                1130                1135

His Asp Leu Lys Ser Gly Leu Ile Thr Ser Phe Ala Val Asp Ile His
        1140                1145                1150

Gln Cys Trp Leu Cys Ile Gly Thr Ser Ser Gly Thr Met Ala Cys Trp
            1155                1160                1165

Asp Met Arg Phe Gln Leu Pro Ile Ser Ser His Cys His Pro Ser Arg
    1170                1175                1180

Ala Arg Ile Arg Arg Leu Ser Met His Pro Leu Tyr Gln Ser Trp Val
1185                1190                1195                1200

Ile Ala Ala Val Gln Gly Asn Asn Glu Val Ser Met Trp Asp Met Glu
            1205                1210                1215

Thr Gly Asp Arg Arg Phe Thr Leu Trp Ala Ser Ser Ala Pro Pro Leu
        1220                1225                1230

Ser Glu Leu Gln Pro Ser Pro His Ser Val His Gly Ile Tyr Cys Ser
    1235                1240                1245

Pro Ala Asp Gly Asn Pro Ile Leu Leu Thr Ala Gly Ser Asp Met Lys
    1250                1255                1260

Ile Arg Phe Trp Asp Leu Ala Tyr Pro Glu Arg Ser Tyr Val Val Ala
1265                1270                1275                1280

Gly Ser Thr Ser Ser Pro Ser Val Ser Tyr Tyr Arg Lys Ile Ile Glu
            1285                1290                1295

Gly Thr Glu Val Val Gln Glu Ile Gln Asn Lys Gln Lys Val Gly Pro
        1300                1305                1310

Ser Asp Asp Thr Pro Arg Arg Gly Pro Glu Ser Leu Pro Val Gly His
        1315                1320                1325

His Asp Ile Ile Thr Asp Val Ala Thr Phe Gln Thr Gln Gly Phe
        1330                1335                1340

Ile Val Thr Ala Ser Arg Asp Gly Ile Val Lys Val Trp Lys
1345                1350                1355

<210> SEQ ID NO 5
<211> LENGTH: 880
<212> TYPE: PRT
<213> ORGANISM: Homo sapiens
<220> FEATURE:
<223> OTHER INFORMATION: phosphatidylinositol 3-kinase (PI3K) p101

<400> SEQUENCE: 5

Met Gln Pro Gly Ala Thr Thr Cys Thr Glu Asp Arg Ile Gln His Ala
1               5                   10                  15

Leu Glu Arg Cys Leu His Gly Leu Ser Leu Ser Arg Arg Ser Thr Ser
            20                  25                  30

Trp Ser Ala Gly Leu Cys Leu Asn Cys Trp Ser Leu Gln Glu Leu Val
        35                  40                  45

Ser Arg Asp Pro Gly His Phe Leu Ile Leu Glu Gln Ile Leu Gln
    50                  55                  60

Lys Thr Arg Glu Val Gln Glu Lys Gly Thr Tyr Asp Leu Leu Thr Pro
65                  70                  75                  80

Leu Ala Leu Leu Phe Tyr Ser Thr Val Leu Cys Thr Pro His Phe Pro
                85                  90                  95
```

```
Pro Asp Ser Asp Leu Leu Leu Lys Ala Ala Ser Thr Tyr His Arg Phe
            100                 105                 110

Leu Thr Trp Pro Val Pro Tyr Cys Ser Ile Cys Gln Glu Leu Leu Thr
        115                 120                 125

Phe Ile Asp Ala Glu Leu Lys Ala Pro Gly Ile Ser Tyr Gln Arg Leu
    130                 135                 140

Val Arg Ala Glu Gln Gly Leu Pro Ile Arg Ser His Arg Ser Ser Thr
145                 150                 155                 160

Val Thr Val Leu Leu Leu Asn Pro Val Glu Val Gln Ala Glu Phe Leu
                165                 170                 175

Ala Val Ala Asn Lys Leu Ser Thr Pro Gly His Ser Pro His Ser Ala
            180                 185                 190

Tyr Thr Thr Leu Leu Leu His Ala Phe Gln Ala Thr Phe Gly Ala His
        195                 200                 205

Cys Asp Val Pro Gly Leu His Cys Arg Leu Gln Ala Lys Thr Leu Ala
    210                 215                 220

Glu Leu Glu Asp Ile Phe Thr Glu Thr Ala Glu Ala Gln Glu Leu Ala
225                 230                 235                 240

Ser Gly Ile Gly Asp Ala Ala Glu Ala Arg Arg Trp Leu Arg Thr Lys
                245                 250                 255

Leu Gln Ala Val Gly Glu Lys Ala Gly Phe Pro Gly Val Leu Asp Thr
            260                 265                 270

Ala Lys Pro Gly Lys Leu His Thr Ile Pro Ile Pro Val Ala Arg Cys
        275                 280                 285

Tyr Thr Tyr Ser Trp Ser Gln Asp Ser Phe Asp Ile Leu Gln Glu Ile
    290                 295                 300

Leu Leu Lys Glu Gln Glu Leu Leu Gln Pro Gly Ile Leu Gly Asp Asp
305                 310                 315                 320

Glu Glu Glu Glu Glu Glu Glu Glu Val Glu Glu Asp Leu Glu Thr
                325                 330                 335

Asp Gly His Cys Ala Glu Arg Asp Ser Leu Leu Ser Thr Ser Ser Leu
            340                 345                 350

Ala Ser His Asp Ser Thr Leu Ser Leu Ala Ser Ser Gln Ala Ser Gly
        355                 360                 365

Pro Ala Leu Ser Arg His Leu Leu Thr Ser Phe Val Ser Gly Leu Ser
    370                 375                 380

Asp Gly Met Asp Ser Gly Tyr Val Glu Asp Ser Glu Ser Ser Ser Ser
385                 390                 395                 400

Glu Trp Pro Trp Arg Arg Gly Ser Gln Glu Arg Arg Gly His Arg Arg
                405                 410                 415

Pro Gly Gln Lys Phe Ile Arg Ile Tyr Lys Leu Phe Lys Ser Thr Ser
            420                 425                 430

Gln Leu Val Leu Arg Arg Asp Ser Arg Ser Leu Glu Gly Ser Ser Asp
        435                 440                 445

Thr Ala Leu Pro Leu Arg Arg Ala Gly Ser Leu Cys Ser Pro Leu Asp
    450                 455                 460

Glu Pro Val Ser Pro Ser Arg Ala Gln Arg Ser Arg Ser Leu Pro
465                 470                 475                 480

Gln Pro Lys Leu Gly Thr Gln Leu Pro Ser Trp Leu Leu Ala Pro Ala
                485                 490                 495

Ser Arg Pro Gln Arg Arg Pro Phe Leu Ser Gly Asp Glu Asp Pro
            500                 505                 510

Lys Ala Ser Thr Leu Arg Val Val Val Phe Gly Ser Asp Arg Ile Ser
```

```
            515                 520                 525
Gly Lys Val Ala Arg Ala Tyr Ser Asn Leu Arg Arg Leu Glu Asn Asn
530                 535                 540

Arg Pro Leu Leu Thr Arg Phe Phe Lys Leu Gln Phe Phe Tyr Val Pro
545                 550                 555                 560

Val Lys Arg Ser His Gly Thr Ser Pro Gly Ala Cys Pro Pro Arg
                565                 570                 575

Ser Gln Thr Pro Ser Pro Pro Thr Asp Ser Pro Arg His Ala Ser Pro
                580                 585                 590

Gly Glu Leu Gly Thr Thr Pro Trp Glu Glu Ser Thr Asn Asp Ile Ser
                595                 600                 605

His Tyr Leu Gly Met Leu Asp Pro Trp Tyr Glu Arg Asn Val Leu Gly
                610                 615                 620

Leu Met His Leu Pro Pro Glu Val Leu Cys Gln Gln Ser Leu Lys Ala
625                 630                 635                 640

Glu Ala Gln Ala Leu Glu Gly Ser Pro Thr Gln Leu Pro Ile Leu Ala
                645                 650                 655

Asp Met Leu Leu Tyr Tyr Cys Arg Phe Ala Ala Arg Pro Val Leu Leu
                660                 665                 670

Gln Val Tyr Gln Thr Glu Leu Thr Phe Ile Thr Gly Glu Lys Thr Thr
                675                 680                 685

Glu Ile Phe Ile His Ser Leu Glu Leu Gly His Ser Ala Ala Thr Arg
690                 695                 700

Ala Ile Lys Ala Ser Gly Pro Gly Ser Lys Arg Leu Gly Ile Asp Gly
705                 710                 715                 720

Asp Arg Glu Ala Val Pro Leu Thr Leu Gln Ile Ile Tyr Ser Lys Gly
                725                 730                 735

Ala Ile Ser Gly Arg Ser Arg Trp Ser Asn Leu Glu Lys Val Cys Thr
                740                 745                 750

Ser Val Asn Leu Asn Lys Ala Cys Arg Lys Gln Glu Glu Leu Asp Ser
                755                 760                 765

Ser Met Glu Ala Leu Thr Leu Asn Leu Thr Glu Val Val Lys Arg Gln
770                 775                 780

Asn Ser Lys Ser Lys Lys Gly Phe Asn Gln Ile Ser Thr Ser Gln Ile
785                 790                 795                 800

Lys Val Asp Lys Val Gln Ile Ile Gly Ser Asn Ser Cys Pro Phe Ala
                805                 810                 815

Val Cys Leu Asp Gln Asp Glu Arg Lys Ile Leu Gln Ser Val Val Arg
                820                 825                 830

Cys Glu Val Ser Pro Cys Tyr Lys Pro Glu Lys Ser Asp Leu Ser Ser
                835                 840                 845

Pro Pro Gln Thr Pro Pro Asp Leu Pro Ala Gln Ala Ala Pro Asp Leu
                850                 855                 860

Cys Ser Leu Leu Cys Leu Pro Ile Met Thr Phe Ser Gly Ala Leu Pro
865                 870                 875                 880

<210> SEQ ID NO 6
<211> LENGTH: 1068
<212> TYPE: PRT
<213> ORGANISM: Homo sapiens
<220> FEATURE:
<223> OTHER INFORMATION: phosphatidylinositol 3-kinase (PI3K) catalytic
      subunit p110alpha

<400> SEQUENCE: 6
```

```
Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Met Asp Cys Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
```

```
            420             425             430
Thr Asp Thr Leu Val Ser Gly Lys Met Ala Leu Asn Leu Trp Pro Val
        435             440             445
Pro His Gly Leu Glu Asp Leu Leu Asn Pro Ile Gly Val Thr Gly Ser
    450             455             460
Asn Pro Asn Lys Glu Thr Pro Cys Leu Glu Leu Glu Phe Asp Trp Phe
465             470             475             480
Ser Ser Val Val Lys Phe Pro Asp Met Ser Val Ile Glu Glu His Ala
            485             490             495
Asn Trp Ser Val Ser Arg Glu Ala Gly Phe Ser Tyr Ser His Ala Gly
        500             505             510
Leu Ser Asn Arg Leu Ala Arg Asp Asn Glu Leu Arg Glu Asn Asp Lys
    515             520             525
Glu Gln Leu Lys Ala Ile Ser Thr Arg Asp Pro Leu Ser Glu Ile Thr
        530             535             540
Glu Gln Glu Lys Asp Phe Leu Trp Ser His Arg His Tyr Cys Val Thr
545             550             555             560
Ile Pro Glu Ile Leu Pro Lys Leu Leu Leu Ser Val Lys Trp Asn Ser
            565             570             575
Arg Asp Glu Val Ala Gln Met Tyr Cys Leu Val Lys Asp Trp Pro Pro
        580             585             590
Ile Lys Pro Glu Gln Ala Met Glu Leu Leu Asp Cys Asn Tyr Pro Asp
    595             600             605
Pro Met Val Arg Gly Phe Ala Val Arg Cys Leu Glu Lys Tyr Leu Thr
        610             615             620
Asp Asp Lys Leu Ser Gln Tyr Leu Ile Gln Leu Val Gln Val Leu Lys
625             630             635             640
Tyr Glu Gln Tyr Leu Asp Asn Leu Leu Val Arg Phe Leu Leu Lys Lys
            645             650             655
Ala Leu Thr Asn Gln Arg Ile Gly His Phe Phe Phe Trp His Leu Lys
        660             665             670
Ser Glu Met His Asn Lys Thr Val Ser Gln Arg Phe Gly Leu Leu Leu
    675             680             685
Glu Ser Tyr Cys Arg Ala Cys Gly Met Tyr Leu Lys His Leu Asn Arg
        690             695             700
Gln Val Glu Ala Met Glu Lys Leu Ile Asn Leu Thr Asp Ile Leu Lys
705             710             715             720
Gln Glu Lys Lys Asp Glu Thr Gln Lys Val Gln Met Lys Phe Leu Val
            725             730             735
Glu Gln Met Arg Arg Pro Asp Phe Met Asp Ala Leu Gln Gly Phe Leu
        740             745             750
Ser Pro Leu Asn Pro Ala His Gln Leu Gly Asn Leu Arg Leu Glu Glu
    755             760             765
Cys Arg Ile Met Ser Ser Ala Lys Arg Pro Leu Trp Leu Asn Trp Glu
        770             775             780
Asn Pro Asp Ile Met Ser Glu Leu Leu Phe Gln Asn Asn Glu Ile Ile
785             790             795             800
Phe Lys Asn Gly Asp Asp Leu Arg Gln Asp Met Leu Thr Leu Gln Ile
            805             810             815
Ile Arg Ile Met Glu Asn Ile Trp Gln Asn Gln Gly Leu Asp Leu Arg
        820             825             830
Met Leu Pro Tyr Gly Cys Leu Ser Ile Gly Asp Cys Val Gly Leu Ile
    835             840             845
```

Glu Val Val Arg Asn Ser His Thr Ile Met Gln Ile Gln Cys Lys Gly
            850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
                900                 905                 910

Ile Gly Asp Arg His Asn Ser Asn Ile Met Val Lys Asp Asp Gly Gln
                915                 920                 925

Leu Phe His Ile Asp Phe Gly His Phe Leu Asp His Lys Lys Lys Lys
            930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975

Phe Glu Arg Phe Gln Glu Met Cys Tyr Lys Ala Tyr Leu Ala Ile Arg
                980                 985                 990

Gln His Ala Asn Leu Phe Ile Asn Leu Phe Ser Met Met Leu Gly Ser
            995                1000                1005

Gly Met Pro Glu Leu Gln Ser Phe Asp Asp Ile Ala Tyr Ile Arg Lys
            1010                1015                1020

Thr Leu Ala Leu Asp Lys Thr Glu Gln Glu Ala Leu Glu Tyr Phe Met
1025                1030                1035                1040

Lys Gln Met Asn Asp Ala His His Gly Gly Trp Thr Thr Lys Met Asp
                1045                1050                1055

Trp Ile Phe His Thr Ile Lys Gln His Ala Leu Asn
                1060                1065

<210> SEQ ID NO 7
<211> LENGTH: 1070
<212> TYPE: PRT
<213> ORGANISM: Homo sapiens
<220> FEATURE:
<223> OTHER INFORMATION: phosphatidylinositol 3-kinase (PI3K) catalytic
      subunit p110beta

<400> SEQUENCE: 7

Met Cys Phe Ser Phe Ile Met Pro Pro Ala Met Ala Asp Ile Leu Asp
 1               5                  10                  15

Ile Trp Ala Val Asp Ser Gln Ile Ala Ser Asp Gly Ser Ile Pro Val
                20                  25                  30

Asp Phe Leu Leu Pro Thr Gly Ile Tyr Ile Gln Leu Glu Val Pro Arg
            35                  40                  45

Glu Ala Thr Ile Ser Tyr Ile Lys Gln Met Leu Trp Lys Gln Val His
        50                  55                  60

Asn Tyr Pro Met Phe Asn Leu Leu Met Asp Ile Asp Ser Tyr Met Phe
65                  70                  75                  80

Ala Cys Val Asn Gln Thr Ala Val Tyr Glu Glu Leu Glu Asp Glu Thr
                85                  90                  95

Arg Arg Leu Cys Asp Val Arg Pro Phe Leu Pro Val Leu Lys Leu Val
                100                 105                 110

Thr Arg Ser Cys Asp Pro Gly Glu Lys Leu Asp Ser Lys Ile Gly Val
            115                 120                 125

Leu Ile Gly Lys Gly Leu His Glu Phe Asp Ser Leu Lys Asp Pro Glu

-continued

```
            130                 135                 140
Val Asn Glu Phe Arg Arg Lys Met Arg Lys Phe Ser Glu Glu Lys Ile
145                 150                 155                 160

Leu Ser Leu Val Gly Leu Ser Trp Met Asp Trp Lys Gln Thr Tyr
                165                 170                 175

Pro Pro Glu His Glu Pro Ser Ile Pro Glu Asn Leu Glu Asp Lys Leu
                180                 185                 190

Tyr Gly Gly Lys Leu Ile Val Ala Val His Phe Glu Asn Cys Gln Asp
                195                 200                 205

Val Phe Ser Phe Gln Val Ser Pro Asn Met Asn Pro Ile Lys Val Asn
210                 215                 220

Glu Leu Ala Ile Gln Lys Arg Leu Thr Ile His Gly Lys Glu Asp Glu
225                 230                 235                 240

Val Ser Pro Tyr Asp Tyr Val Leu Gln Val Ser Gly Arg Val Glu Tyr
                245                 250                 255

Val Phe Gly Asp His Pro Leu Ile Gln Phe Gln Tyr Ile Arg Asn Cys
                260                 265                 270

Val Met Asn Arg Ala Leu Pro His Phe Ile Leu Val Glu Cys Cys Lys
                275                 280                 285

Ile Lys Lys Met Tyr Glu Gln Glu Met Ile Ala Ile Glu Ala Ala Ile
290                 295                 300

Asn Arg Asn Ser Ser Asn Leu Pro Leu Pro Leu Pro Lys Lys Thr
305                 310                 315                 320

Arg Ile Ile Ser His Val Trp Glu Asn Asn Pro Phe Gln Ile Val
                325                 330                 335

Leu Val Lys Gly Asn Lys Leu Asn Thr Glu Thr Val Lys Val His
                340                 345                 350

Val Arg Ala Gly Leu Phe His Gly Thr Glu Leu Leu Cys Lys Thr Ile
                355                 360                 365

Val Ser Ser Glu Val Ser Gly Lys Asn Asp His Ile Trp Asn Glu Pro
                370                 375                 380

Leu Glu Phe Asp Ile Asn Ile Cys Asp Leu Pro Arg Met Ala Arg Leu
385                 390                 395                 400

Cys Phe Ala Val Tyr Ala Val Leu Asp Lys Val Lys Thr Lys Ser
                405                 410                 415

Thr Lys Thr Ile Asn Pro Ser Lys Tyr Gln Thr Ile Arg Lys Ala Gly
                420                 425                 430

Lys Val His Tyr Pro Val Ala Trp Val Asn Thr Met Val Phe Asp Phe
                435                 440                 445

Lys Gly Gln Leu Arg Thr Gly Asp Ile Ile Leu His Ser Trp Ser Ser
                450                 455                 460

Phe Pro Asp Glu Leu Glu Met Leu Asn Pro Met Gly Thr Val Gln
465                 470                 475                 480

Thr Asn Pro Tyr Thr Glu Asn Ala Thr Ala Leu His Val Lys Phe Pro
                485                 490                 495

Glu Asn Lys Lys Gln Pro Tyr Tyr Pro Pro Phe Asp Lys Ile Ile
                500                 505                 510

Glu Lys Ala Ala Glu Ile Ala Ser Ser Asp Ser Ala Asn Val Ser Ser
                515                 520                 525

Arg Gly Gly Lys Lys Phe Leu Pro Val Leu Lys Glu Ile Leu Asp Arg
                530                 535                 540

Asp Pro Leu Ser Gln Leu Cys Glu Asn Glu Met Asp Leu Ile Trp Thr
545                 550                 555                 560
```

```
Leu Arg Gln Asp Cys Arg Glu Ile Phe Pro Gln Ser Leu Pro Lys Leu
                565                 570                 575

Leu Leu Ser Ile Lys Trp Asn Lys Leu Glu Asp Val Ala Gln Leu Gln
            580                 585                 590

Ala Leu Leu Gln Ile Trp Pro Lys Leu Pro Arg Glu Ala Leu Glu
        595                 600                 605

Leu Leu Asp Phe Asn Tyr Pro Asp Gln Tyr Val Arg Glu Tyr Ala Val
    610                 615                 620

Gly Cys Leu Arg Gln Met Ser Asp Glu Glu Leu Ser Gln Tyr Leu Leu
625                 630                 635                 640

Gln Leu Val Gln Val Leu Lys Tyr Glu Pro Phe Leu Asp Cys Ala Leu
                645                 650                 655

Ser Arg Phe Leu Leu Glu Arg Ala Leu Gly Asn Arg Arg Ile Gly Gln
            660                 665                 670

Phe Leu Phe Trp His Leu Arg Ser Glu Val His Ile Pro Ala Val Ser
        675                 680                 685

Val Gln Phe Gly Val Ile Leu Glu Ala Tyr Cys Arg Gly Ser Val Gly
    690                 695                 700

His Met Lys Val Leu Ser Lys Gln Val Glu Ala Leu Asn Lys Leu Lys
705                 710                 715                 720

Thr Leu Asn Ser Leu Ile Lys Leu Asn Ala Val Lys Leu Asn Arg Ala
                725                 730                 735

Lys Gly Lys Glu Ala Met His Thr Cys Leu Lys Gln Ser Ala Tyr Arg
            740                 745                 750

Glu Ala Leu Ser Asp Leu Gln Ser Pro Leu Asn Pro Cys Val Ile Leu
        755                 760                 765

Ser Glu Leu Tyr Val Lys Cys Lys Tyr Met Asp Ser Lys Met Lys
    770                 775                 780

Pro Leu Trp Leu Val Tyr Asn Asn Lys Val Phe Gly Glu Asp Ser Val
785                 790                 795                 800

Gly Val Ile Phe Lys Asn Gly Asp Asp Leu Arg Gln Asp Met Leu Thr
                805                 810                 815

Leu Gln Met Leu Arg Leu Met Asp Leu Leu Trp Lys Glu Ala Gly Leu
            820                 825                 830

Asp Leu Arg Met Leu Pro Tyr Gly Cys Leu Ala Thr Gly Asp Arg Ser
        835                 840                 845

Gly Leu Ile Glu Val Val Ser Thr Ser Glu Thr Ile Ala Asp Ile Gln
    850                 855                 860

Leu Asn Ser Ser Asn Val Ala Ala Ala Ala Phe Asn Lys Asp Ala
865                 870                 875                 880

Leu Leu Asn Trp Leu Lys Glu Tyr Asn Ser Gly Asp Asp Leu Asp Arg
                885                 890                 895

Ala Ile Glu Glu Phe Thr Leu Ser Cys Ala Gly Tyr Cys Val Ala Ser
            900                 905                 910

Tyr Val Leu Gly Ile Gly Asp Arg His Ser Asp Asn Ile Met Val Lys
        915                 920                 925

Lys Thr Gly Gln Leu Phe His Ile Asp Phe Gly His Ile Leu Gly Asn
    930                 935                 940

Phe Lys Ser Lys Phe Gly Ile Lys Arg Glu Arg Val Pro Phe Ile Leu
945                 950                 955                 960

Thr Tyr Asp Phe Ile His Val Ile Gln Gln Gly Lys Thr Gly Asn Thr
                965                 970                 975
```

```
Glu Lys Phe Gly Arg Phe Arg Gln Cys Cys Glu Asp Ala Tyr Leu Ile
            980                 985                 990

Leu Arg Arg His Gly Asn Leu Phe Ile Thr Leu Phe Ala Leu Met Leu
        995                 1000                1005

Thr Ala Gly Leu Pro Glu Leu Thr Ser Val Lys Asp Ile Gln Tyr Leu
    1010                1015                1020

Lys Asp Ser Leu Ala Leu Gly Lys Ser Glu Glu Ala Leu Lys Gln
1025                1030                1035                1040

Phe Lys Gln Lys Phe Asp Glu Ala Leu Arg Glu Ser Trp Thr Thr Lys
            1045                1050                1055

Val Asn Trp Met Ala His Thr Val Arg Lys Asp Tyr Arg Ser
        1060                1065                1070

<210> SEQ ID NO 8
<211> LENGTH: 1102
<212> TYPE: PRT
<213> ORGANISM: Homo sapiens
<220> FEATURE:
<223> OTHER INFORMATION: phosphatidylinositol 3-kinase (PI3K) catalytic
      subunit p110gamma

<400> SEQUENCE: 8

Met Glu Leu Glu Asn Tyr Lys Gln Pro Val Val Leu Arg Glu Asp Asn
1               5                   10                  15

Cys Arg Arg Arg Arg Met Lys Pro Arg Ser Ala Ala Ala Ser Leu
            20                  25                  30

Ser Ser Met Glu Leu Ile Pro Ile Glu Phe Val Leu Pro Thr Ser Gln
        35                  40                  45

Arg Lys Cys Lys Ser Pro Glu Thr Ala Leu Leu His Val Ala Gly His
50                  55                  60

Gly Asn Val Glu Gln Met Lys Ala Gln Val Trp Leu Arg Ala Leu Glu
65                  70                  75                  80

Thr Ser Val Ala Ala Asp Phe Tyr His Arg Leu Gly Pro His His Phe
                85                  90                  95

Leu Leu Leu Tyr Gln Lys Lys Gly Gln Trp Tyr Glu Ile Tyr Asp Lys
            100                 105                 110

Tyr Gln Val Val Gln Thr Leu Asp Cys Leu Arg Tyr Trp Lys Ala Thr
        115                 120                 125

His Arg Ser Pro Gly Gln Ile His Leu Val Gln Arg His Pro Pro Ser
130                 135                 140

Glu Glu Ser Gln Ala Phe Gln Arg Gln Leu Thr Ala Leu Ile Gly Tyr
145                 150                 155                 160

Asp Val Thr Asp Val Ser Asn Val His Asp Asp Glu Leu Glu Phe Thr
                165                 170                 175

Arg Arg Gly Leu Val Thr Pro Arg Met Ala Glu Val Ala Ser Arg Asp
            180                 185                 190

Pro Lys Leu Tyr Ala Met His Pro Trp Val Thr Ser Lys Pro Leu Pro
        195                 200                 205

Glu Tyr Leu Trp Lys Lys Ile Ala Asn Asn Cys Ile Phe Ile Val Ile
210                 215                 220

His Arg Ser Thr Thr Ser Gln Thr Ile Lys Val Ser Pro Asp Asp Thr
225                 230                 235                 240

Pro Gly Ala Ile Leu Gln Ser Phe Phe Thr Lys Met Ala Lys Lys Lys
                245                 250                 255

Ser Leu Met Asp Ile Pro Glu Ser Gln Ser Glu Gln Asp Phe Val Leu
            260                 265                 270
```

```
Arg Val Cys Gly Arg Asp Glu Tyr Leu Val Gly Glu Thr Pro Ile Lys
        275                 280                 285

Asn Phe Gln Trp Val Arg His Cys Leu Lys Asn Gly Glu Glu Ile His
        290                 295                 300

Val Val Leu Asp Thr Pro Pro Asp Pro Ala Leu Asp Glu Val Arg Lys
305                 310                 315                 320

Glu Glu Trp Pro Leu Val Asp Asp Cys Thr Gly Val Thr Gly Tyr His
                325                 330                 335

Glu Gln Leu Thr Ile His Gly Lys Asp His Glu Ser Val Phe Thr Val
                340                 345                 350

Ser Leu Trp Asp Cys Asp Arg Lys Phe Arg Val Lys Ile Arg Gly Ile
        355                 360                 365

Asp Ile Pro Val Leu Pro Arg Asn Thr Asp Leu Thr Val Phe Val Glu
        370                 375                 380

Ala Asn Ile Gln His Gly Gln Gln Val Leu Cys Gln Arg Arg Thr Ser
385                 390                 395                 400

Pro Lys Pro Phe Thr Glu Val Leu Trp Asn Val Trp Leu Glu Phe
                405                 410                 415

Ser Ile Lys Ile Lys Asp Leu Pro Lys Gly Ala Leu Leu Asn Leu Gln
        420                 425                 430

Ile Tyr Cys Gly Lys Ala Pro Ala Leu Ser Ser Lys Ala Ser Ala Glu
        435                 440                 445

Ser Pro Ser Ser Glu Ser Lys Gly Lys Val Gln Leu Leu Tyr Tyr Val
        450                 455                 460

Asn Leu Leu Leu Ile Asp His Arg Phe Leu Leu Arg Arg Gly Glu Tyr
465                 470                 475                 480

Val Leu His Met Trp Gln Ile Ser Gly Lys Gly Glu Asp Gln Gly Ser
                485                 490                 495

Phe Asn Ala Asp Lys Leu Thr Ser Ala Thr Asn Pro Asp Lys Glu Asn
                500                 505                 510

Ser Met Ser Ile Ser Ile Leu Leu Asp Asn Tyr Cys His Pro Ile Ala
        515                 520                 525

Leu Pro Lys His Gln Pro Thr Pro Asp Pro Glu Gly Asp Arg Val Arg
        530                 535                 540

Ala Glu Met Pro Asn Gln Leu Arg Lys Gln Leu Glu Ala Ile Ile Ala
545                 550                 555                 560

Thr Asp Pro Leu Asn Pro Leu Thr Ala Glu Asp Lys Glu Leu Leu Trp
                565                 570                 575

His Phe Arg Tyr Glu Ser Leu Lys His Pro Lys Ala Tyr Pro Lys Leu
                580                 585                 590

Phe Ser Ser Val Lys Trp Gly Gln Gln Glu Ile Val Ala Lys Thr Tyr
        595                 600                 605

Gln Leu Leu Ala Arg Arg Glu Val Trp Asp Gln Ser Ala Leu Asp Val
        610                 615                 620

Gly Leu Thr Met Gln Leu Leu Asp Cys Asn Phe Ser Asp Glu Asn Val
625                 630                 635                 640

Arg Ala Ile Ala Val Gln Lys Leu Glu Ser Leu Glu Asp Asp Val
                645                 650                 655

Leu His Tyr Leu Leu Gln Leu Val Gln Ala Val Lys Phe Glu Pro Tyr
                660                 665                 670

His Asp Ser Ala Leu Ala Arg Phe Leu Leu Lys Arg Gly Leu Arg Asn
        675                 680                 685
```

Lys Arg Ile Gly His Phe Leu Phe Trp Phe Leu Arg Ser Glu Ile Ala
690                 695                 700

Gln Ser Arg His Tyr Gln Gln Arg Phe Ala Val Ile Leu Glu Ala Tyr
705                 710                 715                 720

Leu Arg Gly Cys Gly Thr Ala Met Leu His Asp Phe Thr Gln Gln Val
            725                 730                 735

Gln Val Ile Glu Met Leu Gln Lys Val Thr Leu Asp Ile Lys Ser Leu
            740                 745                 750

Ser Ala Glu Lys Tyr Asp Val Ser Gln Val Ile Ser Gln Leu Lys
        755                 760                 765

Gln Lys Leu Glu Asn Leu Gln Asn Ser Gln Leu Pro Glu Ser Phe Arg
770                 775                 780

Val Pro Tyr Asp Pro Gly Leu Lys Ala Gly Ala Leu Ala Ile Glu Lys
785                 790                 795                 800

Cys Lys Val Met Ala Ser Lys Lys Pro Leu Trp Leu Glu Phe Lys
            805                 810                 815

Cys Ala Asp Pro Thr Ala Leu Ser Asn Glu Thr Ile Gly Ile Phe
            820                 825                 830

Lys His Gly Asp Asp Leu Arg Gln Asp Met Leu Ile Leu Gln Ile Leu
            835                 840                 845

Arg Ile Met Glu Ser Ile Trp Glu Thr Glu Ser Leu Asp Leu Cys Leu
850                 855                 860

Leu Pro Tyr Gly Cys Ile Ser Thr Gly Asp Lys Ile Gly Met Ile Glu
865                 870                 875                 880

Ile Val Lys Asp Ala Thr Thr Ile Ala Lys Ile Gln Gln Ser Thr Val
            885                 890                 895

Gly Asn Thr Gly Ala Phe Lys Asp Glu Val Leu Asn His Trp Leu Lys
            900                 905                 910

Glu Lys Ser Pro Thr Glu Lys Phe Gln Ala Ala Val Glu Arg Phe
        915                 920                 925

Val Tyr Ser Cys Ala Gly Tyr Cys Val Ala Thr Phe Val Leu Gly Ile
            930                 935                 940

Gly Asp Arg His Asn Asp Asn Ile Met Ile Thr Glu Thr Gly Asn Leu
945                 950                 955                 960

Phe His Ile Asp Phe Gly His Ile Leu Gly Asn Tyr Lys Ser Phe Leu
            965                 970                 975

Gly Ile Asn Lys Glu Arg Val Pro Phe Val Leu Thr Pro Asp Phe Leu
            980                 985                 990

Phe Val Met Gly Thr Ser Gly Lys Lys Thr Ser Pro His Phe Gln Lys
            995                 1000                1005

Phe Gln Asp Ile Cys Val Lys Ala Tyr Leu Ala Leu Arg His His Thr
    1010                1015                1020

Asn Leu Leu Ile Ile Leu Phe Ser Met Met Leu Met Thr Gly Met Pro
1025                1030                1035                1040

Gln Leu Thr Ser Lys Glu Asp Ile Glu Tyr Ile Arg Asp Ala Leu Thr
            1045                1050                1055

Val Gly Lys Asn Glu Glu Asp Ala Lys Lys Tyr Phe Leu Asp Gln Ile
            1060                1065                1070

Glu Val Cys Arg Asp Lys Gly Trp Thr Val Gln Phe Asn Trp Phe Leu
            1075                1080                1085

His Leu Val Leu Gly Ile Lys Gln Gly Glu Lys His Ser Ala
            1090                1095                1100

-continued

<210> SEQ ID NO 9
<211> LENGTH: 1044
<212> TYPE: PRT
<213> ORGANISM: Homo sapiens
<220> FEATURE:
<223> OTHER INFORMATION: phosphatidylinositol 3-kinase (PI3K) catalytic
      subunit p110delta

<400> SEQUENCE: 9

```
Met Pro Pro Gly Val Asp Cys Pro Met Glu Phe Trp Thr Lys Glu Glu
 1               5                  10                  15

Asn Gln Ser Val Val Asp Phe Leu Leu Pro Thr Gly Val Tyr Leu
            20                  25                  30

Asn Phe Pro Val Ser Arg Asn Ala Asn Leu Ser Thr Ile Lys Gln Leu
        35                  40                  45

Leu Trp His Arg Ala Gln Tyr Glu Pro Leu Phe His Met Leu Ser Gly
    50                  55                  60

Pro Glu Ala Tyr Val Phe Thr Cys Ile Asn Gln Thr Ala Glu Gln Gln
65                  70                  75                  80

Glu Leu Glu Asp Glu Gln Arg Arg Leu Cys Asp Val Gln Pro Phe Leu
                85                  90                  95

Pro Val Leu Arg Leu Val Ala Arg Glu Gly Asp Arg Val Lys Lys Leu
            100                 105                 110

Ile Asn Ser Gln Ile Ser Leu Leu Ile Gly Lys Gly Leu His Glu Phe
        115                 120                 125

Asp Ser Leu Cys Asp Pro Glu Val Asn Asp Phe Arg Ala Lys Met Cys
    130                 135                 140

Gln Phe Cys Glu Glu Ala Ala Ala Arg Arg Gln Gln Leu Gly Trp Glu
145                 150                 155                 160

Ala Trp Leu Gln Tyr Ser Phe Pro Leu Gln Leu Glu Pro Ser Ala Gln
                165                 170                 175

Thr Trp Gly Pro Gly Thr Leu Arg Leu Pro Asn Arg Ala Leu Leu Val
            180                 185                 190

Asn Val Lys Phe Glu Gly Ser Glu Glu Ser Phe Thr Phe Gln Val Ser
        195                 200                 205

Thr Lys Asp Val Pro Leu Ala Leu Met Ala Cys Ala Leu Arg Lys Lys
    210                 215                 220

Ala Thr Val Phe Arg Gln Pro Leu Val Glu Gln Pro Glu Asp Tyr Thr
225                 230                 235                 240

Leu Gln Val Asn Gly Arg His Glu Tyr Leu Tyr Gly Ser Tyr Pro Leu
                245                 250                 255

Cys Gln Phe Gln Tyr Ile Cys Ser Cys Leu His Ser Gly Leu Thr Pro
            260                 265                 270

His Leu Thr Met Val His Ser Ser Ile Leu Ala Met Arg Asp Glu
        275                 280                 285

Gln Ser Asn Pro Ala Pro Gln Val Gln Lys Pro Arg Ala Lys Pro Pro
    290                 295                 300

Pro Ile Pro Ala Lys Lys Pro Ser Ser Val Ser Leu Trp Ser Leu Glu
305                 310                 315                 320

Gln Pro Phe Arg Ile Glu Leu Ile Gln Gly Ser Lys Val Asn Ala Asp
                325                 330                 335

Glu Arg Met Lys Leu Val Val Gln Ala Gly Leu Phe His Gly Asn Glu
            340                 345                 350

Met Leu Cys Lys Thr Val Ser Ser Glu Val Ser Val Cys Ser Glu
        355                 360                 365
```

-continued

Pro Val Trp Lys Gln Arg Leu Glu Phe Asp Ile Asn Ile Cys Asp Leu
370                 375                 380

Pro Arg Met Ala Arg Leu Cys Phe Ala Leu Tyr Ala Val Ile Glu Lys
385                 390                 395                 400

Ala Lys Lys Ala Arg Ser Thr Lys Lys Ser Lys Lys Ala Asp Cys
                405                 410                 415

Pro Ile Ala Trp Ala Asn Leu Met Leu Phe Asp Tyr Lys Asp Gln Leu
                420                 425                 430

Lys Thr Gly Glu Arg Cys Leu Tyr Met Trp Pro Ser Val Pro Asp Glu
            435                 440                 445

Lys Gly Glu Leu Leu Asn Pro Thr Gly Thr Val Arg Ser Asn Pro Asn
450                 455                 460

Thr Asp Ser Ala Ala Leu Leu Ile Cys Leu Pro Glu Val Ala Pro
465                 470                 475                 480

His Pro Val Tyr Tyr Pro Ala Leu Glu Lys Ile Leu Glu Leu Gly Arg
                485                 490                 495

His Ser Glu Cys Val His Val Thr Glu Glu Gln Leu Gln Leu Arg
            500                 505                 510

Glu Ile Leu Glu Arg Arg Gly Ser Gly Glu Leu Tyr Glu His Glu Lys
            515                 520                 525

Asp Leu Val Trp Lys Leu Arg His Glu Val Gln Glu His Phe Pro Glu
530                 535                 540

Ala Leu Ala Arg Leu Leu Val Thr Lys Trp Asn Lys His Glu Asp
545                 550                 555                 560

Val Ala Gln Met Leu Tyr Leu Leu Cys Ser Trp Pro Glu Leu Pro Val
                565                 570                 575

Leu Ser Ala Leu Glu Leu Leu Asp Phe Ser Phe Pro Asp Cys His Val
            580                 585                 590

Gly Ser Phe Ala Ile Lys Ser Leu Arg Lys Leu Thr Asp Asp Glu Leu
            595                 600                 605

Phe Gln Tyr Leu Leu Gln Leu Val Gln Val Leu Lys Tyr Glu Ser Tyr
            610                 615                 620

Leu Asp Cys Glu Leu Thr Lys Phe Leu Leu Asp Arg Ala Leu Ala Asn
625                 630                 635                 640

Arg Lys Ile Gly His Phe Leu Phe Trp His Leu Arg Ser Glu Met His
                645                 650                 655

Val Pro Ser Val Ala Leu Arg Phe Gly Leu Ile Leu Glu Ala Tyr Cys
                660                 665                 670

Arg Gly Ser Thr His His Met Lys Val Leu Met Lys Gln Gly Glu Ala
            675                 680                 685

Leu Ser Lys Leu Lys Ala Leu Asn Asp Phe Val Lys Leu Ser Ser Gln
690                 695                 700

Lys Thr Pro Lys Pro Gln Thr Lys Glu Leu Met His Leu Cys Met Arg
705                 710                 715                 720

Gln Glu Ala Tyr Leu Glu Ala Leu Ser His Leu Gln Ser Pro Leu Asp
                725                 730                 735

Pro Ser Thr Leu Leu Ala Glu Val Cys Val Glu Gln Cys Thr Phe Met
                740                 745                 750

Asp Ser Lys Met Lys Pro Leu Trp Ile Met Tyr Ser Asn Glu Glu Ala
            755                 760                 765

Gly Ser Gly Gly Ser Val Gly Ile Ile Phe Lys Asn Gly Asp Asp Leu
770                 775                 780

Arg Gln Asp Met Leu Thr Leu Gln Met Ile Gln Leu Met Asp Val Leu

```
             785                 790                 795                 800
Trp Lys Gln Glu Gly Leu Asp Leu Arg Met Thr Pro Tyr Gly Cys Leu
                805                 810                 815
Pro Thr Gly Asp Arg Thr Gly Leu Ile Glu Val Val Leu Arg Ser Asp
                820                 825                 830
Thr Ile Ala Asn Ile Gln Leu Asn Lys Ser Asn Met Ala Ala Thr Ala
                835                 840                 845
Ala Phe Asn Lys Asp Ala Leu Leu Asn Trp Leu Lys Ser Lys Asn Pro
850                 855                 860
Gly Glu Ala Leu Asp Arg Ala Ile Glu Glu Phe Thr Leu Ser Cys Ala
865                 870                 875                 880
Gly Tyr Cys Val Ala Thr Tyr Val Leu Gly Ile Gly Asp Arg His Ser
                885                 890                 895
Asp Asn Ile Met Ile Arg Glu Ser Gly Gln Leu Phe His Ile Asp Phe
                900                 905                 910
Gly His Phe Leu Gly Asn Phe Lys Thr Lys Phe Gly Ile Asn Arg Glu
                915                 920                 925
Arg Val Pro Phe Ile Leu Thr Tyr Asp Phe Val His Val Ile Gln Gln
                930                 935                 940
Gly Lys Thr Asn Asn Ser Glu Lys Phe Glu Arg Phe Arg Gly Tyr Cys
945                 950                 955                 960
Glu Arg Ala Tyr Thr Ile Leu Arg Arg His Gly Leu Leu Phe Leu His
                965                 970                 975
Leu Phe Ala Leu Met Arg Ala Ala Gly Leu Pro Glu Leu Ser Cys Ser
                980                 985                 990
Lys Asp Ile Gln Tyr Leu Lys Asp Ser Leu Ala Leu Gly Lys Thr Glu
                995                 1000                1005
Glu Glu Ala Leu Lys His Phe Arg Val Lys Phe Asn Glu Ala Leu Arg
                1010                1015                1020
Glu Ser Trp Lys Thr Lys Val Asn Trp Leu Ala His Asn Val Ser Lys
1025                1030                1035                1040
Asp Asn Arg Gln

<210> SEQ ID NO 10
<211> LENGTH: 17
<212> TYPE: PRT
<213> ORGANISM: Artificial Sequence
<220> FEATURE:
<223> OTHER INFORMATION: phosphatidylinositol 3-kinase (PI3K) antigen,
      phospho-PI3K p85 acivation state-dependent antibody
      epitope with phosphorylated residue
<220> FEATURE:
<221> NAME/KEY: PHOSPHORYLATION
<222> LOCATION: (10)...(10)
<223> OTHER INFORMATION: phosphotyrosine

<400> SEQUENCE: 10

Cys Gly Phe Ala Glu Pro Tyr Asn Leu Tyr Ser Ser Leu Lys Glu Lys
1               5                   10                  15

Val

<210> SEQ ID NO 11
<211> LENGTH: 15
<212> TYPE: PRT
<213> ORGANISM: Artificial Sequence
<220> FEATURE:
<223> OTHER INFORMATION: phosphatidylinositol 3-kinase (PI3K) antigen,
      phospho-PI3K p85 acivation state-dependent antibody
      epitope with phosphorylated residue
```

-continued

```
<220> FEATURE:
<221> NAME/KEY: PHOSPHORYLATION
<222> LOCATION: (9)...(9)
<223> OTHER INFORMATION: phosphotyrosine

<400> SEQUENCE: 11

Cys Ser Lys Glu Tyr Asp Arg Leu Tyr Glu Glu Tyr Thr Arg Thr
 1               5                  10                  15

<210> SEQ ID NO 12
<211> LENGTH: 126
<212> TYPE: PRT
<213> ORGANISM: Homo sapiens
<220> FEATURE:
<223> OTHER INFORMATION: phosphatidylinositol 3-kinase (PI3K) p110
      antigen

<400> SEQUENCE: 12

Met Pro Pro Arg Pro Ser Ser Gly Glu Leu Trp Gly Ile His Leu Met
 1               5                  10                  15

Pro Pro Arg Ile Leu Val Glu Cys Leu Leu Pro Asn Gly Met Ile Val
                20                  25                  30

Thr Leu Glu Cys Leu Arg Glu Ala Thr Leu Val Thr Ile Lys His Glu
            35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Leu
            100                 105                 110

Asn Arg Glu Ile Gly Phe Ala Ile Gly Met Pro Val Cys Glu
        115                 120                 125
```

What is claimed is:

1. A method for selecting a treatment for a subject having or suspected of having a solid tumor cancer, the method comprising:

(a) measuring the level of dimerization of at least two receptor tyrosine kinases (RTKs) analytes, wherein measuring comprises:

(i) incubating a cellular extract obtained from the subject with one or a plurality of dilution series of capture antibodies to form a plurality of captured analytes;

(ii) incubating the plurality of captured analytes with detection antibodies comprising a first or a plurality of first activation state-independent antibodies and a second or a plurality of second activation state-independent antibodies specific for a first member and a second member, respectively, of a dimerized pair of analytes to form a plurality of detectable captured dimerized analytes, wherein the first activation state-independent antibodies are labeled with a facilitating moiety, the second activation state-independent antibodies are labeled with a first member of a signal amplification pair, and the facilitating moiety generates an oxidizing agent which channels to and reacts with the first member of the signal amplification pair;

(iii) incubating the plurality of detectable captured dimerized analytes with a second member of the signal amplification pair to generate an amplified signal; and (iv) detecting the amplified signal generated from the first and second members of the signal amplification pair; and (b) selecting an anticancer drug by comparing the dimerization of the at least two RTKs to a reference dimerization profile of the same two RTK wherein the reference dimerization profile is generated in the absence of the anticancer drug.

2. The method of claim 1, further comprises calibrating the level of dimerization of at least two RTKs against a standard curve generated for said at least two RTKs.

3. The method of claim 1, wherein the cellular extract is isolated from a subject having cancer after administration of an anticancer drug.

4. The method of claim 1, wherein the cellular extract is contacted with an anticancer drug.

5. The method of claim 1, wherein the anticancer drug is selected from the group consisting of a PI3K modulating compound, a RTK modulating compound, or a combination thereof.

6. The method of claim 1, wherein said at least two RTKs is a member selected form the group consisting of a HER1/HER2 dimer, a HER1/HER3 dimer, a HER2/HER3 dimer, a HER2/HER2 dimer, a HER2/HER4 dimer, a p95HER2/HER3 dimer, and a p95HER2/HER2 dimer.

7. The method of claim 1, wherein the cellular extract is isolated from a subject having or suspected of having a cancer selected from the group consisting of breast, lung, pancreatic, colorectal, or gastric cancer.

8. The method of claim 1, wherein the first activation state-independent antibodies are directly labeled with the facilitating moiety.

9. The method of claim 1, wherein the second activation state-independent antibodies are directly labeled with the first member of the signal amplification pair.

10. The method of claim 1, wherein the second activation state-independent antibodies are labeled with the first member of the signal amplification pair via binding between a first member of a binding pair conjugated to the activation state-independent antibodies and a second member of the binding pair conjugated to the first member of the signal amplification pair.

11. The method of claim 1, wherein the first member of the binding pair is biotin and/or the second member of the binding pair is streptavidin.

12. The method of claim 1, wherein the facilitating moiety is glucose oxidase.

13. The method of claim 12, wherein the glucose oxidase and the activation state-independent antibodies are conjugated to a sulfhydryl-activated dextran molecule.

14. The method of claim 13, wherein the sulfhydryl-activated dextran molecule has a molecular weight of about 500 kDa.

15. The method of claim 1, wherein the capture antibodies are on a solid support, selected from the group consisting of glass, plastic, chips, pins, filters, beads, paper, membrane, fiber bundles, and combinations thereof.

16. The method of claim 15, wherein the capture antibodies are restrained on the solid support in an addressable array.

17. The method of claim 1, wherein the first member of the signal amplification pair is a peroxidase.

18. The method of claim 17, wherein the peroxidase is horseradish peroxidase (HRP).

19. The method of claim 17, wherein the second member of the signal amplification pair is a tyramide reagent.

20. The method of claim 19, wherein the tyramide reagent is biotin-tyramide.

21. The method of claim 20, wherein the amplified signal is generated by peroxidase oxidization of the biotin-tyramide to produce an activated tyramide.

22. The method of claim 21, wherein the activated tyramide is directly detected.

23. The method of claim 21, wherein the activated tyramide is detected upon the addition of a signal-detecting reagent.

24. The method of claim 23, wherein the signal-detecting reagent is a streptavidin-labeled fluorophore.

25. The method of claim 23, wherein the signal-detecting reagent is a combination of a streptavidin-labeled peroxidase and a chromogenic reagent.

26. The method of claim 25, wherein the chromogenic reagent is 3,3',5,5'-tetramethylbenzidine (TMB).

27. A method for selecting a treatment for a subject having or suspected of having a solid tumor cancer, the method comprising:
(a) measuring the level of a PI3K complex activation, wherein said PI3K complex comprises i) dimerization of at least two receptor tyrosine kinases (RTKs) analytes; ii) a PI3K p85 subunit and a PI3K p110 subunit, said measuring comprises:
  (i) incubating a cellular extract obtained from the subject with one or a plurality of dilution series of capture antibodies to form a plurality of captured analytes;
  (ii) incubating the plurality of captured analytes with (1) first detection antibodies comprising a first or a plurality of first activation state-independent antibodies specific for one member of a dimerized receptor tyrosine kinase pair or a PI3K p110 subunit; and (2) second detection antibodies comprising either second or a plurality of second activation state-independent antibodies specific for one member of a dimerized receptor tyrosine kinase pair, a PI3K p85 or a PI3K p110 subunit or activation state-dependent antibodies specific for a PI3K p85 subunit and/or a PI3K p110 subunit to form a plurality of detectable captured dimerized and complexed analytes,
wherein the first detection antibodies are labeled with a facilitating moiety, the second detection antibodies are labeled with a first member of a signal amplification pair, and the facilitating moiety generates an oxidizing agent which channels to and reacts with the first member of the signal amplification pair;
  (iii) incubating the plurality of detectable captured dimerized analytes with a second member of the signal amplification pair to generate an amplified signal; and
  detecting the amplified signal generated from the first and second members of the signal amplification pair; and
(b) selecting an anticancer drug by comparing the level of the PI3K complex activation to a reference PI3K complex activation profile wherein the reference dimerization profile is generated in the absence of the anticancer drug.

* * * * *